US009301526B2

(12) United States Patent
Greul et al.

(10) Patent No.: US 9,301,526 B2
(45) Date of Patent: Apr. 5, 2016

(54) COMPOUNDS WITH NEMATICIDAL ACTIVITY

(71) Applicant: BAYER INTELLECTUAL PROPERTY GMBH, Monheim (DE)

(72) Inventors: Jörg Nico Greul, Leverkusen (DE); Darren Mansfield, Kürten (DE); Martin Füsslein, Düsseldorf (DE); Heiko Rieck, Burscheid (DE); Matthias Riedrich, Köln (DE); Lars Rodefeld, Leverkusen (DE); Kristian Kather, Langenfeld (DE); Olga Malsam, Rösrath (DE); Peter Lösel, Leverkusen (DE); Arnd Voerste, Köln (DE); Hans-Georg Schwarz, Dorsten (DE); Kerstin Ilg, Köln (DE); Ulrich Görgens, Ratingen (DE); Lionel Carles, Tramoyes (FR); Pierre-Yves Coqueron, Lyons (FR); Philippe Desbordes, Lyons (FR); Philippe Meresse, Lyons (FR)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/355,382

(22) PCT Filed: Oct. 29, 2012

(86) PCT No.: PCT/EP2012/071385
§ 371 (c)(1),
(2) Date: Apr. 30, 2014

(87) PCT Pub. No.: WO2013/064460
PCT Pub. Date: May 10, 2013

(65) Prior Publication Data
US 2014/0249149 A1    Sep. 4, 2014

Related U.S. Application Data

(60) Provisional application No. 61/555,127, filed on Nov. 3, 2011.

(30) Foreign Application Priority Data

Nov. 2, 2011  (EP) ..................................... 11187507
Dec. 21, 2011 (EP) ..................................... 11194886

(51) Int. Cl.
*A01N 43/40* (2006.01)
*C07D 213/64* (2006.01)
*A01N 43/84* (2006.01)

(52) U.S. Cl.
CPC ................ *A01N 43/40* (2013.01); *A01N 43/84* (2013.01); *C07D 213/64* (2013.01)

(58) Field of Classification Search
CPC ....... C07D 213/64; A01N 43/40; A01N 43/84
See application file for complete search history.

(56) References Cited

U.S. PATENT DOCUMENTS

| 4,061,642 A | 12/1977 | Fleckenstein et al. |
| 8,815,772 B2 * | 8/2014 | Bereznak et al. .......... 504/116.1 |
| 2008/0103049 A1 | 5/2008 | Witschel et al. |
| 2009/0036311 A1 | 2/2009 | Witschel et al. |
| 2010/0105663 A1 | 4/2010 | Siegel et al. |

FOREIGN PATENT DOCUMENTS

| CA | 2828060 A1 | 9/2012 |
| DE | 2230392 A1 | 1/1974 |
| EP | 1428817 A1 | 6/2004 |
| EP | 1591442 A1 | 11/2005 |
| EP | 1997800 A1 | 12/2008 |
| EP | 2132987 A1 | 12/2009 |
| EP | 2289880 A1 | 3/2011 |
| WO | 8403278 A1 | 8/1984 |
| WO | 0111965 A1 | 2/2001 |
| WO | 2004016088 A2 | 2/2004 |
| WO | 2004074280 A1 | 9/2004 |
| WO | 2005014545 A2 | 2/2005 |
| WO | 2005058828 A1 | 6/2005 |
| WO | 2005058833 A1 | 6/2005 |
| WO | 2005085238 A1 | 9/2005 |
| WO | 2005103004 | * 11/2005 |
| WO | 2005103004 A1 | 11/2005 |
| WO | 2005103006 A1 | 11/2005 |
| WO | 2006008191 A1 | 1/2006 |
| WO | 2006008192 A1 | 1/2006 |
| WO | 2006008193 A1 | 1/2006 |

(Continued)

OTHER PUBLICATIONS

European Search Report dated Oct. 5, 2012, issued in counterpart European Application No. 11194886.5.
European Search Report dated Feb. 16, 2012, issued in counterpart European Application No. 11187507.6.
International Search Report dated Nov. 2, 2011, issued in counterpart International Application No. PCT/EP2012/071385.
Duffey et al., Journal of American Chem. Society, vol. 131, No. 1, p. 14-15 (2009).
Balieu et al., Tetrahedron Letters, vol. 52, p. 2876-2880 (2011).
Journal of American Chem. Society, vol. 72, p. 2804-2806 (1950).

(Continued)

*Primary Examiner* — D M Seaman
(74) *Attorney, Agent, or Firm* — Miles and Stockbridge

(57) ABSTRACT

The present invention relates to the use of known pyridyl carboxamide derivatives and novel pyridyl carboxamide derivatives as nematicides, compositions containing such compounds and methods for the control of nematodes.

12 Claims, 28 Drawing Sheets

(56) References Cited

FOREIGN PATENT DOCUMENTS

| | | | |
|---|---|---|---|
| WO | 2006008194 | A1 | 1/2006 |
| WO | 2006029828 | A1 | 3/2006 |
| WO | 2006067103 | A2 | 6/2006 |
| WO | 2006122952 | * | 11/2006 |
| WO | 2006122952 | A1 | 11/2006 |
| WO | 2006122955 | A1 | 11/2006 |
| WO | 2007060409 | A1 | 5/2007 |
| WO | 2008006479 | A1 | 1/2008 |
| WO | 2010145788 | * | 12/2010 |
| WO | 2012118139 | A1 | 9/2012 |

OTHER PUBLICATIONS

Baur et al., Pesticide Science, vol. 51, pp. 131-152 (1997).
De et al., Tetrahedron letters, vol. 45. p. 7407-7408 (2004).

* cited by examiner

1

COMPOUNDS WITH NEMATICIDAL ACTIVITY

CROSS REFERENCE TO RELATED APPLICATIONS

This application is a §371 National Stage Application of PCT/EP2012/071385, filed Oct. 29, 2012, which claims priority to EP 11187507.6, filed Nov. 2, 2011, which claims the benefit of U.S. Provisional Application No. 61/555,127, filed Nov. 3, 2011 and to EP 1194886.5, filed Dec. 21, 2011.

BACKGROUND

1. Field of the Invention

The present invention relates to the use of predominantly known pyridyl carboxamide derivatives as nematicides, compositions containing such compounds and methods for the control of nematodes.

2. Description of Related Art

Nematodes cause a substantial loss in agricultural product including food and industrial crops and are combated with chemical compounds having nematicidal activity. To be useful in agriculture these compounds should have a high activity, a broad spectrum activity against different strains of nematodes and should not be toxic to non-target organisms.

The use of certain N-2-(pyridyl)ethyl-carboxamide derivatives for controlling nematodes is described in EP 2 132 987 A1.

Most of the compounds of formula (I) described below are known from WO 2001/011965 A1 (later, e.g. in the Tables, referred to as P1), WO 2005/058828 A1 (P2), WO2005/014545 A2 (P3), WO 2005/103004 A1 (P4), WO 2006/122952 A1 (P5), EP 2 289 880 A1 (P6), WO 2006/008191 A1 (P7) and WO 2006/008192 A1 (P8). There it is stated that they can be used as fungicides. Recently WO 2012/118139 was published. It discloses compounds with nematicidal activity.

SUMMARY

Surprisingly it has now been found that these compounds exhibit nematicidal activity and can therefore be used to control nematodes.

It was also found that the compounds of formula (I) exhibit activity against bacteria and viruses and can be used as bactericides and as virucides.

Accordingly, the present invention relates to the use of a compound of formula (I)

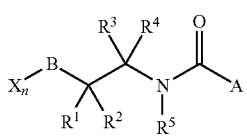

wherein
B represents 2-pyridyl, 3-pyridyl, or 4-pyridyl,
X is selected from the group consisting of halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$ halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —COCNH($C_1$-$C_8$-alkyl), —OCON($C_1$-$C_8$-alkyl)$_2$, —OCONH(O$C_1$-$C_8$-alkyl), —OCO(O$C_1$-$C_8$alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, n is 1, 2, 3 or 4 and if n is 2, 3, or 4 then the substituents X may be the same or different, $R^1$ and $R^2$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-$C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl or $R^1$ and $R^2$ together with the carbon atom to which they are bonded form a 3-, 4-, 5- or 6-membered carbocycle, $R^3$ and $R^4$ are the same or different and are selected from the group consisting of hydrogen, halogen, cyano, hydroxy, amino, —SH, —CHO, —COOH, —CONH$_2$, —CONH (OH), —OCONH$_2$, (hydroxyimino)-$C_1$-$C_6$-alkyl, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_6$- alkyl, $C_1$-$C_6$-alkoxy-$C_1$-$C_6$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2-chlorophenyl-carbonylamino, 2,6-dichlorophenyl-carbonylamino and phenyl;

$R^5$ is selected from the group consisting of hydrogen, cyano, —CHO, —OH, $C_1$-$C_6$-alkyl, $C_1$-$C_6$-halogenoalkyl having 1 to 5 halogen atoms, $C_1$-$C_6$-alkoxy, $C_1$-$C_6$-halogenoalkoxy having 1 to 5 halogen atoms, $C_3$-$C_7$-cycloalkyl, $C_3$-$C_7$-halogenocycloalkyl having 1 to 5 halogen atoms, $C_2$-$C_6$-alkenyl, $C_2$-$C_6$-alkynyl, $C_1$-$C_6$-alkoxy-$C_1$-$C_6$-alkyl, $C_3$-$C_7$-cycloalkyl-$C_1$-$C_6$-alkyl, cyano-$C_1$-$C_6$-alkyl, amino-$C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, $C_1$-$C_6$-alkylcarbonyl, $C_1$-$C_6$-halogenoalkylcarbonyl having 1 to 5 halogen atoms, $C_1$-$C_6$-alkoxycarbonyl, benzyloxycarbonyl, $C_1$-$C_6$-alkoxy-$C_1$-$C_6$-alkylcarbonyl, —S(O)$_2$—$C_1$-$C_6$-alkyl, and —S(O)$_2$—$C_1$-$C_6$-halogenoalkyl having 1 to 5 halogen atoms;

A represents a phenyl group of formula (A1)

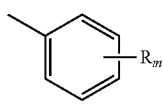

(A1)

wherein

R is selected from the group consisting of halogen, nitro, —OH, NH$_2$, SH, SF$_5$, CHO, OCHO, NHCHO, COOH, cyano, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_3$-$C_6$-cycloalkyl, —S—$C_1$-$C_8$-alkyl, —S—$C_1$-$C_8$-halogenoalkyl having 1 to 5 halogen atoms, $C_1$-$C_8$-alkoxy, $C_1$-$C_8$-halogenoalkoxy having 1 to 5 halogen atoms, $C_1$-$C_8$-alkoxy-$C_2$-$C_8$-alkenyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, $C_1$-$C_8$-alkylsulfonamide, —NH($C_1$-$C_8$-alkyl), N($C_1$-$C_8$-alkyl)$_2$, phenyl (optionally substituted by $C_1$-$C_6$-alkoxy) and phenoxy, or two R bonded to adjacent carbon atoms together represent —O(CH$_2$)$_p$O—, wherein p represents 1 or 2, m is 0, 1, 2, 3, 4 or 5 and if m is 2, 3, 4, or 5 then the substituents R may be the same or different;

with the proviso, that, when B represents 2-pyridyl, then
at least one of $R^1$, $R^2$, $R^3$, $R^4$ and $R^5$ is not a hydrogen atom and
$R^2$ and $R^3$ may also together with the carbon atoms to which they are bonded form a 3-, 4-, 5-, 6- or 7-membered carbocycle, with the proviso, that when B represents 3-pyridyl, then
$R^3$ and $R^4$ may also together with the carbon atom to which they are bonded form a 3-, 4-, 5- or 6-membered carbocycle, with the proviso, that, when B represents 4-pyridyl, then
$R^2$ and $R^3$ may also together with the carbon atoms to which they are bonded form a 3-, 4-, 5-, 6- or 7-membered carbocycle or
$R^3$ and $R^4$ may also together with the carbon atom to which they are bonded form a 3-, 4-, 5- or 6-membered carbocycle, against nematodes.

DETAILED DESCRIPTION OF A PREFERRED EMBODIMENT

Figure 1:
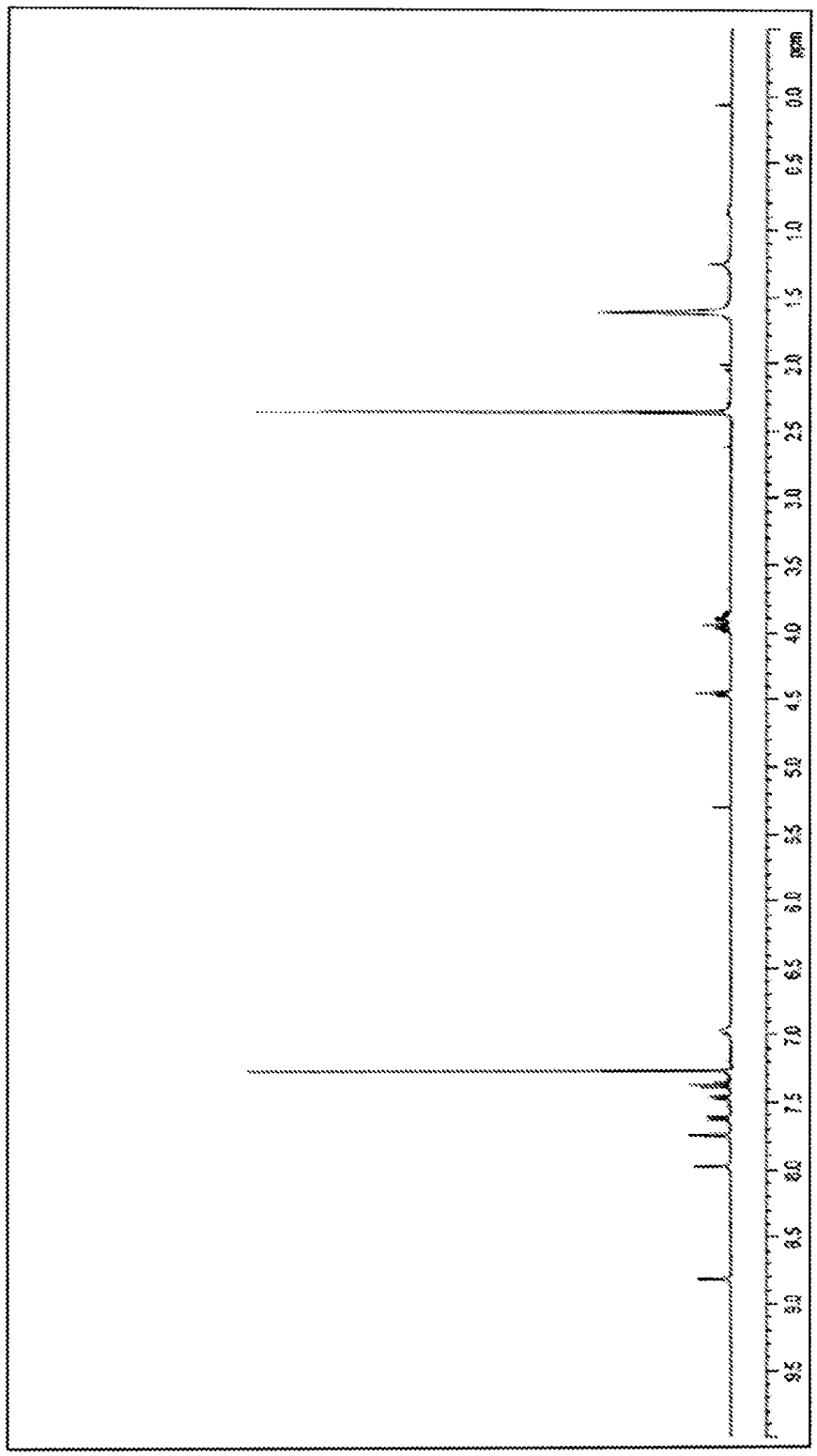
FIGS. 1-16 show chemical structures and mass spectrometry graphs for Compound Nos. Ia-197 through Ia-212, respectively, as further described herein.

In particular the present invention relates to the use of compounds of formula (I) against phytopathogenic nematodes, i.e. against nematodes which damage plants or parts of plants (plant nematodes).

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by a person ordinary skilled in the art.

The invention also relates to the use of salts, N-oxides, metal complexes and metalloid complexes of compounds of formula (I) against nematodes.

A preferred embodiment of the present invention is the use of compounds of formula (Ia)

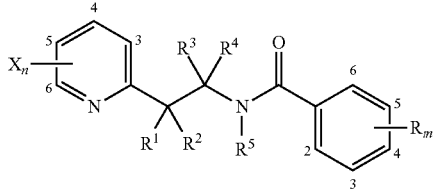
(Ia)

wherein R, $R^1$, $R^2$, $R^3$, $R^4$, $R^5$ X, n, and m have the meanings given above, for the control of nematodes. Another preferred embodiment of the present invention is the use of compounds of formula (Ib)

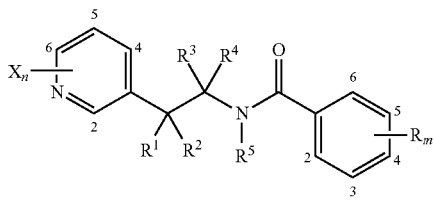
(Ib)

wherein R, $R^1$, $R^2$, $R^3$, $R^4$, $R^5$ X, n, and m have the meanings given above, for the control of nematodes. Another preferred embodiment of the present invention are compounds of formula (Ib-a1)

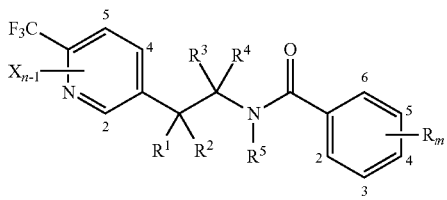
(Ib-a1)

wherein R, $R^1$, $R^2$, $R^3$, $R^4$, $R^5$, n and m have the meanings given above and X represents halogen. Preferably n represents 3 in which case the halogen-atoms (in particular chloroatoms) are in the 2- and 4-position.

Another preferred embodiment of the present invention are compounds of formula (Ib-a2)

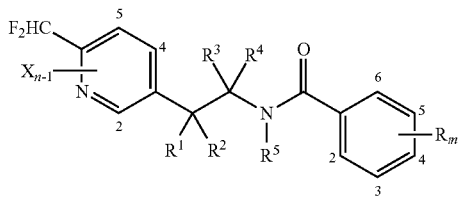
(Ib-a2)

wherein R, $R^1$, $R^2$, $R^3$, $R^4$, $R^5$, n and m have the meanings given above and X represents halogen. Preferably n represents 3 in which case the halogen-atoms (in particular chloroatoms) are in the 2- and 4-position.

Another preferred embodiment of the present invention is the use of compounds of formula (Ic)

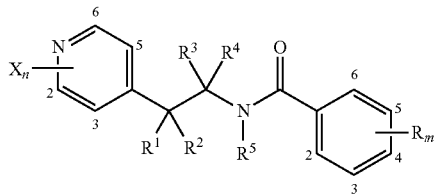
(Ic)

wherein R, $R^1$, $R^2$, $R^3$, $R^4$, $R^5$ X, n, and m have the meanings given above, for the control of nematodes. Other preferred embodiments of the present invention are compounds of formula (I), (Ia), (Ib), (Ib-a1), (Ib-a2) and (Ic) in which $R^1$ and $R^2$ both represent halogen and in particular $R^1$ and $R^2$ both represent fluorine.

Compounds of formula (I) can for example be prepared by reacting a compound of formula (II)

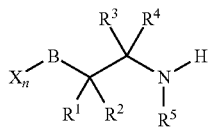
(II)

wherein X, n, $R^1$, $R^2$, $R^3$, $R^4$, and $R^5$ are defined as above, with a compound of formula (III)

(III)

wherein A is defined as above, and
L is a leaving group selected from the group consisting of halogen, hydroxyl, optionally substituted alkyl, optionally substituted benzyl and a group of formula

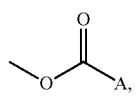

usually in the presence of a base, a condensing agent and in the presence of a solvent.

This process and other processes for the preparation of the compounds of formula (I) as well as intermediates for the preparation of compounds of formula (I) are described in more detail in WO 2001/011965 A1 (P1), WO 2005/058828 A1 (P2), WO2005/014545 A2 (P3), WO 2005/103004 A1 (P4), WO 2006/122952 A1 (P5), EP 2 289 880 A1 (P6), WO 2006/008191 A1 (P7), WO 2006/008192A1 (P8), WO 2004/074280 A1 (P9), WO 2005/058833 A2 (P10), WO 2005/085238 A1 (P11), WO 2005/103006 A1 (P12), WO 2006/122955 A1 (P13), WO 2006/008194 A1 (P14), WO 2006/008193 A1 (P15) and WO 2006/067103 A2 (P16).

In compounds of formula (I), the use of which is preferred, R, $R^1$, $R^2$, $R^3$, $R^4$, $R^5$X, B, n and m have the following meanings.

B represents 2-pyridyl, 3-pyridyl, or 4-pyridyl.

X is selected from the group consisting of halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, n is 1, 2, 3 or 4 and if n is 2, 3, or 4 then the substituents X may be the same or different.

$R^1$ and $R^2$ are the same or different and are selected from the group consisting of hydrogen, halogen, cyano, hydroxy, amino, —CHO, —OCHO, —NHCHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl or $R^1$ and $R^2$ together with the carbon atom to which they are bonded form a 3-, 5- or 6-membered carbocycle, $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, hydroxy-$C_1$-$C_4$-alkyl, $C_1$-$C_4$-alkoxy-$C_1$-$C_3$-alkyl, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2-chlorophenyl-carbonylamino, 2,6-dichlorophenyl-carbonylamino and phenyl;

$R^5$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_2$-$C_4$-alkenyl, $C_2$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di-($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —S(O)$_2$—$C_1$-$C_4$-alkyl, and —S(O)$_2$—$C_1$-$C_4$-halogenoalkyl having 1 to 5 halogen atoms;

A represents a phenyl group of formula (A1)

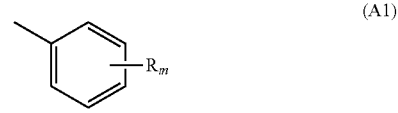

(A1)

wherein

R is selected from the group consisting of halogen, nitro, —OH, CHO, OCHO, NHCHO, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_3$-$C_6$-cycloalkyl, —S—$C_1$-$C_4$-alkyl, —S—$C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkoxy-$C_2$-$C_4$-alkenyl, $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, $C_1$-$C_4$-alkylsulfonamide, —NH($C_1$-$C_4$-alkyl), N($C_1$-$C_4$-alkyl)$_2$, phenyl (optionally substituted by $C_1$-$C_4$-alkoxy) and phenoxy, or two R bonded to adjacent carbon atoms together represent —O(CH$_2$)$_p$O—, wherein p represents 1 or 2, m is 0, 1, 2, 3, 4 or 5 and if m is 2, 3, 4, or 5 then the substituents R may be the same or different.

In compounds of formula (I), the use of which is particularly preferred, R, $R^1$, $R^2$, $R^3$, $R^4$, $R^5$X, B, n and m have the following meanings.

B represents 2-pyridyl, 3-pyridyl, or 4-pyridyl.

X is selected from the group consisting of halogen $C_1$-$C_4$-alkyl, $C_1$-$C_4$-halogenoalkyl having 1 to 5 halogen atoms, $C_1$-$C_4$-alkoxy.

n is 1, 2, 3 or 4 and if n is 2, 3, or 4 then the substituents X may be the same or different.

$R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl or $R^1$ and $R^2$ together with the carbon atom to which they are bonded form a 3- or 5-membered carbocycle.

$R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl.

$R^5$ is selected from the group consisting of hydrogen, $C_3$-$C_6$-cycloalkyl, $C_1$-$C_4$-alkylcarbonyl, and $C_1$-$C_4$-alkoxycarbonyl.

A represents a phenyl group of formula (A1)

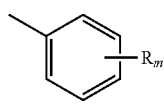

(A1)

wherein

R is selected from the group consisting of halogen, nitro, —OH, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_1$-$C_4$-alkoxycarbonyl, —NH($C_1$-$C_4$-alkyl), phenyl (optionally substituted by $C_1$-$C_4$-alkoxy) and phenoxy.

m is 0, 1, 2 or 3 and if m is 2 or 3 then the substituents R may be the same or different.

The provisos mentioned above apply also with regard to the preferred and particularly preferred definitions.

A "nematicide" as used herein means that the compound is capable of controlling nematodes.

"Controlling nematodes" as used in the present invention means killing nematodes or preventing nematodes to develop or to grow. Controlling nematodes as used herein also encompasses controlling nematode progeny (development of viable cysts and/or egg masses). The compounds described herein, may be used to keep an organism healthy and may be used curatively, pre-emptively or systematically to control nematodes.

The "organism" as mentioned in the above paragraphs may be a plant. When using the compounds described herein, to keep a plant healthy, the controlling of nematodes as used herein encompasses the reduction of damage to plants and/or encompasses increased yield.

Alternatively, the organisms as mentioned above may be a human or an animal. When using the compounds described herein to keep a human or animal healthy, the use encompasses therapeutic use and veterinarian use with the aim to prevent or to cure damage by nematodes.

"Nematodes" as used herein encompass all species of the order Nematoda and in particular species that are parasitic or cause health problems to plants or to fungi (for example species of the orders *Aphelenchida, Meloidogyne, Tylenchida* and others) or to humans and animals (for example species of the orders Ascaradida, Oxyurida, Strongylida, Stronglyloides and Trichocephalida).

Preferably, "nematodes" as used herein, refer to plant nematodes meaning plant parasitic nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonerna* spp.; sedentary parasites such as *Heterodera* spp., *Globoderal* spp., and *Meloidogyne* spp., and stem and leaf endoparasites such as *Ditylenchus* spp., *Aphelenchoides* spp., and *Hirshmaniella* spp. The compounds described herein are distinguished especially for their effective control of halmful root parasitic soil nematodes such as, cystforming nematodes of the genera *Heterodera* or *Globodera*, and/or root knot nematodes of the genus *Meloidogyne*. Harmful species of these genera are for example *Meloidogyne incognata, Heterodera glycines* (soybean cyst nematode), *Globodera pallida* and *Globodera rostochiensis* (potato cyst nematode), which species are effectively controlled with the compounds described herein. However, the use of the compounds described herein is in no way restricted to these genera or species, but also extends in the same manner to other nematodes.

The compounds described herein may have a broad spectrum activity against various genera and/or strains and/or species of nematodes including but not limited to e.g. *Aglenchus agricola, Anguina tritici, Aphelenchoides arachidis, Aphelenchoides fragaria* and the stem and leaf endoparasites *Aphelenchoides* spp. in general, *Belonolaimus gracilis, Belonolaimus longicaudatus, Belonolaimus nortoni, Bursaphelenchus eremus, Bursaphelenchus xylophilus* and *Bursaphelenchus* spp. in general, *Cacopaurus pestis, Criconemella curvata, Criconemella onoensis, Criconemella ornata, Criconemella rusium, Criconemella xenoplax* (=*Mesocriconema xenoplax*) and *Criconemella* spp. in general, *Criconemoides ferniae, Criconemoides onoense, Criconemoides ornatum* and *Criconemoides* spp. in general, *Ditylenchus destructor, Ditylenchus dipsaci, Ditylenchus myceliophagus* and the stem and leaf endoparasites *Ditylenchus* spp. in general, *Dolichodorus heterocephalus, Globodera pallida* (=*Heterodera pallida*), *Globodera rostochiensis* (potato cyst nematode), *Globodera solanacearum, Globodera tabacum, Globodera Virginia* and the sedentary, cyst forming parasites *Globodera* spp. in general *Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicyclio-*

*phora parvana, Heterodera avenae, Heterodera cruciferae, Heterodera glycines* (soybean cyst nematode), *Heterodera oryzae, Heterodera schachtii, Heterodera zeae* and the sedentary, cyst forming parasites *Heterodera* spp. in general, *Hirschmaniella gracilis, Hirschmaniella oryzae Hirschmaniella spinicaudata* and the stem and leaf endoparasites *Hirschmaniella* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and the sedentary parasites *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and the migratory endoparasites *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema*

Nematicides comprising as an active ingredient a compound of formula (I) are suitable for the control of nematodes in soil in the fields of fruit trees, vegetables, other crops and ornamental plants.

Examples of nematodes to which a nematicide of the present invention is applicable include, but are not limited to, nematodes of the genus *Meloidogyne* such as the southern root-knot nematode (*Meloidogyne incognita*), Javanese root-knot nematode (*Meloidogyne javanica*), northern root-knot nematode (*Meloidogyne hapla*), and peanut root-knot nematode (*Meloidogyne arenaria*); nematodes of the genus *Ditylenchus* such as the potato rot nematode (*Ditylenchus destructor*) and bulb and stem nematode (*Ditylenchus dipsaci*); nematodes of the genus *Pratylenchus* such as the cob root-lesion nematode (*Pratylenchus penetrans*), chrysanthemum root-lesion nematode (*Pratylenchus fallax*), coffee root-lesion nematode (*Pratylenchus coffeae*), tea root-lesion nematode (*Pratylenchus loosi*), and walnut root-lesion nematode (*Pratylenchus vulnus*); nematodes of the genus *Globodera* such as the golden nematode (*Globodera rostochiensis*) and potato cyst nematode (*Globodera pallida*); nematodes of the genus *Heterodera* such as the soybean cyst nematode (*Heterodera glycines*) and sugar beet cyst nematode (*Heterodera schachtii*); nematodes of the genus *Aphelenchoides* such as the rice white-tip nematode (*Aphelenchoides besseyi*), chrysanthemum foliar nematode (*Aphelenchoides ritzemabosi*), and strawberry nematode (*Aphelenchoides fragariae*); nematodes of the genus *Aphelenchus* such as the mycophagous nematode (*Aphelenchus avenae*); nematodes of the genus *Radopholus* such as the burrowing nematode (*Radopholus similis*); nematodes of the genus *Tylenchulus* such as the citrus nematode (*Tylenchulus semipenetrans*); nematodes of the genus *Rotylenchulus* such as the reniform nematode (*Rotylenchulus reniformis*); nematodes that occur in trees, such as the pine wood nematode (*Bursaphelenchus xylophilus*), and the like. Furthermore, a nematocidal composition of the present invention is also effective against animal parasitic nematodes such as ascarid, oxyurid, anisakis, filaria, *Wuchereria bancrofti*, *Onchocerca volvulus*, and *Gnathostoma*.

Plants for which a nematicide of the present invention can be used are not particularly limited; for example, plants such as cereals (for example, rice, barley, wheat, rye, oat, corn, kaoliang 5 and the like), beans (soybean, azuki, bean, broad bean, peas, peanuts and the like), fruit trees/fruits (apples, citruses, pears, grapes, peaches, Japanese apricots, cherries, walnuts, almonds, bananas, strawberries and the like), vegetables (cabbage, tomato, spinach, broccoli, lettuce, onion, Welsh onion, pepper and the like), root crops (carrot, potato, sweet potato, radish, lotus root, turnip and the like), industrial crops (cotton, hemp, paper mulberry, mitsumata, rape, beet, hop, sugarcane, sugar beet, olive, rubber, coffee, tobacco, tea and the like), pepos (pumpkin, cucumber, watermelon, melon and the like), pasture plants (orchard grass, sorghum, thimosy, clover, alfalfa and the like), lawn grasses (mascarene grass, bent grass and the like), crops for flavorings etc. (lavender, rosemary, thyme, parsley, pepper, ginger and the like), and flower plants (chrysanthemum, rose, orchids and the like) can be mentioned.

Alternatively, "nematodes" as used herein, refer to nematodes which cause damage to humans or animals.

Specific nematode species harmful to humans or animals are *Ascaris suum, Trichinella spiralis, Trichuris suis* (pig), *Ascaris lumbricoides, Trichinella* sp. (human), *Ostertagia ostertagi, Haemonchus placei, Cooperia oncophora, Dictyocaulus viviparus, Fasciola hepatica* (cattle), *Haemonchus contortus, Nematodirus battus* (sheep), *Strongyloides* sp. (horse), *Ancylostoma caninum, Toxocara canis* (dog), *Toxocara cati, Taenia taeniaeformis* (cat). Moreover, many known nematicides are equally active as anthelmintic and are used to control human and animal parasitic worms, which do not necessarily belong to the group of nematoda. Therefore, it is envisaged by the present invention that the compounds described herein may also be used as anthelmintic.

A further aspect of the invention are nematicidal compositions, comprising an effective amount of at least one compound as defined herein and at least one of the following: surfactant, solid or liquid diluent, characterized in that the surfactant or the diluent is normally used in nematicidal compositions. In an embodiment, said composition comprises at least two compounds as defined herein.

A related aspect of the invention is a method for preparing a nematicidal composition as described herein, comprising the step of mixing at least one compound as described herein with a surfactant or diluent normally used in nematicidal compositions. In an embodiment, said method comprises mixing least two compounds as defined herein with a surfactant or diluent normally used in nematicidal compositions.

In particular, the present invention relates to nematicidal composition developed to be used in agriculture or horticulture. These nematicidal compositions may be prepared in a manner known per se. The present invention further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as Nalkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide. Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives 5 (preferably alkyltaurates), phosphoric esters of polyethoxylated alcohols or phenols, fatty acid esters of polyols, and derivatives of the compounds containing sulphates, sulphonates and phosphates, examples being Alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they areable to penetrate the cuticle of the plant and thereby increase the mobility of the active compounds in thecuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

The compounds are applied in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seeds.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugar beet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemn, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS (tolerance to sulphonylureas, for example maize) Herbicide-resistant plants (plants bred in a conventional manner for herbicide tolerance) which may be mentioned include the varieties sold under the name Clearfield® (for example maize) Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredient may be present in its commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals. The mixtures thus obtained have a broadened spectrum of activity.

Mixtures with fungicides are particularly advantageous. Examples of suitable fungicide mixing partners can be selected from the list consisting of (1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl] 1H-imidazole-1-carbothioate.

(2) inhibitors of the respiratory chain at complex I or II, for example bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1Hpyrazole-4-carboxamide.

(3) inhibitors of the respiratory chain at complex III, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}-ethanamide, (2E)-2-{2-[({[(1E)-1-(3-{[(E)-1-fluoro-2-phenylethenyl]oxy}phenyl)ethylidene]amino}-oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-[({(1E)-1-[3-(trifluoromethyl)phenyl]ethylidenelamino)oxy]methyl}phenyl)-2,4-dihydro-3H-1,2,4-triazol-3-one, methyl (2E)-2-{2-[({cyclopropyl[(4-methoxyphenyl)imino]methyl}-sulfanyl)methyl]phenyl}-3-methoxyprop-2-enoate, N-(3-ethyl-3,5,5-trimethylcyclohexyl)-3-(formyl-amino)-2-hydroxybenzamide, 2-{2-[(2,5-dimethylphenoxy)methyl]phenyl}-2-methoxy-N-methylacetamide and 5 (2R)-2-{2-[(2,5-dimethylphenoxy)methyl]phenyl}-2-methoxy-N-methylacetamide.

(4) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl) [1,2,4]triazolo[1,5-a]pyrimidine and 3-chloro-5-(6-chloropyridin-3-yl)-6-methyl-4-(2,4,6-trifluorophenyl)pyridazine.

(5) Compounds capable to have a multisite action, for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(6) Compounds capable to induce a host defence, for example acibenzolar-S-methyl, isotianil, probenazole and tiadinil.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) Inhibitors of the ATP production, for example fentin acetate, fentin chloride, fentin hydroxide andsilthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon, tricyclazole and 2,2,2-trifluoroethyl {3-methyl-1-[(4-methylbenzoyl)amino]butan-2-yl}carbamate.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen 5 and vinclozolin.

(14) Compounds capable to act as an uncoupler, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propano sine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrroInitrine, tebufloquin, tecloftalam, tolnifanide, triazoxide, trichlamide, zarilamid, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-di-methylbutan-2-yl-1H-imidazole-1-carboxylate, 2,3,5,6-tetrachloro-4-(methylsulfonyl)pyridine, 2,3-dibutyl-6-chlorothieno[2,3-d]pyrimidin-4 (3H)-one, 2,6-dimethyl-1H,5H-[1,4]dithiino[2,3-c:5,6-c] dipyrrole-1,3,5,7 (2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1Hpyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl}piperidin-1-yl) ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)-oxy]pyrimidin-4-amine, 5-fluoro-2-[(4-methylbenzyl)oxy]pyrimidin-4-amine, 5-methyl-6-octyl-[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4- chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)-methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}-piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)-methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)-methylene]amino}oxy)methyl]pyridin-2-yl}carbamate.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

The composition according to the invention comprising a mixture with a bactericide compound may also be particularly advantageous. Examples of suitable bactericide mixing partners may be selected in the list consisting of bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The various aspects of the invention will now be illustrated with reference to the following tables of compounds and examples. The following tables illustrate in a non limiting manner examples of compounds according to the invention.

Abbreviations which are used in the tables include the following:
Me=CH$_3$
Et=C$_2$H$_5$
n-Pr=CH$_2$CH$_2$CH$_3$
tert butyl =C(CH$_3$)$_3$=t-Bu
cyclo-Pr=cyclopropyl
C$_6$H$_5$=phenyl
comm av.=commercially available

TABLE A

Compounds of formula (Ia)

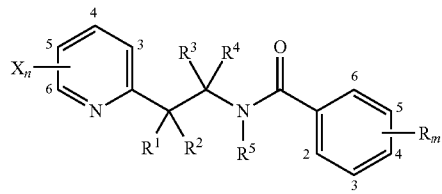

(Ia)

| No. | X$_n$ | R$^1$ | R$^2$ | R$^3$ | R$^4$ | R$^5$ | R$_m$ | cf. |
|---|---|---|---|---|---|---|---|---|
| Ia-1 | 3-Cl 5-CF$_3$ | COOMe | COOMe | H | H | H | 2-CF$_3$ | P16 synthesis procedure |
| Ia-2 | 3-Cl 5-Cl | H | H | CH$_3$ | H | H | 2-CF$_3$ | P3 |
| Ia-3 | 3-Cl 5-Cl | H | H | CH$_3$ | H | H | 2-CF$_3$ | P3 NMR |
| Ia-4 | 3-Cl 5-CF$_3$ | COOEt | COOEt | H | H | H | 2-CF$_3$ | P16 synthesis procedure |
| Ia-5 | 3-Cl 5-CF$_3$ | COOMe | H | H | H | H | 2-CF$_3$ | P2 NMR |
| Ia-6 | 3-Cl 5-CF$_3$ | COOMe | COOEt | H | H | H | 2-CF$_3$ | P2 NMR |
| Ia-7 | 5-Br | OH | H | H | H | H | 2-F 6-F | P3 NMR |
| Ia-8 | 3-Cl 5-CF$_3$ | H | H | CONHEt | H | H | 4-OMe | P1 cpd. 301 |
| Ia-9 | 3-Cl 5-CF$_3$ | H | H | CONHEt | H | H | 2-Cl 6-Cl | P1 cpd. 302 |
| Ia-10 | 3-Cl 5-CF$_3$ | H | H | CONHEt | H | H | H | P1 cpd. 304 |
| Ia-11 | 3-Cl 5-CF$_3$ | H | H | CONHEt | H | H | 4-Cl | P1 cpd. 306 |
| Ia-12 | 3-Cl 5-CF$_3$ | H | H | CONHEt | H | H | 3-NO$_2$ | P1 cpd. 307 |
| Ia-13 | 3-Cl 5-CF$_3$ | H | H | CONHEt | H | H | 3-CF$_3$ | P1 cpd. 308 |

TABLE A-continued

Compounds of formula (Ia)

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-14 | 3-Cl 5-CF$_3$ | H | H | CONHEt | H | H | 4-C$_6$H$_5$ | P1 |
| Ia-15 | 3-Cl 5-CF$_3$ | H | H | CONHEt | H | H | 2-Br | P1 cpd. 310 |
| Ia-16 | 3-Cl 5-CF$_3$ | H | H | CONHMe | H | H | 2-Cl 6-Cl | P1 cpd. 313 |
| Ia-17 | 3-Cl 5-CF$_3$ | H | H | CONHMe | H | H | H | P1 cpd. 314 |
| Ia-18 | 3-Cl 5-CF$_3$ | H | H | CONHMe | H | H | 4-OMe | P1 cpd. 315 |
| Ia-19 | 3-Cl 5-CF$_3$ | H | H | CONHMe | H | H | 4-C$_6$H$_5$ | P1 cpd. 316 |
| Ia-20 | 3-Cl 5-CF$_3$ | H | H | COOMe | H | H | H | P1 cpd. 317 |
| Ia-21 | 3-Cl 5-CF$_3$ | H | H | COOMe | H | H | 2-Cl 6-Cl | P1 cpd. 319 |
| Ia-22 | 3-Cl 5-CF$_3$ | H | H | COOMe | H | H | 4-C$_6$H$_5$ | P1 cpd. 320 |
| Ia-23 | 3-Cl 5-CF$_3$ | H | H | COOMe | H | H | 2-Br | P1 cpd. 321 |
| Ia-24 | 3-Cl 5-CF$_3$ | H | H | COOEt | H | H | 4-OMe | P1 cpd. 323 |
| Ia-25 | 3-Cl 5-CF$_3$ | H | H | COOEt | H | H | 3-CF$_3$ | P1 cpd. 324 |
| Ia-26 | 3-Cl 5-CF$_3$ | H | H | COOEt | H | H | 2-Cl 6-Cl | P1 cpd. 325 |
| Ia-27 | 3-Cl 5-CF$_3$ | H | H | COOEt | H | H | 2-Br | P1 cpd. 326 |
| Ia-28 | 3-Cl 5-CF$_3$ | H | H | COOMe | H | H | 4-OMe | P1 cpd. 328 |
| Ia-29 | 3-Cl 5-CF$_3$ | H | H | COOMe | H | H | 4-Cl | P1 cpd. 329 |
| Ia-30 | 3-Cl 5-CF$_3$ | H | H | COOMe | H | H | 3-NO$_2$ | P1 cpd. 330 |
| Ia-31 | 3-Cl 5-CF$_3$ | H | H | COOMe | H | H | 3-CF$_3$ | P1 cpd. 331 |
| Ia-32 | 3-Cl 5-CF$_3$ | H | H | COOEt | H | H | H | P1 cpd. 333 |
| Ia-33 | 3-Cl 5-CF$_3$ | H | H | COOEt | H | H | 4-Cl | P1 cpd. 334 |
| Ia-34 | 3-Cl 5-CF$_3$ | H | H | COOEt | H | H | 3-NO$_2$ | P1 cpd. 335 |
| Ia-35 | 3-Cl 5-CF$_3$ | H | H | COOEt | H | H | 4-C$_6$H$_5$ | P1 cpd. 336 |
| Ia-36 | 3-Cl 5-CF$_3$ | H | H | CONHMe | H | H | 4-Cl | P1 cpd. 337 |
| Ia-37 | 3-Cl 5-CF$_3$ | H | H | CONHMe | H | H | 3-NO$_2$ | P1 cpd. 338 |
| Ia-38 | 3-Cl 5-CF$_3$ | H | H | CONHMe | H | H | 3-CF$_3$ | P1 cpd. 339 |
| Ia-39 | 3-Cl 5-CF$_3$ | H | H | CONHMe | H | H | 2-Br | P1 cpd. 340 |
| Ia-40 | 3-Cl 5-CF$_3$ | H | H | COOH | H | H | 2-Cl 6-Cl | P2 |
| Ia-41 | 3-Cl 5-CF$_3$ | CH$_3$ | H | H | H | H | 4-CF$_3$ | NMR |
| Ia-42 | 3-Cl 5-CF$_3$ | CH$_3$ | H | H | H | H | 3-CF$_3$ | |
| Ia-43 | 3-Cl 5-CF$_3$ | H | H | Me | H | H | 2-CF$_3$ | P2 cpd. 38 |
| Ia-44 | 5-CF$_3$ | CH$_2$—CH$_2$ | | H | H | H | 2-CF$_3$ | P2 cpd. 65 |
| Ia-45 | 3-Cl 5-Cl | CH$_2$—CH$_2$ | | H | H | H | 2-CF$_3$ | P3 cpd. 67 |

TABLE A-continued

Compounds of formula (Ia)

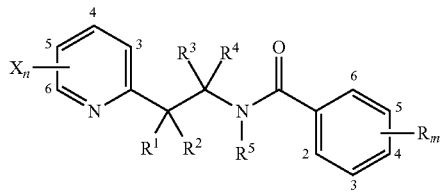

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-46 | 5-CF$_3$ | CH$_3$ | H | H | H | H | 2-CF$_3$ | P2 cpd. 66 |
| Ia-47 | 5-CF$_3$ | CH$_3$ | H | H | H | H | 2-I | P2 cpd. 67 |
| Ia-48 | 5-Cl | CH$_2$—CH$_2$ | | H | H | H | 2-CF$_3$ | P3 cpd. 68 |
| Ia-49 | 5-CF$_3$ 6-Cl | CH$_3$ | H | H | H | H | 2-CF$_3$ | P2 cpd. 62 |
| Ia-50 | 5-CF$_3$ 6-Cl | CH$_3$ | H | H | H | H | 2-I | P2 cpd. 63 |
| Ia-51 | 5-CF$_3$ 6-Cl | CH$_3$ | H | H | H | H | 2-Br | P2 cpd. 64 |
| Ia-52 | 3-Cl 5-CF$_3$ | NHCO-2-C$_6$H$_4$Cl | H | H | H | H | 2-CF$_3$ | P2 cpd. 70 |
| Ia-53 | 3-Cl 5-CF$_3$ | NHCO-2-C$_6$H$_4$Cl | H | H | H | H | 2-I | P2 cpd. 71 |
| Ia-54 | 3-Cl 5-CF$_3$ | NHCO-2-C$_6$H$_4$Cl | H | H | H | H | 2-Br | P2 cpd. 72 |
| Ia-55 | 3-F 5-Cl 6-F | COO-tert butyl | COO-tert butyl | H | H | H | 2-CF$_3$ | P3 NMR |
| Ia-56 | 5-Cl | CH$_3$ | H | H | H | H | 2-Cl 4-F | P3 NMR |
| Ia-57 | 5-Cl | CH$_3$ | H | H | H | H | 2-Cl 5-F | P3 cpd. 7 |
| Ia-58 | 3-Cl 5-CF$_3$ | CH$_3$ | H | H | H | H | 2-Cl 3-Cl | P2 cpd. 1 |
| Ia-59 | 3-Cl 5-CF$_3$ | CH$_3$ | H | H | H | H | 2-Cl 4-Cl | P2 cpd. 2 |
| Ia-60 | 3-Cl 5-CF$_3$ | CH$_3$ | H | H | H | H | 2-Cl 5-Cl | P2 cpd. 3 |
| Ia-61 | 3-Cl 5-CF$_3$ | CH$_3$ | H | H | H | H | 2-OMe | P2 cpd. 4 |
| Ia-62 | 3-Cl 5-CF$_3$ | CH$_3$ | H | H | H | H | 2-OMe 3-OMe | P2 cpd. 5 |
| Ia-63 | 3-Cl 5-CF$_3$ | CH$_3$ | H | H | H | H | 2-OMe 6-OMe | P2 cpd. 6 |
| Ia-64 | 3-Cl 5-CF$_3$ | CH$_3$ | H | H | H | H | 2-Me | P2 cpd. 7 |
| Ia-65 | 3-Cl 5-CF$_3$ | CH$_3$ | H | H | H | H | 2-Me 3-Me | P2 cpd. 8 |
| Ia-66 | 3-Cl 5-CF$_3$ | CH$_3$ | H | H | H | H | 2-Me 4-Me | P2 cpd. 9 |
| Ia-67 | 3-Cl 5-CF$_3$ | CH$_3$ | H | H | H | H | 2-Me 5-Me | P2 cpd. 10 |
| Ia-68 | 3-Cl 5-CF$_3$ | CH$_3$ | H | H | H | H | 2-F 3-Cl | P2 cpd. 11 |
| Ia-69 | 3-Cl 5-CF$_3$ | CH$_3$ | H | H | H | H | 2-Me 3-Cl | P2 cpd. 12 |
| Ia-70 | 3-Cl 5-CF$_3$ | CH$_3$ | H | H | H | H | 2-Me 3-F | P2 cpd. 13 |
| Ia-71 | 3-Cl 5-CF$_3$ | CH$_3$ | H | H | H | H | 2-F 5-Cl | P2 cpd. 14 |
| Ia-72 | 3-Cl 5-CF$_3$ | CH$_3$ | H | H | H | H | 2-Me 3-OH | P2 cpd. 15 |
| Ia-73 | 3-Cl 5-CF$_3$ | C$_2$H$_5$ | H | H | H | H | 2-Cl 3-Cl | P2 cpd. 16 |
| Ia-74 | 3-Cl 5-CF$_3$ | C$_2$H$_5$ | H | H | H | H | 2-Cl 4-Cl | P2 NMR |
| Ia-75 | 3-Cl 5-CF$_3$ | C$_2$H$_5$ | H | H | H | H | 2-Cl 5-Cl | P2 cpd. 18 |
| Ia-76 | 3-Cl 5-CF$_3$ | C$_2$H$_5$ | H | H | H | H | 2-NHMe | P2 cpd. 19 |

TABLE A-continued

Compounds of formula (Ia)

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-77 | 3-Cl 5-CF$_3$ | C$_2$H$_5$ | H | H | H | H | 2-OMe | P2 cpd. 20 |
| Ia-78 | 3-Cl 5-CF$_3$ | C$_2$H$_5$ | H | H | H | H | 2-OMe 3-OMe | P2 cpd. 21 |
| Ia-79 | 2-Cl 5-CF$_3$ | C$_2$H$_5$ | H | H | H | H | 2-OMe 6-OMe | P2 cpd. 22 |
| Ia-80 | 3-Cl 5-CF$_3$ | C$_2$H$_5$ | H | H | H | H | 2-OH | |
| Ia-81 | 3-Cl 5-CF$_3$ | C$_2$H$_5$ | H | H | H | H | 2-OH 4-OMe | NMR |
| Ia-82 | 3-Cl 5-CF$_3$ | C$_2$H$_5$ | H | H | H | H | 2-OH 5-Me | |
| Ia-83 | 3-Cl 5-CF$_3$ | C$_2$H$_5$ | H | H | H | H | 2-Me | P2 cpd. 23 |
| Ia-84 | 3-Cl 5-CF$_3$ | C$_2$H$_5$ | H | H | H | H | 2-Me 3-Me | P2 cpd. 24 |
| Ia-85 | 3-Cl 5-CF$_3$ | C$_2$H$_5$ | H | H | H | H | 2-Me 4-Me | P2 cpd. 25 |
| Ia-86 | 3-Cl F—CF$_3$ | C$_2$H$_5$ | H | H | H | H | 2-F 3-Cl | P2 cpd. 26 |
| Ia-87 | 3-Cl 5-CF$_3$ | C$_2$H$_5$ | H | H | H | H | 2-Me 3-Cl | P2 cpd. 27 |
| Ia-88 | 3-Cl 5-CF$_3$ | C$_2$H$_5$ | H | H | H | H | 2-Me 3-F | P2 cpd. 28 |
| Ia-89 | 3-Cl 5-CF$_3$ | C$_2$H$_5$ | H | H | H | H | 2-F 5-Cl | P2 cpd. 29 |
| Ia-90 | 3-Cl 5-CF$_3$ | C$_2$H$_5$ | H | H | H | H | 2-Me 3-OH | P2 cpd. 30 |
| Ia-91 | 3-Cl 5-CF$_3$ | C$_2$H$_5$ | H | H | H | H | 2-Me 5-Me | P2 cpd. 31 |
| Ia-92 | 3-Cl 5-CF$_3$ | CH$_3$ | H | H | H | H | 2-CF$_3$ | P2 cpd. 32 |
| Ia-93 | 3-Cl 5-CF$_3$ | CH$_3$ | CH$_3$ | H | H | H | 2-CF$_3$ | P2 cpd. 33 |
| Ia-94 | 3-Cl 5-CF$_3$ | CH$_3$ | C$_2$H$_5$ | H | H | H | 2-CF$_3$ | P2 cpd. 34 |
| Ia-95 | 3-Cl 5-CF$_3$ | n-Pr | n-Pr | H | H | H | 2-CF$_3$ | P2 cpd. 35 |
| Ia-96 | 3-Cl 5-CF$_3$ | n-Pr | n-Pr | H | H | H | 2-I | P2 cpd. 36 |
| Ia-97 | 3-Cl 5-CF$_3$ | n-Pr | n-Pr | H | H | H | 2-Br | P2 cpd. 37 |
| Ia-98[1] | 3-Cl 5-CF$_3$ | H | (CH$_2$)$_4$ | | H | H | 2-CF$_3$ | P4 cpd. 1 |
| Ia-99[2] | 3-Cl 5-CF$_3$ | H | (CH$_2$)$_4$ | | H | H | 2-CF$_3$ | P4 cpd. 2 |
| Ia-100 | 3-Cl 5-CF$_3$ | C$_2$H$_5$ | H | H | H | H | 2-CF$_3$ | P2 cpd. 39 |
| Ia-101 | 3-Cl 5-CF$_3$ | C$_2$H$_5$ | H | H | H | H | 2-Br | P2 cpd. 40 |
| Ia-102 | 3-Cl 5-CF$_3$ | C$_2$H$_5$ | H | H | H | H | 2-CHF$_2$ | P2 cpd. 41 |
| Ia-103 | 3-Cl 5-CF$_3$ | n-Pr | H | H | H | H | 2-CF$_3$ | P2 cpd. 42 |
| Ia-104 | 3-Cl 5-CF$_3$ | n-Pr | H | H | H | H | 2-Br | P2 cpd. 43 |
| Ia-105 | 3-Cl 5-CF$_3$ | n-Pr | H | H | H | H | 2-CHF$_2$ | P2 cpd. 44 |
| Ia-106 | 3-Cl 5-CF$_3$ | CH$_3$ | CH$_3$ | H | H | H | 2-CHF$_2$ | P2 cpd. 46 |
| Ia-107 | 3-Cl 5-CF$_3$ | H | (CH$_2$)$_4$ | | H | H | 2-CHF$_2$ | P4 cpd. 3 |
| Ia-108[1] | 3-Cl 5-CF$_3$ | H | (CH$_2$)$_4$ | | H | H | 2-I | P4 cpd. 4 |

TABLE A-continued

Compounds of formula (Ia)

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-109[2] | 3-Cl 5-CF$_3$ | H | (CH$_2$)$_4$ | | H | H | 2-I | P4 cpd. 5 |
| Ia-110 | 3-Cl 5-CF$_3$ | H | H | C$_2$H$_5$ | H | H | 2-CF$_3$ | P2 cpd. 47 |
| Ia-111 | 3-Cl 5-CF$_3$ | H | H | OMe | H | H | 2-CF$_3$ | P2 NMR |
| Ia-112 | 3-Cl 5-CF$_3$ | H | H | OC(O)Me | H | H | 2-CF$_3$ | P2 NMR |
| Ia-113 | 3-Cl 5-Cl | CH$_3$ | H | H | H | H | 2-CF$_3$ | P3 cpd. 60 |
| Ia-114 | 3-Cl 5-Cl | CH$_3$ | H | H | H | H | 2-I | P3 cpd. 61 |
| Ia-115 | 3-Cl 5-CF$_3$ | H | H | C$_6$H$_5$ | H | H | 2-CF$_3$ | P2 cpd. 49 |
| Ia-116 | 3-Cl 5-CF$_3$ | H | H | C$_6$H$_5$ | H | H | 2-I | P2 cpd. 50 |
| Ia-117 | 3-Cl 5-CF$_3$ | NHCO-2,6-C$_6$H$_3$Cl$_2$ | H | H | H | H | 2-I | P2 cpd. 51 |
| Ia-118 | 3-Cl 5-CF$_3$ | NHCO-2,6-C$_6$H$_3$Cl$_2$ | H | H | H | H | 2-Br | P2 cpd. 52 |
| Ia-119 | 3-Cl 5-CF$_3$ | NHCO-2,6-C$_6$H$_3$Cl$_2$ | H | H | H | H | 2-CHF$_2$ | P2 cpd. 53 |
| Ia-120 | 3-Cl 5-CF$_3$ | CN | COOMe | H | H | H | 2-CF$_3$ | P2 cpd. 54 |
| Ia-121 | 3-Cl 5-CF$_3$ | CN | H | H | H | H | 2-CF$_3$ | P2 cpd. 55 |
| Ia-122[3] | 3-Cl 5-CF$_3$ | H | H | CH$_3$ | H | H | 2-CF$_3$ | P2 cpd. 57 |
| Ia-123[3] | 3-Cl 5-CF$_3$ | H | H | CH$_3$ | H | H | 2-CF$_3$ | P2 cpd. 56 |
| Ia-124 | 5-Cl | CH$_3$ | H | H | H | H | 2-I | P3 cpd. 65 |
| Ia-125 | 5-Cl | CH$_3$ | H | H | H | H | 2-CF$_3$ | P3 cpd. 66 |
| Ia-126 | 3-Cl 5-CF$_3$ | CH$_3$ | H | CH$_3$ | H | H | 2-CF$_3$ | P2 cpd. 58 |
| Ia-127 | 3-Cl 5-CF$_3$ | CH$_3$ | H | CH$_3$ | H | H | 2-I | P2 cpd. 59 |
| Ia-128 | 3-Cl 5-CF$_3$ | H | (CH$_2$)$_5$ | | H | H | 2-CF$_3$ | P4 cpd. 6 |
| Ia-129 | 3-Cl 5-CF$_3$ | H | (CH$_2$)$_5$ | | H | H | 2-I | P4 cpd. 7 |
| Ia-130 | 5-Cl | C$_6$H$_5$ | H | H | H | H | 2-CF$_3$ | P3 NMR |
| Ia-131 | 5-Cl | C$_2$H$_5$ | H | H | H | H | 2-CF$_3$ | P3 NMR |
| Ia-132 | 6-Cl 5-CF$_3$ | H | H | CH$_3$ | H | H | 2-CF$_3$ | P2 cpd. 61 |
| Ia-133 | 3-Cl 5-CF$_3$ | H | H | CF$_3$ | H | H | 2-CF$_3$ | P2 cpd. 60 |
| Ia-134 | 5-Cl | (CH$_2$)$_4$ | | H | H | H | 2-CF$_3$ | P3 NMR |
| Ia-135 | 3-Cl 5-CF$_3$ | H | H | CH$_3$ | H | cyclo-Pr | 2-CF$_3$ | P2 cpd. 68 |
| Ia-136 | 3-Cl 5-CF$_3$ | H | H | CH$_3$ | H | cyclo-Pr | 2-I | P2 cpd. 69 |
| Ia-137 | 3-Cl 5-Cl | H | (CH$_2$)$_4$ | | H | H | 2-CF$_3$ | P5 cpd. 1 |
| Ia-138 | 3-Cl 5-CF$_3$ | C$_2$H$_5$ | H | H | H | H | H | |
| Ia-139 | 3-Cl 5-Cl | F | F | H | H | H | 2-CF$_3$ | P3 NMR |
| Ia-140 | 3-Cl 5-CF$_3$ | H | H | CH$_3$ | H | H | 2-I | P2 NMR |

TABLE A-continued

Compounds of formula (Ia)

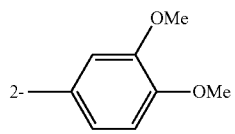

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-141 | 3-Cl 5-CF$_3$ | H | H | CH$_3$ | H | H | 2-Cl | P2 NMR |
| Ia-142 | 3-Cl 5-Cl | F | F | H | H | H | 2-I | P3 NMR |
| Ia-143[4] | 3-Cl 5-CF$_3$ | CH$_2$-cyclo-Pr | H | CH$_3$ | H | H | 2-CF$_3$ | NMR |
| Ia-144[4] | 3-Cl 5-CF$_3$ | CH$_2$—CH=CH$_2$ | H | CH$_3$ | H | H | 2-CF$_3$ | P2 NMR |
| Ia-145[4] | 3-Cl 5-CF$_3$ | CH$_2$—CH=CH$_2$ | H | CH$_3$ | H | H | 2-Cl | P2 |
| Ia-146[4] | 3-Cl 5-CF$_3$ | CH$_2$-cyclo-Pr | H | CH$_3$ | H | H | 2-Cl | NMR |
| Ia-147[2] | 3-Cl 5-Cl | H | CH$_2$ | | H | H | 2-CF$_3$ | P5 cpd. 2 |
| Ia-148 | 3-Cl 5-CF$_3$ | F | F | H | H | H | 2-CF$_3$ | P2 NMR |
| Ia-149 | 3-Cl 5-Cl | H | CH$_2$ | | H | H | 2-I | P5 NMR |
| Ia-150 | 3-Cl 5-CF$_3$ | F | F | H | H | H | 2-I | P2 NMR |
| Ia-151 | 3-Cl 5-Cl | H | CH$_2$ | | H | H | 2-I | P5 cpd. 4 |
| Ia-152[2] | 3-Cl 5-Cl | H | CH$_2$ | | H | H | 2-I | P5 cpd. 3 |
| Ia-153 | 3-Cl 5-CF$_3$ | H | H | CH$_3$ | H | H | 2-Br | P2 NMR |
| Ia-154 | 3-Cl 5-CF$_3$ | H | H | CH$_3$ | H | H | 2-CHF$_2$ | P2 NMR |
| Ia-155[4] | 3-Cl 5-CF$_3$ | CH$_2$—C≡CH | H | CH$_3$ | H | H | 2-Br | P2 NMR |
| Ia-156[4] | 3-Cl 5-CF$_3$ | CH$_2$—C≡CH | H | CH$_3$ | H | H | 2-CHF$_2$ | P2 NMR |
| Ia-157 | 3-Cl 5-CF$_3$ | C$_2$H$_5$ | H | H | H | H | 2-(3,4-diOMe-C$_6$H$_3$) | NMR |
| Ia-158 | 3-Cl 5-CF$_3$ | OC(O)Me | H | H | H | H | 2-CF$_3$ | P2 |
| Ia-159 | 3-Cl 5-CF$_3$ | OC(O)Me | H | H | H | COMe | 2-CF$_3$ | P2 |
| Ia-160 | 3-Cl 5-CF$_3$ | Cl | H | H | H | H | 2-CF$_3$ | P2 |
| Ia-161[4] | 3-Cl 5-CF$_3$ | H | (CH$_2$)$_4$ | | H | H | H | P4 NMR |
| Ia-162[4] | 3-Cl 5-CF$_3$ | H | (CH$_2$)$_4$ | | H | H | 4-Cl | P4 NMR |
| Ia-163[4] | 3-Cl 5-CF$_3$ | H | (CH$_2$)$_4$ | | H | H | 4-OMe | PR NMR |
| Ia-164[4] | 3-Cl 5-CF$_3$ | H | (CH$_2$)$_4$ | | H | H | 2-Br | P4 NMR |
| Ia-165[4] | 3-Cl 5-CF$_3$ | H | (CH$_2$)$_4$ | | H | H | 4-C$_6$H$_5$ | NMR |
| Ia-166[4] | 3-Cl 5-CF$_3$ | H | (CH$_2$)$_4$ | | H | H | 3-NO$_2$ | P4 NMR |
| Ia-167 | 3-Cl 5-CF$_3$ | COOEt | H | H | H | H | 2-CF$_3$ | P2 |
| Ia-168 | 3-Cl 5-CF$_3$ | OEt | H | H | H | H | 2-CF$_3$ | P2 |
| Ia-169 | 3-Cl 5-CF$_3$ | H | H | COOH | H | H | 2-Br | P2 NMR |

TABLE A-continued

Compounds of formula (Ia)

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-170 | 3-Cl<br>5-CF$_3$ | H | H | CH$_3$ | H | H | 2-F<br>6-F | P2<br>NMR |
| Ia-171 | 3-Cl<br>5-CF$_3$ | H | H | CH$_3$ | H | H | 2-F<br>4-F<br>6-F | P2<br>NMR |
| Ia-172 | 3-Cl<br>5-CF$_3$ | H | H | CH$_3$ | H | H | 2-F | P2<br>NMR |
| Ia-173 | 3-Cl<br>5-CF$_3$ | H | H | CH$_3$ | H | H | 2-Cl<br>6-Cl | P2<br>NMR |
| Ia-174 | 3-Cl<br>5-CF$_3$ | H | H | CH$_3$ | H | H | 2-F<br>6-CF$_3$ | P2<br>NMR |
| Ia-175 | 3-Cl<br>5-CF$_3$ | H | H | CH$_3$ | H | H | 2-CH$_2$CF$_3$ | P2<br>NMR |
| Ia-176 | 3-Cl<br>5-CF$_3$ | H | H | CH$_3$ | H | H | 2-Cl<br>4-Cl | P2<br>NMR |
| Ia-177 | 3-Cl<br>5-CF$_3$ | CH$_3$ | H | H | H | H | 2-I | P2<br>NMR |
| Ia-178 | 3-Cl<br>5-CF$_3$ | CH$_3$ | H | C$_2$H$_5$ | H | H | 2-I | P2<br>NMR |
| Ia-179 | 3-Cl<br>5-CF$_3$ | CH$_3$ | H | C$_2$H$_5$ | H | H | 2-CF$_3$ | P2 |
| Ia-180 | 3-Cl<br>5-Cl | CH$_3$ | H | C$_2$H$_5$ | H | H | 2-I | P3 |
| Ia-181 | 3-Cl<br>5-Cl | CH$_3$ | H | C$_2$H$_5$ | H | H | 2-CF$_3$ | P3 |
| Ia-182 | 3-Cl<br>5-Cl | C$_2$H$_5$ | H | CH$_3$ | H | H | 2-I | P3 |
| Ia-183 | 3-Cl<br>5-Cl | C$_2$H$_5$ | H | CH$_3$ | H | H | 2-CF$_3$ | P3 |
| Ia-184 | 5-F | CH$_3$ | H | CH$_3$ | H | H | 2-I | P3 |
| Ia-185 | 5-F | CH$_3$ | H | CH$_3$ | H | H | 2-CF$_3$ | P3 |
| Ia-186 | 3-Cl | CH$_3$ | H | CH$_3$ | H | H | 2-I | P3 |
| Ia-187 | 3-Cl | CH$_3$ | H | CH$_3$ | H | H | 2-CF$_3$ | P3 |
| Ia-188 | 5-CF$_3$ | CH$_3$ | H | CH$_3$ | H | H | 2-I | P2 |
| Ia-189 | 5-CF$_3$ | CH$_3$ | H | CH$_3$ | H | H | 2-CF$_3$ | P2 |
| Ia-190 | 3-Cl<br>5-Cl | H | H | CH$_2$—OCH$_3$ | H | H | 2-I | P3 |
| Ia-191 | 3-Cl<br>5-Cl | H | H | CH$_2$—OCH$_3$ | H | H | 2-CF$_3$ | P3 |
| Ia-192 | 3-Cl<br>5-Cl | H | H | C$_2$H$_5$ | H | H | 2-I | P3 |
| Ia-193 | 3-Cl<br>5-Cl | H | H | C$_2$H$_5$ | H | H | 2-CF$_3$ | P3 |
| Ia-194 | 3-Cl<br>5-CF$_3$ | H | H | CH$_2$—OH | H | H | 2-I | P2 |
| Ia-195 | 3-Cl<br>5-CF$_3$ | H | H | CH$_2$—OH | H | H | 2-CF$_3$ | P2 |
| Ia-196 | 3-Cl<br>5-CF$_3$ | H | H | CH$_3$ | H | H | 2-NO$_2$ | P2<br>NMR |
| Ia-197 | 3-Cl<br>5-CF$_3$ | N(CH$_3$)$_2$ | H | H | H | H | 3-Cl | P2<br>NMR |
| Ia-198 | 3-Cl<br>5-CF$_3$ | N(CH$_3$)$_2$ | H | H | H | H | 2-F<br>6-F | P2<br>NMR |
| Ia-199 | 3-Cl<br>5-CF$_3$ | N(CH$_3$)$_2$ | H | H | H | H | H | P2<br>NMR |
| Ia-200 | 3-Cl<br>5-CF$_3$ | N(CH$_3$)$_2$ | H | H | H | H | 4-Cl | P2<br>NMR |
| Ia-201 | 3-Cl<br>5-CF$_3$ | N(CH$_3$)$_2$ | H | H | H | H | 2-Cl<br>4-Cl | P2<br>NMR |
| Ia-202 | 3-Cl<br>5-CF$_3$ | N(CH$_3$)$_2$ | H | H | H | H | 2-Cl<br>6-Cl | P2<br>NMR |

TABLE A-continued

Compounds of formula (Ia)

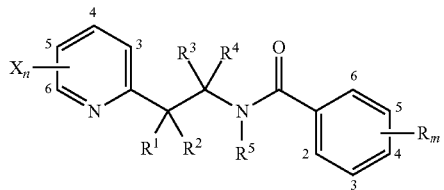

(Ia)

| No. | $X_n$ | $R^1$ | $R^2$ | $R^3$ | $R^4$ | $R^5$ | $R_m$ | cf. |
|---|---|---|---|---|---|---|---|---|
| Ia-203 | 3-Cl 5-CF$_3$ | morpholine | H | H | H | H | H | P2 NMR |
| Ia-204 | 3-Cl 5-CF$_3$ | morpholine | H | H | H | H | 2-Cl 4-Cl | P2 NMR |
| Ia-205 | 3-Cl 5-CF$_3$ | morpholine | H | H | H | H | 2-CF$_3$ | P2 NMR |
| Ia-206 | 3-Cl 5-CF$_3$ | morpholine | H | H | H | H | 4-Cl | P2 NMR |
| Ia-207 | 3-Cl 5-CF$_3$ | morpholine | H | H | H | H | 2-F 6-F | P2 NMR |
| Ia-208 | 3-Cl 5-CF$_3$ | morpholine | H | H | H | H | 2-Cl 6-Cl | P2 NMR |
| Ia-209 | 3-Cl 5-CF$_3$ | morpholine | H | H | H | H | 2-Cl | P2 NMR |
| Ia-210 | 3-Cl 5-CF$_3$ | morpholine | H | H | H | H | 3-Cl | P2 NMR |
| Ia-211 | 3-Cl 5-CF$_3$ | N(CH$_3$)$_2$ | H | H | H | H | 2-Cl | P2 NMR |
| Ia-212 | 3-Cl 5-CF$_3$ | N(CH$_3$)$_2$ | H | H | H | H | 2-CF$_3$ | P2 NMR |
| Ia-213 | 3-Cl 5-Cl | 4-Cl—Phenyl | H | H | H | H | 2-CF$_3$ | P3 NMR |
| Ia-214 | 3-Cl 5-Cl | CH$_3$ | H | H | H | H | 2-NO$_2$ | P3 NMR |
| Ia-215 | 3-Cl 5-CF$_3$ | CH$_3$ | H | C$_2$H$_5$ | H | H | 2-NO$_2$ | P2 NMR |
| Ia-216 | 3-Cl 5-CF$_3$ | CH$_3$ | H | C$_2$H$_5$ | H | H | 2-F 6-F | P2 NMR |
| Ia-217 | 3-Cl 5-Cl | CH$_3$ | COOEt | H | H | H | 2-NO$_2$ | |
| Ia-218 | 3-Cl 5-Cl | CH$_3$ | COOEt | H | H | H | 2-CF$_3$ | |

[1] cis-isomer,
[2] trans-isomer,
[3] pure enantiomer, absolute configuration not determined,
[4] mixture of diastereomers $^1$H-NMR Data $^1$H-NMR-data were determined with a Bruker Avance 400 equipped with a flow cell (60 μl volume) or with a Bruker AVIII 400 equipped with 1.7 mm cryo-CPTCI probe head or with a Bruker AVII 600 (600.13 MHz) equipped with a cyroTCI probe head or with a Bruker AVIII 600 (601.6 MHz)

equipped with a cryo CPMNP probe head with tetramethylsilane as reference (0.0) and the solvents $CD_3CN$, $CDCl_3$, $[D_6]$-DMSO.

NMR-data of selected examples are listed in classic format (chemical shift δ, multiplicity, number of hydrogen atoms) or as NMR-peak-lists.

NMR-Peak-Lists:

If NMR-data of selected examples are provided in form of $^1$H-NMR-peak lists, then for every peak first the chemical shift δ in ppm and then, separated by a blank, the intensity of the signal in round brackets is listed.

The peak list of an example is therefore listed as: $δ_1$ (intensity$_1$); $δ_2$ (intensity$_2$) ... $δ_i$ (intensity$_i$); ... ; $δ_n$(intensity$_n$).

The solvent, in which the NMR-spectrum was measured, is specified in squared brackets.

No. Ia-3, Solvent: <$CDCl_3$>, Spectrometer: 400.13 MHz
8.3588 (6.16); 8.3534 (6.06); 7.7243 (6.40); 7.7189 (6.17); 7.6848 (2.78); 7.6655 (3.42); 7.5937 (1.05); 7.5755 (2.97); 7.5578 (2.63); 7.5355 (2.44); 7.5166 (2.76); 7.4977 (0.98); 7.4512 (3.33); 7.4333 (2.42); 7.2634 (2.41); 6.6512 (1.15); 6.6315 (1.14); 5.0999 (0.41); 4.7466 (0.67); 4.7297 (1.27); 4.7163 (1.28); 4.7129 (1.54); 4.7097 (1.17); 4.6961 (1.28); 4.6792 (0.66); 3.2377 (1.21); 3.2202 (1.07); 3.2013 (4.18); 3.1838 (4.36); 3.1756 (4.15); 3.1627 (4.10); 3.1392 (1.14); 3.1263 (1.01); 2.3460 (0.70); 1.6114 (12.84); 1.3745 (0.37); 1.3578 (0.39); 1.3402 (0.63); 1.3242 (16.00); 1.3075 (15.48); 1.2746 (0.33); 1.2579 (0.50); 0.0003 (3.34)

No. Ia-5, Solvent: <$[D_6]$-DMSO>, Spectrometer: 400.13 MHz
8.9835 (1.54); 8.9815 (1.84); 8.9787 (1.83); 8.9770 (1.62); 8.6360 (0.51); 8.6218 (1.05); 8.6071 (0.51); 8.5524 (1.78); 8.5512 (1.90); 8.5475 (1.89); 7.7486 (1.10); 7.7291 (1.53); 7.7187 (0.54); 7.7000 (1.28); 7.6813 (0.92); 7.6405 (0.91); 7.6217 (1.13); 7.6026 (0.42); 7.3990 (1.32); 7.3803 (1.18); 4.7833 (0.83); 4.7684 (1.05); 4.7628 (1.12); 4.7478 (0.91); 4.0732 (0.39); 4.0582 (0.77); 4.0429 (0.56); 4.0400 (0.66); 4.0249 (1.00); 4.0100 (0.49); 3.8681 (0.51); 3.8536 (0.59); 3.8473 (0.54); 3.8335 (0.79); 3.8205 (0.45); 3.8140 (0.45); 3.7996 (0.38); 3.6409 (16.00); 3.3266 (32.02); 3.3028 (1.01); 2.5161 (4.83); 2.5116 (10.58); 2.5070 (14.78); 2.5024 (10.69); 2.4978 (4.94); 0.0054 (7.40)

No. Ia-6, Solvent: <$CD_3CN$>, Spectrometer: 600.13 MHz
8.7760 (2.18); 8.1985 (1.98); 8.1964 (2.12); 7.6884 (1.37); 7.6756 (1.67); 7.6082 (0.57); 7.5958 (1.48); 7.5841 (1.09); 7.5704 (1.14); 7.5578 (1.37); 7.5453 (0.49); 7.1727 (1.48); 7.1603 (1.37); 7.0970 (0.46); 7.0878 (0.75); 7.0782 (0.48); 4.4917 (2.35); 4.4862 (2.57); 4.4808 (2.44); 4.4753 (2.50); 4.2907 (0.69); 4.2845 (0.54); 4.2789 (0.71); 4.2727 (1.47); 4.2609 (1.45); 4.2555 (0.54); 4.2490 (0.52); 4.2436 (1.49); 4.2317 (1.50); 4.2256 (0.72); 4.2199 (0.52); 4.2137 (0.69); 3.7701 (16.00); 2.1546 (2.03); 1.9495 (1.18); 1.9454 (2.18); 1.9413 (3.16); 1.9373 (2.23); 1.9332 (1.15); 1.2383 (0.62); 1.2333 (4.10); 1.2265 (1.26); 1.2215 (8.17); 1.2147 (0.72); 1.2096 (4.00); −0.0001 (1.33)

No. Ia-7, Solvent: <$CD_3CN$>, Spectrometer: 400.13 MHz
3.65 (m, 1H); 3.8 (m, 1H); 4.2 (br., 1H); 4.85 (m, 1H); 7.1 (m, 3H); 7.5 (m, 2H); 7.95 (d, 1H); 9.65 (s, 1H)

No. Ia-41, Solvent: <$[D_6]$-DMSO>, Spectrometer: 601.6 MHz 8.9659 (4.86); 8.9642 (4.79); 8.7601 (1.29); 8.7505 (2.33); 8.7409 (1.27); 8.3952 (5.03); 8.3925 (4.80); 8.1322 (0.89); 8.1190 (0.97); 8.0721 (0.51); 7.9561 (5.51); 7.9426 (6.83); 7.8960 (0.41); 7.8818 (0.60); 7.8684 (0.64); 7.8546 (0.61); 7.8347 (7.13); 7.8210 (5.73); 7.8128 (0.46); 3.9028 (7.65); 3.8937 (1.28); 3.8823 (2.48); 3.8709 (2.50); 3.8584 (1.34); 3.7085 (1.13); 3.7036 (0.40); 3.6979 (2.13); 3.6928 (0.48); 3.6870 (2.49); 3.6762 (2.51); 3.6655 (1.22); 3.6223 (0.34); 3.5141 (1.42); 3.5051 (1.76); 3.5019 (1.48); 3.4926 (2.55); 3.4834 (1.28); 3.4801 (1.30); 3.4712 (1.09); 3.3176 (207.29); 3.1726 (1.00); 3.1639 (0.98); 2.6191 (1.05); 2.6160 (2.21); 2.6130 (3.06); 2.6099 (2.20); 2.6069 (1.04); 2.5405 (0.77); 2.5369 (0.54); 2.5335 (0.53); 2.5223 (6.53); 2.5192 (8.17); 2.5161 (8.37); 2.5073 (168.28); 2.5043 (360.66); 2.5012 (494.89); 2.4982 (361.70); 2.4952 (167.19); 2.4764 (0.47); 2.4735 (0.50); 2.4705 (0.43); 2.3914 (0.99); 2.3885 (2.14); 2.3854 (2.98); 2.3824 (2.08); 2.3794 (0.91); 1.9084 (1.16); 1.8473 (0.77); 1.5141 (2.61); 1.2701 (15.85); 1.2587 (16.00); 1.2495 (0.54); 1.2354 (0.88); 1.1515 (0.35); 1.1471 (0.35); 1.1405 (0.34); 0.0965 (1.43); 0.0154 (0.41); 0.0052 (11.38); −0.0002 (375.37); −0.0058 (11.58); −0.1001 (1.41)

No. Ia-55, Solvent: <$[D_6]$-DMSO>, Spectrometer: 399.95 MHz
7.6988 (0.40); 7.6728 (0.32); 7.2565 (0.33); 4.1621 (0.60); 4.1462 (0.60); 3.9041 (1.02); 3.3405 (58.94); 2.5249 (0.54); 2.5115 (8.95); 2.5072 (17.93); 2.5026 (23.78); 2.4981 (17.89); 2.4937 (9.15); 1.4320 (16.00); −0.0002 (0.43)

No. Ia-56, Solvent: <$[D_6]$-DMSO>, Spectrometer: 601.6 MHz
8.5658 (4.95); 8.5654 (4.95); 8.5617 (4.99); 8.4576 (1.18); 8.4481 (2.33); 8.4386 (1.21); 7.8566 (4.17); 7.8523 (4.09); 7.8427 (4.48); 7.8384 (4.48); 7.4698 (3.43); 7.4656 (3.45); 7.4548 (3.52); 7.4506 (3.39); 7.3845 (3.04); 7.3742 (3.28); 7.3703 (3.89); 7.3598 (8.90); 7.3456 (5.16); 7.2631 (2.19); 7.2589 (2.02); 7.2490 (3.96); 7.2448 (3.53); 7.2348 (1.86); 7.2306 (1.67); 3.9026 (6.02); 3.5174 (0.87); 3.5074 (1.18); 3.5048 (1.09); 3.4954 (2.30); 3.4857 (1.80); 3.4830 (2.06); 3.4731 (1.76); 3.4528 (1.54); 3.4428 (2.23); 3.4419 (2.22); 3.4317 (2.45); 3.4199 (1.21); 3.4102 (0.94); 3.3171 (138.62); 3.2192 (1.29); 3.2075 (2.45); 3.1957 (2.36); 3.1839 (1.18); 3.1722 (1.35); 3.1635 (1.12); 2.6186 (0.59); 2.6157 (1.28); 2.6126 (1.81); 2.6096 (1.30); 2.6066 (0.60); 2.5402 (0.35); 2.5219 (3.33); 2.5188 (4.20); 2.5157 (4.13); 2.5069 (96.83); 2.5039 (210.66); 2.5008 (291.97); 2.4978 (214.78); 2.4948 (100.92); 2.4790 (0.83); 2.4757 (0.63); 2.3911 (0.58); 2.3881 (1.28); 2.3850 (1.78); 2.3820 (1.27); 2.3790 (0.58); 1.2550 (16.00); 1.2434 (15.96); 0.0965 (0.80); 0.0052 (6.40); −0.0002 (215.80); −0.0058 (6.79); −0.1001 (0.81)

No. Ia-74, Solvent: <$[D_6]$-DMSO>, Spectrometer: 601.6 MHz
8.9682 (4.75); 8.9663 (4.63); 8.4727 (1.40); 8.4628 (2.53); 8.4538 (1.23); 8.4155 (5.01); 8.4126 (4.95); 7.6249 (7.08); 7.6215 (7.26); 7.4590 (3.83); 7.4556 (3.69); 7.4453 (4.62); 7.4419 (4.53); 7.3280 (8.14); 7.3143 (6.76); 3.9026 (7.66); 3.7407 (0.42); 3.7316 (1.01); 3.7269 (0.98); 3.7223 (0.93); 3.7179 (1.98); 3.7061 (2.35); 3.7017 (1.31); 3.6966 (2.24); 3.6863 (1.91); 3.6761 (2.04); 3.6666 (1.04); 3.5023 (0.88); 3.4936 (1.41); 3.4897 (1.30); 3.4811 (1.94); 3.4728 (1.19); 3.4594 (0.84); 3.3170 (195.39); 3.1723 (0.90); 3.1635 (0.88); 2.6186 (0.85); 2.6156 (1.76); 2.6126 (2.41); 2.6097 (1.74); 2.6067 (0.83); 2.5403 (0.54); 2.5219 (5.10); 2.5189 (6.50); 2.5157 (7.21); 2.5069 (137.75); 2.5039 (284.67); 2.5009 (387.37); 2.4979 (283.44); 2.4949 (133.11); 2.4736 (0.46); 2.4707 (0.36); 2.3910 (0.81); 2.3881 (1.70); 2.3851 (2.34); 2.3821 (1.66); 2.3792 (0.76); 1.8030 (0.34); 1.7935 (0.75); 1.7808 (2.09); 1.7716 (1.80); 1.7683 (2.94); 1.7592 (1.88); 1.7557 (2.41); 1.7424 (1.48); 1.7324 (0.71); 1.7198 (0.45); 1.2492 (0.39); 1.2371 (0.41); 0.8756 (0.42); 0.8625 (0.46); 0.8429 (0.33); 0.7843 (7.42); 0.7720 (16.00); 0.7596 (7.12); 0.0965 (1.05); 0.0052 (9.03); −0.0002 (243.85); −0.0057 (7.74); −0.1001 (1.06)

No. Ia-81, Solvent: <$[D_6]$-DMSO>, Spectrometer: 399.95 MHz
12.8703 (4.77); 8.9950 (1.95); 8.9924 (1.93); 8.6551 (0.54); 8.6403 (1.00); 8.4049 (1.99); 8.4011 (1.99); 7.6614 (2.23); 7.6391 (2.31); 6.4387 (1.26); 6.4324 (1.56); 6.4166

(1.13); 6.4103 (1.65); 6.3856 (3.14); 6.3793 (2.36); 3.9046 (4.60); 3.7499 (16.00); 3.7327 (1.24); 3.7186 (1.12); 3.7037 (0.97); 3.6889 (0.43); 3.5358 (0.63); 3.5232 (0.34); 3.5099 (0.42); 3.4888 (0.61); 3.4654 (1.14); 3.4518 (1.49); 3.3753 (509.95); 3.3070 (0.98); 3.2883 (0.52); 3.1753 (0.37); 3.1623 (0.35); 2.6787 (0.41); 2.6744 (0.58); 2.6699 (0.45); 2.5445 (0.44); 2.5276 (1.80); 2.5142 (33.64); 2.5098 (67.47); 2.5053 (89.50); 2.5007 (67.49); 2.4964 (34.39); 2.3364 (0.41); 2.3321 (0.57); 2.3275 (0.43); 1.8053 (0.65); 1.7868 (1.09); 1.7753 (0.81); 1.7697 (0.91); 1.7569 (0.74); 0.7697 (2.72); 0.7512 (6.02); 0.7327 (2.60); 0.0080 (0.48); −0.0002 (14.94); −0.0085 (0.58)

No. Ia-111, Solvent: <[$D_6$]-DMSO>, Spectrometer: 601.6 MHz 9.0203 (11.61); 9.0185 (11.20); 8.9667 (2.43); 8.9650 (2.35); 8.6215 (3.27); 8.6118 (6.51); 8.6021 (3.30); 8.5154 (12.22); 8.5128 (11.85); 8.4716 (0.71); 8.4623 (3.85); 8.4599 (3.24); 8.4527 (0.71); 7.7470 (7.69); 7.7340 (9.42); 7.7263 (1.85); 7.7226 (1.18); 7.7167 (1.58); 7.7119 (4.99); 7.6979 (8.94); 7.6909 (1.02); 7.6848 (8.21); 7.6798 (1.16); 7.6750 (1.36); 7.6722 (1.32); 7.6698 (1.47); 7.6327 (5.10); 7.6197 (8.03); 7.6066 (4.02); 7.5920 (0.67); 7.4281 (8.48); 7.4155 (7.71); 5.7556 (3.53); 5.7447 (3.76); 5.2952 (0.61); 5.2843 (1.53); 5.2738 (1.50); 5.2632 (0.59); 5.0565 (6.07); 5.0459 (13.85); 5.0353 (6.18); 4.1466 (1.04); 4.1368 (1.88); 4.1266 (0.99); 4.0928 (0.71); 4.0841 (0.72); 3.9026 (16.00); 3.7770 (2.33); 3.7666 (4.70); 3.7552 (5.92); 3.7445 (8.27); 3.7341 (5.29); 3.7239 (0.88); 3.7124 (0.89); 3.6988 (4.18); 3.6887 (7.05); 3.6784 (5.13); 3.6665 (4.07); 3.6565 (2.38); 3.5088 (0.43); 3.3681 (0.67); 3.3397 (0.63); 3.3171 (689.18); 3.2528 (117.91); 3.2245 (1.99); 3.1722 (2.82); 3.1635 (2.76); 3.1559 (0.60); 3.1327 (0.59); 2.6186 (2.55); 2.6156 (5.43); 2.6126 (7.49); 2.6096 (5.36); 2.6065 (2.45); 2.5402 (1.59); 2.5371 (1.17); 2.5219 (15.43); 2.5188 (19.70); 2.5157 (21.11); 2.5069 (420.79); 2.5039 (890.63); 2.5008 (1223.62); 2.4978 (888.21); 2.4948 (411.55); 2.3911 (2.47); 2.3881 (5.31); 2.3850 (7.32); 2.3820 (5.20); 2.3790 (2.32); 1.6412 (0.40); 1.6313 (0.57); 1.6212 (0.48); 1.3667 (0.74); 1.3605 (0.71); 1.3544 (0.88); 1.3495 (0.87); 1.3433 (0.73); 1.3375 (0.87); 1.3310 (0.38); 1.3252 (0.48); 1.3094 (0.73); 1.2983 (1.17); 1.2896 (1.35); 1.2807 (2.84); 1.2725 (1.79); 1.2585 (0.90); 1.2492 (0.56); 1.2353 (1.12); 0.8881 (2.92); 0.8757 (6.74); 0.8629 (5.73); 0.8507 (1.40); 0.0965 (3.63); 0.0225 (0.38); 0.0052 (32.50); −0.0002 (952.74); −0.0057 (29.02); −0.0204 (0.67); −0.1001 (3.64)

No. Ia-112, Solvent: <[$D_6$]-DMSO>, Spectrometer: 601.6 MHz 8.9887 (1.73); 8.9869 (1.69); 8.7992 (0.52); 8.7896 (1.07); 8.7800 (0.52); 8.5363 (1.82); 8.5338 (1.80); 7.7743 (1.17); 7.7612 (1.43); 7.7431 (0.58); 7.7305 (1.28); 7.7179 (0.81); 7.6580 (0.76); 7.6453 (1.15); 7.6325 (0.50); 7.4801 (1.25); 7.4675 (1.17); 6.2241 (0.89); 6.2137 (1.93); 6.2032 (0.91); 3.9026 (6.05); 3.7678 (1.45); 3.7576 (2.76); 3.7475 (1.53); 3.3168 (89.87); 3.2338 (0.53); 3.1722 (0.83); 3.1635 (0.81); 2.8902 (0.77); 2.7310 (0.64); 2.7304 (0.62); 2.6186 (0.49); 2.6156 (1.02); 2.6126 (1.43); 2.6095 (1.02); 2.6065 (0.47); 2.5402 (0.37); 2.5219 (2.81); 2.5188 (3.51); 2.5157 (3.50); 2.5069 (75.50); 2.5039 (163.70); 2.5008 (226.40); 2.4977 (165.47); 2.4947 (76.62); 2.3911 (0.43); 2.3881 (0.95); 2.3850 (1.34); 2.3820 (0.94); 2.3789 (0.41); 2.0649 (16.00); 0.0965 (0.75); 0.0053 (6.49); −0.0002 (207.49); −0.0057 (6.19); −0.0112 (0.39); −0.1001 (0.74)

No. Ia-130, Solvent: <[$D_6$]-DMSO>, Spectrometer: 399.95 MHz 8.6046 (7.41); 8.5984 (7.56); 8.5868 (2.07); 8.5730 (3.82); 8.5590 (1.92); 8.3186 (0.67); 8.8642 (5.22); 8.8577 (5.14); 7.8432 (5.90); 7.8367 (5.89); 7.7237 (3.90); 7.7054 (5.17); 7.6580 (1.69); 7.6410 (4.36); 7.6229 (3.59); 7.6046 (3.58); 7.5859 (3.93); 7.5675 (1.36); 7.4291 (7.83); 7.4081 (7.23); 7.3816 (4.66); 7.3780 (6.53); 7.3602 (11.56); 7.3291 (6.92); 7.3109 (11.09); 7.2914 (5.38); 7.2394 (3.87); 7.2362 (2.41); 7.2265 (1.80); 7.2213 (5.14); 7.2034 (1.98); 7.2001 (1.46); 7.1909 (4.67); 7.1728 (4.22); 4.5055 (2.44); 4.4863 (4.81); 4.4667 (2.80); 4.0209 (1.10); 4.0074 (1.26); 4.0001 (1.16); 3.9875 (2.86); 3.9745 (2.10); 3.9672 (2.14); 3.9537 (1.84); 3.9245 (1.95); 3.9042 (16.00); 3.8915 (3.15); 3.8746 (1.57); 3.8589 (1.20); 3.5064 (0.41); 3.4749 (0.39); 3.4328 (0.62); 3.4171 (0.80); 3.3476 (878.83); 3.1746 (0.72); 3.1615 (0.69); 2.8909 (0.33); 2.6767 (1.29); 2.6722 (1.76); 2.6677 (1.33); 2.6634 (0.68); 2.5424 (1.42); 2.5254 (6.09); 2.5119 (100.43); 2.5076 (199.36); 2.5031 (262.29); 2.4986 (196.12); 2.4943 (99.99); 2.3344 (1.21); 2.3298 (1.67); 2.3253 (1.23); 1.2358 (0.56); 0.1460 (0.49); 0.0080 (3.93); −0.0002 (113.14); −0.0084 (4.92); −0.1497 (0.49)

No. Ia-131, Solvent: <[$D_6$]-DMSO>, Spectrometer: 399.95 MHz 8.5906 (5.70); 8.5844 (5.75); 8.4842 (1.51); 8.4702 (2.90); 8.4563 (1.45); 8.3185 (0.38); 7.8649 (3.87); 7.8584 (3.85); 7.8440 (4.25); 7.8376 (4.21); 7.7437 (3.41); 7.7242 (4.55); 7.6973 (1.50); 7.6792 (3.81); 7.6607 (2.71); 7.6239 (2.76); 7.6050 (3.41); 7.5860 (1.22); 7.3523 (4.04); 7.3336 (3.64); 7.3098 (6.13); 7.2889 (5.79); 3.9044 (6.34); 3.8609 (0.58); 3.5428 (0.60); 3.5272 (1.04); 3.5102 (2.46); 3.4933 (4.19); 3.4773 (3.39); 3.4569 (2.50); 3.4387 (1.10); 3.4238 (1.13); 3.3485 (625.63); 3.1679 (0.53); 3.0143 (0.56); 2.9955 (1.23); 2.9784 (1.52); 2.9607 (1.20); 2.9430 (0.52); 2.6767 (0.94); 2.6723 (1.29); 2.6679 (0.97); 2.5424 (0.96); 2.5076 (148.60); 2.5032 (194.96); 2.4989 (148.25); 2.3343 (0.91); 2.3300 (1.23); 2.3256 (0.92); 1.7698 (0.56); 1.7567 (0.90); 1.7517 (0.86); 1.7365 (1.79); 1.7233 (1.48); 1.7176 (1.76); 1.7051 (1.44); 1.6956 (1.65); 1.6769 (1.70); 1.6726 (1.56); 1.6540 (1.52); 1.6432 (0.78); 1.6384 (0.91); 1.6203 (0.61); 1.2355 (0.33); 0.7481 (7.51); 0.7298 (16.00); 0.7113 (7.05); −0.0002 (2.90)

No. Ia-134, Solvent: <[$D_6$]-DMSO>, Spectrometer: 399.95 MHz 8.5462 (11.12); 8.5406 (11.10); 8.5398 (11.10); 8.3185 (1.04); 8.2753 (2.63); 8.2601 (5.36); 8.2449 (2.70); 7.8320 (8.11); 7.8255 (8.06); 7.8107 (9.13); 7.8041 (9.22); 7.7278 (6.43); 7.7083 (8.76); 7.6948 (3.05); 7.6767 (7.36); 7.6581 (5.25); 7.6137 (5.15); 7.5948 (6.58); 7.5757 (2.48); 7.4454 (11.97); 7.4240 (10.87); 7.3676 (7.62); 7.3490 (6.84); 3.9040 (14.31); 3.7076 (0.57); 3.5508 (15.92); 3.5352 (16.00); 3.5065 (0.73); 3.3414 (883.65); 3.2711 (0.52); 3.2537 (0.42); 3.1680 (0.57); 2.6763 (1.74); 2.6717 (2.44); 2.6673 (1.82); 2.5418 (1.18); 2.5251 (6.73); 2.5115 (136.11); 2.5072 (278.03); 2.5027 (372.71); 2.4982 (284.40); 2.4939 (149.41); 2.3339 (1.86); 2.3294 (2.53); 2.3249 (1.93); 2.0557 (1.58); 2.0513 (1.60); 2.0359 (3.17); 2.0194 (5.14); 2.0055 (5.97); 1.9868 (4.11); 1.9586 (3.51); 1.9432 (6.01); 1.9285 (5.70); 1.9123 (3.39); 1.8957 (2.42); 1.8061 (0.70); 1.7939 (0.96); 1.7609 (5.50); 1.7500 (5.62); 1.7333 (3.76); 1.7041 (1.02); 1.6372 (1.13); 1.6073 (3.94); 1.5903 (5.63); 1.5823 (5.03); 1.5698 (3.07); 1.5361 (0.61); 1.2583 (0.36); 1.2356 (1.05); 0.8443 (1.46); 0.8319 (0.71); 0.8216 (0.51); −0.0002 (7.27); −0.0084 (0.33)

No. Ia-139, Solvent: <$CDCl_3$>, Spectrometer: 399.95 MHz 8.4335 (15.00); 8.4286 (14.43); 7.9358 (0.35); 7.9306 (0.33); 7.8857 (16.00); 7.8806 (15.14); 7.7021 (7.63); 7.6839 (9.09); 7.6488 (0.41); 7.6298 (0.43); 7.6142 (2.47); 7.5968 (7.48); 7.5791 (8.69); 7.5629 (7.19); 7.5440 (9.01); 7.5376 (11.36); 7.5191 (5.73); 7.2622 (8.31); 6.3961 (3.82); 4.5048 (0.47); 4.4884 (6.71); 4.4724 (6.53); 4.4550 (13.60); 4.4391

(13.10); 4.4217 (6.83); 4.4057 (6.61); 4.1302 (0.63); 4.1122 (0.65); 2.0462 (2.67); 1.6193 (1.18); 1.5689 (56.34); 1.5190 (0.44); 1.3024 (0.37); 1.2775 (1.16); 1.2597 (2.46); 1.2421 (0.84); 0.8817 (0.36); 0.0499 (0.57); 0.0003 (28.74); 0.0074 (0.96)

No. Ia-140, Solvent: <[$D_6$]-DMSO>, Spectrometer: 399.95 MHz 8.9225 (5.80); 8.9198 (5.67); 8.4400 (3.51); 8.4297 (6.60); 8.4258 (6.84); 8.4197 (3.92); 7.8525 (4.87); 7.8506 (4.89); 7.8327 (5.27); 7.8309 (5.00); 7.4473 (2.29); 7.4447 (2.29); 7.4369 (0.46); 7.4285 (5.23); 7.4260 (5.05); 7.4098 (3.29); 7.4073 (3.04); 7.2334 (4.31); 7.2296 (4.93); 7.2145 (3.91); 7.2106 (3.91); 7.1650 (2.79); 7.1609 (2.53); 7.1459 (4.26); 7.1420 (3.90); 7.1267 (2.42); 7.1226 (2.14); 4.6110 (0.79); 4.5938 (1.81); 4.5765 (2.08); 4.5737 (2.08); 4.5562 (1.82); 4.5390 (0.80); 3.9051 (1.70); 3.3798 (0.55); 3.3440 (240.69); 3.2456 (0.37); 3.2264 (0.41); 3.2078 (5.64); 3.1908 (6.06); 3.1718 (0.70); 3.1544 (0.34); 2.6768 (0.40); 2.6724 (0.54); 2.6684 (0.42); 2.5427 (0.46); 2.5257 (1.67); 2.5121 (31.82); 2.5078 (62.50); 2.5033 (81.97); 2.4988 (61.27); 2.4945 (30.93); 2.3345 (0.40); 2.3301 (0.55); 2.3254 (0.41); 1.2187 (16.00); 1.2019 (15.91); 0.0080 (1.69); −0.0002 (48.66); −0.0085 (1.95)

No. Ia-141, Solvent: <[$D_6$]-DMSO>, Spectrometer: 399.95 MHz 8.8990 (5.34); 8.8964 (5.32); 8.4834 (2.91); 8.4622 (2.94); 8.4236 (5.49); 8.4198 (5.36); 8.3178 (0.61); 7.4597 (1.67); 7.4558 (2.43); 7.4399 (4.96); 7.4363 (5.97); 7.4304 (2.77); 7.4259 (2.79); 7.4130 (4.29); 7.4084 (4.13); 7.3938 (2.12); 7.3876 (3.61); 7.3825 (2.32); 7.3686 (4.15); 7.3645 (4.18); 7.3510 (2.19); 7.3470 (2.08); 7.3233 (4.77); 7.3196 (4.18); 7.3052 (2.84); 7.3005 (2.29); 4.6432 (0.68); 4.6246 (1.47); 4.6072 (1.96); 4.5873 (1.44); 4.5704 (0.71); 3.9040 (5.33); 3.5083 (0.36); 3.4618 (0.48); 3.3500 (780.94); 3.2887 (0.38); 3.2821 (0.36); 3.2319 (0.67); 3.2158 (0.85); 3.1974 (3.64); 3.1833 (5.39); 3.1659 (3.45); 3.1505 (0.74); 3.1310 (0.71); 2.6770 (1.01); 2.6725 (1.40); 2.6680 (1.07); 2.5257 (4.84); 2.5122 (82.88); 2.5080 (164.24); 2.5035 (215.96); 2.4990 (163.69); 2.4949 (85.43); 2.3346 (0.99); 2.3303 (1.35); 2.3258 (1.03); 1.3504 (0.81); 1.3357 (0.44); 1.2976 (0.44); 1.2584 (0.71); 1.2490 (0.68); 1.2319 (4.97); 1.2245 (16.00); 1.2077 (15.18); 0.1459 (0.33); 0.0079 (2.65); −0.0002 (76.85); −0.0084 (3.51); −0.1496 (0.35)

No. Ia-142, Solvent: <$CDCl_3$>, Spectrometer: 399.95 MHz 8.4650 (9.39); 8.4599 (9.26); 7.8820 (10.40); 7.8768 (10.81); 7.8715 (8.62); 7.8518 (7.67); 7.4341 (0.32); 7.3845 (16.00); 7.3831 (15.33); 7.3727 (14.19); 7.3531 (0.59); 7.2616 (21.64); 7.1372 (0.67); 7.1283 (3.64); 7.1174 (4.90); 7.1083 (4.06); 7.1054 (3.40); 7.0982 (3.77); 7.0957 (3.15); 7.0855 (2.92); 7.0763 (0.37); 6.3489 (2.26); 4.4928 (4.48); 4.4767 (4.23); 4.4594 (9.24); 4.4433 (8.95); 4.4260 (4.66); 4.4099 (4.50); 2.0467 (0.46); 1.6063 (2.16); 1.5565 (156.08); 1.5063 (1.18); 1.2600 (1.50); 0.8981 (0.36); 0.8818 (0.84); 0.8640 (0.42); 0.0692 (0.47); 0.0496 (0.84); 0.0078 (2.84); 0.0003 (67.58); 0.0085 (2.21); 0.0504 (0.47)

No. Ia-143, Solvent: <[$D_6$]-DMSO>, Spectrometer: 399.95 MHz 9.0182 (6.34); 9.0154 (6.20); 8.9462 (2.28); 8.9435 (2.23); 8.5984 (3.78); 8.5759 (3.83); 8.4682 (6.60); 8.4645 (6.48); 8.4248 (2.35); 8.4211 (2.35); 8.3084 (1.33); 8.2861 (1.34); 7.7964 (4.07); 7.7758 (6.05); 7.7536 (4.60); 7.7349 (3.10); 7.7233 (1.58); 7.7034 (1.93); 7.6900 (0.73); 7.6720 (4.51); 7.6530 (5.07); 7.6337 (1.59); 7.6165 (1.14); 7.5974 (1.37); 7.5782 (0.50); 7.5215 (4.61); 7.5028 (3.99); 7.2237 (1.59); 7.2051 (1.47); 4.4982 (0.51); 4.4803 (0.83); 4.4589 (0.95); 4.4489 (1.22); 4.4412 (1.16); 4.4319 (1.33); 4.4257 (2.04); 4.4093 (1.98); 4.4031 (1.34); 4.3861 (1.07); 3.9050 (4.43); 3.7905 (0.59); 3.7795 (0.84); 3.7722 (1.82); 3.7639 (2.30); 3.7462 (2.83); 3.7390 (2.63); 3.7217 (1.39); 3.7130 (1.30); 3.5082 (0.40); 3.4742 (0.41); 3.4338 (0.91); 3.3509 (631.09); 2.6774 (0.85); 2.6730 (1.17); 2.6687 (0.94); 2.5433 (1.31); 2.5262 (4.07); 2.5128 (67.28); 2.5084 (132.47); 2.5039 (174.70); 2.4994 (130.98); 2.4950 (66.06); 2.3352 (0.79); 2.3307 (1.09); 2.3261 (0.78); 1.8760 (1.05); 1.8611 (1.11); 1.8429 (1.92); 1.8274 (1.78); 1.8162 (1.74); 1.8005 (1.50); 1.6952 (1.31); 1.6866 (1.57); 1.6778 (1.50); 1.6688 (1.60); 1.6619 (1.32); 1.6531 (1.10); 1.6435 (1.21); 1.6346 (1.05); 1.6241 (0.60); 1.6129 (0.58); 1.6059 (0.59); 1.5943 (0.64); 1.5797 (0.43); 1.5715 (0.47); 1.5616 (0.39); 1.2585 (0.37); 1.2491 (0.47); 1.2355 (0.69); 1.1652 (5.70); 1.1483 (5.69); 0.8893 (16.00); 0.8727 (15.96); 0.8343 (0.45); 0.8128 (0.39); 0.4165 (0.43); 0.3989 (0.65); 0.3810 (0.53); 0.3373 (0.54); 0.3256 (1.23); 0.3040 (2.09); 0.2923 (2.93); 0.2811 (2.62); 0.2713 (3.00); 0.2610 (2.50); 0.2494 (1.84); 0.2271 (0.85); 0.2126 (0.60); 0.2030 (0.82); 0.1929 (0.86); 0.1847 (1.46); 0.1719 (1.73); 0.1621 (2.28); 0.1529 (2.03); 0.1430 (1.82); 0.1334 (0.83); 0.1299 (0.86); 0.1198 (0.64); 0.0239 (0.43); 0.0080 (3.07); −0.0002 (77.98); −0.0086 (4.19); −0.0219 (2.21); −0.0336 (2.67); −0.0445 (2.43); −0.0552 (1.60); −0.0672 (0.70); −0.1497 (0.35); −0.2507 (0.69); −0.2610 (0.97); −0.2731 (0.90); −0.2836 (0.56); −0.3358 (0.83); −0.3478 (1.84); −0.3584 (2.64); −0.3705 (2.52); −0.3811 (1.59); −0.3934 (0.65)

No. Ia-144, Solvent: <[$D_6$]-DMSO>, Spectrometer: 399.95 MHz 9.0148 (6.47); 9.0122 (6.38); 8.9501 (2.71); 8.6572 (3.88); 8.6346 (3.92); 8.4527 (6.79); 8.4488 (6.66); 8.4142 (2.80); 8.4104 (2.75); 8.3541 (1.57); 8.3322 (1.57); 8.3178 (0.91); 7.8446 (0.52); 7.8251 (0.73); 7.8020 (4.48); 7.7822 (6.08); 7.7575 (5.02); 7.7386 (3.68); 7.7260 (2.01); 7.7062 (2.50); 7.6961 (1.03); 7.6774 (4.93); 7.6584 (5.38); 7.6394 (1.62); 7.6189 (1.37); 7.5999 (1.66); 7.5806 (0.70); 7.5644 (4.83); 7.5456 (4.08); 7.2520 (1.87); 7.2334 (1.73); 5.6333 (0.53); 5.6258 (0.45); 5.6143 (0.96); 5.6087 (1.03); 5.5910 (1.57); 5.5716 (1.52); 5.5467 (1.49); 5.5273 (1.34); 5.5109 (0.81); 4.8985 (1.57); 4.8611 (2.14); 4.8415 (1.69); 4.8218 (8.38); 4.7922 (4.18); 4.7841 (3.68); 4.5076 (0.61); 4.4902 (1.16); 4.4706 (1.71); 4.4542 (2.58); 4.4375 (2.31); 4.4153 (1.17); 4.3981 (0.35); 3.9042 (10.96); 3.7700 (0.72); 3.7563 (2.00); 3.7461 (2.33); 3.7307 (3.13); 3.7225 (2.66); 3.7071 (1.73); 3.6973 (1.46); 3.5079 (0.64); 3.4806 (0.88); 3.3506 (1539.96); 3.1747 (0.47); 3.1615 (0.38); 2.6769 (2.71); 2.6724 (3.49); 2.6681 (3.03); 2.6456 (2.15); 2.6348 (1.87); 2.6195 (2.28); 2.5989 (2.90); 2.5734 (3.11); 2.5576 (2.26); 2.5078 (314.33); 2.5034 (415.06); 2.4990 (317.53); 2.3345 (1.98); 2.3301 (2.73); 2.3258 (2.07); 1.2573 (0.38); 1.2354 (1.00); 1.1947 (6.71); 1.1777 (6.67); 0.9275 (15.94); 0.9109 (16.00); 0.8543 (0.50); 0.8349 (0.38); 0.0080 (1.12); −0.0002 (34.56); −0.0082 (1.78)

No. Ia-146, Solvent: <[$D_6$]-DMSO>, Spectrometer: 399.95 MHz 9.0142 (6.23); 9.0116 (6.15); 8.9482 (2.09); 8.9457 (2.07); 8.5225 (3.77); 8.4998 (3.90); 8.4605 (6.55); 8.4565 (6.53); 8.4135 (2.13); 8.4093 (2.19); 8.3184 (0.92); 8.2788 (1.23); 8.2567 (1.24); 7.5093 (3.45); 7.4903 (7.03); 7.4754 (0.52); 7.4671 (2.06); 7.4558 (4.52); 7.4445 (4.20); 7.4365 (2.70); 7.4253 (3.89); 7.4113 (15.73); 7.4015 (8.21); 7.3900 (1.78); 7.3858 (1.60); 7.3701 (0.69); 7.3662 (0.76); 7.3560 (1.18); 7.3519 (1.39); 7.3395 (3.06); 7.3337 (1.50); 7.3207 (0.68); 7.3164 (0.64); 7.2010 (1.51); 7.1830 (1.25); 7.1790 (1.17); 7.1428 (0.41); 7.1210 (0.45); 6.8656 (0.51); 6.8446 (0.44); 4.5472 (1.59); 4.4999 (0.42); 4.4816 (0.99); 4.4648 (1.57); 4.4423 (2.44); 4.4257 (2.12); 4.4200 (1.38); 4.4027 (1.12);

4.1062 (0.45); 4.0962 (0.54); 4.0844 (0.45); 3.9041 (14.00); 3.8000 (0.48); 3.7891 (0.62); 3.7719 (1.98); 3.7635 (2.13); 3.7461 (3.00); 3.7390 (2.70); 3.7221 (1.41); 3.7136 (1.29); 3.5958 (2.06); 3.5070 (0.34); 3.4478 (0.40); 3.4332 (0.55); 3.3426 (1142.35); 3.3072 (1.35); 3.1742 (0.43); 3.1616 (0.47); 2.6765 (1.85); 2.6722 (2.55); 2.6678 (1.90); 2.5420 (1.67); 2.5253 (7.87); 2.5075 (293.89); 2.5031 (387.92); 2.4987 (294.83); 2.3342 (1.83); 2.3298 (2.51); 2.3257 (1.90); 1.9533 (0.47); 1.8934 (0.89); 1.8787 (1.27); 1.8607 (1.93); 1.8519 (1.58); 1.8447 (2.00); 1.8338 (1.80); 1.8182 (1.75); 1.8021 (0.54); 1.7372 (1.44); 1.7285 (1.69); 1.7195 (1.63); 1.7110 (1.76); 1.7041 (1.39); 1.6950 (1.14); 1.6853 (1.24); 1.6765 (1.07); 1.6312 (0.52); 1.6209 (0.61); 1.6130 (0.59); 1.6023 (0.64); 1.5868 (0.44); 1.5792 (0.48); 1.5683 (0.44); 1.3237 (4.19); 1.2987 (0.39); 1.2585 (0.71); 1.2352 (1.57); 1.1783 (5.21); 1.1614 (5.23); 0.9074 (15.90); 0.8908 (16.00); 0.8541 (0.68); 0.8348 (0.56); 0.8110 (0.45); 0.3987 (0.60); 0.3812 (0.51); 0.3619 (0.33); 0.3419 (0.57); 0.3234 (1.27); 0.3117 (2.04); 0.3032 (2.12); 0.2946 (2.97); 0.2827 (2.73); 0.2736 (2.93); 0.2638 (2.47); 0.2517 (2.00); 0.2301 (0.79); 0.2128 (0.64); 0.2026 (0.81); 0.1890 (1.48); 0.1786 (1.82); 0.1757 (1.81); 0.1657 (2.30); 0.1566 (2.17); 0.1462 (1.88); 0.1335 (0.97); 0.1237 (0.73); 0.0113 (0.68); −0.0002 (6.98); −0.0088 (1.80); −0.0207 (2.12); −0.0309 (2.64); −0.0419 (2.71); −0.0529 (1.74); −0.0646 (0.80); −0.2481 (0.65); −0.2586 (0.88); −0.2705 (0.84); −0.2818 (0.55); −0.3254 (0.82); −0.3372 (1.89); −0.3481 (2.68); −0.3600 (2.61); −0.3711 (1.68); −0.3829 (0.74)

No. Ia-148, Solvent: <$CDCl_3$>, Spectrometer: 399.95 MHz 12.1118 (0.35); 8.7402 (14.50); 8.1121 (15.45); 8.1081 (14.80); 7.7497 (0.34); 7.7007 (8.47); 7.6990 (8.09); 7.6821 (10.13); 7.6799 (9.91); 7.6350 (0.37); 7.6191 (2.60); 7.6163 (2.70); 7.6004 (8.15); 7.5990 (7.85); 7.5826 (9.85); 7.5790 (7.73); 7.5664 (8.00); 7.5495 (8.37); 7.5479 (8.24); 7.5346 (13.14); 7.5329 (12.31); 7.5180 (5.94); 7.5163 (6.36); 7.5151 (6.18); 7.2665 (5.62); 7.2652 (4.92); 6.4220 (4.29); 5.3030 (1.17); 5.3017 (1.06); 4.5320 (7.56); 4.5159 (7.44); 4.4986 (16.00); 4.4825 (15.56); 4.4651 (8.14); 4.4490 (7.86); 3.1322 (2.22); 3.1201 (2.53); 3.1140 (6.90); 3.1019 (7.07); 3.0956 (7.14); 3.0836 (6.95); 3.0773 (2.59); 3.0652 (2.32); 1.6283 (12.44); 1.4506 (0.34); 1.4316 (14.62); 1.4133 (29.08); 1.3949 (13.80); 1.2600 (0.52); 1.1402 (0.36); 1.1247 (0.36); 0.0070 (0.52); 0.0001 (9.53); 0.0011 (8.75); 0.0084 (0.32)

No. Ia-149, Solvent: <$CDCl_3$>, Spectrometer: 399.95 MHz 8.4128 (0.38); 8.3052 (5.56); 8.2999 (5.51); 8.2711 (12.61); 8.2655 (12.40); 8.1285 (0.33); 8.1235 (0.37); 7.8650 (3.06); 7.8627 (2.95); 7.8453 (3.20); 7.8430 (2.98); 7.8259 (6.27); 7.8230 (6.17); 7.8058 (6.43); 7.8033 (6.73); 7.7201 (0.44); 7.7084 (16.00); 7.7030 (14.65); 7.6616 (7.36); 7.6563 (6.59); 7.5300 (0.38); 7.5242 (0.41); 7.4276 (1.14); 7.4226 (1.63); 7.4086 (4.01); 7.4036 (3.92); 7.3969 (2.83); 7.3943 (2.60); 7.3880 (0.64); 7.3792 (2.89); 7.3765 (2.92); 7.3603 (1.27); 7.3575 (1.27); 7.3516 (3.29); 7.3489 (3.25); 7.3328 (7.04); 7.3301 (7.11); 7.3142 (4.58); 7.3113 (4.76); 7.2640 (7.84); 7.2558 (0.49); 7.2455 (0.34); 7.1922 (6.37); 7.1881 (6.94); 7.1732 (5.47); 7.1689 (5.38); 7.1252 (3.28); 7.1200 (3.21); 7.1073 (3.32); 7.1054 (3.66); 7.1023 (3.12); 7.1004 (3.09); 7.0878 (5.90); 7.0835 (4.55); 7.0684 (5.39); 7.0641 (5.02); 7.0496 (3.54); 7.0453 (3.35); 6.0486 (1.15); 5.3029 (4.65); 4.0587 (1.41); 4.0444 (1.79); 4.0393 (4.03); 4.0251 (4.45); 4.0199 (4.36); 4.0057 (4.23); 4.0006 (1.74); 3.9864 (1.54); 3.4701 (0.38); 3.4556 (0.40); 3.4484 (0.73); 3.4393 (1.10); 3.4364 (1.03); 3.4287 (1.60); 3.4199 (1.63); 3.4175 (1.00); 3.4124 (0.97); 3.4085 (1.12); 3.4004 (0.78); 2.9428 (2.59); 2.9265 (3.20); 2.9237 (2.99); 2.9204 (3.21); 2.9075 (3.21); 2.9041 (3.23); 2.9013 (3.09); 2.8850 (2.69); 2.8073 (1.12); 2.7995 (1.13); 2.7924 (1.28); 2.7843 (2.31); 2.7765 (1.28); 2.7691 (1.24); 2.7614 (1.22); 1.7678 (1.40); 1.7529 (1.85); 1.7487 (1.61); 1.7397 (1.61); 1.7354 (1.81); 1.7339 (1.83); 1.7205 (1.45); 1.6272 (2.78); 1.6131 (3.94); 1.6074 (3.42); 1.6048 (3.57); 1.5978 (26.24); 1.5936 (5.45); 1.5909 (4.57); 1.5849 (2.93); 1.5709 (3.39); 1.5407 (3.53); 1.5265 (6.62); 1.5105 (6.34); 1.4963 (2.49); 1.4779 (1.57); 1.4652 (2.38); 1.4545 (1.86); 1.4421 (2.35); 1.4295 (1.34); 1.2526 (0.50); 1.1400 (0.44); 1.1250 (0.50); 0.9871 (0.57); 0.9690 (1.11); 0.9507 (0.52); 0.0701 (0.44); 0.0079 (0.46); 0.0001 (15.35); 0.0086 (0.54)

No. Ia-150, Solvent: <[$D_6$]-DMSO>, Spectrometer: 399.95 MHz 11.1731 (1.33); 9.0841 (12.31); 8.9033 (3.70); 8.8879 (7.50); 8.8723 (3.60); 8.7050 (12.28); 8.3192 (1.25); 7.9894 (0.94); 7.9699 (1.00); 7.8724 (10.64); 7.8528 (10.82); 7.7116 (0.68); 7.6926 (0.80); 7.4949 (0.65); 7.4751 (1.21); 7.4594 (5.22); 7.4428 (9.78); 7.4407 (10.56); 7.4242 (6.04); 7.4219 (6.34); 7.2494 (8.81); 7.2456 (10.46); 7.2304 (8.32); 7.2266 (8.52); 7.1903 (5.35); 7.1862 (5.12); 7.1711 (8.53); 7.1672 (8.25); 7.1520 (4.57); 7.1479 (4.24); 4.3075 (3.68); 4.2918 (3.75); 4.2717 (8.18); 4.2561 (7.95); 4.2358 (4.19); 4.2202 (3.92); 3.9043 (16.00); 3.8516 (0.57); 3.8407 (1.96); 3.8129 (0.36); 3.7487 (0.54); 3.7391 (0.43); 3.7265 (0.39); 3.6394 (0.43); 3.6268 (0.50); 3.6159 (0.41); 3.6034 (0.93); 3.5074 (0.47); 3.3387 (1026.61); 3.1742 (0.54); 3.1612 (0.58); 3.0696 (0.43); 3.0443 (0.87); 2.6762 (2.98); 2.6718 (4.12); 2.6674 (3.18); 2.6340 (0.35); 2.5248 (14.13); 2.5111 (232.92); 2.5072 (460.71); 2.5027 (612.49); 2.4983 (472.74); 2.3338 (2.78); 2.3295 (3.90); 2.3250 (3.00); 2.0454 (0.51); 1.8055 (0.53); 1.2583 (0.49); 1.2348 (1.42); 1.1757 (0.43); 0.9940 (0.33); 0.8531 (0.40); 0.8333 (0.36); 0.8113 (0.33); 0.1459 (1.11); 0.0079 (9.33); −0.0002 (254.08); −0.0083 (14.39); −0.1497 (1.17)

No. Ia-153, Solvent: <[$D_6$]-DMSO>, Spectrometer: 601.6 MHz 8.9083 (5.11); 8.9065 (4.94); 8.4567 (2.74); 8.4426 (2.78); 8.4208 (5.30); 8.4180 (5.17); 7.6128 (4.22); 7.6114 (4.38); 7.5995 (4.66); 7.5981 (4.67); 7.4243 (1.86); 7.4226 (1.95); 7.4119 (4.63); 7.4102 (4.68); 7.3995 (3.15); 7.3978 (3.05); 7.3413 (2.52); 7.3384 (2.95); 7.3283 (3.35); 7.3254 (3.80); 7.3156 (1.92); 7.3127 (1.98); 7.2914 (4.60); 7.2886 (4.08); 7.2290 (3.86); 7.2761 (3.36); 4.6202 (0.74); 4.6087 (1.66); 4.5971 (1.91); 4.5951 (1.83); 4.5834 (1.65); 4.5719 (0.76); 3.9026 (6.07); 3.3171 (223.65); 3.1949 (7.63); 3.1831 (6.86); 3.1722 (1.05); 3.1635 (0.89); 2.6185 (1.04); 2.6156 (2.08); 2.6126 (2.85); 2.6096 (2.08); 2.6066 (1.01); 2.5403 (0.83); 2.5372 (0.68); 2.5219 (6.48); 2.5188 (8.19); 2.5157 (9.01); 2.5068 (160.09); 2.5039 (331.73); 2.5009 (452.12); 2.4978 (329.79); 2.4949 (153.83); 2.4782 (0.36); 2.4749 (0.32); 2.3910 (0.90); 2.3880 (1.95); 2.3850 (2.69); 2.3820 (1.91); 2.3791 (0.82); 1.5476 (0.39); 1.5366 (0.37); 1.2882 (0.36); 1.2771 (0.38); 1.2361 (0.39); 1.2171 (16.00); 1.2060 (15.94); 0.0965 (1.35); 0.0052 (12.24); −0.0002 (325.94); −0.0057 (9.64); −0.1001 (1.33)

No. Ia-154, Solvent: <[$D_6$]-DMSO>, Spectrometer: 601.6 MHz 8.8555 (5.44); 8.6307 (2.84); 8.6166 (2.88); 8.4223 (5.65); 8.4195 (5.52); 7.6722 (1.94); 7.6649 (2.57); 7.6572 (3.20); 7.6175 (0.95); 7.6093 (6.69); 7.6051 (4.23); 7.6010 (4.49); 7.5942 (6.40); 7.5860 (0.66); 7.5175 (2.72); 7.5101 (2.57); 7.5030 (1.90); 7.0726 (2.06); 6.9801 (4.50); 6.8874 (2.26); 4.6398 (0.61); 4.6262 (1.34); 4.6156 (1.78); 4.6049 (1.33); 4.5913 (0.61); 3.9026 (3.58); 3.3209 (181.50); 3.2624 (1.73); 3.2529 (1.79); 3.2394 (2.85); 3.2299 (2.69); 3.1750 (2.88); 3.1612 (2.83); 3.1522 (1.80); 3.1383 (1.76); 2.6159 (1.79);

2.6129 (2.44); 2.6100 (1.75); 2.6071 (0.83); 2.5405 (0.48); 2.5221 (4.59); 2.5191 (5.85); 2.5160 (6.45); 2.5070 (142.10); 2.5041 (292.87); 2.5012 (399.12); 2.4982 (293.67); 2.4954 (140.67); 2.3911 (0.81); 2.3883 (1.71); 2.3854 (2.33); 2.3824 (1.68); 1.9083 (0.77); 1.2597 (15.95); 1.2485 (16.00); 0.0966 (1.23); 0.0150 (0.36); 0.0051 (9.69); −0.0002 (255.35); −0.0055 (8.45); −0.1000 (1.23)

No. Ia-155, Solvent: <[D$_6$]-DMSO>, Spectrometer: 601.6 MHz 9.0356 (2.97); 9.0336 (2.88); 8.9848 (1.48); 8.9829 (1.43); 8.5686 (1.85); 8.5537 (1.88); 8.4968 (3.17); 8.4940 (3.14); 8.4490 (1.50); 8.4462 (1.48); 8.3871 (0.40); 8.3128 (0.86); 8.2983 (0.88); 7.6666 (2.50); 7.6653 (2.60); 7.6533 (2.77); 7.6520 (2.77); 7.6444 (0.33); 7.6422 (0.40); 7.6289 (0.45); 7.5974 (1.22); 7.5959 (1.26); 7.5841 (1.37); 7.5826 (1.34); 7.4662 (0.88); 7.4645 (0.88); 7.4538 (2.41); 7.4523 (2.37); 7.4418 (2.42); 7.4401 (2.35); 7.4280 (2.82); 7.4248 (3.49); 7.4155 (1.68); 7.4122 (1.43); 7.4070 (0.77); 7.4051 (0.69); 7.3944 (1.41); 7.3927 (1.37); 7.3821 (2.56); 7.3791 (1.77); 7.3690 (2.02); 7.3668 (1.72); 7.3658 (1.73); 7.3570 (1.45); 7.3536 (1.56); 7.3506 (0.52); 7.3410 (0.56); 7.3380 (0.36); 7.3307 (0.89); 7.3279 (0.93); 7.3178 (1.03); 7.3149 (1.07); 7.3050 (0.57); 7.3021 (0.58); 7.1939 (1.16); 7.1911 (1.16); 7.1815 (1.08); 7.1786 (1.01); 6.9987 (0.51); 6.9696 (0.56); 4.4933 (0.34); 4.4814 (0.56); 4.4672 (0.56); 4.4553 (0.36); 4.4181 (0.58); 4.4145 (0.38); 4.4067 (0.65); 4.4032 (1.13); 4.3920 (1.12); 4.3884 (0.68); 4.3773 (0.64); 4.0931 (0.33); 4.0843 (0.34); 3.9025 (16.00); 3.8959 (0.51); 3.8905 (0.46); 3.8861 (1.17); 3.8793 (1.10); 3.8714 (0.92); 3.8679 (1.18); 3.8651 (1.07); 3.8615 (0.87); 3.8534 (0.76); 3.8466 (0.70); 3.8320 (0.42); 3.3451 (0.36); 3.3174 (340.37); 3.1722 (1.32); 3.1635 (1.31); 2.8902 (2.45); 2.8379 (0.67); 2.8334 (0.82); 2.8313 (0.88); 2.8268 (0.75); 2.8101 (1.24); 2.8057 (1.40); 2.7991 (1.04); 2.7920 (0.39); 2.7857 (0.55); 2.7815 (0.58); 2.7686 (0.53); 2.7643 (0.56); 2.7306 (2.10); 2.7265 (1.05); 2.7221 (1.16); 2.7145 (0.73); 2.7117 (0.82); 2.7079 (1.42); 2.7040 (1.15); 2.6989 (0.76); 2.6944 (0.84); 2.6869 (0.50); 2.6804 (0.91); 2.6764 (0.82); 2.6421 (1.14); 2.6378 (2.23); 2.6335 (1.13); 2.6301 (2.33); 2.6258 (4.49); 2.6214 (2.04); 2.6187 (1.51); 2.6156 (2.75); 2.6126 (3.76); 2.6096 (2.72); 2.6066 (1.30); 2.5701 (0.33); 2.5402 (1.04); 2.5371 (0.89); 2.5219 (7.48); 2.5188 (9.25); 2.5157 (10.08); 2.5069 (200.87); 2.5039 (426.09); 2.5008 (586.76); 2.4978 (430.22); 2.4948 (201.99); 2.4749 (0.44); 2.3911 (1.16); 2.3880 (2.51); 2.3850 (3.47); 2.3820 (2.47); 2.3791 (1.11); 2.0349 (0.67); 1.9081 (1.99); 1.5019 (0.96); 1.4905 (0.94); 1.3550 (1.78); 1.2368 (0.55); 1.1785 (3.96); 1.1671 (3.95); 1.1039 (0.39); 1.0934 (0.38); 1.0336 (0.35); 1.0223 (0.35); 0.9666 (8.39); 0.9554 (8.40); 0.0965 (1.58); 0.0052 (12.30); −0.0002 (385.32); −0.0057 (12.48); −0.1001 (1.59)

No. Ia-156, Solvent: <[D$_6$]-DMSO>, Spectrometer: 601.6 MHz 9.0101 (5.83); 9.0081 (5.82); 8.9980 (2.67); 8.9960 (2.65); 8.6976 (3.45); 8.6827 (3.53); 8.5010 (6.06); 8.4982 (6.05); 8.4471 (1.52); 8.4356 (3.24); 8.4328 (4.10); 8.3932 (0.47); 7.7377 (0.53); 7.7312 (0.55); 7.7186 (2.22); 7.7125 (2.80); 7.7107 (2.99); 7.7042 (3.39); 7.6990 (1.17); 7.6893 (0.51); 7.6808 (0.38); 7.6604 (0.53); 7.6547 (1.94); 7.6492 (6.23); 7.6435 (6.56); 7.6389 (7.17); 7.6338 (13.74); 7.6300 (6.83); 7.6229 (2.57); 7.6208 (2.26); 7.6133 (1.10); 7.6090 (1.05); 7.6045 (0.99); 7.5958 (2.95); 7.5922 (2.31); 7.5875 (2.71); 7.5836 (1.64); 7.5806 (2.71); 7.5718 (0.43); 7.4239 (1.20); 7.4160 (1.23); 7.4095 (0.96); 7.3266 (2.17); 7.2424 (0.53); 7.2339 (5.19); 7.1413 (2.45); 7.0524 (0.98); 7.0031 (0.57); 6.9683 (0.72); 6.9597 (2.20); 6.8671 (1.10); 4.5365 (0.59); 4.5247 (0.94); 4.5102 (0.93); 4.4985 (0.63); 4.4896 (0.35); 4.4788 (1.09); 4.4645 (2.08); 4.4531 (2.09); 4.4388 (1.20); 4.4272 (0.35); 4.0928 (0.70); 4.0841 (0.72); 3.9390 (1.34); 3.9262 (3.38); 3.9127 (3.23); 3.9026 (14.71); 3.8954 (0.79); 3.8877 (0.77); 3.8830 (0.70); 3.8785 (0.82); 3.8756 (0.85); 3.8710 (0.72); 3.8664 (0.67); 3.8586 (0.62); 3.8320 (0.61); 3.8256 (0.47); 3.3928 (0.38); 3.3837 (0.40); 3.3171 (427.45); 3.2943 (0.33); 3.1723 (2.63); 3.1636 (2.55); 2.8902 (1.49); 2.8003 (0.60); 2.7961 (0.63); 2.7833 (0.70); 2.7792 (0.67); 2.7726 (1.02); 2.7684 (1.11); 2.7632 (0.45); 2.7559 (0.96); 2.7516 (1.04); 2.7304 (1.68); 2.7222 (5.24); 2.7180 (5.88); 2.7097 (6.05); 2.7057 (5.90); 2.6865 (0.65); 2.6821 (0.84); 2.6791 (0.64); 2.6745 (0.70); 2.6548 (1.98); 2.6505 (3.79); 2.6462 (1.56); 2.6340 (4.29); 2.6298 (8.45); 2.6255 (3.49); 2.6186 (2.08); 2.6156 (4.12); 2.6126 (5.64); 2.6096 (4.15); 2.6066 (2.07); 2.5922 (0.33); 2.5868 (0.35); 2.5703 (0.46); 2.5479 (1.41); 2.5403 (1.64); 2.5371 (1.08); 2.5219 (11.27); 2.5188 (15.59); 2.5158 (14.35); 2.5069 (297.70); 2.5039 (635.76); 2.5009 (882.93); 2.4979 (649.72); 2.4949 (308.19); 2.3911 (1.69); 2.3881 (3.75); 2.3851 (5.21); 2.3820 (3.75); 2.3791 (1.72); 2.0329 (1.17); 1.9082 (2.25); 1.5226 (1.09); 1.5110 (1.11); 1.4253 (0.68); 1.4148 (0.66); 1.3551 (1.93); 1.3480 (0.49); 1.2584 (0.44); 1.2492 (0.50); 1.2368 (1.03); 1.2100 (6.90); 1.1986 (6.84); 1.1692 (0.35); 1.1574 (0.35); 1.1171 (0.45); 1.1049 (0.41); 1.0999 (0.35); 1.0919 (0.47); 1.0835 (0.62); 1.0723 (0.54); 1.0023 (15.91); 0.9910 (16.00); 0.8857 (0.37); 0.8753 (0.41); 0.8541 (0.46); 0.8496 (0.41); 0.8377 (0.34); 0.0965 (2.60); 0.0052 (19.58); −0.0002 (622.08); −0.0057 (21.19); −0.0229 (0.38); −0.1001 (2.59)

No. Ia-157, Solvent: <[D$_6$]-DMSO>, Spectrometer: 399.95 MHz 8.9161 (2.44); 8.9134 (2.43); 8.4066 (2.54); 8.4026 (2.54); 8.3194 (0.38); 8.1660 (0.72); 8.1516 (1.38); 8.1394 (0.63); 7.4632 (0.59); 7.4598 (0.62); 7.4415 (1.52); 7.4259 (1.36); 7.4225 (1.35); 7.3789 (2.42); 7.3621 (2.03); 7.3465 (1.83); 7.3285 (1.04); 7.3254 (0.97); 7.2769 (2.12); 7.2607 (1.29); 7.2582 (1.27); 6.9653 (3.16); 6.9613 (4.81); 6.9412 (3.49); 6.8907 (2.08); 6.8857 (1.89); 6.8701 (1.24); 6.8651 (1.15); 3.9043 (10.96); 3.7696 (16.00); 3.7474 (15.83); 3.4839 (0.52); 3.4625 (0.72); 3.4555 (1.09); 3.4407 (0.96); 3.4247 (1.07); 3.4088 (1.24); 3.3930 (0.82); 3.3421 (236.37); 3.1678 (0.75); 2.6764 (0.71); 2.6720 (0.97); 2.6677 (0.72); 2.5422 (0.78); 2.5251 (3.31); 2.5074 (120.85); 2.5029 (157.12); 2.4985 (119.23); 2.3342 (0.70); 2.3297 (0.96); 2.3251 (0.73); 1.5826 (0.42); 1.5671 (0.61); 1.5478 (0.75); 1.5285 (0.54); 1.5021 (0.47); 1.4903 (0.55); 1.4838 (0.56); 1.4711 (0.66); 1.4562 (0.41); 1.4511 (0.40); 0.6361 (2.94); 0.6178 (6.36); 0.5993 (2.78); −0.0002 (2.26)

No. Ia-161, Solvent: <[D$_6$]-DMSO>, Spectrometer: 399.95 MHz 8.8663 (9.30); 8.8638 (9.53); 8.7395 (5.78); 8.7369 (5.94); 8.3408 (6.05); 8.3364 (6.10); 8.3187 (1.49); 8.3083 (10.01); 8.3043 (10.09); 8.1596 (5.73); 8.1377 (5.90); 7.9539 (3.11); 7.9311 (3.18); 7.5737 (12.55); 7.5561 (15.19); 7.5526 (12.67); 7.5203 (7.44); 7.5030 (9.49); 7.4993 (8.55); 7.4784 (1.57); 7.4659 (1.23); 7.4598 (4.83); 7.4542 (2.68); 7.4508 (2.97); 7.4453 (3.23); 7.4417 (4.35); 7.4385 (3.95); 7.4323 (8.11); 7.4272 (2.86); 7.4174 (3.94); 7.4142 (6.47); 7.4003 (7.84); 7.3813 (10.18); 7.3736 (12.70); 7.3638 (4.93); 7.3545 (16.00); 7.3368 (5.95); 4.7201 (1.60); 4.7119 (1.82); 4.6983 (1.85); 4.6889 (1.67); 4.4259 (0.70); 4.4159 (0.83); 4.3967 (2.03); 4.3679 (2.10); 4.3491 (0.94); 4.3386 (0.78); 3.9044 (14.38); 3.6454 (1.19); 3.6370 (2.25); 3.6285 (1.46); 3.6163 (1.43); 3.6081 (2.40); 3.5995 (1.41); 3.5857 (1.80); 3.5779 (1.91); 3.5571 (3.44); 3.5492 (3.27); 3.5297 (1.96); 3.5210 (1.78); 3.4731 (0.36); 3.4545 (0.40); 3.4376 (0.40); 3.4305 (0.52); 3.4159 (0.73); 3.3460 (1897.15); 3.2820 (1.56); 3.2468 (0.81); 3.2297 (0.61); 3.2141 (0.48); 3.2048 (0.56); 3.1746 (0.57); 3.1617 (0.53); 2.6770 (2.71); 2.6725 (3.77);

2.6680 (2.92); 2.5256 (12.19); 2.5120 (206.18); 2.5079 (415.84); 2.5034 (557.11); 2.4989 (428.11); 2.4281 (1.03); 2.4196 (1.06); 2.3896 (1.81); 2.3623 (1.81); 2.3345 (3.32); 2.3301 (4.27); 2.3257 (3.44); 2.2755 (0.36); 1.9555 (2.62); 1.9237 (3.13); 1.8728 (6.33); 1.8483 (7.65); 1.8420 (7.73); 1.8104 (6.64); 1.7882 (3.76); 1.7636 (2.67); 1.7292 (0.82); 1.6867 (1.07); 1.6613 (2.24); 1.6231 (3.15); 1.5986 (4.24); 1.5920 (3.89); 1.5671 (4.01); 1.5603 (3.75); 1.5293 (2.66); 1.5033 (1.63); 1.4446 (3.08); 1.4122 (3.14); 1.3879 (3.08); 1.3632 (2.73); 1.3313 (1.97); 1.2983 (0.91); 1.2579 (0.56); 1.2486 (0.52); 1.2350 (0.88); 0.8533 (0.32); 0.1459 (1.04); 0.0079 (7.59); −0.0002 (217.92); −0.0084 (10.31); −0.1498 (0.95)

No. Ia-162, Solvent: <[$D_6$]-DMSO>, Spectrometer: 399.95 MHz 8.8583 (1.81); 8.7329 (5.95); 8.7304 (6.05); 8.3343 (6.22); 8.3303 (6.17); 8.3188 (1.03); 8.3030 (1.96); 8.2994 (1.93); 8.2562 (1.07); 8.2345 (1.11); 8.0584 (3.21); 8.0353 (3.31); 7.6113 (3.08); 7.5899 (4.20); 7.5601 (8.98); 7.5558 (3.71); 7.5437 (4.08); 7.5388 (15.31); 7.4792 (2.18); 7.4736 (15.45); 7.4688 (4.71); 7.4524 (12.47); 7.4367 (1.27); 7.4321 (3.43); 4.7086 (1.62); 4.7003 (1.81); 4.6864 (1.84); 4.6778 (1.63); 4.3863 (0.39); 4.3599 (0.39); 3.9045 (16.00); 3.6407 (1.20); 3.6325 (2.19); 3.6235 (1.42); 3.6117 (1.48); 3.6029 (2.30); 3.5946 (1.29); 3.5676 (0.37); 3.5593 (0.38); 3.5385 (0.73); 3.5309 (0.63); 3.5099 (0.43); 3.4327 (0.44); 3.4078 (0.81); 3.3462 (1127.30); 3.3027 (1.61); 3.2801 (0.85); 3.2576 (0.51); 3.2438 (0.48); 3.2143 (0.35); 3.2038 (0.33); 3.1746 (0.44); 3.1617 (0.40); 2.8913 (0.73); 2.7313 (0.60); 2.6770 (1.69); 2.6726 (2.33); 2.6681 (1.75); 2.5426 (1.67); 2.5257 (7.59); 2.5122 (130.42); 2.5080 (260.11); 2.5035 (343.43); 2.4990 (259.45); 2.4949 (134.03); 2.4160 (0.74); 2.4083 (0.81); 2.3784 (1.67); 2.3503 (1.71); 2.3398 (1.49); 2.3347 (2.04); 2.3303 (2.58); 2.3257 (2.16); 1.9568 (0.63); 1.9232 (0.85); 1.8790 (4.19); 1.8517 (5.50); 1.7997 (2.41); 1.7888 (1.78); 1.7645 (2.03); 1.7307 (0.66); 1.6826 (0.43); 1.6472 (0.62); 1.6028 (1.90); 1.5948 (1.98); 1.5588 (2.26); 1.5489 (2.03); 1.5297 (1.75); 1.5180 (1.73); 1.5077 (1.52); 1.4582 (1.63); 1.4455 (1.41); 1.4326 (1.50); 1.3632 (0.73); 1.3361 (0.64); 1.2972 (0.52); 1.2583 (0.55); 1.2491 (0.53); 1.2359 (1.07); 0.8540 (0.55); 0.8336 (0.50); 0.8119 (0.39); 0.1458 (0.63); 0.0078 (5.13); −0.0002 (135.93); −0.0084 (5.81); −0.1497 (0.61)

No. Ia-163, Solvent: <[$D_6$]-DMSO>, Spectrometer: 399.95 MHz 8.8541 (0.45); 8.7226 (2.15); 8.3320 (2.27); 8.3282 (2.26); 8.3190 (0.33); 8.2910 (0.47); 8.2873 (0.46); 7.7519 (1.22); 7.7294 (1.25); 7.5766 (0.74); 7.5541 (1.00); 7.5445 (3.60); 7.5226 (3.90); 6.9256 (3.98); 6.9037 (3.85); 6.8975 (1.31); 6.8754 (0.79); 4.6898 (0.58); 4.6819 (0.67); 4.6685 (0.70); 4.6594 (0.59); 3.9043 (4.05); 3.8240 (0.44); 3.7774 (16.00); 3.7510 (3.27); 3.6365 (0.43); 3.6286 (0.77); 3.6198 (0.52); 3.6081 (0.51); 3.5994 (0.80); 3.3443 (321.39); 2.6724 (0.66); 2.6681 (0.50); 2.5076 (78.48); 2.5033 (102.38); 2.4991 (78.45); 2.4142 (0.33); 2.3859 (0.62); 2.3568 (0.63); 2.3300 (0.90); 1.8997 (0.70); 1.8695 (1.72); 1.8401 (1.35); 1.8073 (0.65); 1.7710 (0.62); 1.7425 (0.68); 1.6001 (0.68); 1.5652 (0.66); 1.5378 (0.63); 1.5279 (0.65); 1.5039 (0.53); 1.4559 (0.54); 1.4257 (0.54); 1.4035 (0.33); 0.0079 (1.37); −0.0002 (38.31); −0.0075 (2.02)

No. Ia-164, Solvent: <[$D_6$]-DMSO>, Spectrometer: 399.95 MHz 8.9220 (2.84); 8.9193 (2.87); 8.8586 (3.86); 8.8560 (3.92); 8.4089 (2.03); 8.3782 (3.69); 8.3724 (4.25); 8.3701 (4.73); 8.3648 (4.30); 8.3174 (0.87); 8.2320 (1.68); 8.2104 (1.73); 7.5459 (2.85); 7.5436 (3.08); 7.5261 (3.56); 7.5237 (3.81); 7.5200 (2.73); 7.5174 (2.58); 7.4999 (2.66); 7.4975 (2.72); 7.3912 (1.27); 7.3887 (1.47); 7.3727 (3.30); 7.3700 (3.40); 7.3541 (2.37); 7.3513 (2.34); 7.3451 (1.26); 7.3292 (2.52); 7.3265 (2.61); 7.3080 (3.72); 7.3038 (2.64); 7.2886 (2.72); 7.2842 (2.94); 7.2753 (1.83); 7.2703 (2.77); 7.2652 (1.54); 7.2558 (2.05); 7.2513 (2.19); 7.2368 (1.01); 7.2325 (0.96); 7.0803 (2.96); 7.0760 (3.08); 7.0615 (2.77); 7.0573 (2.64); 7.0095 (2.19); 7.0051 (2.29); 6.9907 (2.05); 6.9865 (2.00); 4.7814 (1.12); 4.7653 (1.10); 4.7586 (1.09); 4.4042 (0.61); 4.3815 (0.59); 3.9040 (16.00); 3.7706 (0.39); 3.5758 (1.44); 3.5675 (0.99); 3.5537 (0.99); 3.5455 (1.52); 3.5376 (0.87); 3.4672 (0.91); 3.4601 (1.07); 3.4389 (1.58); 3.4327 (1.90); 3.4116 (2.15); 3.3535 (1518.02); 3.2301 (0.61); 3.2082 (0.48); 3.1746 (0.78); 3.1614 (0.74); 2.9991 (0.39); 2.8911 (1.68); 2.7527 (0.35); 2.7310 (1.43); 2.6770 (1.70); 2.6725 (2.34); 2.6681 (1.77); 2.5426 (1.45); 2.5257 (7.32); 2.5122 (131.26); 2.5080 (262.37); 2.5035 (346.79); 2.4990 (261.86); 2.4947 (135.18); 2.3571 (0.80); 2.3346 (2.55); 2.3302 (3.24); 2.3258 (2.69); 2.3006 (1.13); 2.2709 (0.55); 2.0326 (0.83); 2.0097 (1.14); 1.8773 (1.09); 1.8459 (2.25); 1.7961 (3.38); 1.7748 (3.83); 1.7195 (0.42); 1.5855 (1.33); 1.5555 (1.74); 1.5191 (1.89); 1.4904 (1.46); 1.4606 (2.03); 1.4331 (2.01); 1.4086 (1.39); 1.3765 (0.99); 1.3459 (0.80); 1.3358 (0.74); 1.3150 (0.64); 1.2980 (0.48); 1.2821 (0.40); 1.2582 (0.45); 1.2489 (0.49); 1.2357 (0.91); 0.8539 (0.41); 0.8346 (0.37); 0.1459 (0.56); 0.0080 (4.49); −0.0002 (127.38); −0.0084 (5.49); −0.1498 (0.55)

No. Ia-165, Solvent: <[$D_6$]-DMSO>, Spectrometer: 601.6 MHz 8.8748 (0.36); 8.7588 (3.03); 8.7569 (2.94); 8.3468 (3.31); 8.3441 (3.22); 8.3118 (0.37); 8.3090 (0.36); 7.9844 (1.84); 7.9694 (1.88); 7.7026 (3.83); 7.7004 (5.27); 7.6970 (6.13); 7.6938 (2.31); 7.6886 (5.52); 7.6867 (6.10); 7.6829 (8.69); 7.6799 (1.70); 7.6764 (1.76); 7.6688 (1.31); 7.6639 (0.69); 7.6382 (1.38); 7.6354 (7.88); 7.6321 (2.19); 7.6244 (1.81); 7.6213 (5.04); 7.6182 (0.68); 7.4972 (2.76); 7.4941 (1.08); 7.4848 (5.32); 7.4776 (0.59); 7.4743 (1.50); 7.4716 (3.50); 7.4686 (0.66); 7.4652 (0.66); 7.4519 (0.38); 7.4130 (1.11); 7.4111 (2.02); 7.4092 (1.12); 7.4016 (0.99); 7.3988 (2.89); 7.3960 (1.05); 7.3885 (0.67); 7.3866 (1.26); 7.3845 (0.83); 4.7343 (0.80); 4.7281 (0.90); 4.7198 (0.92); 4.7133 (0.80); 3.9026 (16.00); 3.6593 (0.62); 3.6536 (1.14); 3.6475 (0.69); 3.6402 (0.72); 3.6342 (1.16); 3.6284 (0.63); 3.3463 (0.51); 3.3376 (1.16); 3.3211 (651.14); 3.3028 (0.46); 3.2939 (0.35); 3.1726 (1.09); 3.1639 (1.07); 2.8903 (0.51); 2.7305 (0.42); 2.6191 (0.76); 2.6161 (1.61); 2.6130 (2.26); 2.6100 (1.62); 2.6069 (0.75); 2.5406 (0.54); 2.5376 (0.34); 2.5223 (4.43); 2.5192 (5.60); 2.5161 (5.54); 2.5073 (120.28); 2.5043 (260.75); 2.5012 (361.94); 2.4982 (262.79); 2.4952 (120.86); 2.4804 (0.46); 2.4773 (0.33); 2.4001 (0.69); 2.3915 (0.87); 2.3885 (1.75); 2.3854 (2.62); 2.3824 (2.25); 2.3794 (1.31); 1.9214 (0.80); 1.9145 (0.63); 1.8991 (1.61); 1.8825 (1.38); 1.8779 (1.36); 1.8626 (1.06); 1.8571 (0.91); 1.7996 (0.57); 1.7863 (0.62); 1.7801 (0.92); 1.7740 (0.57); 1.6197 (0.80); 1.6148 (0.82); 1.5976 (0.81); 1.5916 (0.77); 1.5526 (0.69); 1.5461 (0.71); 1.5380 (0.59); 1.5292 (0.60); 1.4688 (0.63); 1.4463 (0.67); 1.2370 (0.58); 0.0965 (1.10); 0.0052 (9.36); −0.0002 (304.01); −0.0057 (8.67); −0.1001 (1.09)

No. Ia-166, Solvent: <[$D_6$]-DMSO>, Spectrometer: 601.6 MHz 8.8723 (1.07); 8.8704 (1.04); 8.7359 (2.75); 8.7341 (2.70); 8.5624 (0.62); 8.5481 (0.64); 8.4200 (0.78); 8.4168 (1.22); 8.4136 (0.85); 8.3850 (1.49); 8.3696 (1.53); 8.3505 (2.99); 8.3477 (2.96); 8.3276 (1.30); 8.3260 (1.46); 8.3237 (1.54); 8.3222 (1.50); 8.3140 (1.37); 8.3124 (1.51); 8.3083 (2.77); 8.3039 (1.66); 8.2955 (0.59); 8.2930 (0.61); 8.2917 (0.59); 8.2901 (0.55); 8.2711 (2.37); 8.2680 (3.24); 8.2647 (2.06); 8.0373 (0.50); 8.0354 (0.70); 8.0331 (0.52); 8.0244 (0.57);

8.0221 (0.75); 8.0202 (0.54); 7.9479 (1.39); 7.9460 (1.92); 7.9437 (1.39); 7.9352 (1.59); 7.9331 (2.09); 7.9309 (1.51); 7.7162 (2.20); 7.7029 (3.69); 7.6897 (2.04); 7.6869 (1.53); 7.6737 (0.76); 4.7369 (0.71); 4.7309 (0.80); 4.7221 (0.68); 4.7161 (0.72); 3.9027 (16.00); 3.6700 (0.55); 3.6640 (1.04); 3.6580 (0.63); 3.6506 (0.65); 3.6446 (1.07); 3.6387 (0.58); 3.5663 (0.35); 3.5614 (0.33); 3.3175 (221.82); 3.1725 (1.12); 3.1638 (1.11); 2.8905 (1.15); 2.7312 (0.91); 2.6190 (0.76); 2.6159 (1.63); 2.6129 (2.29); 2.6099 (1.62); 2.6069 (0.72); 2.5405 (0.33); 2.5222 (4.25); 2.5191 (5.20); 2.5160 (5.26); 2.5072 (123.83); 2.5042 (267.21); 2.5011 (369.74); 2.4981 (271.90); 2.4951 (127.84); 2.4687 (0.36); 2.4070 (0.34); 2.3914 (1.31); 2.3883 (2.25); 2.3854 (2.79); 2.3824 (1.88); 2.3793 (0.90); 2.3693 (0.71); 2.3497 (0.32); 1.9679 (0.33); 1.9632 (0.32); 1.9079 (1.47); 1.9042 (1.00); 1.8871 (2.16); 1.8702 (1.54); 1.8508 (0.59); 1.8455 (0.62); 1.8244 (0.91); 1.8054 (0.70); 1.7995 (1.11); 1.7936 (0.76); 1.6394 (0.36); 1.6192 (0.98); 1.5974 (0.97); 1.5578 (0.70); 1.5512 (0.72); 1.5431 (0.60); 1.5347 (0.58); 1.4752 (0.68); 1.4545 (0.88); 1.4338 (0.54); 1.3815 (0.37); 1.3605 (0.32); 1.2368 (0.60); 0.0965 (1.05); 0.0053 (8.03); −0.0002 (270.63); −0.0057 (8.98); −0.0161 (0.38); −0.1000 (1.09)

No. Ia-169, Solvent: <[$D_6$]-DMSO>, Spectrometer: 601.6 MHz 8.9767 (0.56); 8.9635 (0.56); 8.9111 (0.84); 8.9093 (0.80); 8.8782 (2.83); 8.4619 (0.89); 8.4591 (0.87); 8.4062 (2.45); 7.6285 (0.72); 7.6269 (0.74); 7.6152 (0.92); 7.6135 (0.95); 7.6089 (2.72); 7.6076 (2.83); 7.5958 (3.00); 7.5942 (2.98); 7.4431 (0.40); 7.4413 (0.40); 7.4338 (1.30); 7.4320 (1.48); 7.4289 (0.96); 7.4214 (3.11); 7.4196 (3.08); 7.4166 (0.77); 7.4090 (2.10); 7.4072 (1.98); 7.3675 (0.51); 7.3645 (0.61); 7.3546 (0.72); 7.3501 (1.74); 7.3472 (2.04); 7.3417 (0.61); 7.3374 (2.12); 7.3343 (2.82); 7.3246 (3.94); 7.3217 (3.40); 7.3170 (1.00); 7.3124 (2.40); 7.3096 (1.88); 7.3046 (0.65); 5.1644 (0.47); 5.1543 (0.47); 4.9767 (0.32); 3.9026 (16.00); 3.6657 (7.14); 3.5971 (0.34); 3.5868 (1.32); 3.5774 (1.13); 3.5715 (0.52); 3.5619 (1.62); 3.5528 (1.24); 3.4486 (0.47); 3.4347 (0.48); 3.4227 (0.41); 3.4090 (0.45); 3.3878 (0.44); 3.3182 (78.27); 3.1713 (1.87); 3.1645 (1.79); 2.6186 (1.19); 2.6157 (2.18); 2.6126 (2.88); 2.6096 (2.11); 2.6065 (1.11); 2.5402 (2.27); 2.5219 (9.18); 2.5188 (11.21); 2.5157 (12.58); 2.5069 (157.14); 2.5039 (318.96); 2.5009 (429.75); 2.4978 (309.68); 2.4948 (140.64); 2.4738 (0.49); 2.3911 (0.92); 2.3881 (1.89); 2.3851 (2.55); 2.3820 (1.80); 2.3790 (0.80); 1.9077 (1.13); 0.0965 (0.90); 0.0197 (0.52); 0.0052 (9.06); −0.0002 (226.43); −0.0058 (7.18); −0.1001 (0.86)

No. Ia-170, Solvent: <$CD_3CN$>, Spectrometer: 601.6 MHz 8.7668 (3.74); 8.7654 (4.02); 8.1011 (3.83); 8.0988 (4.21); 7.4459 (0.72); 7.4350 (1.47); 7.4317 (1.62); 7.4241 (0.89); 7.4209 (2.95); 7.4178 (1.36); 7.4100 (1.43); 7.4068 (1.78); 7.3960 (0.74); 7.0524 (0.87); 7.0434 (0.92); 7.0386 (0.87); 7.0101 (0.61); 7.0080 (0.88); 7.0032 (4.53); 6.9958 (0.77); 6.9938 (1.10); 6.9899 (5.73); 6.9893 (6.18); 6.9762 (4.22); 6.9716 (0.84); 6.9696 (0.63); 4.7280 (0.62); 4.7168 (1.11); 4.7154 (1.15); 4.7139 (1.12); 4.7042 (1.41); 4.7027 (1.60); 4.6930 (0.91); 4.6915 (1.17); 4.6901 (1.32); 4.6790 (0.70); 3.2613 (0.50); 3.2486 (0.43); 3.2377 (3.27); 3.2297 (3.42); 3.2253 (3.85); 3.2191 (3.37); 3.2062 (0.53); 3.1954 (0.40); 2.1626 (62.51); 1.9668 (0.83); 1.9587 (0.70); 1.9545 (1.19); 1.9508 (12.12); 1.9467 (23.29); 1.9425 (35.28); 1.9385 (25.62); 1.9344 (13.22); 1.4358 (2.83); 1.3009 (0.36); 1.2853 (15.91); 1.2741 (16.00); 0.0053 (0.38); −0.0002 (10.70)

No. Ia-171, Solvent: <$CD_3CN$>, Spectrometer: 601.6 MHz 8.7612 (3.44); 8.7597 (3.43); 8.0992 (3.58); 8.0967 (3.55); 7.0668 (0.73); 7.0554 (0.74); 6.8801 (0.40); 6.8735 (1.27); 6.8711 (3.55); 6.8648 (0.57); 6.8584 (4.75); 6.8558 (4.83); 6.8494 (0.54); 6.8431 (3.52); 6.8406 (1.27); 6.8342 (0.36); 4.7084 (0.68); 4.6970 (1.34); 4.6943 (0.90); 4.6852 (1.45); 4.6828 (1.49); 4.6738 (0.89); 4.6712 (1.33); 4.6597 (0.69); 3.2282 (5.69); 3.2165 (6.69); 2.3799 (0.44); 2.1624 (73.49); 1.9670 (2.60); 1.9589 (1.66); 1.9546 (2.27); 1.9509 (16.54); 1.9468 (29.63); 1.9427 (42.17); 1.9385 (29.54); 1.9344 (15.17); 1.4362 (0.94); 1.2963 (0.32); 1.2823 (15.88); 1.2712 (16.00); −0.0002 (7.00)

No. Ia-172, Solvent: <$CD_3CN$>, Spectrometer: 601.6 MHz 8.7526 (4.03); 8.7512 (4.01); 8.0886 (4.13); 8.0863 (4.09); 7.7081 (1.42); 7.7050 (1.51); 7.6953 (2.88); 7.6923 (2.99); 7.6825 (1.52); 7.6795 (1.53); 7.5110 (0.76); 7.5079 (0.78); 7.5023 (0.86); 7.4989 (1.67); 7.4972 (1.38); 7.4957 (1.32); 7.4943 (1.14); 7.4899 (1.18); 7.4884 (1.31); 7.4868 (1.42); 7.4852 (1.74); 7.4819 (0.96); 7.4762 (0.91); 7.4732 (0.85); 7.2537 (2.11); 7.2522 (2.22); 7.2411 (3.58); 7.2397 (3.75); 7.2286 (1.83); 7.2271 (1.89); 7.1811 (2.51); 7.1797 (2.53); 7.1673 (2.50); 7.1659 (2.47); 7.1621 (2.54); 7.1607 (2.45); 7.1483 (1.88); 7.1469 (1.82); 4.7179 (0.47); 4.7161 (0.55); 4.7048 (1.29); 4.6934 (1.69); 4.6821 (1.29); 4.6707 (0.55); 4.6690 (0.49); 3.2755 (5.47); 3.2642 (6.91); 2.3808 (0.54); 2.1904 (21.04); 1.9698 (0.38); 1.9574 (0.47); 1.9537 (2.99); 1.9496 (5.35); 1.9455 (7.70); 1.9414 (5.29); 1.9373 (2.69); 1.4327 (1.74); 1.3035 (15.97); 1.2923 (16.00); −0.0002 (1.55)

No. Ia-173, Solvent: <$CD_3CN$>, Spectrometer: 601.6 MHz 8.7812 (3.35); 8.7796 (3.32); 8.1041 (3.51); 8.1014 (3.46); 7.3701 (0.41); 7.3658 (3.78); 7.3625 (4.77); 7.3505 (10.61); 7.3285 (6.10); 7.3176 (2.86); 7.3131 (2.07); 7.3021 (1.78); 6.9434 (0.72); 6.9310 (0.72); 4.7837 (0.57); 4.7805 (0.33); 4.7729 (0.88); 4.7695 (1.12); 4.7662 (0.34); 4.7621 (0.76); 4.7586 (1.61); 4.7551 (0.74); 4.7510 (0.34); 4.7478 (1.15); 4.7443 (0.87); 4.7368 (0.34); 4.7336 (0.58); 3.3260 (1.57); 3.3120 (1.55); 3.3022 (2.32); 3.2882 (2.29); 3.2063 (1.95); 3.1961 (1.96); 3.1824 (1.34); 3.1723 (1.29); 2.1576 (119.10); 2.0528 (0.40); 1.9665 (1.61); 1.9584 (1.44); 1.9541 (2.37); 1.9504 (25.69); 1.9463 (48.19); 1.9422 (68.94); 1.9381 (47.97); 1.9340 (24.54); 1.9253 (0.44); 1.8275 (0.39); 1.4363 (0.47); 1.3133 (15.99); 1.3022 (16.00); 0.0052 (0.95); −0.0002 (26.47); −0.0058 (0.87)

No. Ia-174, Solvent: <$CD_3CN$>, Spectrometer: 601.6 MHz 8.7742 (3.29); 8.7725 (3.22); 8.1109 (3.41); 8.1083 (3.35); 7.6015 (0.57); 7.6002 (0.55); 7.5923 (0.69); 7.5909 (0.78); 7.5877 (1.37); 7.5871 (1.37); 7.5788 (1.37); 7.5779 (1.41); 7.5745 (1.13); 7.5732 (1.05); 7.5654 (1.06); 7.5643 (1.02); 7.5406 (3.50); 7.5275 (1.96); 7.4252 (1.47); 7.4106 (2.52); 7.3965 (1.20); 7.0567 (0.70); 7.0444 (0.70); 4.7588 (0.63); 4.7478 (1.09); 4.7458 (0.98); 4.7365 (0.92); 4.7346 (1.41); 4.7318 (0.85); 4.7226 (1.01); 4.7206 (1.05); 4.7095 (0.64); 3.3021 (1.45); 3.2892 (1.43); 3.2782 (2.23); 3.2653 (2.18); 3.1896 (1.98); 3.1788 (1.98); 3.1657 (1.32); 3.1549 (1.29); 2.3799 (0.47); 2.1618 (46.74); 1.9668 (0.93); 1.9587 (0.78); 1.9544 (1.27); 1.9507 (15.41); 1.9466 (28.43); 1.9425 (41.41); 1.9384 (29.18); 1.9343 (14.76); 1.9296 (0.51); 1.4361 (0.64); 1.2668 (16.00); 1.2556 (15.90); 0.0053 (0.50); −0.0002 (15.34); −0.0058 (0.45)

No. Ia-175, Solvent: <$CD_3CN$>, Spectrometer: 601.6 MHz 8.7747 (3.18); 8.7730 (3.19); 8.0989 (3.26); 8.0963 (3.27); 7.4582 (0.88); 7.4548 (1.00); 7.4464 (1.94); 7.4431 (2.47); 7.4348 (2.26); 7.4312 (4.21); 7.4225 (4.59); 7.4198 (2.66); 7.4159 (3.19); 7.4134 (3.92); 7.4044 (1.93); 7.4023 (1.84); 7.4009 (1.34); 7.3917 (0.77); 7.3893 (0.89); 7.3843 (2.45);

7.3719 (1.71); 6.9376 (0.75); 6.9243 (0.75); 4.7032 (0.66); 4.6918 (1.22); 4.6888 (0.81); 4.6800 (1.38); 4.6775 (1.32); 4.6688 (0.85); 4.6657 (1.26); 4.6544 (0.69); 3.8577 (0.37); 3.8388 (1.19); 3.8331 (0.59); 3.8199 (1.29); 3.8142 (1.66); 3.8010 (0.51); 3.7953 (1.66); 3.7764 (0.55); 3.7144 (0.50); 3.6955 (1.60); 3.6899 (0.48); 3.6766 (1.70); 3.6709 (1.22); 3.6576 (0.63); 3.6520 (1.18); 3.6330 (0.39); 3.2491 (6.82); 3.2374 (5.79); 2.3799 (0.46); 2.1823 (0.42); 2.1750 (0.37); 2.1572 (186.69); 2.0568 (0.51); 2.0526 (0.76); 2.0485 (0.54); 1.9738 (0.38); 1.9664 (17.99); 1.9582 (3.41); 1.9541 (4.80); 1.9503 (48.40); 1.9462 (92.40); 1.9421 (138.36); 1.9380 (95.38); 1.9339 (47.38); 1.9196 (0.38); 1.8315 (0.52); 1.8273 (0.75); 1.8232 (0.54); 1.4365 (0.37); 1.2918 (15.91); 1.2806 (16.00); 1.2693 (0.38); 0.0053 (1.20); −0.0002 (36.79); −0.0058 (1.45)

No. Ia-176, Solvent: <[D$_6$]-DMSO>, Spectrometer: 399.95 MHz 8.8966 (5.59); 8.8938 (5.51); 8.5417 (3.13); 8.5206 (3.20); 8.4215 (5.74); 8.4174 (5.77); 7.6428 (9.29); 7.6378 (9.91); 7.4898 (4.58); 7.4847 (4.25); 7.4693 (6.24); 7.4642 (6.09); 7.3673 (10.56); 7.3468 (7.77); 4.6262 (0.66); 4.6071 (1.47); 4.5904 (1.96); 4.5731 (1.35); 4.5536 (0.68); 3.3354 (237.36); 3.3119 (1.60); 3.2342 (0.90); 3.2179 (0.99); 3.1991 (3.34); 3.1823 (3.73); 3.1785 (4.03); 3.1585 (3.24); 3.1435 (1.00); 3.1238 (1.01); 2.6719 (0.41); 2.5255 (0.69); 2.5208 (1.04); 2.5115 (23.17); 2.5074 (44.64); 2.5032 (61.62); 2.4990 (42.97); 2.4949 (21.41); 2.3298 (0.37); 1.2257 (16.00); 1.2089 (15.91); −0.0002 (5.08)

No. Ia-177, Solvent: <[D$_6$]-DMSO>, Spectrometer: 399.95 MHz 8,9455 (2,86); 8,4485 (0,81); 8,4342 (1,51); 8,4115 (3,07); 8,407 (2,97); 7,8472 (2,44); 7,8278 (2,54); 7,4273 (1,1); 7,4086 (2,46); 7,3899 (1,48); 7,2365 (2); 7,2327 (2,33); 7,2176 (1,78); 7,2138 (1,84); 7,1552 (1,23); 7,1512 (1,17); 7,1361 (1,99); 7,1323 (1,94); 7,117 (1,04); 7,1129 (0,95); 3,8587 (0,62); 3,8416 (1,33); 3,8244 (1,42); 3,8073 (0,77); 3,6417 (0,68); 3,626 (0,86); 3,6096 (1,33); 3,5935 (1,66); 3,5774 (0,81); 3,5514 (0,9); 3,5377 (1,1); 3,5334 (0,99); 3,5193 (1,3); 3,5053 (0,54); 3,5008 (0,53); 3,4871 (0,43); 3,3215 (13,79); 2,5063 (29,88); 2,5019 (40,17); 2,4977 (31,28); 1,3977 (16); 1,2884 (8,04); 1,2712 (8,13); 1,25 (0,36); −0,0002 (4,31)

No. Ia-178, Solvent: <[D$_6$]-DMSO>, Spectrometer: 399.95 MHz 8,9756 (5,13); 8,9728 (5,03); 8,926 (0,68); 8,9231 (0,67); 8,421 (5,24); 8,42 (5,34); 8,4161 (5,35); 8,4063 (0,81); 8,4011 (0,75); 8,3389 (3,04); 8,3154 (3,1); 8,1383 (0,39); 8,1158 (0,4); 7,8914 (4,34); 7,8892 (4,55); 7,8717 (4,72); 7,8694 (4,62); 7,8367 (0,58); 7,8345 (0,61); 7,8148 (0,89); 7,4926 (2,08); 7,49 (2,04); 7,4739 (4,73); 7,4712 (4,55); 7,4551 (2,92); 7,4525 (2,79); 7,4095 (0,56); 7,3907 (0,77); 7,3881 (0,65); 7,3719 (0,43); 7,3693 (0,41); 7,3283 (4,08); 7,3243 (4,56); 7,3094 (3,53); 7,3054 (3,46); 7,1932 (2,56); 7,189 (2,51); 7,1741 (3,84); 7,17 (3,66); 7,1548 (2,23); 7,1507 (2,06); 7,1442 (0,41); 7,1401 (0,4); 7,1251 (0,51); 7,1209 (0,56); 7,0261 (0,64); 7,0224 (0,74); 7,0073 (0,57); 7,0034 (0,56); 5,7579 (7,98); 5,4406 (0,56); 4,4159 (1,06); 4,4037 (1,28); 4,3915 (1,41); 4,3816 (1,52); 4,3698 (1,46); 4,36 (1,55); 4,3469 (0,67); 4,337 (0,64); 3,7614 (0,44); 3,6957 (0,51); 3,6787 (2,04); 3,6613 (2,4); 3,6585 (2,31); 3,641 (1,99); 3,624 (0,5); 3,3297 (15,94); 2,5281 (0,43); 2,5232 (0,68); 2,5148 (8,4); 2,5103 (16,86); 2,5058 (22,24); 2,5012 (16,14); 2,4967 (7,78); 1,4116 (0,54); 1,3933 (0,82); 1,3886 (0,6); 1,3771 (1,42); 1,358 (1,86); 1,3546 (1,84); 1,3381 (3,73); 1,3279 (1,86); 1,3113 (16); 1,2942 (15,41); 1,2709 (2,34); 1,2599 (0,96); 1,2505 (2,24); 1,2345 (0,46);

0,9763 (0,94); 0,9581 (1,98); 0,9396 (0,9); 0,9187 (6,94); 0,9005 (14,55); 0,882 (5,81); 0,0079 (0,54); −0,0002 (15,36); −0,0085 (0,52)

No. Ia-196, Solvent: <CD$_3$CN>, Spectrometer: 399.95 MHz 8,786 (4,01); 8,1069 (4,22); 8,103 (4,26); 7,9518 (2,96); 7,9507 (3,07); 7,9326 (3,25); 7,9305 (3,41); 7,7274 (1,41); 7,7249 (1,52); 7,7086 (3,43); 7,7061 (3,51); 7,6898 (2,33); 7,6872 (2,27); 7,6288 (2,08); 7,6254 (2,3); 7,6093 (2,86); 7,6077 (2,82); 7,6059 (3,15); 7,5897 (1,43); 7,5863 (1,36); 7,4708 (3,43); 7,4676 (3,53); 7,452 (2,98); 7,4487 (3,04); 7,0951 (0,92); 7,0824 (0,9); 4,6789 (0,67); 4,6619 (1,28); 4,6414 (1,59); 4,6232 (1,33); 4,6058 (0,72); 3,3012 (0,7); 3,2824 (0,55); 3,266 (3,62); 3,2478 (4,63); 3,2358 (3,7); 3,2164 (0,73); 3,2005 (0,58); 2,3794 (0,7); 2,2514 (1,45); 2,075 (0,58); 1,9652 (0,39); 1,9532 (4,68); 1,9471 (8,95); 1,941 (12,67); 1,9348 (9,06); 1,9287 (4,89); 1,2996 (15,95); 1,2828 (16); 1,1849 (0,7); 1,174 (0,55); 1,1689 (0,68); −0,0002 (0,36)

No. Ia-197, Solvent: <CDCl$_3$>, Spectrometer: 400 MHz
See FIG. 1

Figure 2:
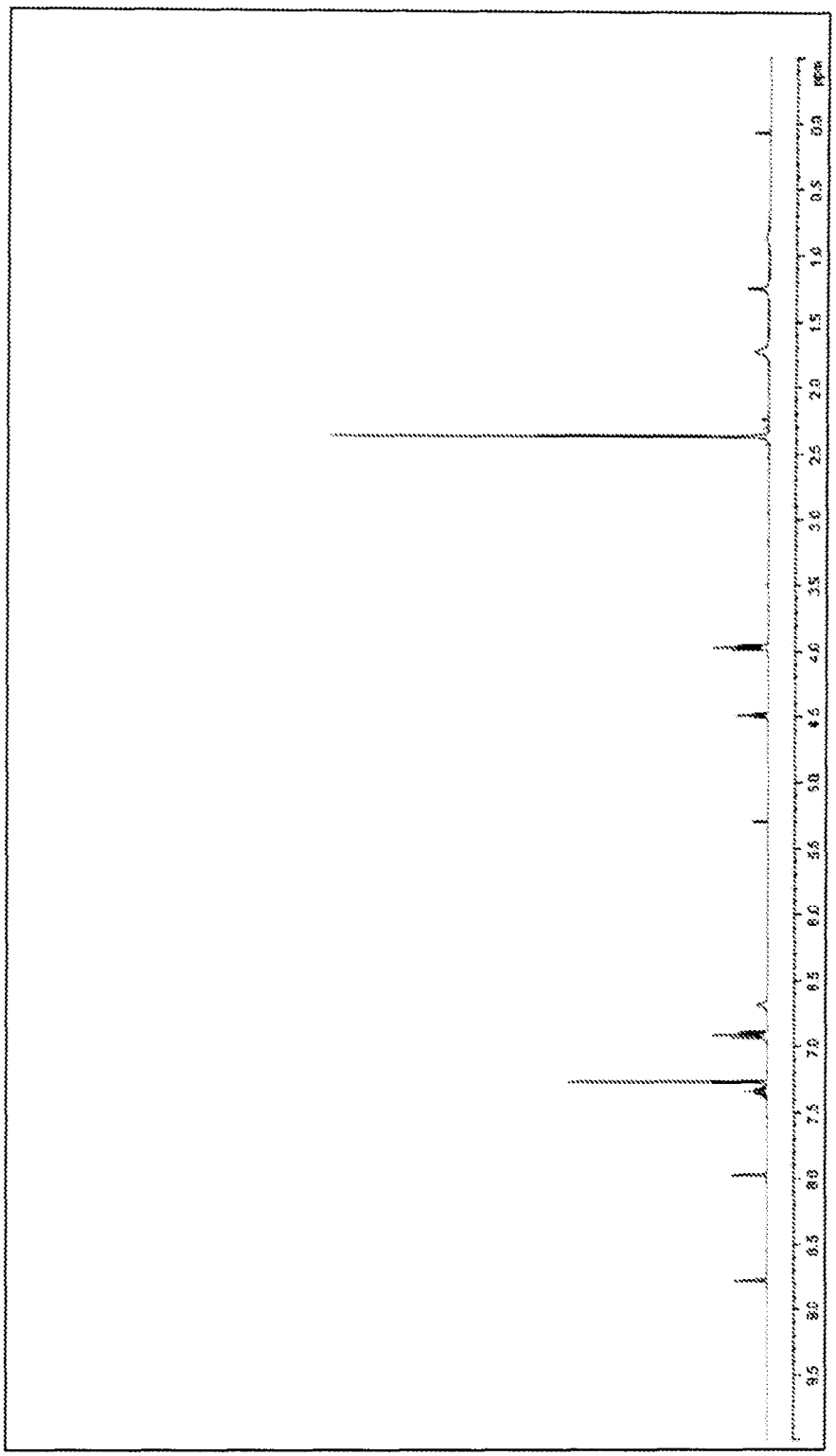

No. Ia-198, Solvent: <CDCl$_3$>, Spectrometer: 400 MHz
See FIG. 2

Figure 3:
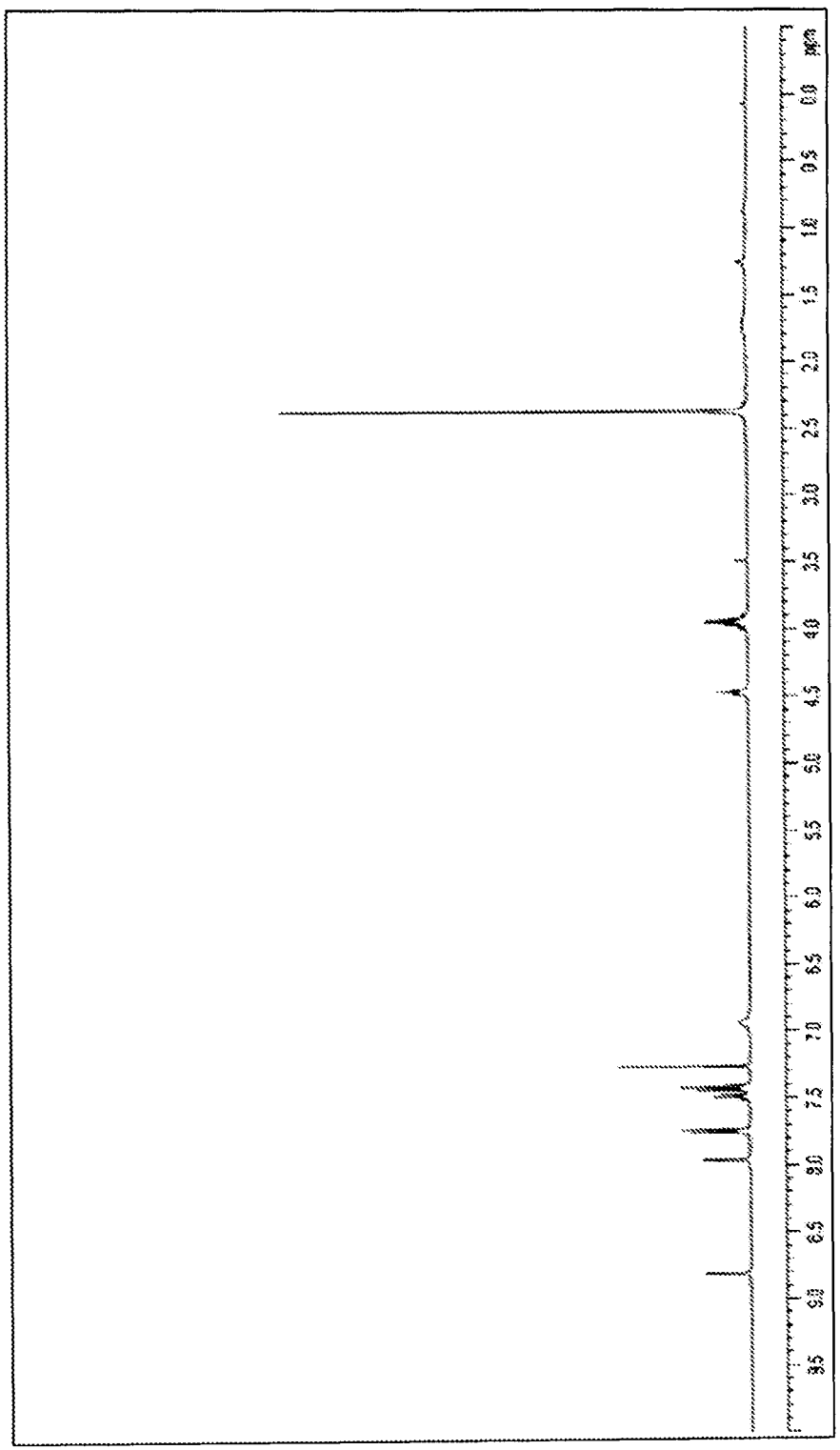

No. Ia-199, Solvent: <CDCl$_3$>, Spectrometer: 400 MHz
See FIG. 3

Figure 4:
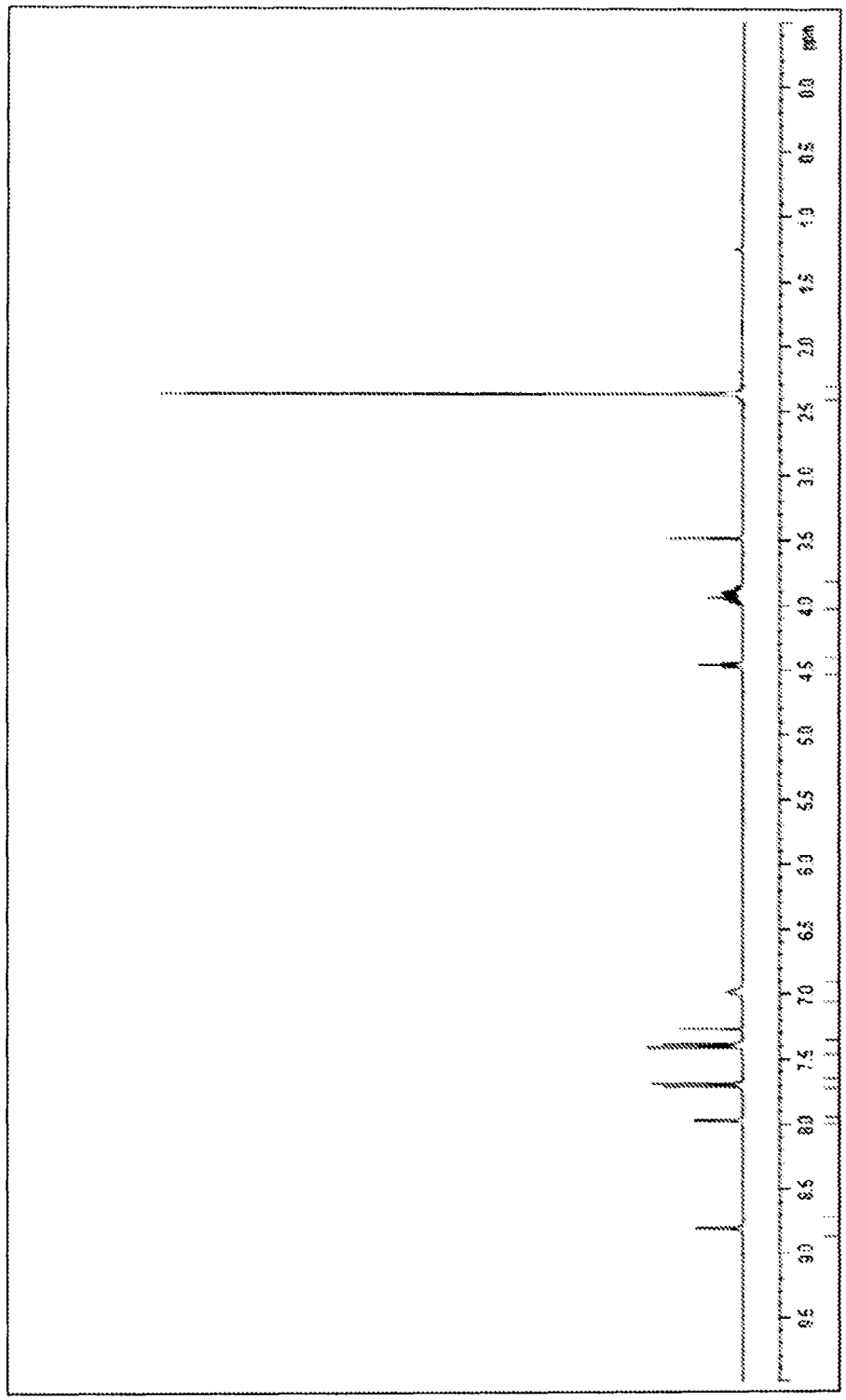

No. Ia-200, Solvent: <CDCl$_3$>, Spectrometer: 400 MHz
See FIG. 4

Figure 5:
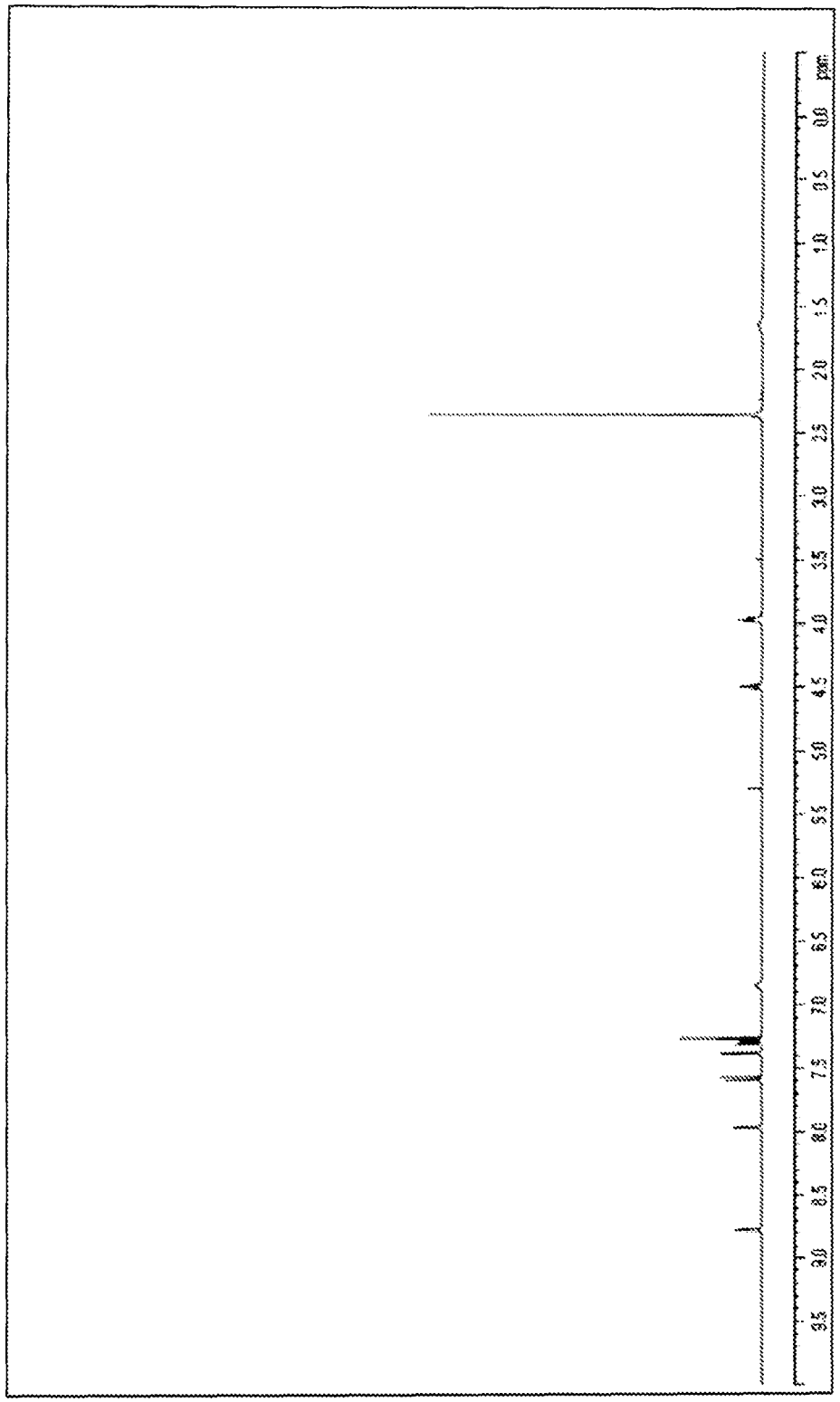

No. Ia-201, Solvent: <CDCl$_3$>, Spectrometer: 400 MHz
See FIG. 5

Figure 6:
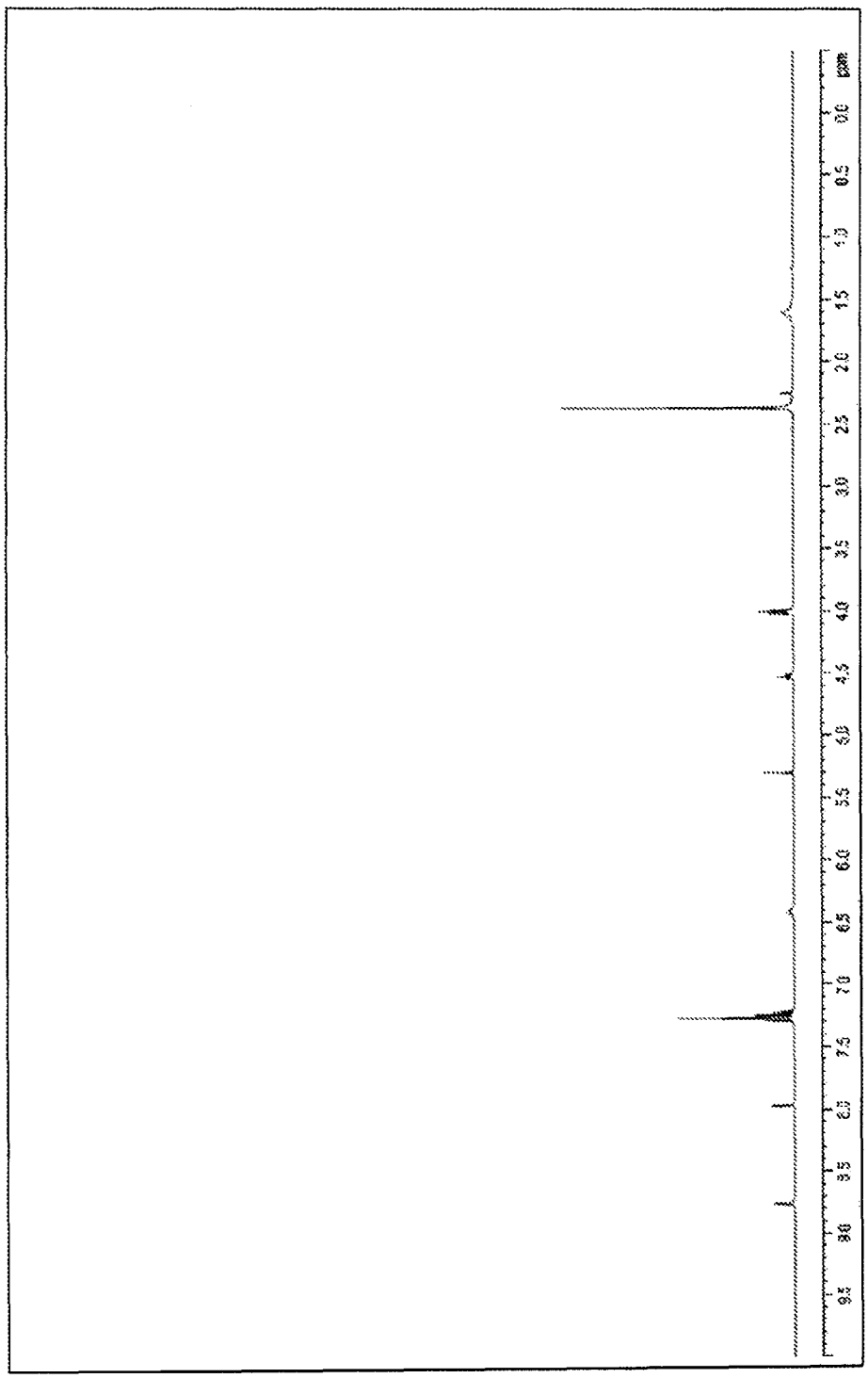

No. Ia-202, Solvent: <CDCl$_3$>, Spectrometer: 400 MHz
See FIG. 6

Figure 7:
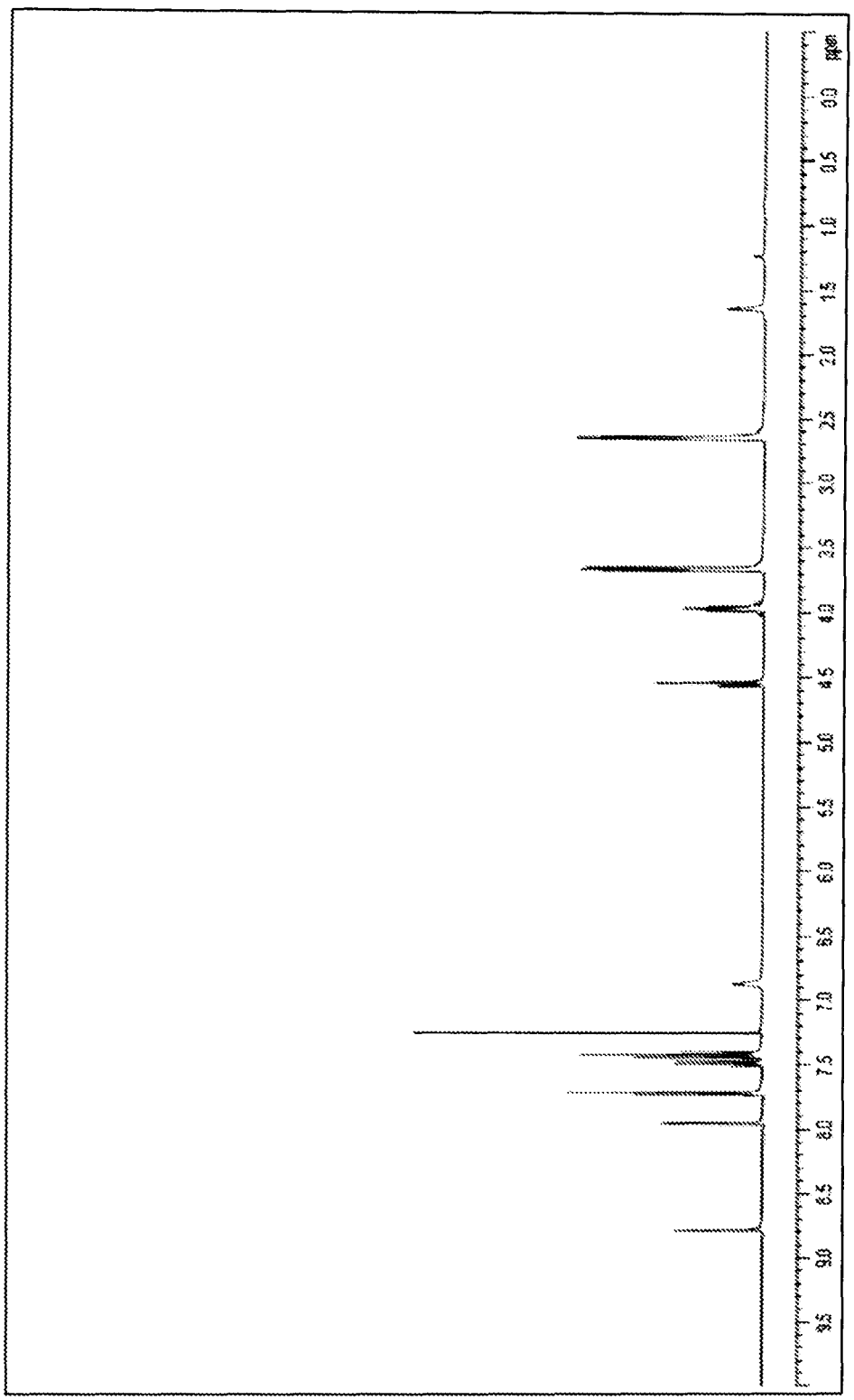

No. Ia-203, Solvent: <CDCl$_3$>, Spectrometer: 400 MHz
See FIG. 7

Figure 8:
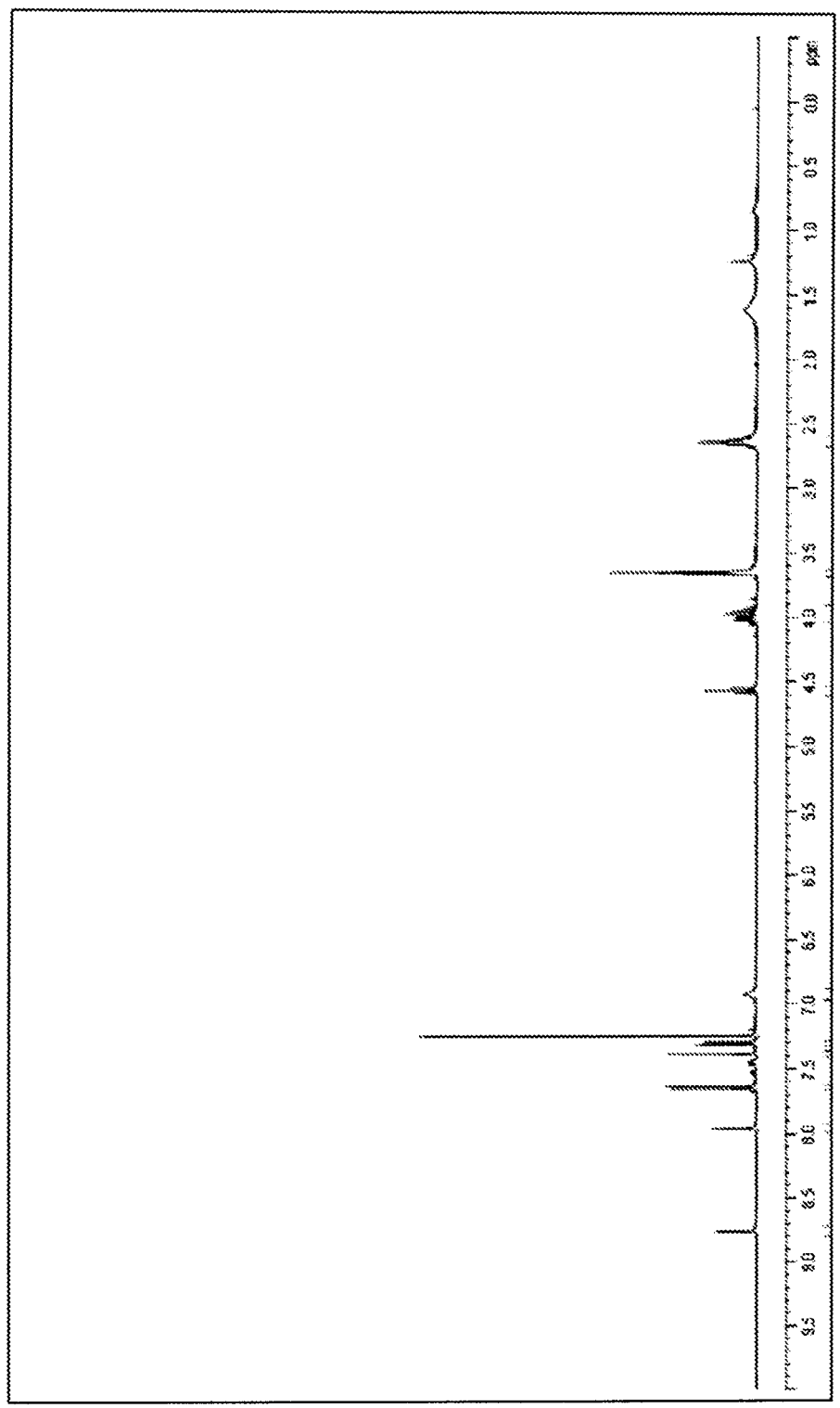

No. Ia-204, Solvent: <CDCl$_3$>, Spectrometer: 400 MHz
See FIG. 8

Figure 9:
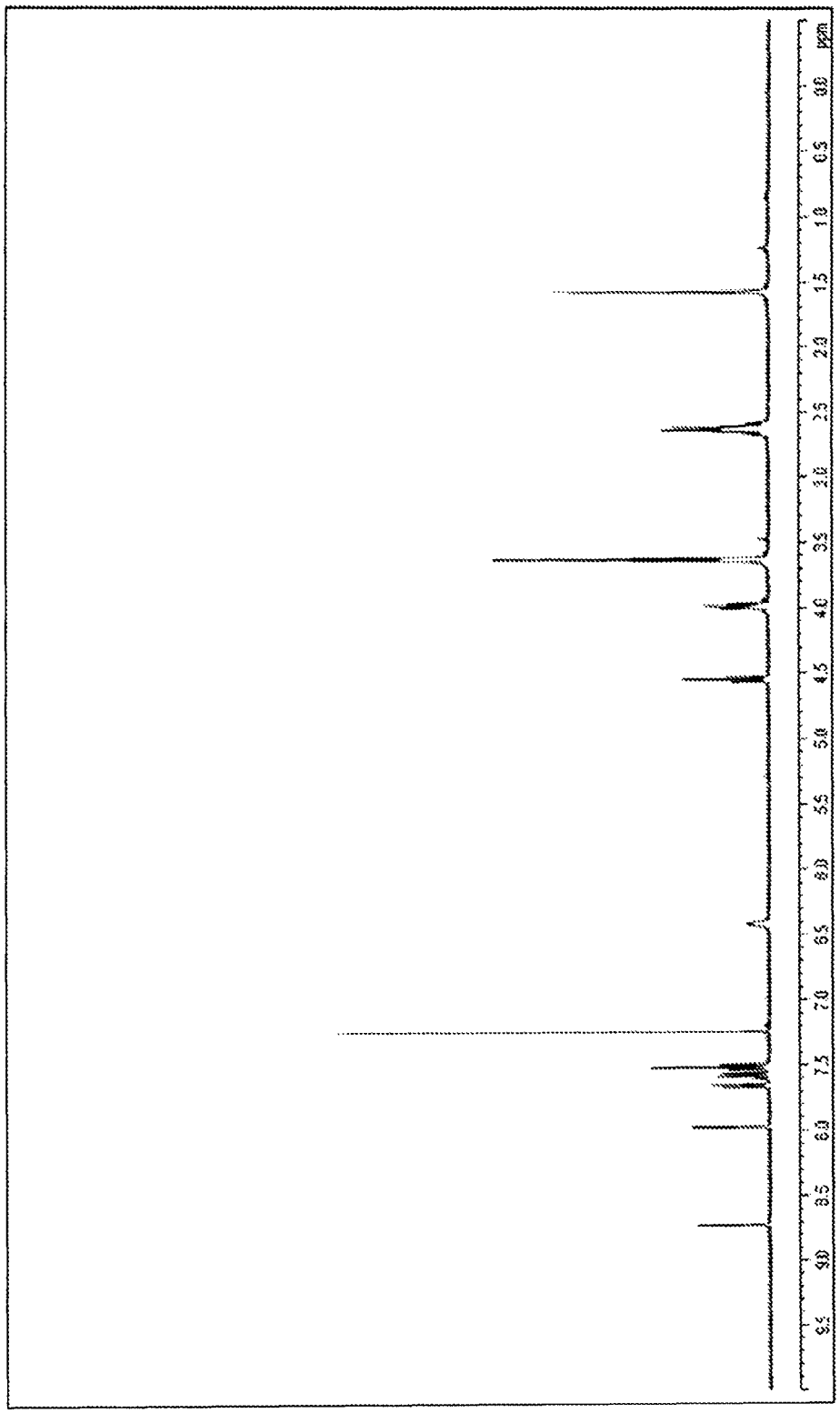

No. Ia-205, Solvent: <CDCl$_3$>, Spectrometer: 400 MHz
See FIG. 9

Figure 10:
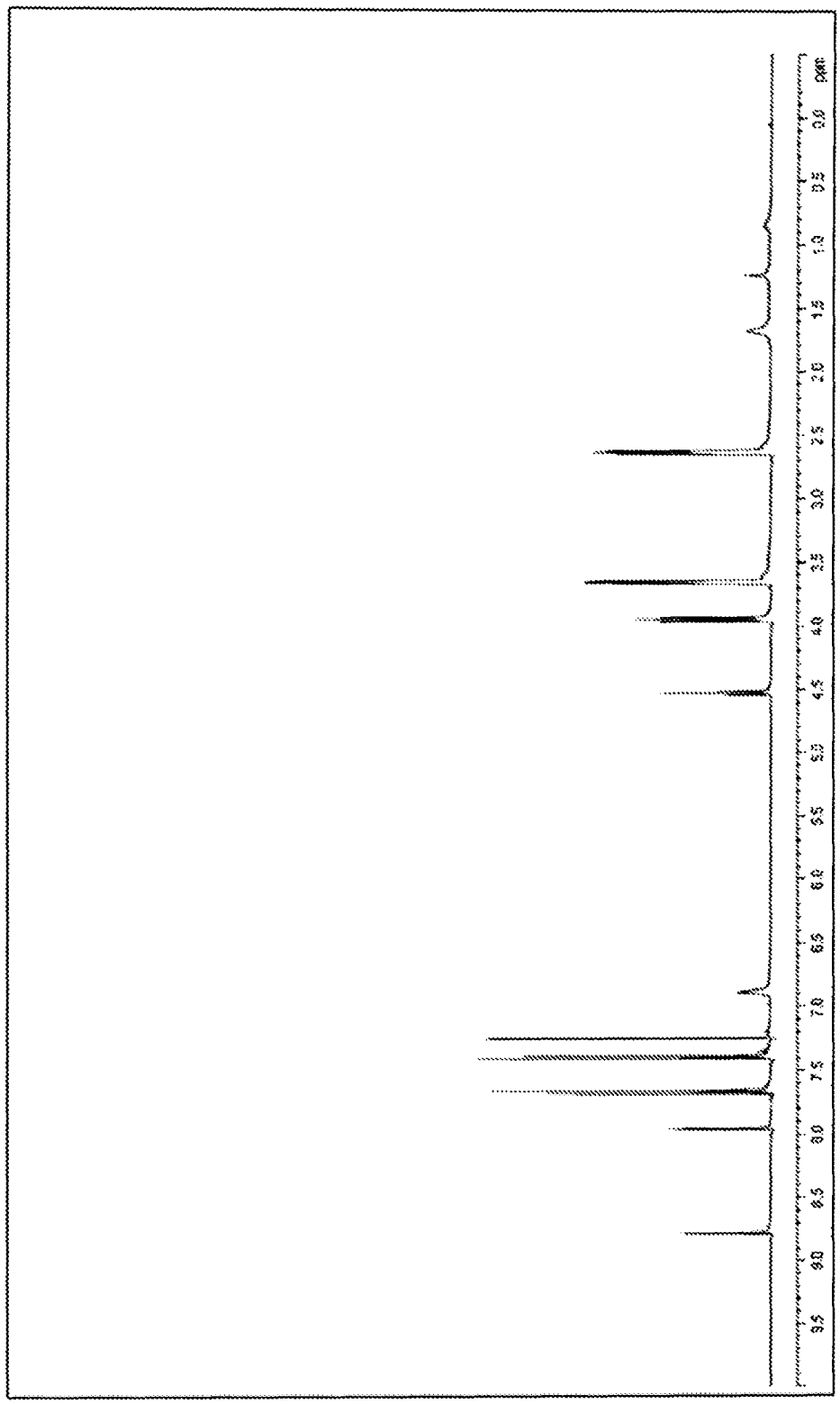

No. Ia-206, Solvent: <CDCl$_3$>, Spectrometer: 400 MHz
See FIG. 10

Figure 11:
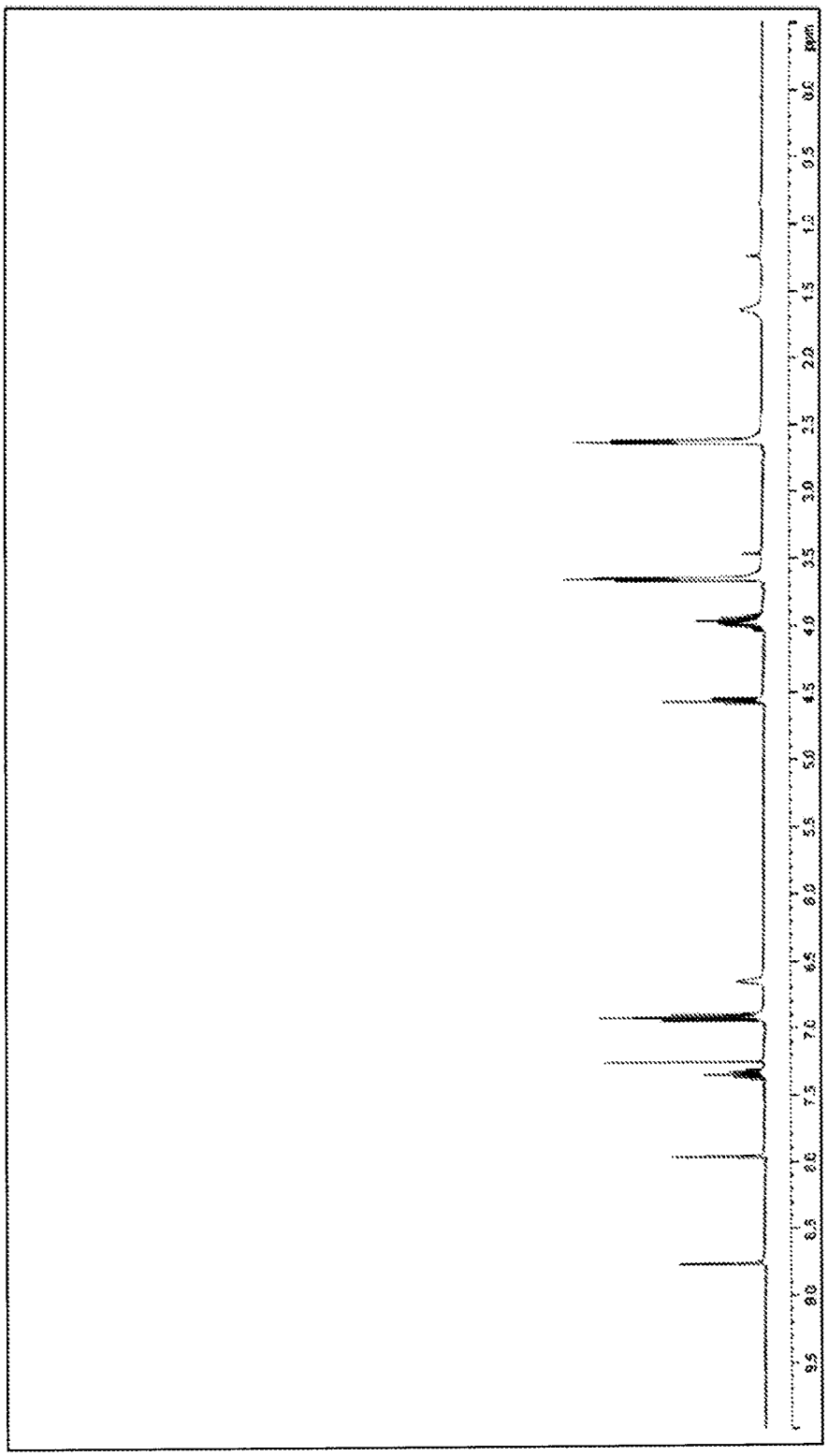

No. Ia-207, Solvent: <CDCl$_3$>, Spectrometer: 400 MHz
See FIG. 11

Figure 12:
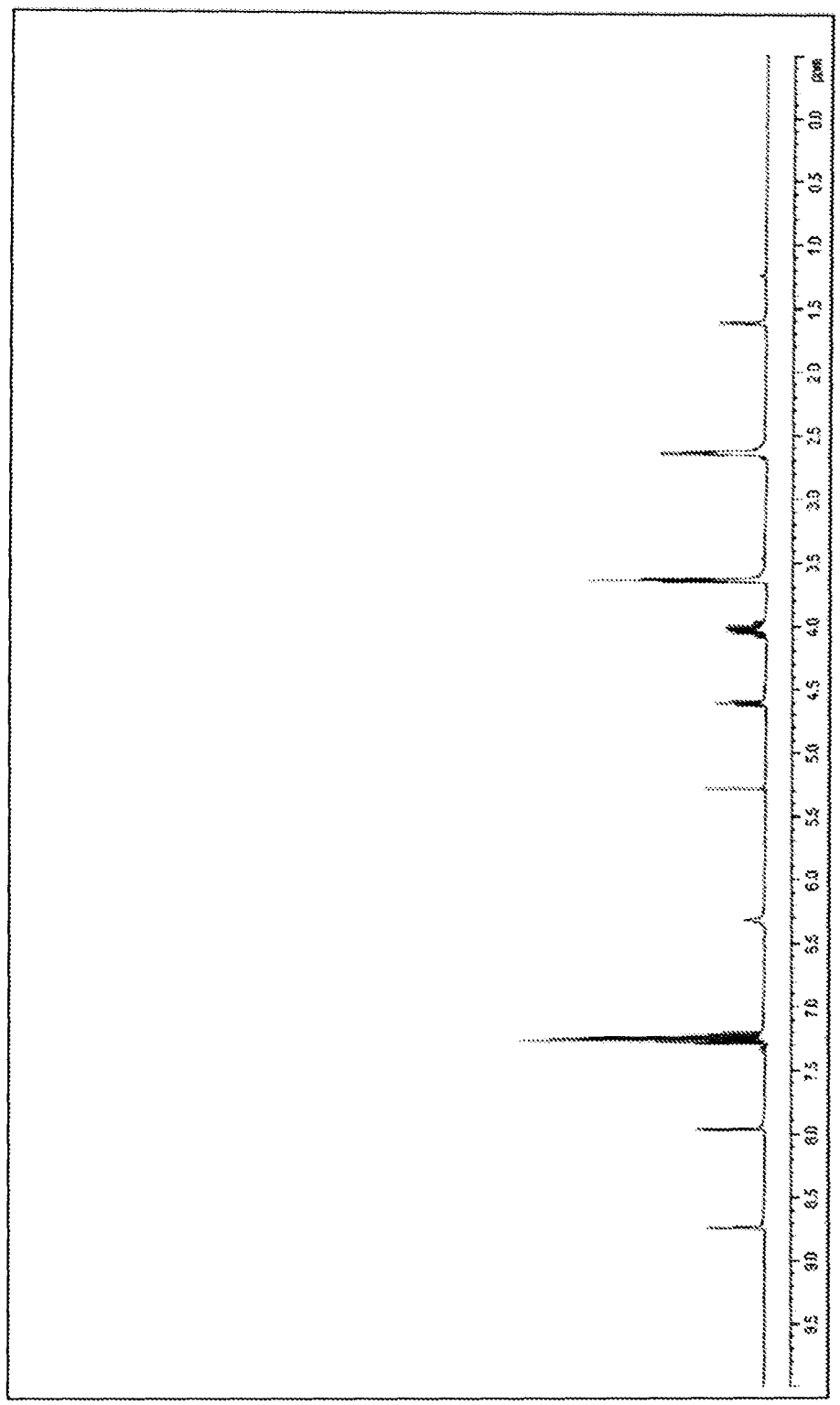

No. Ia-208, Solvent: <CDCl$_3$>, Spectrometer: 400 MHz
See FIG. 12

Figure 13:
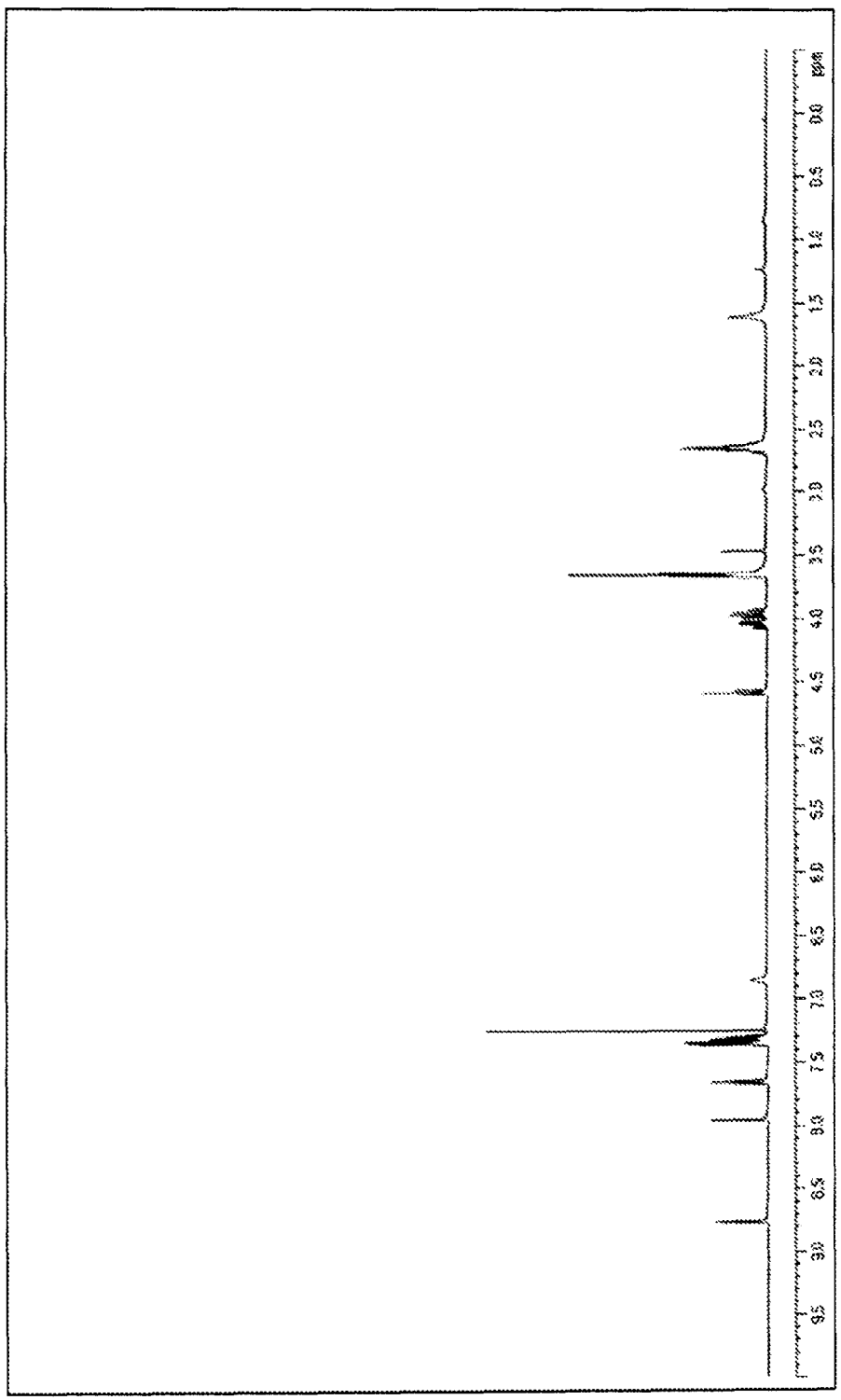

No. Ia-209, Solvent: <CDCl$_3$>, Spectrometer: 400 MHz
See FIG. 13

Figure 14:
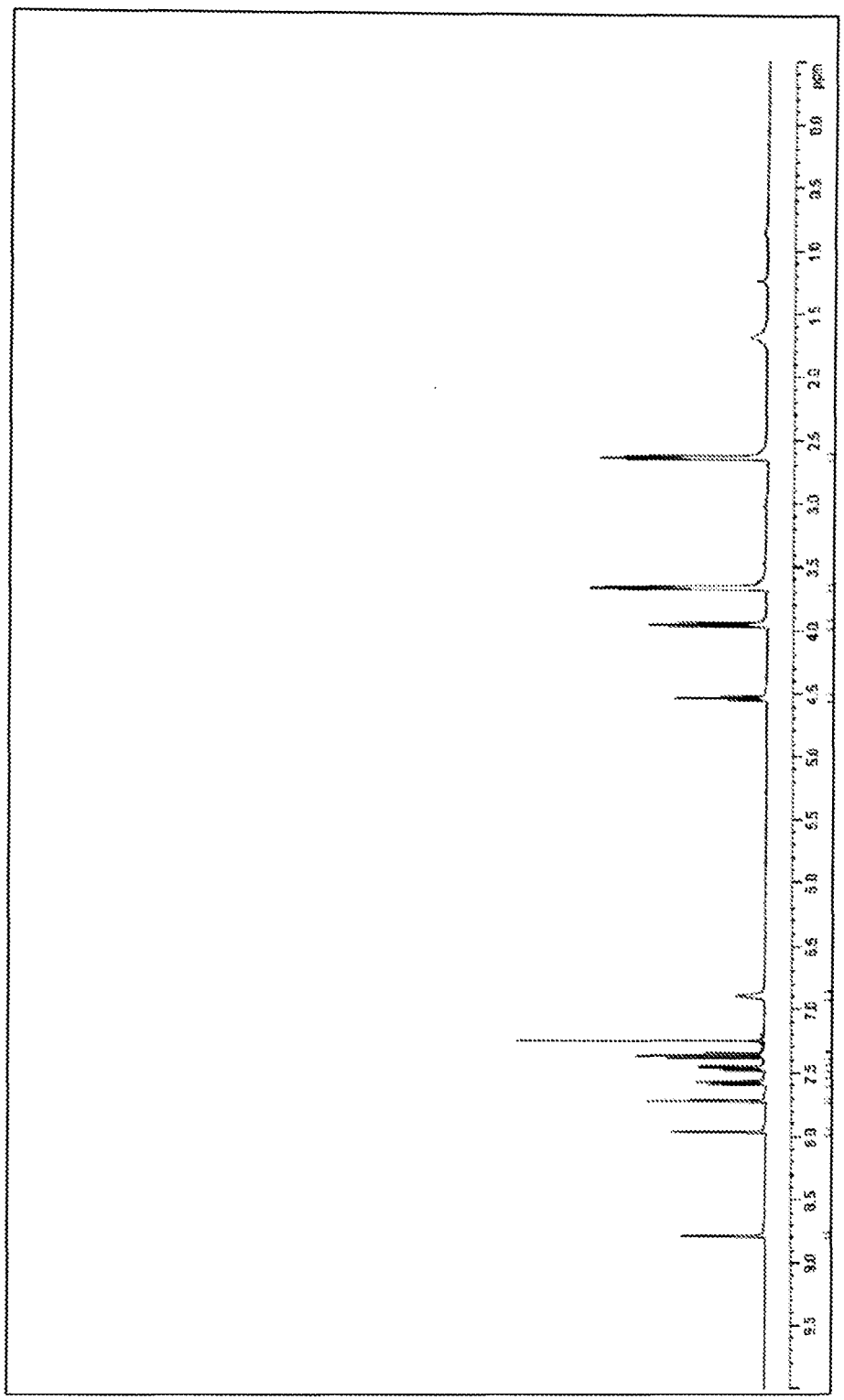

No. Ia-210, Solvent: <CDCl$_3$>, Spectrometer: 400 MHz
See FIG. 14

Figure 15:
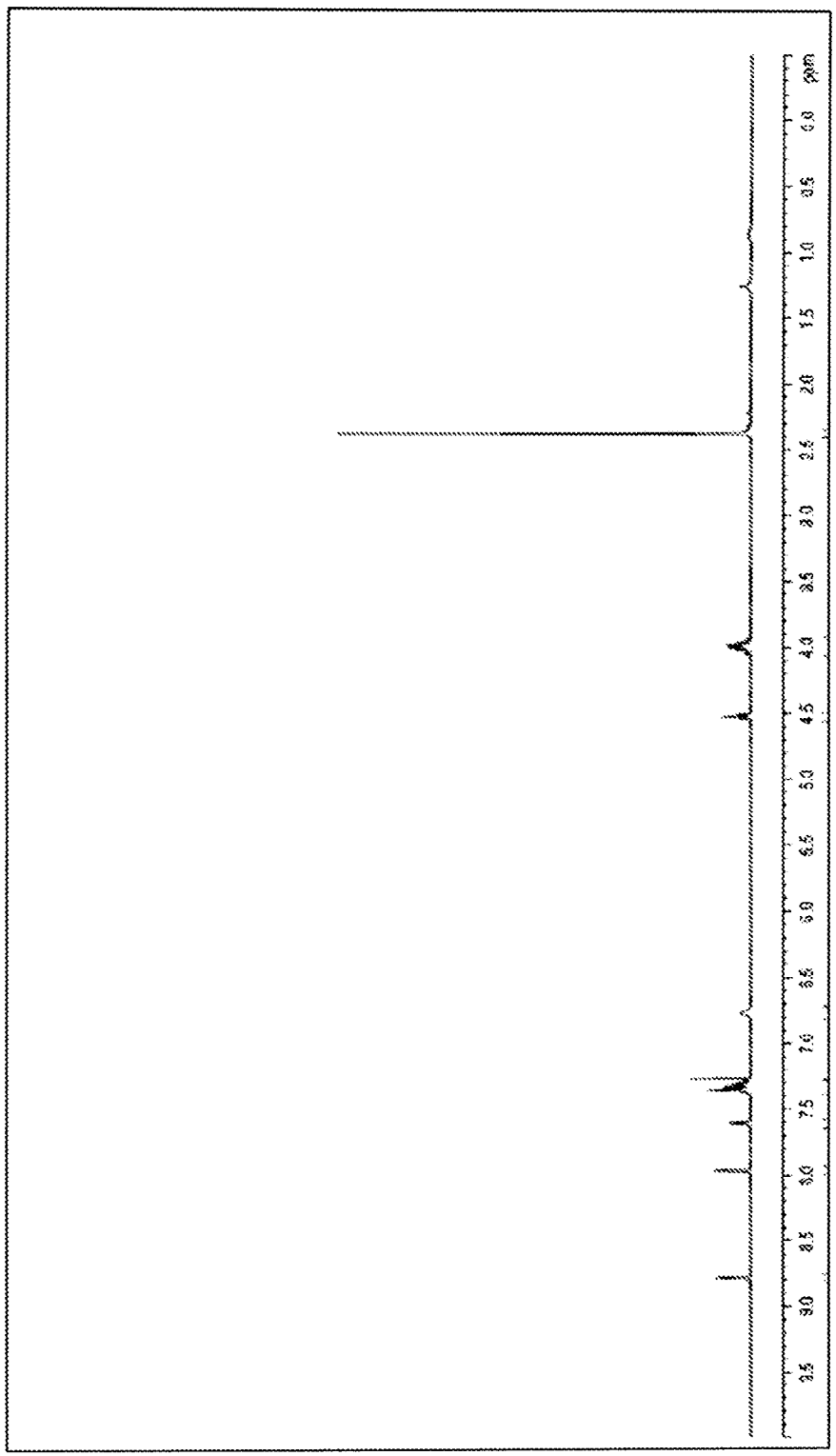

No. Ia-211, Solvent: <CDCl$_3$>, Spectrometer: 400 MHz
See FIG. 15

Figure 16:
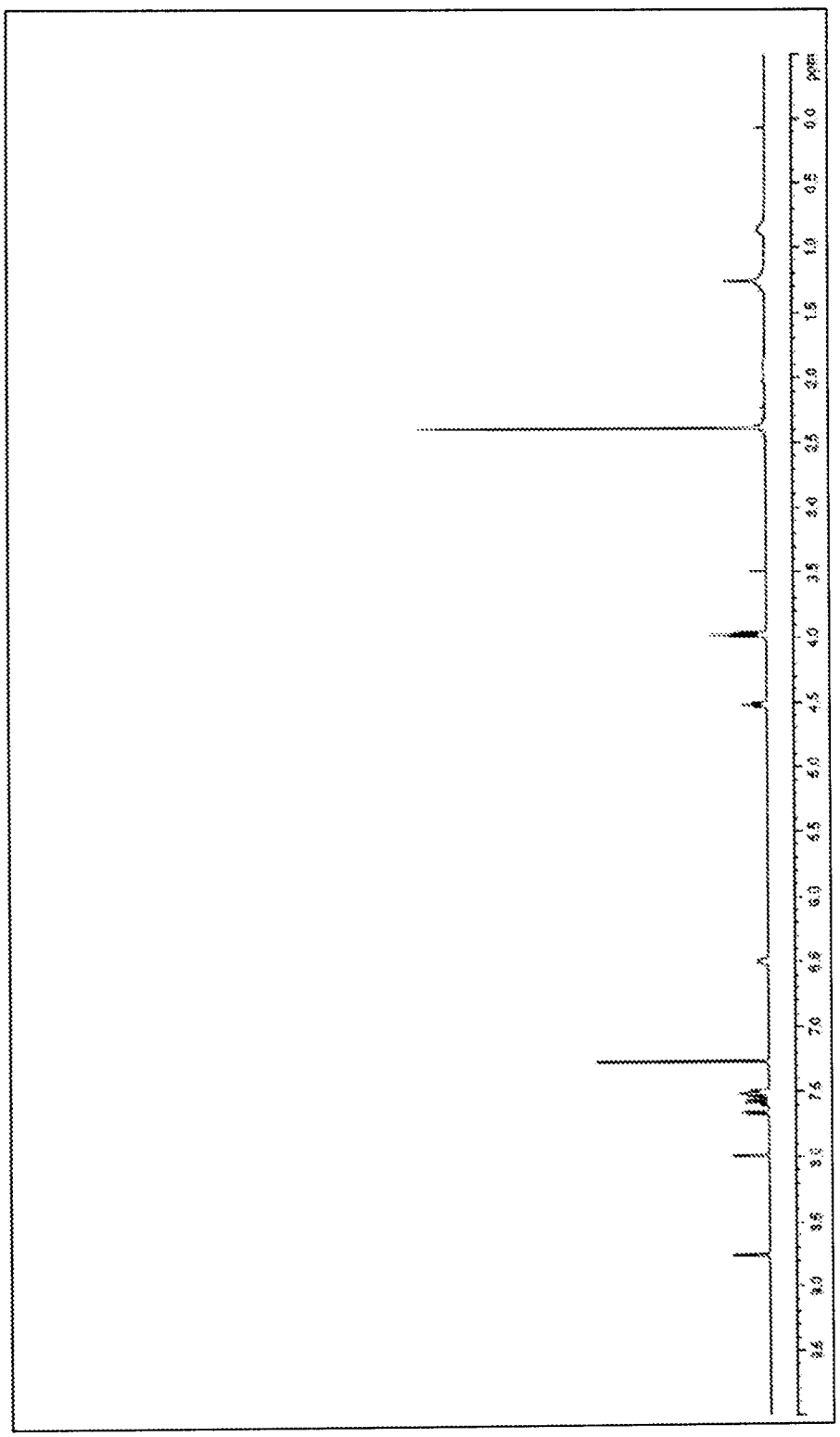

No. Ia-212, Solvent: <CDCl$_3$>, Spectrometer: 400 MHz
See FIG. 16

No. Ia-213, Solvent: <[D$_6$]-DMSO>, Spectrometer: 399.95 MHz 8,6943 (8,93); 8,6888 (9,05); 8,6009 (1,67); 8,5867 (3,15); 8,5731 (1,64); 8,2203 (10); 8,2149 (9,72); 7,8099 (0,45); 7,7973 (0,88); 7,7781 (1,1); 7,7536 (0,77); 7,7284 (4,43); 7,7186 (1,69); 7,7084 (5,04); 7,6823 (1,99); 7,6649 (4,35); 7,6464 (3,2); 7,616 (3,13); 7,5969 (3,64); 7,5782 (1,32); 7,4598 (0,35); 7,4046 (1); 7,3985 (8,03); 7,3937 (3,04); 7,3823 (3,96); 7,3772 (16); 7,3715 (2,34); 7,3364 (2,39); 7,3306 (14,49); 7,3256 (3,91); 7,3141 (2,91); 7,3092 (7,85); 7,2958 (0,38); 7,2736 (4,1); 7,2551 (3,75); 4,9169 (2,2); 4,8984 (4,83); 4,8795 (2,36); 4,0561 (0,58); 4,0383 (1,73); 4,0205 (1,76); 4,0027 (0,6); 3,9703 (0,43); 3,9572 (0,56); 3,9507 (0,49); 3,9376 (2,62); 3,9251 (3,85); 3,9181 (2,73); 3,908 (4,02); 3,8922 (2,42); 3,8766 (0,67); 3,8595 (0,42); 3,3261 (17,26); 3,2703 (0,43); 3,2514 (0,34); 2,9988 (0,41);

2,6761 (0,54); 2,6715 (0,73); 2,667 (0,53); 2,5247 (2,33); 2,5114 (41,27); 2,507 (82,25); 2,5024 (109,07); 2,4978 (79,67); 2,4933 (38,17); 2,3337 (0,54); 2,3292 (0,74); 2,3246 (0,53); 1,9894 (7,57); 1,9097 (0,36); 1,2582 (0,41); 1,2347 (2,64); 1,1929 (2,21); 1,1752 (4,25); 1,1666 (0,44); 1,1573 (2,14); 1,1483 (0,64); 1,1383 (0,88); 1,1299 (0,35); 1,1207 (1,65); 1,103 (0,79); 1,0907 (0,34); 0,9999 (0,82); 0,9822 (1,67); 0,9644 (0,77); 0,8533 (0,36); 0,0127 (0,97); 0,008 (1,58); −0,0002 (41,92); −0,0085 (1,25)

No. Ia-214, Solvent: <CD$_3$CN>, Spectrometer: 399.95 MHz 8,4875 (4,24); 8,482 (4,18); 7,9367 (2,27); 7,9342 (2,26); 7,9164 (2,61); 7,9139 (2,58); 7,8839 (4,89); 7,8785 (4,73); 7,7042 (1,16); 7,7012 (1,22); 7,6854 (2,98); 7,6824 (2,95); 7,6666 (2,11); 7,6635 (1,96); 7,6175 (1,82); 7,6138 (1,98); 7,5973 (2,27); 7,5938 (2,28); 7,5784 (1,13); 7,5747 (1,08); 7,4476 (2,8); 7,4442 (2,7); 7,4287 (2,35); 7,4254 (2,29); 7,0253 (0,67); 3,7929 (0,73); 3,7759 (1,23); 3,7737 (1,16); 3,7588 (1,48); 3,7418 (1,14); 3,7249 (0,36); 3,7042 (0,45); 3,6888 (0,57); 3,6713 (2,64); 3,6605 (3,07); 3,6558 (3,58); 3,6458 (2,92); 3,6409 (3,72); 3,6261 (2,05); 3,6128 (0,43); 3,6078 (0,39); 3,593 (0,34); 2,1486 (7,16); 1,9646 (1,08); 1,9586 (1,68); 1,9526 (7,29); 1,9465 (12,8); 1,9404 (16,77); 1,9342 (11,52); 1,928 (5,9); 1,3719 (1,32); 1,2751 (16); 1,258 (14,71); −0,0002 (5,3)

No. Ia-215, Solvent: <[D$_6$]-DMSO>, Spectrometer: 399.95 MHz 8,9706 (5,11); 8,9678 (4,99); 8,6618 (3,04); 8,6383 (3,13); 8,4281 (5,48); 8,4241 (5,31); 8,029 (4,06); 8,0264 (4,31); 8,0087 (4,72); 8,0061 (4,7); 7,8357 (1,84); 7,8328 (1,9); 7,8168 (4,61); 7,814 (4,53); 7,798 (3,08); 7,7951 (2,91); 7,7164 (2,76); 7,7129 (3,18); 7,6966 (3,55); 7,6933 (3,81); 7,6773 (1,94); 7,6738 (1,94); 7,6084 (4,41); 7,6051 (4,33); 7,5896 (3,89); 7,5862 (3,56); 5,7574 (6,85); 4,3974 (0,53); 4,3871 (0,66); 4,3746 (1,41); 4,3645 (1,53); 4,3529 (1,46); 4,3429 (1,55); 4,3303 (0,61); 4,3201 (0,57); 3,7051 (0,52); 3,6881 (2,04); 3,6707 (2,39); 3,668 (2,31); 3,6505 (1,99); 3,6334 (0,5); 3,326 (27,53); 2,5266 (0,81); 2,5218 (1,29); 2,5133 (16,19); 2,5088 (32,58); 2,5043 (43,11); 2,4997 (31,19); 2,4951 (14,91); 1,4144 (0,55); 1,3971 (1,75); 1,3799 (1,46); 1,3612 (1,92); 1,3572 (1,87); 1,3374 (6,02); 1,3247 (1,82); 1,3143 (1,91); 1,3081 (1,41); 1,2939 (16); 1,2769 (15,49); 1,2664 (1,44); 1,2594 (2,06); 1,2501 (5,13); 1,2355 (0,93); 1,1889 (0,47); 1,1713 (0,46); 1,1543 (0,33); 0,9491 (0,33); 0,9309 (0,65); 0,9124 (0,35); 0,8904 (7,07); 0,8721 (15,21); 0,8537 (6,13); 0,0079 (1,02); −0,0002 (28,13); −0,0086 (0,94)

No. Ia-216, Solvent: <[D$_6$]-DMSO>, Spectrometer: 399.95 MHz 8,9643 (4,8); 8,9615 (4,68); 8,8829 (0,53); 8,8801 (0,52); 8,6458 (2,66); 8,622 (2,69); 8,4325 (4,78); 8,431 (5,11); 8,4273 (4,96); 8,4261 (4,8); 8,4128 (0,32); 8,3664 (0,57); 8,3627 (0,55); 7,7485 (0,53); 7,7269 (0,53); 7,7053 (0,5); 7,5536 (0,84); 7,5369 (1,78); 7,5323 (1,52); 7,5202 (1,21); 7,5158 (3,18); 7,5115 (1,2); 7,499 (1,56); 7,4947 (1,93); 7,478 (0,85); 7,4304 (0,37); 7,3462 (0,73); 7,3247 (1,35); 7,318 (0,34); 7,3154 (0,48); 7,3127 (0,82); 7,3035 (0,66); 7,2909 (1,39); 7,2693 (0,77); 7,2665 (0,46); 7,2164 (1,2); 7,2065 (0,69); 7,2033 (0,91); 7,1957 (5,58); 7,1768 (6,54); 7,175 (6,19); 7,156 (4,57); 7,1481 (0,78); 7,0912 (0,63); 7,0725 (0,74); 7,0705 (0,69); 7,0517 (0,53); 5,7584 (12,48); 4,4502 (0,5); 4,44 (0,63); 4,427 (1,47); 4,4169 (1,67); 4,4039 (1,51); 4,3937 (1,61); 4,3807 (0,57); 4,3703 (0,56); 3,6379 (0,5); 3,6208 (1,89); 3,6037 (2,07); 3,5984 (1,95); 3,5813 (1,83); 3,5643 (0,49); 3,3287 (16,59); 2,5285 (0,62); 2,5238 (0,99); 2,5152 (11,55); 2,5106 (23,37); 2,506 (30,99); 2,5014 (22,41); 2,4969 (10,69); 1,338 (1,67); 1,3318 (0,57); 1,3131 (0,71); 1,3079 (0,51); 1,297 (1,53); 1,2895 (1,08); 1,2779 (2,31); 1,2634 (16); 1,2505 (7,89); 1,2463 (15,64); 1,2248 (0,92); 1,2181 (0,67); 1,2073 (0,4); 1,1486 (0,34); 0,9363 (0,72); 0,9181 (1,57); 0,8997 (0,68); 0,8502 (6,65); 0,8321 (14,24); 0,8136 (5,57); 0,008 (0,83); −0,0002 (23,6); −0,0085 (0,75)

TABLE B

Compounds of formula (Ib)

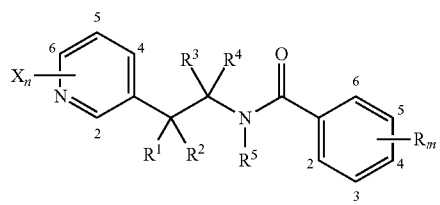

(Ib)

| No. | $X_n$ | $R^1$ | $R^2$ | $R^3$ | $R^4$ | $R^5$ | $R_m$ | cf. |
|---|---|---|---|---|---|---|---|---|
| Ib-1 | 5-Cl 6-OMe | H | H | COOMe | H | H | H | P7 |
| Ib-2 | 5-Cl 6-OMe | H | H | COOMe | H | H | 4-OMe | P7 |
| Ib-3 | 5-Cl 6-OMe | H | H | COOMe | H | H | 4-Cl | P7 |
| Ib-4 | 5-Cl 6-OMe | H | H | COOMe | H | H | 3-CF$_3$ | P7 |
| Ib-5 | 5-Cl 6-OMe | H | H | COOMe | H | H | 2-Cl | P7 |
| Ib-6 | 5-Cl 6-OMe | H | H | COOMe | H | H | 4-C$_6$H$_5$ | P7 |
| Ib-7 | 5-Cl 6-OMe | H | H | COOMe | H | H | 2-Br | P7 |
| Ib-8 | 5-Cl 6-OMe | H | H | CONHEt | H | H | H | P7 |

TABLE B-continued

Compounds of formula (Ib)

(Ib)

| No. | $X_n$ | $R^1$ | $R^2$ | $R^3$ | $R^4$ | $R^5$ | $R_m$ | cf. |
|---|---|---|---|---|---|---|---|---|
| Ib-9 | 5-Cl<br>6-OMe | H | H | CONHEt | H | H | 4-OMe | P7 |
| Ib-10 | 5-Cl<br>6-OMe | H | H | CONHEt | H | H | 2-Cl | P7 |
| Ib-11 | 5-Cl<br>6-OMe | H | H | CONHEt | H | H | 4-C$_6$H$_5$ | |
| Ib-12 | 5-Cl<br>6-OMe | H | H | CONHEt | H | H | 4-Cl | P7<br>NMR |
| Ib-13 | 5-Cl<br>6-OMe | H | H | CONHEt | H | H | 3-NO$_2$ | P7<br>NMR |
| Ib-14 | 5-Cl<br>6-OMe | H | H | CONHEt | H | H | 3-CF$_3$ | P7<br>NMR |
| Ib-15 | 5-Cl<br>6-OMe | H | H | CONHEt | H | H | 2-Br | P7 |
| Ib-16 | 5-Cl<br>6-OMe | H | H | CONHMe | H | H | 4-OMe | P7<br>NMR |
| Ib-17 | 5-Cl<br>6-OMe | H | H | CONHMe | H | H | 4-Cl | P7<br>NMR |
| Ib-18 | 5-Cl<br>6-OMe | H | H | COOMe | H | H | 3-NO$_2$ | P7<br>(M + 1) = 394 |
| Ib-19 | 5-Cl<br>6-OMe | H | H | CONHMe | H | H | H | P7<br>NMR |
| Ib-20 | 5-Cl<br>6-OMe | H | H | CONHMe | H | H | 3-NO$_2$ | P7<br>(M + 1) = 393 |
| Ib-21 | 5-Cl<br>6-OMe | H | H | CONHMe | H | H | 3-CF$_3$ | P7<br>NMR |
| Ib-22 | 5-Cl<br>6-OMe | H | H | CONHMe | H | H | 2-Cl<br>6-Cl | P7<br>NMR |
| Ib-23 | 5-Cl<br>6-OMe | H | H | CONHMe | H | H | 4-C$_6$H$_5$ | P7<br>NMR |
| Ib-24 | 5-Cl<br>6-OMe | H | H | CONHMe | H | H | 2-Br | P7<br>NMR |
| Ib-25 | 5-Cl<br>6-OMe | H | H | COOEt | H | H | H | P7<br>NMR |
| Ib-26 | 5-Cl<br>6-OMe | H | H | COOEt | H | H | 4-OMe | P7<br>NMR |
| Ib-27 | 5-Cl<br>6-OMe | H | H | COOEt | H | H | 4-Cl | P7 |
| Ib-28 | 5-Cl<br>6-OMe | H | H | COOEt | H | H | 3-CF$_3$ | P7<br>NMR |
| Ib-29 | 5-Cl<br>6-OMe | H | H | COOEt | H | H | 2-Cl<br>6-Cl | P7<br>NMR |
| Ib-30 | 5-Cl<br>6-OMe | H | H | COOEt | H | H | 2-Br | P7<br>NMR |
| Ib-31 | 5-Cl<br>6-OMe | H | H | COOEt | H | H | 3-NO$_2$ | P7 |
| Ib-32 | 5-Cl<br>6-OMe | H | H | COOEt | H | H | 4-C$_6$H$_5$ | NMR |
| Ib-33 | 6-CF$_3$ | H | H | H | H | H | 2-Cl | P7<br>cpd. 1 |
| Ib-34 | 6-CF$_3$ | H | H | H | H | H | 2-Me | P7<br>cpd. 2 |
| Ib-35 | 6-CF$_3$ | H | H | H | H | H | 2-Br | P7<br>cpd. 3 |
| Ib-36 | 6-CF$_3$ | H | H | H | H | H | 2-CF$_3$ | P7<br>cpd. 4 |
| Ib-37 | 6-Cl | H | H | H | H | H | 2-Cl | P7<br>cpd. 5 |
| Ib-38 | 6-Cl | H | H | H | H | H | 2-CF$_3$ | P7<br>cpd. 6 |
| Ib-39 | 6-Cl | CH$_3$ | H | H | H | H | 2-Cl | P7<br>cpd. 7 |
| Ib-40 | 6-Cl | CH$_3$ | H | H | H | H | 2-Me | P7<br>cpd. 8 |

TABLE B-continued

Compounds of formula (Ib)

(Ib)

| No. | $X_n$ | $R^1$ | $R^2$ | $R^3$ | $R^4$ | $R^5$ | $R_m$ | cf. |
|---|---|---|---|---|---|---|---|---|
| Ib-41 | 6-Cl | CH₃ | H | H | H | H | 2-Br | P7 cpd. 9 |
| Ib-42 | 6-Cl | CH₃ | H | H | H | H | 2-I | P7 cpd. 10 |
| Ib-43 | 6-Cl | CH₃ | H | H | H | H | 2-CF₃ | P7 cpd. 11 |
| Ib-44 | 6-Cl | H | H | H | H | H | 2-I | P7 cpd. 12 |
| Ib-45 | 2-Cl 4-Cl | H | H | H | H | H | 2-CF₃ | P7 cpd. 13 |
| Ib-46 | 6-CH₂CH₂CF₃ | H | H | H | H | H | 2-CF₃ | P7 |
| Ib-47 | 4-Cl 6-CF₃ | H | H | H | H | H | 2-CF₃ | P7 NMR |
| Ib-48 | 4-Cl 6-CF₃ | H | H | H | H | H | 2-F | P7 NMR |
| Ib-49 | 4-Cl 6-CF₃ | H | H | H | H | H | 2-Cl | P7 NMR |
| Ib-50 | 4-Cl 6-CF₃ | H | H | H | H | H | 2-CHF₂ | P7 NMR |
| Ib-51 | 4-Cl 6-CF₃ | H | H | H | H | H | 2-F 6-F | P7 NMR |
| Ib-52 | 4-Cl 6-CF₃ | H | H | H | H | H | 2-Br | P7 NMR |
| Ib-53[4] | 4-Cl 6-CF₃ | H | H | H | H | H | 2-CF₃ | P7 NMR |
| Ib-54[4] | 4-Cl 6-CF₃ | H | H | H | H | H | 2-Cl | P7 NMR |
| Ib-55[4] | 6-Cl | H | H | H | H | H | 2-CF₃ | P7 NMR |
| Ib-56[4] | 6-Cl | H | H | H | H | H | 2-Cl | P7 NMR |
| Ib-57 | 4-Cl 6-CF₃ | H | H | H | H | H | 2-I | P7 NMR |
| Ib-58 | 4-Cl 6-CF₃ | H | H | H | H | H | 2-NO₂ | P7 NMR |
| Ib-59 | 2-Cl 6-CF₃ | H | H | H | H | H | 2-F | P7 NMR |
| Ib-60 | 2-Cl 6-CF₃ | H | H | H | H | H | 2-Br | P7 NMR |
| Ib-61 | 2-Cl 6-CF₃ | H | H | H | H | H | 2-I | P7 NMR |
| Ib-62 | 2-Cl 6-CF₃ | H | H | H | H | H | 2-Cl | P7 NMR |
| Ib-63 | 2-Cl 6-CF₃ | H | H | H | H | H | 2-CF₃ | P7 NMR |
| Ib-64 | 2-Cl 6-CF₃ | H | H | H | H | H | 2-F 6-F | P7 NMR |
| Ib-65 | 6-Cl | H | H | H | H | H | 2-F | P7 NMR |
| Ib-66 | 6-Cl | H | H | H | H | H | 2-F 6-F | P7 NMR |
| Ib-67 | 6-Cl | F | F | H | H | H | 2-F | P7 NMR |
| Ib-68 | 6-Cl | F | F | H | H | H | 2-Cl | P7 NMR |
| Ib-69 | 6-Cl | F | F | H | H | H | 2-Br | P7 NMR |
| Ib-70 | 6-Cl | F | F | H | H | H | 2-I | P7 NMR |

TABLE B-continued

Compounds of formula (Ib)

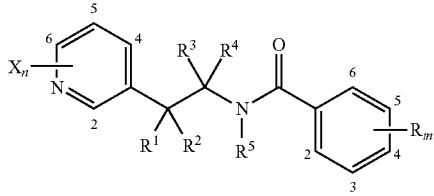

(Ib)

| No. | $X_n$ | $R^1$ | $R^2$ | $R^3$ | $R^4$ | $R^5$ | $R_m$ | cf. |
|---|---|---|---|---|---|---|---|---|
| Ib-71 | 6-Cl | F | F | H | H | H | 2-F 6-F | P7 NMR |
| Ib-72 | 6-Cl | F | F | H | H | H | 2-CF$_3$ | P7 NMR |

[1] cis-isomer,
[2] trans-isomer,
[3] pure enantiomer, absolute configuration not determined,
[4] pyridine-N-oxide No. Ib-12, Solvent: <[D$_6$]-DMSO>, Spectrometer: 399.95 MHz 8.7081 (1.30); 8.6868 (1.31); 8.1108 (0.66); 8.0971 (1.28); 8.0834 (0.66); 8.0247 (2.59); 8.0197 (2.72); 7.8521 (3.87); 7.8474 (1.47); 7.8309 (6.58); 7.8274 (3.63); 7.5532 (4.52); 7.5486 (1.47); 7.5363 (1.29); 7.5316 (3.92); 4.6267 (0.40); 4.6147 (0.47); 4.6017 (0.70); 4.5929 (0.63); 4.5800 (0.52); 4.5683 (0.42); 3.9157 (0.79); 3.9048 (2.55); 3.8670 (16.00); 3.4210 (0.47); 3.4047 (0.73); 3.3512 (429.39); 3.2870 (0.35); 3.1741 (0.47); 3.1615 (0.46); 3.1386 (0.41); 3.1202 (1.09); 3.1024 (1.53); 3.0883 (1.53); 3.0706 (1.12); 3.0525 (0.51); 3.0450 (0.63); 3.0329 (0.73); 3.0105 (1.02); 2.9990 (0.94); 2.9441 (0.99); 2.9185 (0.98); 2.9102 (0.67); 2.8842 (0.57); 2.6770 (0.54); 2.6726 (0.75); 2.6682 (0.56); 2.5427 (0.40); 2.5258 (2.39); 2.5123 (43.73); 2.5080 (87.18); 2.5035 (115.46); 2.4989 (87.25); 2.4946 (44.61); 2.3347 (0.56); 2.3302 (0.76); 2.3257 (0.57); 1.0197 (3.85); 1.0016 (8.14); 0.9836 (3.69); 0.0080 (1.58); −0.0002 (48.07); −0.0084 (2.10)

No. Ib-13, Solvent: <[D$_6$]-DMSO>, Spectrometer: 399.95 MHz 9.0780 (1.32); 9.0568 (1.36); 8.6799 (1.57); 8.6753 (2.45); 8.6706 (1.64); 8.4021 (0.99); 8.4000 (1.12); 8.3965 (1.03); 8.3943 (1.01); 8.3817 (1.10); 8.3795 (1.17); 8.3760 (1.13); 8.3738 (1.05); 8.3291 (0.60); 8.3069 (0.75); 8.2603 (1.40); 8.2403 (1.53); 8.1683 (0.69); 8.1545 (1.36); 8.1407 (0.73); 8.0530 (0.70); 8.0281 (2.99); 8.0231 (3.08); 8.0000 (0.35); 7.8454 (3.03); 7.8402 (3.22); 7.8344 (0.65); 7.7983 (1.57); 7.7862 (0.45); 7.7784 (2.70); 7.7583 (1.39); 7.7490 (0.33); 4.6852 (0.40); 4.6730 (0.49); 4.6603 (0.71); 4.6512 (0.67); 4.6390 (0.58); 4.6266 (0.48); 3.9162 (0.71); 3.9054 (3.69); 3.8649 (16.00); 3.8213 (1.05); 3.3927 (0.57); 3.3496 (216.43); 3.3122 (0.42); 3.1753 (0.99); 3.1622 (1.00); 3.1508 (0.50); 3.1323 (1.24); 3.1141 (1.80); 3.0998 (1.82); 3.0820 (1.61); 3.0730 (0.91); 3.0633 (0.67); 3.0499 (1.20); 3.0385 (1.09); 2.9682 (1.03); 2.9603 (0.36); 2.9427 (1.01); 2.9338 (0.83); 2.9081 (0.60); 2.6732 (0.41); 2.6689 (0.32); 2.5436 (0.36); 2.5264 (1.42); 2.5130 (23.96); 2.5087 (47.10); 2.5042 (62.08); 2.4997 (46.70); 2.4953 (23.70); 2.3310 (0.39); 1.0256 (4.45); 1.0076 (9.29); 0.9895 (4.28); 0.0079 (1.01); −0.0002 (28.58); −0.0085 (1.15)

No. Ib-14, Solvent: <[D$_6$]-DMSO>, Spectrometer: 399.95 MHz 8.9422 (1.43); 8.9209 (1.46); 8.1610 (2.48); 8.1363 (1.44); 8.1160 (1.50); 8.0955 (1.46); 8.0288 (2.69); 8.0239 (2.86); 7.9215 (1.16); 7.9022 (1.40); 7.8486 (3.05); 7.8436 (2.94); 7.7377 (1.07); 7.7182 (1.82); 7.6987 (0.82); 4.6651 (0.42); 4.6532 (0.51); 4.6401 (0.73); 4.6316 (0.70); 4.6186 (0.55); 4.6064 (0.44); 3.9052 (1.22); 3.8643 (16.00); 3.4142 (0.61); 3.3555 (340.93); 3.1471 (0.45); 3.1289 (1.16); 3.1109 (1.69); 3.0967 (1.72); 3.0791 (1.62); 3.0692 (0.88); 3.0610 (0.57); 3.0466 (1.22); 3.0349 (1.02); 2.9529 (1.05); 2.9270 (1.04); 2.9185 (0.77); 2.8926 (0.64); 2.6779 (0.36); 2.6734 (0.51); 2.6690 (0.39); 2.5264 (1.85); 2.5088 (59.40); 2.5043 (78.01); 2.4999 (60.22); 2.3353 (0.37); 2.3311 (0.49); 2.3266 (0.39); 1.0241 (3.87); 1.0061 (8.14); 0.9880 (3.75); 0.0079 (1.02); −0.0002 (26.03); −0.0084 (1.39)

No. Ib-16, Solvent: <[D$_6$]-DMSO>, Spectrometer: 399.95 MHz 8.4798 (1.13); 8.4584 (1.17); 8.0295 (2.43); 8.0245 (2.77); 8.0135 (0.99); 8.0018 (0.93); 7.8354 (2.64); 7.8303 (2.67); 7.8187 (3.54); 7.8137 (1.26); 7.8015 (1.18); 7.7965 (3.83); 7.7893 (0.67); 7.0036 (0.40); 6.9966 (3.76); 6.9920 (1.40); 6.9792 (1.13); 6.9744 (3.68); 4.6138 (0.35); 4.6028 (0.40); 4.5878 (0.60); 4.5814 (0.54); 4.5771 (0.49); 4.5663 (0.44); 4.5549 (0.37); 3.9047 (1.74); 3.8626 (14.76); 3.8018 (16.00); 3.3632 (276.64); 3.2965 (0.46); 3.1750 (0.73); 3.1619 (0.69); 3.0520 (0.49); 3.0409 (0.56); 3.0173 (0.93); 3.0063 (0.82); 2.9486 (0.89); 2.9221 (0.90); 2.9142 (0.62); 2.8875 (0.53); 2.7614 (0.32); 2.7501 (0.33); 2.6781 (0.32); 2.6736 (0.44); 2.6688 (0.33); 2.6175 (5.51); 2.6060 (5.57); 2.5267 (1.28); 2.5134 (23.37); 2.5090 (46.94); 2.5044 (62.47); 2.4998 (46.91); 2.4954 (23.71); 2.3311 (0.41); −0.0002 (8.81); −0.0085 (0.33)

No. Ib-17, Solvent: <[D$_6$]-DMSO>, Spectrometer: 399.95 MHz 8.7458 (1.28); 8.7244 (1.32); 8.0523 (1.00); 8.0408 (1.04); 8.0245 (2.71); 8.0195 (2.83); 7.8547 (1.05); 7.8484 (3.91); 7.8439 (1.48); 7.8302 (4.29); 7.8266 (6.63); 7.5593 (0.59); 7.5531 (4.64); 7.5485 (1.68); 7.5456 (1.30); 7.5362 (1.39); 7.5316 (4.14); 7.5242 (1.04); 4.6308 (0.39); 4.6196 (0.46); 4.6047 (0.68); 4.5984 (0.63); 4.5936 (0.56); 4.5833 (0.50); 4.5721 (0.43); 3.9051 (1.64); 3.8649 (16.00); 3.3508 (201.96); 3.3106 (0.39); 3.1750 (0.33); 3.1619 (0.33); 3.0725 (0.61); 3.0612 (0.68); 3.0378 (0.98); 3.0269 (0.91); 2.9392 (0.97); 2.9126 (0.99); 2.9047 (0.75); 2.8781 (0.62); 2.7819

(1.26); 2.7705 (1.26); 2.6730 (0.41); 2.6684 (0.33); 2.6200 (6.12); 2.6086 (6.22); 5431 (0.32); 2.5263 (1.23); 2.5127 (21.10); 2.5084 (42.38); 2.5039 (56.72); 2.4994 (43.28); 2.4952 (22.48); 2.3308 (0.37); 0.0079 (0.55); −0.0002 (15.44); −0.0085 (0.60)

No. Ib-19, Solvent: <[$D_6$]-DMSO>, Spectrometer: 399.95 MHz 8.6395 (1.24); 8.6180 (1.28); 8.0415 (3.06); 8.0364 (3.32); 7.8506 (2.78); 7.8456 (2.71); 7.8333 (0.67); 7.8248 (2.81); 7.8163 (0.79); 7.8121 (1.14); 7.8072 (3.23); 7.8035 (2.48); 7.5435 (0.65); 7.5314 (0.54); 7.5253 (1.75); 7.5198 (0.66); 7.5102 (0.98); 7.5070 (1.47); 7.4722 (2.61); 7.4530 (3.46); 7.4354 (1.40); 4.6402 (0.39); 4.6293 (0.45); 4.6138 (0.66); 4.6078 (0.61); 4.6029 (0.54); 4.5924 (0.50); 4.5813 (0.41); 3.9168 (0.32); 3.9053 (1.31); 3.8643 (16.00); 3.3427 (95.11); 3.0750 (0.57); 3.0639 (0.63); 3.0404 (1.00); 3.0294 (0.93); 2.9599 (1.03); 2.9332 (1.00); 2.9255 (0.70); 2.8987 (0.60); 2.7860 (0.94); 2.7746 (0.93); 2.6723 (0.38); 2.6235 (6.01); 2.6120 (6.08); 2.5257 (1.19); 2.5121 (22.21); 2.5078 (43.72); 2.5032 (57.55); 2.4987 (43.42); 2.4944 (22.25); 2.3681 (1.03); 2.3300 (0.39); 0.0080 (0.99); −0.0002 (28.08); −0.0085 (1.11)

No. Ib-21, Solvent: <[$D_6$]-DMSO>, Spectrometer: 399.95 MHz 8.9695 (1.24); 8.9479 (1.29); 8.1545 (2.08); 8.1069 (1.22); 8.0869 (2.19); 8.0752 (1.07); 8.0267 (2.48); 8.0217 (2.73); 7.9210 (1.05); 7.9014 (1.27); 7.8465 (2.92); 7.8414 (2.89); 7.7368 (1.01); 7.7171 (1.71); 7.6976 (0.79); 4.6676 (0.38); 4.6564 (0.44); 4.6415 (0.63); 4.6350 (0.60); 4.6199 (0.47); 4.6086 (0.41); 3.9053 (1.50); 3.8614 (16.00); 3.3939 (0.45); 3.3490 (290.87); 3.3092 (0.64); 3.2958 (0.38); 3.1100 (0.62); 3.0987 (0.69); 3.0751 (0.94); 3.0639 (0.86); 2.9455 (0.91); 2.9189 (0.94); 2.9111 (0.73); 2.8844 (0.65); 2.8167 (1.36); 2.8053 (1.36); 2.6775 (0.44); 2.6729 (0.61); 2.6684 (0.45); 2.6275 (5.97); 2.6161 (6.07); 2.5263 (1.78); 2.5215 (2.70); 2.5128 (31.36); 2.5084 (63.47); 2.5038 (84.85); 2.4992 (64.40); 2.4948 (32.96); 2.3350 (0.39); 2.3306 (0.54); 2.3259 (0.41); 0.0080 (1.06); −0.0002 (31.60); −0.0085 (1.22)

No. Ib-22, Solvent: <[$D_6$]-DMSO>, Spectrometer: 399.95 MHz 9.0341 (1.33); 9.0124 (1.36); 8.0081 (2.52); 8.0031 (2.63); 7.9140 (0.98); 7.9018 (0.98); 7.8032 (2.87); 7.7981 (2.73); 7.4588 (1.79); 7.4526 (2.49); 7.4357 (5.98); 7.4108 (3.01); 7.3952 (1.47); 7.3872 (0.98); 7.3715 (0.77); 4.6991 (0.41); 4.6880 (0.50); 4.6740 (0.71); 4.6660 (0.67); 4.6526 (0.53); 4.6405 (0.43); 3.9268 (0.34); 3.9165 (0.58); 3.9001 (16.00); 3.4522 (0.39); 3.4401 (0.53); 3.4313 (0.61); 3.3563 (474.53); 3.1741 (0.53); 3.1610 (0.48); 2.9868 (0.63); 2.9753 (0.68); 2.9513 (0.96); 2.9403 (0.87); 2.8399 (0.95); 2.8137 (0.99); 2.8048 (0.75); 2.7787 (0.66); 2.6773 (0.59); 2.6726 (0.80); 2.6683 (0.64); 2.6431 (6.26); 2.6315 (6.25); 2.5428 (0.54); 2.5258 (2.45); 2.5122 (43.02); 2.5081 (83.08); 2.5036 (108.82); 2.4991 (82.09); 2.4951 (42.14); 2.3691 (2.06); 2.3347 (0.55); 2.3303 (0.72); 2.3260 (0.54); 0.0079 (1.19); −0.0002 (32.40); −0.0084 (1.36)

No. Ib-23, Solvent: <[$D_6$]-DMSO>, Spectrometer: 399.95 MHz 8.6987 (1.44); 8.6774 (1.48); 8.0542 (3.80); 8.0496 (3.59); 8.0417 (1.36); 7.9331 (3.68); 7.9120 (4.79); 7.8633 (3.15); 7.8583 (3.05); 7.7810 (4.76); 7.7760 (2.35); 7.7599 (3.87); 7.7547 (1.45); 7.7460 (2.54); 7.7427 (3.55); 7.7246 (3.89); 7.5140 (1.89); 7.4957 (4.08); 7.4763 (2.61); 7.4284 (1.54); 7.4102 (2.00); 7.3919 (0.69); 4.6700 (0.41); 4.6586 (0.47); 4.6433 (0.72); 4.6375 (0.65); 4.6221 (0.51); 4.6109 (0.44); 3.9051 (3.70); 3.8681 (16.00); 3.4085 (0.33); 3.4016 (0.39); 3.3887 (0.75); 3.3489 (271.39); 3.3009 (0.38); 3.0919 (0.58); 3.0808 (0.67); 3.0571 (1.05); 3.0466 (0.95); 2.9791 (1.00);

2.9525 (1.04); 2.9448 (0.75); 2.9180 (0.60); 2.8110 (1.37); 2.7997 (1.39); 2.6772 (0.44); 2.6728 (0.59); 2.6684 (0.47); 2.6352 (6.31); 2.6237 (6.34); 2.5431 (0.43); 2.5259 (1.88); 2.5081 (66.01); 2.5036 (86.70); 2.4992 (66.22); 2.3347 (0.42); 2.3302 (0.56); 2.3261 (0.42); 0.0080 (1.11); −0.0002 (31.01); −0.0084 (1.35)

No. Ib-24, Solvent: <[$D_6$]-DMSO>, Spectrometer: 399.95 MHz 8.6898 (1.32); 8.6684 (1.34); 8.0175 (2.45); 8.0125 (2.61); 7.9650 (1.00); 7.9533 (0.99); 7.8234 (2.83); 7.8183 (2.72); 7.6525 (0.38); 7.6324 (0.47); 7.6169 (1.58); 7.6150 (1.67); 7.5973 (1.86); 7.5952 (1.84); 7.4405 (0.74); 7.4380 (0.78); 7.4219 (1.93); 7.4195 (1.95); 7.4036 (1.63); 7.4010 (1.54); 7.3862 (0.35); 7.3811 (0.58); 7.3661 (0.57); 7.3613 (1.24); 7.3568 (1.22); 7.3418 (1.43); 7.3374 (1.47); 7.3230 (0.75); 7.3184 (0.65); 7.2901 (1.65); 7.2858 (1.52); 7.2715 (1.33); 7.2672 (1.16); 4.6353 (0.40); 4.6243 (0.47); 4.6098 (0.67); 4.6024 (0.64); 4.5881 (0.49); 4.5770 (0.41); 3.9163 (0.43); 3.9037 (16.00); 3.3464 (193.76); 3.3056 (0.33); 3.0340 (0.64); 3.0230 (0.71); 2.9992 (0.90); 2.9882 (0.84); 2.8336 (0.89); 2.8074 (0.96); 2.7988 (0.76); 2.7727 (0.67); 2.7474 (1.80); 2.7357 (1.81); 2.6765 (0.36); 2.6720 (0.49); 2.6676 (0.41); 2.6625 (0.32); 2.6494 (6.07); 2.6379 (6.11); 2.5252 (1.37); 2.5074 (49.14); 2.5029 (64.74); 2.4985 (49.24); 2.3725 (0.39); 2.3296 (0.41); 0.0079 (0.86); −0.0002 (25.17); −0.0085 (1.11)

No. Ib-25, Solvent: <[$D_6$]-DMSO>, Spectrometer: 399.95 MHz 8.8661 (1.30); 8.8463 (1.31); 8.0392 (2.43); 8.0342 (2.61); 7.8950 (2.84); 7.8898 (2.67); 7.7992 (2.71); 7.7817 (3.25); 7.7779 (2.45); 7.5649 (0.52); 7.5617 (0.34); 7.5527 (0.38); 7.5467 (1.63); 7.5413 (0.51); 7.5315 (0.86); 7.5284 (1.36); 7.5252 (0.72); 7.4909 (2.41); 7.4718 (3.41); 7.4540 (1.42); 4.6810 (0.42); 4.6671 (0.52); 4.6614 (0.54); 4.6558 (0.66); 4.6474 (0.59); 4.6419 (0.56); 4.6361 (0.59); 4.6222 (0.46); 4.1404 (0.58); 4.1334 (0.77); 4.1226 (1.88); 4.1160 (1.98); 4.1048 (2.07); 4.0984 (1.87); 4.0870 (0.75); 4.0808 (0.59); 3.9049 (1.54); 3.8789 (16.00); 3.8558 (1.43); 3.3958 (0.33); 3.3719 (1.20); 3.3424 (214.24); 3.3091 (0.58); 3.1740 (0.38); 3.1670 (0.58); 3.1611 (0.42); 3.1534 (0.66); 3.1323 (1.08); 3.1186 (0.98); 3.0684 (1.05); 3.0431 (1.04); 3.0335 (0.63); 3.0082 (0.61); 2.6764 (0.45); 2.6719 (0.62); 2.6674 (0.48); 2.5422 (0.62); 2.5253 (2.03); 2.5204 (3.13); 2.5117 (36.22); 2.5073 (72.41); 2.5028 (96.50); 2.4983 (72.77); 2.4939 (37.02); 2.3304 (0.45); 2.3296 (0.62); 2.3250 (0.45); 1.1692 (4.11); 1.1515 (8.68); 1.1337 (4.00); 0.0080 (0.95); −0.0002 (29.70); −0.0085 (1.23)

No. Ib-26, Solvent: <[$D_6$]-DMSO>, Spectrometer: 399.95 MHz 8.7059 (1.18); 8.6862 (1.21); 8.0300 (2.23); 8.0249 (2.49); 7.8833 (2.52); 7.8782 (2.47); 7.8063 (0.41); 7.7991 (3.52); 7.7941 (1.34); 7.7819 (1.26); 7.7769 (3.93); 7.0211 (0.39); 7.0139 (3.71); 7.0090 (1.29); 6.9917 (3.80); 6.9848 (0.53); 6.9721 (0.43); 4.6475 (0.36); 4.6337 (0.46); 4.6281 (0.48); 4.6226 (0.60); 4.6142 (0.53); 4.6089 (0.52); 4.6031 (0.55); 4.5889 (0.40); 4.1302 (0.51); 4.1225 (0.75); 4.1124 (1.74); 4.1051 (1.91); 4.0945 (1.96); 4.0875 (1.79); 4.0770 (0.80); 4.0698 (0.58); 4.0604 (0.33); 3.9051 (1.06); 3.8771 (15.24); 3.8536 (1.79); 3.8064 (16.00); 3.7952 (2.16); 3.3428 (133.18); 3.1472 (0.54); 3.1333 (0.58); 3.1123 (1.04); 3.0986 (0.92); 3.0577 (0.95); 3.0324 (0.95); 3.0229 (0.59); 2.9975 (0.55); 2.6765 (0.37); 2.6719 (0.55); 2.6675 (0.42); 2.5253 (1.46); 2.5206 (2.35); 2.5119 (29.81); 2.5075 (61.46); 2.5029 (83.10); 2.4984 (63.59); 2.4940 (33.08); 2.3343 (0.45); 2.3297 (0.60); 2.3251 (0.47); 1.2337 (0.33); 1.1621 (4.05); 1.1443 (8.60); 1.1266 (3.94); 0.0081 (1.26); −0.0002 (41.65); −0.0084 (1.87)

No. Ib-28, Solvent: <[D$_6$]-DMSO>, Spectrometer: 399.95 MHz 9.1636 (1.35); 9.1440 (1.36); 8.1192 (2.21); 8.1047 (1.32); 8.0846 (1.34); 8.0358 (2.56); 8.0308 (2.91); 7.9487 (1.08); 7.9290 (1.30); 7.9016 (3.05); 7.8965 (2.83); 7.7604 (1.02); 7.7409 (1.71); 7.7215 (0.82); 4.7215 (0.44); 4.7072 (0.55); 4.7023 (0.59); 4.6969 (0.68); 4.6879 (0.61); 4.6827 (0.60); 4.6775 (0.64); 4.6633 (0.46); 4.1486 (0.60); 4.1412 (0.80); 4.1307 (1.90); 4.1239 (1.99); 4.1129 (2.06); 4.1063 (1.89); 4.0952 (0.80); 4.0886 (0.62); 3.9052 (1.46); 3.8981 (0.54); 3.8773 (16.00); 3.8533 (2.03); 3.3378 (153.38); 3.1866 (0.69); 3.1734 (0.97); 3.1610 (0.46); 3.1518 (1.17); 3.1379 (1.06); 3.0726 (1.04); 3.0477 (1.04); 3.0380 (0.69); 3.0128 (0.61); 2.6764 (0.63); 2.6719 (0.88); 2.6675 (0.67); 2.5422 (0.88); 2.5252 (2.88); 2.5116 (48.87); 2.5073 (97.47); 2.5028 (129.89); 2.4983 (98.96); 2.4941 (51.62); 2.3341 (0.60); 2.3296 (0.83); 2.3250 (0.61); 1.2340 (0.40); 1.1692 (4.17); 1.1515 (8.67); 1.1338 (4.02); 0.0080 (2.02); −0.0002 (60.25); −0.0084 (2.75)

No. Ib-29, Solvent: <[D$_6$]-DMSO>, Spectrometer: 399.95 MHz 9.1954 (1.30); 9.1746 (1.34); 8.0381 (2.34); 8.0330 (2.52); 7.8784 (2.75); 7.8732 (2.64); 7.4792 (1.56); 7.4733 (2.21); 7.4561 (5.33); 7.4430 (0.55); 7.4294 (2.83); 7.4135 (1.17); 7.4058 (0.92); 7.3900 (0.80); 4.8001 (0.43); 4.7882 (0.51); 4.7794 (0.51); 4.7734 (0.66); 4.7674 (0.63); 4.7618 (0.54); 4.7527 (0.55); 4.7409 (0.45); 4.1860 (0.34); 4.1769 (0.52); 4.1669 (0.75); 4.1591 (1.75); 4.1490 (1.84); 4.1412 (1.93); 4.1312 (1.73); 4.1230 (0.84); 4.1135 (0.58); 4.1042 (0.37); 3.9045 (2.70); 3.9001 (16.00); 3.8806 (1.15); 3.3346 (86.46); 3.3078 (0.32); 3.1589 (0.71); 3.1464 (0.73); 3.1227 (0.89); 3.1113 (0.88); 2.9215 (0.89); 2.8948 (0.91); 2.8861 (0.76); 2.8593 (0.68); 2.6759 (0.45); 2.6712 (0.64); 2.6666 (0.48); 2.5414 (0.37); 2.5245 (2.01); 2.5196 (3.04); 2.5110 (35.89); 2.5066 (72.87); 2.5021 (97.93); 2.4975 (74.69); 2.4932 (38.68); 2.3335 (0.45); 2.3289 (0.64); 2.3242 (0.49); 1.2346 (0.33); 1.2189 (4.13); 1.2011 (8.73); 1.1834 (4.07); 0.0080 (1.82); −0.0002 (56.52); −0.0084 (2.53)

No. Ib-30, Solvent: <[D$_6$]-DMSO>, Spectrometer: 399.95 MHz 8.9351 (1.28); 8.9149 (1.29); 8.0433 (2.39); 8.0382 (2.57); 7.8890 (2.88); 7.8838 (2.64); 7.6469 (1.49); 7.6446 (1.56); 7.6270 (1.77); 7.6247 (1.76); 7.4629 (0.62); 7.4602 (0.67); 7.4442 (1.66); 7.4415 (1.69); 7.4256 (1.21); 7.4227 (1.22); 7.3833 (1.01); 7.3788 (1.14); 7.3638 (1.27); 7.3592 (1.39); 7.3447 (0.65); 7.3403 (0.63); 7.2150 (1.52); 7.2106 (1.55); 7.1963 (1.35); 7.1920 (1.28); 4.6796 (0.43); 4.6666 (0.52); 4.6592 (0.52); 4.6535 (0.65); 4.6466 (0.61); 4.6407 (0.55); 4.6333 (0.56); 4.6205 (0.44); 4.1711 (0.59); 4.1665 (0.68); 4.1533 (1.94); 4.1488 (2.02); 4.1354 (2.09); 4.1312 (1.98); 4.1176 (0.73); 4.1135 (0.68); 3.9085 (16.00); 3.8791 (1.63); 3.3344 (76.80); 3.1562 (0.72); 3.1436 (0.76); 3.1211 (0.92); 3.1085 (0.85); 2.9544 (0.93); 2.9283 (0.93); 2.9192 (0.74); 2.8931 (0.66); 2.6758 (0.46); 2.6711 (0.63); 2.6666 (0.46); 2.5414 (0.39); 2.5246 (2.00); 2.5197 (3.00); 2.5110 (35.62); 2.5066 (71.89); 2.5021 (96.27); 2.4976 (72.83); 2.4932 (37.31); 2.3331 (0.45); 2.3289 (0.63); 2.3244 (0.47); 1.2345 (0.37); 1.2187 (4.11); 1.2010 (8.65); 1.1832 (4.02); 0.0080 (1.80); −0.0002 (56.41); −0.0085 (2.45)

No. Ib-32, Solvent: <[D$_6$]-DMSO>, Spectrometer: 399.95 MHz 8.9265 (1.50); 8.9067 (1.52); 8.0520 (2.80); 8.0469 (2.87); 8.0333 (0.53); 7.9113 (6.23); 7.9064 (4.20); 7.8900 (4.65); 7.8456 (0.51); 7.8243 (0.49); 7.7965 (4.81); 7.7754 (3.46); 7.7701 (1.12); 7.7586 (0.42); 7.7548 (0.56); 7.7474 (2.44); 7.7441 (3.11); 7.7262 (3.55); 7.7099 (0.46); 7.5172 (1.75); 7.4992 (3.66); 7.4798 (2.28); 7.4328 (1.41); 7.4145 (1.84); 7.3962 (0.62); 4.7105 (0.43); 4.6963 (0.53); 4.6908 (0.58); 4.6853 (0.71); 4.6770 (0.61); 4.6715 (0.59); 4.6659 (0.60); 4.6518 (0.46); 4.3495 (0.44); 4.3317 (0.44); 4.1526 (0.60); 4.1455 (0.81); 4.1347 (1.97); 4.1283 (2.05); 4.1168 (2.09); 4.1107 (1.98); 4.0991 (0.82); 4.0931 (0.62); 3.9048 (1.77); 3.8975 (0.34); 3.8828 (16.00); 3.8574 (1.67); 3.4020 (0.77); 3.3495 (396.68); 3.3019 (0.52); 3.2926 (0.33); 3.1844 (0.58); 3.1704 (0.75); 3.1616 (0.37); 3.1491 (1.12); 3.1357 (0.96); 3.0907 (1.03); 3.0655 (1.04); 3.0560 (0.67); 3.0307 (0.58); 2.6770 (0.53); 2.6725 (0.73); 2.6681 (0.55); 2.5425 (0.46); 2.5256 (2.44); 2.5119 (43.79); 2.5079 (86.57); 2.5034 (114.86); 2.4989 (87.47); 2.4948 (45.39); 2.3345 (0.56); 2.3301 (0.76); 2.3257 (0.55); 1.3616 (0.46); 1.3438 (0.99); 1.3260 (0.49); 1.2335 (0.40); 1.1795 (4.19); 1.1617 (8.75); 1.1440 (4.08); 0.0080 (1.35); −0.0002 (42.89); −0.0085 (1.96)

No. Ib-47, Solvent: <[D$_6$]-DMSO>, Spectrometer: 399.95 MHz 8,71 (11,84); 8,6412 (1,72); 8,627 (3,39); 8,6129 (1,72); 8,1225 (16); 7,7682 (4,09); 7,7487 (5,54); 7,7348 (1,85); 7,7163 (4,7); 7,6976 (3,3); 7,6519 (3,32); 7,6328 (4,22); 7,6137 (1,55); 7,4483 (4,9); 7,4295 (4,28); 4,056 (0,42); 4,0381 (1,33); 4,0203 (1,34); 4,0026 (0,46); 3,6184 (2,6); 3,6021 (7,21); 3,5866 (7,43); 3,5705 (2,9); 3,3223 (81,02); 3,0794 (4,88); 3,0628 (9,46); 3,0462 (4,26); 2,6754 (0,54); 2,6709 (0,75); 2,6664 (0,54); 2,541 (0,34); 2,5242 (2,53); 2,5193 (3,97); 2,5109 (43,46); 2,5064 (86,25); 2,5018 (112,35); 2,4972 (79,7); 2,4927 (37,52); 2,3331 (0,55); 2,3286 (0,74); 2,324 (0,54); 1,9889 (5,92); 1,336 (0,32); 1,2497 (0,43); 1,1928 (1,6); 1,175 (3,17); 1,1572 (1,57); 0,146 (0,42); 0,008 (3,8); −0,0002 (102,72); −0,0085 (3,28); −0,1497 (0,44)

No. Ib-48, Solvent: <[D$_6$]-DMSO>, Spectrometer: 399.95 MHz 8,6827 (12,03); 8,4604 (1,46); 8,4481 (2,66); 8,4349 (1,47); 8,3168 (0,32); 8,1057 (16); 7,5365 (5,11); 7,5205 (6,84); 7,5175 (8,28); 7,5025 (5,08); 7,4981 (4,67); 7,4849 (2); 7,4804 (1,11); 7,2896 (3,19); 7,2772 (4); 7,2749 (4,11); 7,2699 (3,14); 7,2642 (4,2); 7,2579 (7,4); 7,24 (5,58); 3,6166 (2,62); 3,6008 (7,34); 3,5851 (7,57); 3,5692 (2,96); 3,3244 (32,92); 3,1008 (5,22); 3,0845 (9,74); 3,0681 (4,58); 2,6721 (0,39); 2,5254 (1,12); 2,5205 (1,8); 2,512 (22,07); 2,5076 (43,98); 2,503 (57,42); 2,4985 (41,01); 2,494 (19,58); 2,3298 (0,37); 1,9896 (1,03); 1,3371 (0,32); 1,2501 (0,39); 1,1757 (0,55); 0,0079 (1,96); −0,0002 (53,1); −0,0085 (1,74)

No. Ib-49, Solvent: <[D$_6$]-DMSO>, Spectrometer: 399.95 MHz 8,7171 (12); 8,5614 (1,7); 8,5469 (3,3); 8,5325 (1,68); 8,1125 (16); 7,4807 (2,72); 7,477 (3,64); 7,4609 (6,5); 7,4574 (7,22); 7,444 (3,26); 7,4393 (3,54); 7,4264 (5,28); 7,4217 (5,43); 7,407 (2,8); 7,4019 (3,2); 7,3943 (3,03); 7,3902 (2,8); 7,3756 (5,88); 7,3719 (5,67); 7,358 (3,56); 7,3543 (3,3); 7,3423 (7,15); 7,3376 (6,18); 7,3237 (3,58); 7,3189 (2,63); 4,0384 (0,37); 4,0206 (0,37); 3,6198 (2,7); 3,604 (7,27); 3,5882 (7,4); 3,5723 (3,02); 3,3231 (38,85); 3,092 (5,02); 3,0757 (9,22); 3,0595 (4,42); 2,6711 (0,42); 2,5244 (1,25); 2,5196 (2); 2,5111 (24,27); 2,5066 (48,3); 2,502 (62,98); 2,4975 (44,73); 2,493 (21,09); 2,3288 (0,41); 1,9891 (1,61); 1,1931 (0,44); 1,1753 (0,86); 1,1575 (0,43); 0,0079 (2,25); −0,0002 (59,88); −0,0085 (1,86)

No. Ib-50, Solvent: <[D$_6$]-DMSO>, Spectrometer: 399.95 MHz 8,7483 (1,69); 8,7342 (3,34); 8,7195 (1,74); 8,6992 (12,09); 8,3167 (0,59); 8,1159 (16); 7,7065 (2,33); 7,6992 (2,97); 7,684 (4,34); 7,646 (1,05); 7,641 (1,56); 7,6274 (5,27); 7,6224 (7,45); 7,6133 (7,34); 7,6046 (7,28); 7,5998 (3,97); 7,586 (1,12); 7,5811 (0,8); 7,5239 (3,85); 7,5161 (1,96);

7,5095 (2,84); 7,5023 (2,23); 7,2782 (3,52); 7,1391 (7,94); 6,9999 (3,89); 3,6308 (2,55); 3,6153 (6,9); 3,5993 (7,01); 3,5837 (2,88); 3,3231 (37,97); 3,1043 (4,91); 3,0881 (8,87); 3,072 (4,35); 2,6757 (0,35); 2,6713 (0,48); 2,6667 (0,34); 2,5247 (1,35); 2,5198 (2,15); 2,5112 (27,33); 2,5068 (54,91); 2,5022 (72,12); 2,4976 (51,68); 2,4931 (24,6); 2,3334 (0,35); 2,329 (0,48); 2,3242 (0,34); 1,9891 (0,8); 1,3364 (0,36); 1,2497 (0,44); 1,1752 (0,44); 0,0079 (2,52); −0,0002 (71,05); −0,0086 (2,3)

No. Ib-51, Solvent: <[D$_6$]-DMSO>, Spectrometer: 399.95 MHz 8,8402 (1,65); 8,8259 (3,17); 8,8113 (1,61); 8,6709 (11, 61); 8,3159 (0,68); 8,1132 (16); 7,533 (1,12); 7,5163 (2,4); 7,5117 (2,16); 7,4996 (1,58); 7,4951 (4,56); 7,4908 (1,64); 7,4784 (2,2); 7,474 (2,67); 7,4574 (1,21); 7,1788 (0,92); 7,1756 (1,29); 7,1683 (7,79); 7,1486 (10,07); 7,1282 (6,58); 7,1206 (1,09); 3,6314 (2,61); 3,6156 (7,08); 3,5998 (7,25); 3,584 (2,94); 3,3218 (62,92); 3,0811 (4,99); 3,0648 (9,2); 3,0484 (4,38); 2,6753 (0,51); 2,6709 (0,69); 2,6662 (0,5); 2,5242 (2,16); 2,5108 (38,97); 2,5063 (78,04); 2,5018 (102, 47); 2,4972 (73,54); 2,4927 (35,05); 2,3331 (0,49); 2,3286 (0,67); 2,3241 (0,49); 1,9888 (0,79); 1,2497 (0,38); 1,1751 (0,42); 0,1459 (0,41); 0,008 (3,43); −0,0002 (95,23); −0,0085 (3,18); −0,1497 (0,42)

No. Ib-52, Solvent: <[D$_6$]-DMSO>, Spectrometer: 399.95 MHz 8,735 (12,42); 8,5559 (1,8); 8,5414 (3,47); 8,5272 (1,75); 8,1151 (16); 7,6382 (5,43); 7,6359 (5,64); 7,6185 (6,39); 7,6159 (6,32); 7,4387 (2,21); 7,4359 (2,37); 7,4201 (6,17); 7,4173 (6,15); 7,4016 (5); 7,3986 (4,62); 7,3614 (3,67); 7,3567 (4,91); 7,342 (4,58); 7,3372 (6,02); 7,3228 (2,52); 7,3182 (2,79); 7,3121 (6,94); 7,3076 (5,55); 7,2936 (5,02); 7,2891 (4,16); 4,0381 (0,77); 4,0203 (0,79); 3,6118 (2,76); 3,596 (7,53); 3,5802 (7,71); 3,5643 (3,07); 3,3227 (57,87); 3,0933 (5,24); 3,077 (9,76); 3,0606 (4,57); 2,6754 (0,43); 2,6708 (0,59); 2,6663 (0,44); 2,5241 (1,89); 2,5108 (34,46); 2,5063 (68,68); 2,5018 (89,88); 2,4972 (64,22); 2,4927 (30, 4); 2,333 (0,41); 2,3285 (0,58); 2,3238 (0,41); 1,9889 (3,37); 1,2496 (0,4); 1,1929 (0,92); 1,1751 (1,84); 1,1573 (0,89); 0,1458 (0,36); 0,0079 (3,22); −0,0002 (86,56); −0,0086 (2,66); −0,1498 (0,37)

No. Ib-53, Solvent: <[D$_6$]-DMSO>, Spectrometer: 399.95 MHz 8,6073 (1,8); 8,593 (3,58); 8,5783 (1,81); 8,4839 (12,08); 8,1481 (16); 7,7765 (4,12); 7,7568 (5,61); 7,7426 (1,86); 7,7239 (4,66); 7,7053 (3,28); 7,6591 (3,26); 7,64 (4,2); 7,621 (1,54); 7,4957 (4,97); 7,477 (4,24); 3,6068 (2,39); 3,5914 (6,39); 3,5755 (6,56); 3,56 (2,64); 3,321 (52,6); 2,9483 (4,62); 2,9322 (8,3); 2,9163 (4,2); 2,6746 (0,75); 2,6702 (1,04); 2,6657 (0,79); 2,5055 (121,35); 2,5011 (159,35); 2,4966 (118,42); 2,3323 (0,8); 2,3278 (1,09); 2,3235 (0,84); 0,0079 (2,63); −0,0002 (67,13); −0,0084 (2,64)

No. Ib-54, Solvent: <[D$_6$]-DMSO>, Spectrometer: 399.95 MHz 8,5344 (1,76); 8,5199 (3,45); 8,5052 (1,8); 8,4841 (12,28); 8,1391 (16); 7,4886 (3,29); 7,4696 (8,29); 7,4508 (2,72); 7,4424 (3,04); 7,4369 (3,7); 7,4285 (4,71); 7,422 (1,4); 7,4182 (2,28); 7,4087 (3,08); 7,4039 (1,31); 7,4003 (1,51); 7,3849 (6,98); 7,3809 (9,79); 7,3711 (9,42); 7,3694 (8,95); 7,3612 (0,97); 5,7577 (0,78); 3,6096 (2,52); 3,5947 (6,25); 3,5787 (6,28); 3,5633 (2,68); 3,3226 (17,91); 2,9589 (4,78); 2,9429 (7,65); 2,9275 (4,26); 2,6704 (0,38); 2,5231 (1,48); 2,5101 (22,28); 2,5058 (43,23); 2,5013 (56,03); 2,4968 (40, 53); 2,4924 (19,73); 2,328 (0,35); 0,0077 (1,19); −0,0002 (27,66); −0,0083 (0,95)

No. Ib-55, Solvent: <[D$_6$]-DMSO>, Spectrometer: 399.95 MHz 8,5704 (2,81); 8,5566 (5,41); 8,5427 (2,81); 8,3833 (12,61); 8,379 (12,95); 7,7702 (6,68); 7,7507 (9,01); 7,7359 (13,52); 7,7291 (3,52); 7,7148 (16); 7,6915 (5,36); 7,6498 (5,33); 7,6308 (6,77); 7,6119 (2,49); 7,445 (7,93); 7,4263 (6,9); 7,2906 (7,56); 7,286 (7,73); 7,2696 (6,89); 7,265 (7,01); 5,7576 (9,66); 3,5338 (4,38); 3,5181 (11,17); 3,5024 (11,27); 3,4867 (4,7); 3,3245 (71,55); 2,8019 (8,21); 2,7855 (15,04); 2,7692 (7,46); 2,6752 (0,51); 2,6707 (0,7); 2,6661 (0,54); 2,5239 (2,59); 2,5106 (38,66); 2,5062 (77,48); 2,5016 (102,24); 2,4971 (75,05); 2,4927 (37,56); 2,3329 (0,47); 2,3284 (0,65); 2,3238 (0,48); 1,2357 (0,36); 1,1644 (0,44); 0,0079 (1,85); −0,0002 (49,42); −0,0085 (2)

No. Ib-56, Solvent: <[D$_6$]-DMSO>, Spectrometer: 399.95 MHz 8,4973 (2,91); 8,4834 (5,5); 8,4696 (2,87); 8,3873 (13,9); 8,383 (13,77); 7,733 (14,28); 7,712 (15,72); 7,4828 (4,98); 7,4795 (6,03); 7,4629 (11,4); 7,46 (12,04); 7,4439 (5,46); 7,4391 (5,93); 7,4265 (8,95); 7,4216 (9,12); 7,4135 (0,61); 7,407 (4,7); 7,4017 (5,42); 7,3921 (4,94); 7,3882 (4,5); 7,3734 (10,12); 7,3698 (10,05); 7,3558 (6,62); 7,3523 (6,34); 7,3446 (12,51); 7,3396 (10,59); 7,3261 (5,43); 7,3211 (3,87); 7,3017 (8,41); 7,2971 (8,35); 7,2808 (7,62); 7,2761 (7,55); 5,756 (6,39); 3,5354 (5,05); 3,5201 (12,51); 3,504 (12,4); 3,4886 (5,35); 3,431 (0,33); 3,4159 (0,45); 3,41 (0,48); 3,3903 (0,78); 3,3444 (450,13); 3,3013 (0,54); 3,2882 (0,35); 2,8175 (9,11); 2,8012 (16); 2,7851 (8,34); 2,6764 (0,49); 2,6718 (0,68); 2,6673 (0,51); 2,5249 (2,28); 2,5116 (39,17); 2,5073 (77,08); 2,5027 (99,94); 2,4982 (71,55); 2,4937 (34, 05); 2,3339 (0,45); 2,3294 (0,63); 2,3249 (0,44); 1,2345 (0,42); 1,1804 (0,38); 1,1661 (0,58); 0,0079 (2,09); −0,0002 (55,95); −0,0085 (1,74)

No. Ib-57, Solvent: <[D$_6$]-DMSO>, Spectrometer: 399.95 MHz 8,7559 (12,12); 8,5226 (1,96); 8,508 (3,73); 8,4935 (1,86); 8,1191 (16); 7,873 (5,78); 7,8709 (6); 7,8533 (6,23); 7,8512 (6,09); 7,4503 (2,79); 7,4477 (2,86); 7,4315 (6,31); 7,4289 (6,32); 7,4128 (3,92); 7,4102 (3,8); 7,2493 (5,43); 7,2453 (6,19); 7,2303 (4,84); 7,2264 (4,86); 7,1761 (3,53); 7,1719 (3,31); 7,1568 (5,23); 7,1527 (4,84); 7,1378 (3,03); 7,1336 (2,7); 4,0378 (0,46); 4,02 (0,47); 3,5951 (2,67); 3,5789 (7,35); 3,5634 (7,56); 3,5473 (2,95); 3,3221 (35,97); 3,1008 (5,09); 3,0845 (9,62); 3,068 (4,37); 2,6796 (0,33); 2,6751 (0,63); 2,6705 (0,85); 2,666 (0,63); 2,5237 (3,84); 2,5105 (49,85); 2,5061 (96,07); 2,5015 (124,05); 2,4969 (89,44); 2,4925 (43,13); 2,3328 (0,61); 2,3282 (0,82); 2,3237 (0,58); 1,9889 (2,05); 1,2495 (0,37); 1,1924 (0,58); 1,1747 (1,11); 1,1568 (0,55); 0,008 (1,16); −0,0002 (26,92); −0,0085 (0,92)

No. Ib-58, Solvent: <[D$_6$]-DMSO>, Spectrometer: 399.95 MHz 8,8309 (1,95); 8,8165 (3,81); 8,802 (1,9); 8,74 (12,45); 8,1262 (16); 8,0252 (5,3); 8,0227 (5,51); 8,005 (6,13); 8,0025 (6,06); 7,8045 (2,35); 7,802 (2,44); 7,7858 (5,97); 7,7831 (5,83); 7,767 (4,06); 7,7643 (3,8); 7,7061 (3,66); 7,7026 (3,99); 7,6865 (4,95); 7,6831 (5,22); 7,667 (2,39); 7,6636 (2,31); 7,544 (5,91); 7,5406 (5,92); 7,5252 (5,25); 7,5217 (4,92); 5,759 (0,69); 3,6065 (2,75); 3,5903 (7,6); 3,5748 (7,83); 3,5587 (3); 3,3276 (15,72); 3,0946 (5,19); 3,0781 (9,93); 3,0615 (4,49); 2,5254 (1,02); 2,5121 (16,86); 2,5078 (32,46); 2,5033 (41,79); 2,4987 (30,1); 2,4944 (14,48); 1,2349 (0,45); 0,0079 (0,61); −0,0002 (15,01); −0,0081 (0,47)

No. Ib-59, Solvent: <[D$_6$]-DMSO>, Spectrometer: 399.95 MHz 8,4395 (2,05); 8,4271 (3,53); 8,4148 (2,01); 8,0663 (6,7); 8,0468 (8,84); 7,9199 (13,89); 7,9004 (10,87); 7,55 (2,51); 7,5458 (4,01); 7,537 (2,67); 7,5322 (5,59); 7,5275 (8,22); 7,5185 (4,54); 7,5164 (3,81); 7,5121 (4,94); 7,5081 (5,1); 7,5044 (4,9); 7,498 (4,2); 7,4932 (2,19); 7,4845 (2,72);

No. Ib-60, Solvent: <[$D_6$]-DMSO>, Spectrometer: 399.95 MHz 7,4799 (1,87); 7,2861 (4,8); 7,2773 (5,85); 7,2748 (5,7); 7,2651 (4,97); 7,2584 (16); 7,2388 (9,85); 3,6313 (3,64); 3,6153 (10,06); 3,5998 (10,35); 3,5839 (4,07); 3,5604 (0,33); 3,3245 (118,47); 3,0774 (6,8); 3,061 (12,97); 3,0446 (6,19); 2,6759 (0,65); 2,6714 (0,93); 2,6667 (0,66); 2,5248 (2,6); 2,52 (4,21); 2,5114 (50,63); 2,5069 (101,96); 2,5023 (135, 03); 2,4977 (97,51); 2,4932 (46,2); 2,3337 (0,65); 2,329 (0,89); 2,3246 (0,65); 1,3362 (0,42); 1,2987 (0,71); 1,2588 (1); 1,2496 (0,45); 0,0079 (2,24); −0,0002 (64,63); −0,0086 (1,97)

No. Ib-60, Solvent: <[$D_6$]-DMSO>, Spectrometer: 399.95 MHz 8,5326 (2,71); 8,5185 (5,3); 8,5041 (2,67); 8,1283 (7,82); 8,109 (9,69); 7,9488 (16); 7,9293 (13,14); 7,6361 (7,96); 7,6342 (8,92); 7,6168 (9,21); 7,6142 (9,76); 7,4365 (3,52); 7,4335 (3,78); 7,4272 (0,58); 7,4179 (10,04); 7,415 (8,8); 7,4087 (0,68); 7,4055 (0,7); 7,3994 (8,61); 7,3963 (7,91); 7,3603 (5,75); 7,3555 (8,7); 7,3412 (6,93); 7,3362 (11,78); 7,3267 (11,72); 7,322 (9,96); 7,317 (5,01); 7,3085 (7,94); 7,3042 (6,09); 5,7571 (0,4); 3,6279 (4,2); 3,6118 (11,36); 3,5964 (11,72); 3,5804 (4,68); 3,324 (93,87); 3,0758 (7,44); 3,0594 (14,17); 3,043 (6,62); 2,6756 (0,6); 2,671 (0,82); 2,6664 (0,59); 2,5244 (2,3); 2,5197 (3,52); 2,511 (44,16); 2,5065 (89,44); 2,5019 (118,65); 2,4973 (85,56); 2,4927 (40, 42); 2,3333 (0,56); 2,3287 (0,78); 2,324 (0,55); 1,2587 (0,45); 1,2351 (0,69); 0,008 (2,12); −0,0002 (64,08); −0,0085 (1,93)

No. Ib-61, Solvent: <[$D_6$]-DMSO>, Spectrometer: 399.95 MHz 8,4995 (3,2); 8,4854 (6,21); 8,4713 (3,15); 8,1467 (8,78); 8,1273 (10,62); 7,9524 (16); 7,9329 (13,42); 7,8696 (10,05); 7,8676 (10,3); 7,8498 (10,79); 7,8478 (10,48); 7,4473 (4,68); 7,4447 (4,79); 7,4285 (10,65); 7,4259 (10,54); 7,4098 (6,71); 7,4072 (6,44); 7,2649 (9,35); 7,261 (10,18); 7,246 (8,09); 7,2421 (7,87); 7,1743 (5,78); 7,1702 (5,48); 7,155 (8,68); 7,151 (7,99); 7,1361 (5,02); 7,1319 (4,5); 5,7569 (0,85); 3,6158 (4,46); 3,5996 (12,38); 3,5843 (12,87); 3,5682 (4,99); 3,3235 (85,29); 3,0832 (8,22); 3,0667 (15,87); 3,0502 (7,29); 2,6755 (0,71); 2,6709 (0,96); 2,6664 (0,69); 2,5241 (3,13); 2,5107 (54,99); 2,5064 (107,18); 2,5018 (139,98); 2,4973 (102,13); 2,4929 (49,36); 2,3332 (0,69); 2,3287 (0,95); 2,3241 (0,69); 2,3199 (0,33); 1,2986 (0,42); 1,2588 (0,56); 1,2496 (0,38); 1,2351 (0,45); 0,008 (2,63); −0,0002 (66,5); −0,0085 (2,19)

No. Ib-62, Solvent: <[$D_6$]-DMSO>, Spectrometer: 399.95 MHz 8,5395 (2,58); 8,5252 (4,93); 8,5108 (2,52); 8,3923 (0,53); 8,1113 (7,36); 8,0919 (9,23); 8,0634 (0,35); 7,9415 (14,61); 7,933 (0,71); 7,922 (11,86); 7,8581 (0,39); 7,6527 (0,4); 7,6326 (0,46); 7,4791 (3,84); 7,476 (4,94); 7,4604 (8,27); 7,459 (9,64); 7,4569 (10,62); 7,4435 (5,17); 7,4381 (5,56); 7,4267 (8,35); 7,4212 (8,53); 7,4073 (4,11); 7,4014 (5,4); 7,3936 (3,92); 7,3897 (3,52); 7,3835 (1,14); 7,3748 (9,27); 7,3712 (9,59); 7,3551 (16); 7,351 (9,88); 7,3497 (9,36); 7,3371 (3,87); 7,332 (2,17); 7,2501 (0,41); 7,2307 (0,36); 3,6337 (3,97); 3,6177 (10,79); 3,6022 (11,12); 3,5863 (4,5); 3,5501 (0,37); 3,5347 (0,36); 3,3236 (83,87); 3,0733 (7,12); 3,0569 (13,42); 3,0407 (6,46); 2,6756 (0,6); 2,671 (0,82); 2,6664 (0,59); 2,5244 (2,32); 2,5196 (3,8); 2,511 (45,88); 2,5065 (92,41); 2,5019 (122,6); 2,4973 (89,05); 2,4928 (42, 5); 2,3378 (0,33); 2,3331 (0,72); 2,3262 (1,59); 1,3361 (1,23); 1,2986 (0,73); 1,2587 (1,07); 1,2496 (1,57); 1,2347 (1,25); 0,008 (2,13); −0,0002 (60,39); −0,0085 (1,9)

No. Ib-63, Solvent: <[$D_6$]-DMSO>, Spectrometer: 399.95 MHz 8,6202 (3); 8,6061 (5,74); 8,5918 (2,88); 8,1068 (8,17); 8,0874 (10,4); 7,9414 (16); 7,9219 (12,84); 7,7685 (6,9); 7,7491 (9,24); 7,7317 (3,07); 7,7131 (7,95); 7,6944 (5,65); 7,6513 (5,62); 7,6322 (7,06); 7,6132 (2,59); 7,4626 (8,39); 7,4438 (7,26); 3,6312 (4,41); 3,6148 (12,14); 3,5996 (12,53); 3,5834 (4,84); 3,3237 (93,22); 3,0608 (7,95); 3,0442 (15,43); 3,0276 (7,03); 2,6756 (0,8); 2,6711 (1,08); 2,6665 (0,78); 2,6621 (0,37); 2,5244 (3,4); 2,5111 (61,64); 2,5066 (119,84); 2,502 (155,26); 2,4974 (112,22); 2,4929 (53); 2,3377 (0,36); 2,3333 (0,76); 2,3288 (1,04); 2,3242 (0,73); 1,299 (0,36); 1,2588 (0,54); 0,0079 (2,86); −0,0002 (73,47); −0,0085 (2,4)

No. Ib-64, Solvent: <[$D_6$]-DMSO>, Spectrometer: 399.95 MHz 8,8194 (2,58); 8,8053 (4,81); 8,791 (2,46); 8,3159 (0,39); 8,0717 (0,51); 8,0616 (7,23); 8,0422 (9,66); 7,932 (16); 7,9125 (12,14); 7,5319 (1,91); 7,5252 (0,33); 7,5153 (4,11); 7,5107 (3,36); 7,4987 (2,75); 7,4941 (7,6); 7,4897 (2,59); 7,4774 (3,53); 7,473 (4,46); 7,4564 (2,03); 7,2157 (0,33); 7,1754 (1,57); 7,1722 (2,09); 7,1649 (12,75); 7,1537 (2,1); 7,1455 (15,63); 7,1388 (2,76); 7,1355 (1,84); 7,1246 (10,66); 7,1171 (1,81); 4,056 (0,41); 4,0381 (1,25); 4,0203 (1,25); 4,0025 (0,42); 3,6494 (4,13); 3,6333 (11,08); 3,6179 (11,36); 3,6018 (4,59); 3,3239 (196,04); 3,061 (7,4); 3,0446 (14); 3,0281 (6,76); 2,8573 (1,13); 2,6802 (0,38); 2,6757 (0,8); 2,6711 (1,12); 2,6665 (0,81); 2,6618 (0,37); 2,5245 (3,38); 2,5197 (5,4); 2,5111 (62); 2,5066 (123,95); 2,502 (163,34); 2,4974 (116,58); 2,4928 (54,33); 2,3378 (0,38); 2,3333 (0,81); 2,3288 (1,12); 2,3242 (0,8); 2,3198 (0,36); 1,989 (5,63); 1,3361 (1,05); 1,2497 (1,36); 1,1929 (1,52); 1,1751 (3,06); 1,1573 (1,51); 0,9346 (0,32); 0,008 (1,37); −0,0002 (40,17); −0,0086 (1,16)

No. Ib-65, Solvent: <[$D_6$]-DMSO>, Spectrometer: 399.95 MHz 8,3879 (3,25); 8,2878 (9,04); 8,2822 (9,29); 7,769 (6,03); 7,7628 (5,97); 7,7486 (6,92); 7,7423 (6,82); 7,535 (7,46); 7,519 (9,68); 7,516 (11,22); 7,5011 (6,87); 7,4991 (6,76); 7,4964 (6,5); 7,4921 (2,5); 7,4833 (3,07); 7,4787 (1,78); 7,4585 (11,12); 7,438 (9,73); 7,2896 (4,5); 7,2783 (5,72); 7,2758 (5,96); 7,27 (4,42); 7,2645 (5,82); 7,259 (10,08); 7,2574 (10,06); 7,2407 (9,4); 3,5267 (4,03); 3,5099 (10,59); 3,495 (10,9); 3,4784 (4,43); 3,3283 (1617,53); 2,8704 (7,94); 2,8534 (16); 2,8363 (7,21); 2,7109 (1,84); 2,6796 (1,87); 2,6752 (3,83); 2,6706 (5,21); 2,6661 (3,7); 2,6615 (1,75); 2,5409 (518,88); 2,524 (17,12); 2,5192 (25,92); 2,5106 (285, 07); 2,5061 (570,05); 2,5015 (752,38); 2,4969 (542,38); 2,4924 (257,8); 2,3672 (1,77); 2,3375 (1,65); 2,3329 (3,54); 2,3283 (4,89); 2,3237 (3,5); 2,3192 (1,62); 2,2883 (0,4); 2,0743 (7,92); 1,2352 (0,6); 1,1469 (0,52); 0,008 (1,56); −0,0002 (42,99); −0,0086 (1,14)

No. Ib-66, Solvent: <[$D_6$]-DMSO>, Spectrometer: 399.95 MHz 8,7858 (2,25); 8,7724 (4,17); 8,7588 (2,25); 8,2839 (9,88); 8,2781 (9,91); 7,7725 (6,59); 7,7662 (6,47); 7,752 (7,47); 7,7457 (7,3); 7,5306 (1,8); 7,5139 (3,83); 7,5092 (3,26); 7,4972 (2,4); 7,4927 (7,29); 7,4884 (2,54); 7,476 (3,39); 7,4716 (4,42); 7,4588 (12,42); 7,4383 (10,69); 7,1771 (1,33); 7,1739 (1,9); 7,1663 (11,98); 7,1555 (1,88); 7,1528 (2,46); 7,147 (14,39); 7,1369 (1,74); 7,1263 (9,98); 7,1185 (1,59); 3,5346 (4,43); 3,518 (11,27); 3,5032 (11,43); 3,4867 (4,88); 3,397 (0,48); 3,3308 (1140,9); 3,2844 (0,72); 3,2737 (0,57); 3,2547 (0,35); 2,9958 (0,58); 2,9811 (0,77); 2,9779 (0,63); 2,9638 (0,69); 2,8528 (8,19); 2,836 (16); 2,8193 (7,39); 2,7108 (0,38); 2,6798 (0,96); 2,6754 (2,06); 2,6708 (2,79); 2,6662 (1,99); 2,6616 (0,98); 2,5411 (103,07); 2,5242 (8,02); 2,5194 (12,49); 2,5108 (150,38); 2,5063 (305,14); 2,5017 (406,07); 2,4971 (294,04); 2,4926 (140,57); 2,3671 (0,41); 2,3375 (0,92); 2,3331 (1,92); 2,3285 (2,69); 2,3239 (1,93); 2,3193 (0,89); 2,1265 (0,74); 2,1235 (0,75); 2,0743 (3,08); 0,985 (0,82); 0,9671 (1,65); 0,9492 (0,75); −0,0002 (8,3)

No. Ib-67, Solvent: <[D₆]-DMSO>, Spectrometer: 399.95 MHz 8,8337 (3,52); 8,8182 (6,62); 8,8032 (3,46); 8,6156 (13,41); 8,6105 (13,29); 8,3153 (2,45); 8,0624 (8,74); 8,0559 (8,57); 8,0414 (9,73); 8,035 (9,45); 7,6903 (14,73); 7,6694 (13,09); 7,5533 (2,6); 7,5487 (3,01); 7,54 (2,9); 7,5352 (6,09); 7,5323 (4,64); 7,5304 (4,97); 7,528 (4,47); 7,5209 (4,47); 7,5196 (4,48); 7,5171 (5,06); 7,5143 (6,71); 7,5095 (4,05); 7,5008 (3,34); 7,4962 (3,75); 7,4806 (5,18); 7,4761 (5,03); 7,4621 (9,85); 7,4576 (9,55); 7,443 (6,83); 7,4388 (5,58); 7,2942 (7,89); 7,2753 (16); 7,2699 (9,32); 7,2673 (8,23); 7,2585 (14,56); 7,2567 (14,13); 7,2489 (6,49); 7,2466 (6,51); 7,24 (7,34); 7,2375 (6,11); 5,7557 (10,13); 4,1288 (5,48); 4,113 (5,53); 4,0945 (12,26); 4,0785 (12); 4,06 (6,11); 4,0442 (5,86); 3,3248 (1190,69); 2,9433 (0,87); 2,6754 (4,56); 2,6708 (6,4); 2,6663 (4,66); 2,6618 (2,12); 2,5925 (0,37); 2,5242 (18,56); 2,5194 (29,27); 2,5108 (351,41); 2,5063 (715,6); 2,5018 (950,6); 2,4972 (690,72); 2,4927 (332,12); 2,3463 (0,38); 2,3377 (2,12); 2,3331 (4,58); 2,3285 (6,31); 2,3239 (4,59); 2,3196 (2,17); 2,0602 (0,54); 2,0407 (0,54); 1,9887 (0,44); 1,3357 (0,72); 1,2495 (0,96); 1,2354 (0,44); 1,1481 (0,65); −0,0002 (4,84)

No. Ib-68, Solvent: <[D₆]-DMSO>, Spectrometer: 399.95 MHz 8,969 (1,7); 8,9534 (3,45); 8,9378 (1,74); 8,6458 (5,79); 8,6406 (5,82); 8,0957 (3,84); 8,0893 (3,78); 8,0747 (4,24); 8,0683 (4,19); 7,6981 (6,4); 7,6773 (5,78); 7,4815 (1,68); 7,4777 (2,72); 7,4616 (6,89); 7,4577 (8,42); 7,4515 (4,51); 7,4384 (5,67); 7,4341 (5,58); 7,4187 (2,44); 7,4142 (2,56); 7,4052 (0,34); 7,3985 (3,41); 7,3939 (3,09); 7,3798 (5,2); 7,3756 (5,2); 7,3624 (3,05); 7,3582 (2,82); 7,3076 (5,68); 7,3044 (5,33); 7,3035 (5,19); 7,2893 (4,2); 7,2851 (3,7); 5,7564 (16); 4,1402 (2,33); 4,1244 (2,37); 4,1058 (5,25); 4,0899 (5,14); 4,0712 (2,65); 4,0557 (2,74); 4,0393 (1,7); 4,0215 (1,67); 4,0037 (0,56); 3,331 (20,27); 2,5256 (0,45); 2,5208 (0,68); 2,5122 (9,03); 2,5077 (18,47); 2,5031 (24,58); 2,4986 (17,96); 2,4941 (8,72); 1,9902 (7,11); 1,3383 (0,35); 1,2502 (0,45); 1,1937 (1,94); 1,1759 (3,85); 1,1581 (1,89)

No. Ib-69, Solvent: <[D₆]-DMSO>, Spectrometer: 399.95 MHz 8,9514 (2,59); 8,9359 (5,01); 8,9203 (2,52); 8,6573 (8,16); 8,652 (8,12); 8,1054 (5,02); 8,0991 (4,89); 8,0844 (5,51); 8,0781 (5,28); 7,7001 (8,53); 7,6792 (7,69); 7,6361 (6,74); 7,634 (6,74); 7,6164 (7,88); 7,6141 (7,62); 7,4426 (2,67); 7,4401 (2,82); 7,4241 (7,27); 7,4215 (7,1); 7,4056 (5,68); 7,4028 (5,2); 7,3727 (4,48); 7,3681 (5,23); 7,3533 (5,75); 7,3488 (6,25); 7,3342 (2,63); 7,3298 (2,47); 7,2738 (7,29); 7,2694 (6,91); 7,2552 (5,88); 7,2508 (5,35); 5,7565 (16); 4,1348 (3,13); 4,1191 (3,25); 4,1004 (6,83); 4,0847 (6,63); 4,0659 (3,51); 4,0502 (3,3); 4,0391 (1,09); 4,0212 (0,89); 3,33 (33,34); 2,5072 (28,26); 2,5028 (35,81); 2,4984 (26,54); 1,99 (3,54); 1,1935 (0,96); 1,1757 (1,86); 1,1579 (0,92); 0,0077 (0,44); −0,0002 (7,87); −0,008 (0,34)

No. Ib-70, Solvent: <[D₆]-DMSO>, Spectrometer: 399.95 MHz 8,8969 (4,38); 8,8813 (8,71); 8,8657 (4,26); 8,6686 (13,99); 8,6633 (13,97); 8,1124 (9,29); 8,106 (9,08); 8,0914 (10,2); 8,085 (9,97); 7,8694 (13,07); 7,8674 (13,94); 7,8498 (14,07); 7,8476 (14,06); 7,6994 (15,35); 7,6785 (13,93); 7,4539 (6,71); 7,4512 (6,94); 7,4351 (14,5); 7,4324 (14,87); 7,4164 (9,23); 7,4136 (9); 7,2064 (11,15); 7,2026 (15,43); 7,1855 (15,65); 7,1836 (16); 7,1665 (13,3); 7,1623 (10,55); 7,1473 (7,61); 7,1432 (6,23); 5,7565 (15,75); 4,124 (5,3); 4,1082 (5,4); 4,0896 (11,97); 4,0738 (11,61); 4,0552 (6,19); 4,0388 (6,97); 4,0208 (1,65); 4,003 (0,54); 3,3288 (88,01); 2,6762 (0,43); 2,6715 (0,57); 2,667 (0,42); 2,525 (2,07); 2,5201 (3,23); 2,5116 (33,32); 2,5071 (66,4); 2,5025 (87,11); 2,4979 (62,89); 2,4934 (29,87); 2,3338 (0,4); 2,3292 (0,54); 2,3247 (0,4); 1,9897 (6,59); 1,3372 (0,74); 1,2498 (0,96); 1,2345 (0,33); 1,1932 (1,83); 1,1754 (3,67); 1,1576 (1,81); −0,0002 (2,39)

No. Ib-71, Solvent: <[D₆]-DMSO>, Spectrometer: 399.95 MHz 9,2461 (2,68); 9,2306 (5,36); 9,2149 (2,67); 8,6158 (9,19); 8,6104 (9,21); 8,0665 (6,24); 8,0601 (6,07); 8,0456 (6,92); 8,0391 (6,74); 7,7008 (10,46); 7,68 (9,37); 7,5481 (1,93); 7,5315 (4,04); 7,5269 (3,46); 7,5148 (2,58); 7,5103 (7,56); 7,5058 (2,6); 7,4936 (3,56); 7,4891 (4,43); 7,4725 (2,02); 7,1799 (1,5); 7,1768 (2,12); 7,1697 (12,91); 7,1502 (16); 7,1294 (10,62); 7,122 (1,82); 5,7571 (2,86); 4,1737 (3,76); 4,1579 (3,78); 4,1391 (8,52); 4,1233 (8,32); 4,1045 (4,27); 4,0887 (4,1); 3,3284 (45,35); 2,6721 (0,4); 2,5256 (1,16); 2,5207 (1,77); 2,5122 (21,98); 2,5076 (44,63); 2,503 (59,06); 2,4984 (42,43); 2,4939 (20,05); 2,3298 (0,38); 1,3375 (0,7); 1,2501 (0,89)

No. Ib-72, Solvent: <[D₆]-DMSO>, Spectrometer: 399.95 MHz 9,0228 (3,31); 9,0075 (6,42); 8,992 (3,26); 8,6489 (10,42); 8,6438 (10,34); 8,1 (6,18); 8,0938 (6,06); 8,079 (6,82); 8,0728 (6,54); 7,7725 (6,98); 7,753 (9,71); 7,7396 (3,47); 7,7211 (8,18); 7,7015 (16); 7,6804 (9,97); 7,665 (6,09); 7,6459 (7,34); 7,6269 (2,65); 7,4169 (8,41); 7,3983 (7,43); 5,7573 (5,45); 4,1488 (3,87); 4,133 (4,06); 4,1139 (8,42); 4,0982 (8,16); 4,0789 (4,34); 4,0632 (4,05); 4,039 (1,25); 4,0212 (1,19); 4,0034 (0,41); 3,331 (62,98); 2,6722 (0,4); 2,5073 (45,84); 2,503 (57,55); 2,4988 (43,55); 2,3297 (0,36); 1,9898 (4,83); 1,3379 (0,49); 1,2501 (0,58); 1,1934 (1,32); 1,1756 (2,54); 1,1578 (1,25); −0,0002 (11,89)

TABLE C

Compounds of formula (Ic)

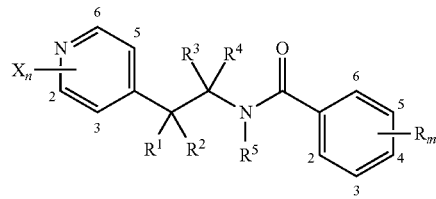

(Ic)

| No. | $X_n$ | $R^1$ | $R^2$ | $R^3$ | $R^4$ | $R^5$ | $R_m$ | cf. |
|---|---|---|---|---|---|---|---|---|
| Ic-1 | 2-F<br>3-F<br>5-F<br>6-F | H | H | H | H | H | 2-CF₃ | P8<br>cpd. 4 |
| Ic-2 | 2-F<br>3-F<br>5-F<br>6-F | H | H | H | H | H | 2-I | P8<br>cpd. 5 |
| Ic-3 | 2-F<br>3-F<br>5-F<br>6-F | H | H | H | H | H | 2-Br | P8<br>cpd. 6 |
| Ic-4 | 2-F<br>3-F<br>5-F<br>6-F | H | H | H | H | H | 2-Cl | P8<br>cpd. 7 |
| Ic-5 | 2-Me<br>5-Cl | H | H | H | H | H | 2-CF₃ | P8<br>cpd. 1 |
| Ic-6 | 2-Me<br>5-Cl | H | H | H | H | H | H | P8<br>cpd. 2 |
| Ic-7 | 2-F<br>5-F | H | H | H | H | H | 2-CF₃ | P8<br>cpd. 3 |

TABLE C-continued

Compounds of formula (Ic)

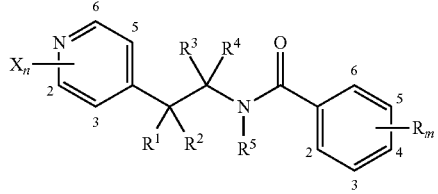

(Ic)

| No. | $X_n$ | $R^1$ | $R^2$ | $R^3$ | $R^4$ | $R^5$ | $R_m$ | cf. |
|---|---|---|---|---|---|---|---|---|
| Ic-8[2] | 2-F<br>3-F<br>5-F<br>6-F | H | (CH$_2$)$_4$ | H | H |  | 2-CF$_3$ | NMR |
| Ic-9 | 3-Cl<br>5-Cl | H | H | H | H | H | 2-CF$_3$ | P8<br>NMR |
| Ic-10 | 3-Cl<br>5-Cl | H | H | H | H | H | H | P8<br>NMR |
| Ic-11 | 3-Cl<br>5-Cl | H | H | H | H | H | 3-Cl | P8<br>NMR |
| Ic-12 | 3-Cl<br>5-Cl | H | H | H | H | H | 4-Cl | P8<br>NMR |
| Ic-13 | 3-Cl<br>5-Cl | H | H | H | H | H | 3-Cl<br>4-Cl | P8<br>NMR |
| Ic-14 | 3-Cl | H | H | H | H | H | 2-CF$_3$ | P8<br>NMR |
| Ic-15 | 3-Cl | H | H | H | H | H | H | P8<br>NMR |
| Ic-16 | 3-Cl | H | H | H | H | H | 4-Me | P8<br>NMR |
| Ic-17 | 3-Cl<br>5-Cl | H | H | H | H | H | 2-F | P8<br>NMR |
| Ic-18 | 3-Cl<br>5-Cl | H | H | H | H | H | 4-t-Bu | P8<br>NMR |
| Ic-19 | 3-Cl<br>5-Cl | H | H | H | H | H | 3-OMe<br>5-OMe | P8<br>NMR |
| Ic-20 | 3-Cl<br>5-Cl | H | H | H | H | H | 3-Br | P8<br>NMR |
| Ic-21 | 3-Cl<br>5-Cl | H | H | H | H | H | 3-OMe | P8<br>NMR |
| Ic-22 | 3-Cl<br>5-Cl | H | H | H | H | H | 2-OMe | P8<br>NMR |
| Ic-23 | 3-Cl<br>5-Cl | H | H | H | H | H | 3-Me | P8<br>NMR |
| Ic-24 | 3-Cl<br>5-Cl | H | H | H | H | H | 2-F<br>5-Cl | P8<br>NMR |
| Ic-25 | 3-Cl<br>5-Cl | H | H | H | H | H | 2-F<br>4-Cl | P8<br>NMR |
| Ic-26 | 3-Cl<br>5-Cl | H | H | H | H | H | 3-F<br>4-F | P8<br>NMR |
| Ic-27 | 3-Cl<br>5-Cl | H | H | H | H | H | 2-Me | P8<br>NMR |
| Ic-28 | 3-Cl<br>5-Cl | H | H | H | H | H | 2-Cl | P8<br>NMR |
| Ic-29 | 3-Cl<br>5-Cl | H | H | H | H | H | 2-Cl<br>4-F | P8<br>NMR |
| Ic-30 | 3-Cl<br>5-Cl | H | H | H | H | H | 4-CF$_3$ | P8<br>NMR |
| Ic-31 | 3-Cl<br>5-Cl | H | H | H | H | H | 3-CF$_3$ | P8<br>NMR |
| Ic-32 | 3-Cl<br>5-Cl | H | H | H | H | H | 2-Cl<br>4-Cl | P8<br>NMR |
| Ic-33 | 3-Cl<br>5-Cl | H | H | H | H | H | 3-Cl<br>5-Cl | P8<br>NMR |
| Ic-34 | 3-Cl<br>5-Cl | H | H | H | H | H | 3,4-OCH$_2$—O— | NMR |
| Ic-35 | 3-Cl<br>5-Cl | H | H | H | H | H | 4-Et | P8<br>NMR |
| Ic-36 | 3-Cl<br>5-Cl | H | H | H | H | H | 2-F<br>4-F | P8<br>NMR |
| Ic-37 | 3-Cl<br>5-Cl | H | H | H | H | H | 4-F | P8<br>NMR |
| Ic-38 | 3-Cl<br>5-Cl | H | H | H | H | H | 4-NO$_2$ | P8<br>NMR |
| Ic-39 | 3-Cl<br>5-Cl | H | H | H | H | H | 3-F | P8<br>NMR |
| Ic-40 | 3-Cl<br>5-Cl | H | H | H | H | H | 4-Br | P8<br>NMR |
| Ic-41 | 3-Cl<br>5-Cl | H | H | H | H | H | 3-OMe<br>4-OMe | P8<br>NMR |
| Ic-42 | 3-Cl<br>5-Cl | H | H | H | H | H | 2-F<br>6-F | P8<br>NMR |
| Ic-43 | 3-Cl<br>5-Cl | H | H | H | H | H | 3-CN | P8<br>NMR |
| Ic-44 | 3-Cl | H | H | H | H | H | 4-OMe | P8<br>NMR |
| Ic-45 | 3-Cl | H | H | H | H | H | 4-NO$_2$ | P8<br>NMR |
| Ic-46 | 3-Cl | H | H | H | H | H | 4-Me | P8<br>NMR |
| Ic-47 | 3-Cl<br>5-Cl | H | H | H | H | H | 4-OMe | P8<br>NMR |
| Ic-48 | 3-Cl<br>5-Cl | H | H | H | H | H | 4-CN | P8<br>NMR |
| Ic-49 | 3-Cl<br>5-Cl | H | H | H | H | H | 3-F<br>5-F | P8<br>NMR |
| Ic-50 | 2-OMe | H | H | H | H | H | 4-F | P8<br>NMR |
| Ic-51 | 2-OMe | H | H | H | H | H | 4-OMe | P8<br>NMR |
| Ic-52 | 2-OMe | H | H | H | H | H | 3-Cl<br>4-Cl | P8<br>NMR |
| Ic-53 | 2-OMe | H | H | H | H | H | 2-F | P8<br>NMR |
| Ic-54 | 2-OMe | H | H | H | H | H | 4-t-Bu | P8<br>NMR |
| Ic-55 | 2-OMe | H | H | H | H | H | 3-OMe<br>5-OMe | P8<br>NMR |
| Ic-56 | 2-OMe | H | H | H | H | H | 3-CF$_3$ | P8<br>NMR |
| Ic-57 | 2-OMe | H | H | H | H | H | 3,4-OCH$_2$O— | P8<br>NMR |
| Ic-58 | 2-OMe | H | H | H | H | H | 4-Et | P8<br>NMR |
| Ic-59 | 2-OMe | H | H | H | H | H | 2-OMe | P8<br>NMR |
| Ic-60 | 2-OMe | H | H | H | H | H | 4-CF$_3$ | P8<br>NMR |
| Ic-61 | 2-OMe | H | H | H | H | H | 3-Me | P8<br>NMR |
| Ic-62 | 2-OMe | H | H | H | H | H | 2-F<br>4-F | P8<br>NMR |
| Ic-63 | 2-OMe | H | H | H | H | H | 3-F<br>5-F | P8<br>NMR |
| Ic-64 | 2-OMe | H | H | H | H | H | 2-F<br>5-Cl | P8<br>NMR |
| Ic-65 | 2-OMe | H | H | H | H | H | 3-Br | P8<br>NMR |
| Ic-66 | 2-OMe | H | H | H | H | H | 4-Br | P8<br>NMR |
| Ic-67 | 2-OMe | H | H | H | H | H | 2-F<br>6-F | P8<br>NMR |
| Ic-68 | 2-OMe | H | H | H | H | H | 3-CN | P8<br>NMR |
| Ic-69 | 2-OMe | H | H | H | H | H | 2-Cl<br>4-F | P8<br>NMR |
| Ic-70 | 2-OMe | H | H | H | H | H | 4-CN | P8<br>NMR |

TABLE C-continued

Compounds of formula (Ic)

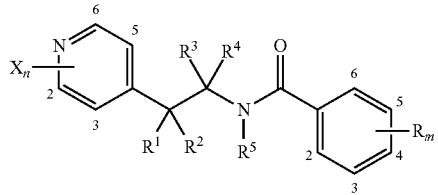

(Ic)

| No. | $X_n$ | $R^1$ | $R^2$ | $R^3$ | $R^4$ | $R^5$ | $R_m$ | cf. |
|---|---|---|---|---|---|---|---|---|
| Ic-71 | 2-OMe | H | H | H | H | H | 4-NO$_2$ | P8 NMR |
| Ic-72 | 2-OMe | H | H | H | H | H | 3-F | P8 NMR |
| Ic-73 | 2-OMe | H | H | H | H | H | 3-F 4-F | P8 NMR |
| Ic-74 | 2-OMe | H | H | H | H | H | 2-Cl | P8 NMR |
| Ic-75 | 2-OMe | H | H | H | H | H | 3-Cl | P8 NMR |
| Ic-76 | 2-OMe | H | H | H | H | H | 2-CF$_3$ | P8 NMR |
| Ic-77 | 2-OMe | H | H | H | H | H | 3-OMe 4-OMe | P8 NMR |
| Ic-78 | 2-Me | H | H | H | H | H | H | P8 |
| Ic-79 | 2-Me | H | H | H | H | H | 4-F | P8 NMR |
| Ic-80 | 2-Me | H | H | H | H | H | 2-Cl | P8 NMR |
| Ic-81 | 2-Me | H | H | H | H | H | 2-Cl 4-Cl | P8 NMR |
| Ic-82 | 2-Me | H | H | H | H | H | 4-Cl | P8 NMR |
| Ic-83 | 2-Me | H | H | H | H | H | 4-Me | P8 NMR |
| Ic-84 | 2-Me | H | H | H | H | H | 2-F | P8 NMR |
| Ic-85 | 2-Me | H | H | H | H | H | 4-t-Bu | P8 NMR |
| Ic-86 | 2-Me | H | H | H | H | H | 3-F | P8 NMR |
| Ic-87 | 2-Me | H | H | H | H | H | 3-CF$_3$ | P8 NMR |
| Ic-88 | 2-Me | H | H | H | H | H | 4-Et | P8 NMR |
| Ic-89 | 2-Me | H | H | H | H | H | 2-OMe | P8 NMR |
| Ic-90 | 2-Me | H | H | H | H | H | 4-CF$_3$ | P8 NMR |
| Ic-91 | 2-Me | H | H | H | H | H | 3-Cl | P8 NMR |
| Ic-92 | 2-Me | H | H | H | H | H | 3-Cl 5-Cl | P8 NMR |
| Ic-93 | 2-Me | H | H | H | H | H | 3-Me | P8 NMR |
| Ic-94 | 2-Me | H | H | H | H | H | 2-F 4-F | P8 NMR |
| Ic-95 | 2-Me | H | H | H | H | H | 3-F 5-F | P8 NMR |
| Ic-96 | 2-OMe | H | H | H | H | H | 2-Cl 4-Cl | P8 NMR |
| Ic-97 | 2-OMe | H | H | H | H | H | 4-Me | P8 NMR |
| Ic-98 | 2-OMe | H | H | H | H | H | 2-Me | P8 NMR |
| Ic-99 | 2-OMe | H | H | H | H | H | 3-Cl 5-Cl | P8 NMR |
| Ic-100 | 2-OMe | H | H | H | H | H | 2-F 4-Cl | P8 |
| Ic-101 | 2-Me | H | H | H | H | H | 3,4-OCH$_2$O— | NMR |
| Ic-102 | 2-Me | H | H | H | H | H | 4-OMe | NMR |
| Ic-103 | 2-Me | H | H | H | H | H | 4-NO$_2$ | NMR |
| Ic-104 | 2-Me | H | H | H | H | H | 2-Me | P8 NMR |

TABLE C-continued

Compounds of formula (Ic)

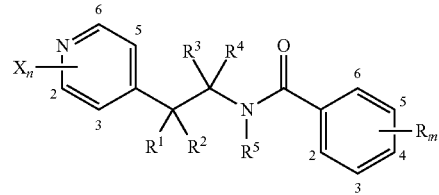

(Ic)

| No. | $X_n$ | $R^1$ | $R^2$ | $R^3$ | $R^4$ | $R^5$ | $R_m$ | cf. |
|---|---|---|---|---|---|---|---|---|
| Ic-105 | 2-OMe | H | H | H | H | H | 4-Cl | P8 NMR |
| Ic-106 | 2-OMe | H | H | H | H | H | H | P8 NMR |
| Ic-107 | 3-Cl | H | H | H | H | H | 2-Cl | P8 NMR |
| Ic-108 | 2-Cl | H | H | H | H | H | 2-CF$_3$ | P8 NMR |
| Ic-109[1] | 2-F 3-F 5-F 6-F | H | (CH$_2$)$_4$ | H | H | | 2-CF$_3$ | NMR |

[1]cis-isomer
[2]trans-isomer
[3]pure enantiomer, absolute configuration not determined No. Ic-8, Solvent: <[D$_6$]-DMSO>, Spectrometer: 399.95 MHz 8.5930 (4.34); 8.5707 (4.41); 7.7028 (8.47); 7.6835 (16.00); 7.6655 (4.47); 7.6110 (4.48); 7.5913 (5.42); 7.5730 (2.07); 7.2373 (6.21); 7.2186 (5.84); 5.3244 (0.33); 4.4056 (0.79); 4.3800 (1.82); 4.3569 (1.80); 4.3305 (0.63); 3.9048 (6.89); 3.3360 (479.87); 3.1736 (0.62); 3.1604 (0.68); 3.1489 (1.45); 3.1394 (1.64); 3.1192 (2.90); 3.1105 (2.96); 3.0903 (1.65); 3.0811 (1.51); 2.6756 (1.66); 2.6712 (2.34); 2.6667 (1.75); 2.5413 (0.95); 2.5245 (6.66); 2.5109 (134.72); 2.5066 (273.38); 2.5021 (365.93); 2.4976 (278.63); 2.4933 (145.18); 2.3994 (0.37); 2.3334 (1.82); 2.3289 (2.52); 2.3243 (1.93); 2.0254 (0.62); 2.0069 (1.36); 1.9871 (2.76); 1.9665 (2.96); 1.9321 (1.94); 1.8998 (3.15); 1.8817 (1.60); 1.8399 (4.69); 1.8093 (6.61); 1.7758 (3.24); 1.5172 (0.77); 1.4855 (3.06); 1.4571 (5.83); 1.4327 (3.35); 1.4074 (0.75); 1.3982 (0.77); 1.3501 (2.04); 1.3353 (1.26); 1.3157 (2.03); 1.2974 (2.27); 1.2881 (2.12); 1.2579 (2.77); 1.2350 (5.39); 0.8696 (0.63); 0.8537 (1.55); 0.8437 (2.14); 0.8297 (1.15); 0.1460 (0.61); 0.0080 (4.41); −0.0002 (143.78); −0.0084 (6.48); −0.1496 (0.61)

No. Ic-9, Solvent: <[D$_6$]-DMSO>, Spectrometer: 399.95 MHz 8.7437 (0.80); 8.7287 (1.51); 8.7138 (0.77); 8.6146 (16.00); 7.9526 (0.57); 7.8348 (0.41); 7.8014 (0.44); 7.7850 (2.05); 7.7657 (2.79); 7.7486 (1.15); 7.7304 (2.24); 7.7120 (1.56); 7.6618 (1.47); 7.6426 (1.92); 7.6235 (0.76); 7.5051 (2.18); 7.4861 (1.86); 3.5364 (1.18); 3.5202 (2.74); 3.5029 (2.78); 3.4866 (1.32); 3.3917 (0.38); 3.3412 (248.53); 3.1741 (2.47); 3.1559 (4.29); 3.1386 (2.16); 3.1252 (0.41); 2.8905 (3.70); 2.7303 (3.06); 2.6762 (0.67); 2.6717 (0.93); 2.6673 (0.68); 2.5573 (0.44); 2.5439 (0.90); 2.5251 (2.73); 2.5115 (51.58); 2.5072 (104.60); 2.5027 (139.39); 2.4981 (105.49); 2.4938 (54.29); 2.3338 (0.65); 2.3294 (0.92); 2.3250 (0.70); 1.2757 (2.27); 1.2592 (4.69); 1.2434 (2.97); 1.2272 (0.68); −0.0002 (4.60)

No. Ic-10, Solvent: <[D$_6$]-DMSO>, Spectrometer: 399.95 MHz 8.6707 (0.84); 8.6560 (1.61); 8.6414 (0.83); 8.5785 (16.00); 7.9562 (0.62); 7.9386 (0.67); 7.9351 (0.57); 7.7769 (4.33); 7.7644 (1.31); 7.7595 (5.10); 7.7557 (3.83); 7.6278 (0.35); 7.5298 (0.83); 7.5267 (0.69); 7.5235 (0.71); 7.5186 (0.78); 7.5117 (2.64); 7.5057 (1.32); 7.4970 (1.50); 7.4936 (2.32); 7.4901 (1.36); 7.4854 (0.55); 7.4641 (3.97); 7.4488 (2.80); 7.4452 (5.11); 7.4277 (2.04); 7.4247 (1.31); 7.0865 (0.38); 3.9048 (2.88); 3.5875 (1.26); 3.5712 (3.56); 3.5556 (3.77); 3.5394 (1.48); 3.4332 (0.35); 3.4199 (0.36); 3.4045 (0.47); 3.3452 (310.51); 3.3142 (0.85); 3.3054 (0.57); 3.1913 (2.57); 3.1747 (5.54); 3.1581 (2.33); 3.0945 (0.45); 2.6767 (0.49); 2.6721 (0.67); 2.6678 (0.52); 2.5425 (0.52); 2.5256 (2.19); 2.5119 (37.75); 2.5076 (75.85); 2.5031 (101.60); 2.4986 (77.57); 2.4943 (40.42); 2.3343 (0.47); 2.3299 (0.65); 2.3253 (0.49); 1.2556 (1.25); 1.2420 (0.57); 0.0080 (1.47); −0.0002 (45.73); −0.0084 (2.12)

No. Ic-11, Solvent: <[D$_6$]-DMSO>, Spectrometer: 399.95 MHz 8.8063 (0.83); 8.7917 (1.61); 8.7769 (0.81); 8.5860 (16.00); 7.8070 (2.28); 7.8026 (3.91); 7.7982 (2.60); 7.7484 (1.49); 7.7456 (2.09); 7.7420 (1.40); 7.7291 (1.79); 7.7262 (2.41); 7.7227 (1.61); 7.6090 (1.19); 7.6065 (1.41); 7.6039 (1.27); 7.6013 (1.19); 7.5890 (1.93); 7.5865 (1.98); 7.5839 (2.05); 7.5813 (1.67); 7.5175 (2.80); 7.4979 (4.03); 7.4783 (1.64); 3.9051 (3.31); 3.5847 (1.17); 3.5681 (3.41); 3.5526 (3.59); 3.5363 (1.39); 3.4329 (0.42); 3.3952 (0.51); 3.3789 (0.94); 3.3438 (293.68); 3.1874 (2.56); 3.1708 (5.25); 3.1614 (1.13); 3.1541 (2.20); 2.6767 (0.52); 2.6722 (0.74); 2.6678 (0.55); 2.5425 (0.73); 2.5255 (2.47); 2.5120 (42.26); 2.5077 (84.20); 2.5031 (111.68); 2.4986 (83.66); 2.4942 (42.26); 2.3344 (0.55); 2.3299 (0.76); 2.3253 (0.55); 0.0080 (0.91); −0.0002 (27.99); −0.0085 (1.11)

No. Ic-12, Solvent: <[D$_6$]-DMSO>, Spectrometer: 399.95 MHz 8.7565 (0.82); 8.7414 (1.62); 8.7271 (0.82); 8.5776 (16.00); 7.8035 (0.73); 7.7972 (5.79); 7.7924 (1.99); 7.7805 (2.09); 7.7757 (6.96); 7.7695 (0.95); 7.5502 (0.90); 7.5439 (6.93); 7.5391 (2.12); 7.5271 (1.91); 7.5224 (5.70); 7.5161 (0.75); 3.9050 (1.40); 3.5809 (1.11); 3.5645 (3.23); 3.5490 (3.39); 3.5329 (1.30); 3.3418 (270.48); 3.1828 (2.40); 3.1663 (4.89); 3.1496 (2.09); 2.6766 (0.50); 2.6720 (0.69); 2.6677 (0.52); 2.5424 (0.59); 2.5254 (2.28); 2.5118 (40.03); 2.5075 (79.52); 2.5030 (105.40); 2.4984 (79.26); 2.4941 (40.40); 2.3343 (0.51); 2.3297 (0.70); 2.3251 (0.53); 0.0080 (0.65); −0.0002 (19.46); −0.0084 (0.79)

No. Ic-13, Solvent: <[D$_6$]-DMSO>, Spectrometer: 399.95 MHz 8.8751 (0.80); 8.8604 (1.60); 8.8455 (0.78); 8.5862 (16.00); 7.9988 (4.31); 7.7783 (0.33); 7.7590 (10.22); 3.9052 (1.47); 3.5818 (1.05); 3.5654 (3.06); 3.5499 (3.21); 3.5336 (1.21); 3.3395 (192.38); 3.1835 (2.28); 3.1742 (1.35); 3.1670 (4.62); 3.1616 (1.59); 3.1502 (1.97); 2.6766 (0.48); 2.6721 (0.64); 2.6677 (0.49); 2.5254 (2.15); 2.5119 (37.34); 2.5076 (74.52); 2.5030 (98.82); 2.4985 (74.38); 2.4942 (37.75); 2.3343 (0.45); 2.3298 (0.64); 2.3252 (0.47); 0.0080 (1.65); −0.0002 (47.71); −0.0084 (1.91)

No. Ic-14, Solvent: <[D$_6$]-DMSO>, Spectrometer: 399.95 MHz 8.6647 (2.06); 8.6506 (3.86); 8.6368 (2.04); 8.5931 (16.00); 8.5044 (0.38); 8.4640 (10.04); 8.4517 (10.35); 8.3181 (0.64); 7.7765 (4.86); 7.7570 (6.43); 7.7324 (2.14); 7.7146 (5.42); 7.6961 (3.92); 7.6541 (3.85); 7.6351 (4.91); 7.6163 (1.80); 7.4531 (5.81); 7.4337 (13.16); 7.4212 (8.31); 4.1212 (0.51); 4.1079 (0.54); 3.9042 (7.57); 3.5770 (3.40); 3.5600 (8.74); 3.5450 (8.96); 3.5281 (3.81); 3.5074 (0.45); 3.4928 (0.41); 3.4753 (0.51); 3.4636 (0.52); 3.3496 (924.79); 3.1746 (1.88); 3.1615 (1.81); 2.9922 (6.46); 2.9751 (13.01); 2.9578 (5.78); 2.6769 (1.24); 2.6724 (1.71); 2.6679 (1.28); 2.5255 (6.45); 2.5120 (98.13); 2.5078 (193.12); 2.5033 (253.14); 2.4988 (190.30); 2.4946 (98.00); 2.3345 (1.15); 2.3300 (1.58); 2.3256 (1.16); 1.2340 (0.54); 0.0080 (1.62); −0.0002 (45.40); −0.0084 (2.00)

No. Ic-15, Solvent: <[D$_6$]-DMSO>, Spectrometer: 399.95 MHz 8.6193 (1.99); 8.6057 (3.70); 8.5915 (2.12); 8.5763 (16.00); 8.4281 (10.40); 8.4158 (10.70); 7.7918 (10.51); 7.7791 (3.12); 7.7743 (12.51); 7.7705 (9.25); 7.5360 (1.87); 7.5328 (1.24); 7.5243 (1.39); 7.5177 (6.36); 7.5121 (1.95); 7.5030 (3.39); 7.4997 (5.46); 7.4963 (2.94); 7.4689 (9.50); 7.4535 (6.81); 7.4498 (12.53); 7.4362 (2.00); 7.4323 (4.79); 7.4293 (2.96); 7.3925 (8.63); 7.3801 (8.38); 3.9046 (2.69); 3.5931 (3.60); 3.5761 (8.94); 3.5613 (9.14); 3.5444 (3.99); 3.5057 (0.69); 3.4727 (0.82); 3.3661 (1017.90); 3.2658 (0.81); 3.1752 (0.38); 3.1622 (0.41); 3.0236 (6.63); 3.0064 (13.35); 2.9892 (5.93); 2.6781 (0.86); 2.6736 (1.15); 2.6692 (0.86); 2.5267 (3.88); 2.5133 (64.82); 2.5090 (128.41); 2.5045 (170.09); 2.4999 (128.14); 2.4957 (64.96); 2.3357 (0.76); 2.3312 (1.07); 2.3268 (0.79); 1.3370 (0.93); 0.0080 (0.58); −0.0002 (17.36); −0.0084 (0.70)

No. Ic-16, Solvent: <[D$_6$]-DMSO>, Spectrometer: 399.95 MHz 8.5852 (1.08); 8.5710 (16.00); 8.5565 (0.84); 7.6836 (4.56); 7.6632 (5.03); 7.3119 (0.32); 7.2540 (4.18); 7.2341 (3.79); 3.9042 (6.08); 3.5694 (1.02); 3.5531 (2.93); 3.5375 (3.08); 3.5213 (1.17); 3.3887 (0.37); 3.3419 (195.96); 3.3075 (0.39); 3.1780 (2.20); 3.1615 (4.47); 3.1447 (2.00); 2.6766 (0.46); 2.6721 (0.65); 2.6676 (0.49); 2.5459 (0.40); 2.5423 (0.47); 2.5253 (2.13); 2.5118 (38.50); 2.5075 (77.27); 2.5030 (102.02); 2.4985 (76.68); 2.4941 (39.32); 2.4528 (0.39); 2.3708 (0.62); 2.3585 (0.37); 2.3383 (14.18); 2.3205 (0.72); 1.2748 (1.06); 1.2587 (2.17); 1.2434 (1.46); 1.2265 (0.35); −0.0002 (1.87)

No. Ic-17, Solvent: <[D$_6$]-DMSO>, Spectrometer: 399.95 MHz 8.5824 (16.00); 8.5035 (0.68); 8.4912 (1.14); 8.4745 (0.81); 7.5908 (0.90); 7.5865 (1.06); 7.5720 (1.76); 7.5678 (2.16); 7.5534 (0.95); 7.5492 (1.23); 7.5422 (0.68); 7.5377 (0.61); 7.5290 (0.67); 7.5241 (1.21); 7.5210 (1.04); 7.5101 (1.07); 7.5044 (1.26); 7.4984 (0.75); 7.4899 (0.78); 7.4852 (0.64); 7.2876 (1.87); 7.2833 (2.07); 7.2623 (4.60); 7.2430 (2.09); 3.9043 (4.72); 3.5792 (1.14); 3.5629 (3.33); 3.5471 (2.09); 3.5309 (1.35); 3.3857 (0.42); 3.3405 (201.36); 3.3041 (0.42); 3.1916 (2.54); 3.1750 (5.07); 3.1582 (2.20); 2.6765 (0.56); 2.6720 (0.76); 2.6675 (0.58); 2.5478 (0.38); 2.5422 (0.44); 2.5251 (2.43); 2.5116 (43.28); 2.5074 (86.53); 2.5029 (114.33); 2.4984 (86.20); 2.4941 (44.54); 2.3340 (0.50); 2.3297 (0.72); 2.3250 (0.52); 1.2558 (0.89); 1.2424 (0.39); −0.0002 (2.13)

No. Ic-18, Solvent: <[D$_6$]-DMSO>, Spectrometer: 399.95 MHz 8.5759 (4.09); 7.7112 (1.20); 7.6901 (1.44); 7.4659 (1.46); 7.4448 (1.23); 3.9043 (1.66); 3.5627 (0.72); 3.5471 (0.75); 3.3404 (62.88); 3.1826 (0.52); 3.1662 (1.10); 3.1496 (0.47); 2.5254 (0.64); 2.5118 (12.09); 2.5075 (24.49); 2.5030 (32.61); 2.4985 (24.74); 2.4944 (12.95); 1.3575 (0.33); 1.2999 (2.89); 1.2890 (16.00); 1.2585 (0.63); 1.2434 (0.44); −0.0002 (0.57)

No. Ic-19, Solvent: <[D$_6$]-DMSO>, Spectrometer: 399.95 MHz 8.6176 (0.64); 8.6035 (0.32); 8.5840 (5.48); 6.9277 (2.87); 6.9220 (2.99); 6.6303 (0.81); 6.6247 (1.45); 6.6190 (0.75); 3.9044 (1.28); 3.7852 (1.09); 3.7651 (16.00); 3.7540 (0.81);

3.5641 (0.35); 3.5474 (1.02); 3.5318 (1.07); 3.5157 (0.41); 3.3359 (43.29); 3.1785 (0.78); 3.1618 (1.59); 3.1450 (0.69); 2.5112 (16.86); 2.5071 (33.02); 2.5026 (43.23); 2.4981 (32.46); 2.4941 (16.67); 1.2581 (0.61); 1.2432 (0.42); 0.0080 (0.71); −0.0002 (20.22); −0.0084 (0.93)

No. Ic-20, Solvent: <[D$_6$]-DMSO>, Spectrometer: 399.95 MHz 8.8040 (0.82); 8.7895 (1.65); 8.7749 (0.86); 8.5854 (16.00); 8.3200 (0.35); 8.0339 (0.34); 7.9469 (2.27); 7.9425 (4.13); 7.9383 (2.77); 7.7854 (2.02); 7.7656 (2.27); 7.7353 (1.69); 7.7329 (1.67); 7.7306 (1.52); 7.7154 (1.87); 7.7129 (1.96); 7.4512 (2.51); 7.4315 (4.15); 7.4118 (1.94); 3.9045 (5.21); 3.5801 (1.17); 3.5636 (3.36); 3.5480 (3.50); 3.5319 (1.35); 3.3375 (180.73); 3.1852 (2.50); 3.1686 (5.03); 3.1519 (2.20); 2.6762 (0.68); 2.6719 (0.96); 2.6675 (0.72); 2.5420 (0.49); 2.5249 (3.02); 2.5073 (111.61); 2.5028 (148.09); 2.4983 (112.69); 2.3339 (0.75); 2.3296 (1.01); 2.3252 (0.77); 1.2553 (1.25); 1.2351 (0.80); 1.2098 (0.75); 1.1937 (0.62); 0.0079 (1.42); −0.0002 (43.13); −0.0084 (1.96)

No. Ic-21, Solvent: <[D$_6$]-DMSO>, Spectrometer: 399.95 MHz 8.6590 (0.53); 8.6439 (1.02); 8.6293 (0.52); 8.5814 (10.01); 7.3801 (0.43); 7.3612 (1.98); 7.3545 (1.43); 7.3512 (1.69); 7.3449 (3.80); 7.3360 (0.40); 7.3323 (0.48); 7.3178 (1.51); 7.3104 (1.83); 7.0860 (0.80); 7.0789 (1.19); 7.0717 (1.06); 7.0633 (1.25); 7.0565 (0.68); 3.9045 (2.70); 3.7840 (16.00); 3.7713 (0.76); 3.5774 (0.69); 3.5606 (2.00); 3.5450 (2.10); 3.5288 (0.79); 3.3369 (64.12); 3.1857 (1.50); 3.1692 (3.05); 3.1616 (0.77); 3.1523 (1.28); 2.6762 (0.40); 2.6719 (0.55); 2.6676 (0.41); 2.5251 (1.88); 2.5116 (31.24); 2.5073 (62.40); 2.5028 (82.51); 2.4983 (62.20); 2.4940 (31.96); 2.3341 (0.38); 2.3295 (0.53); 2.3250 (0.40); 1.2554 (0.48); 0.0080 (1.12); −0.0002 (33.46); −0.0082 (1.48)

No. Ic-22, Solvent: <[D$_6$]-DMSO>, Spectrometer: 399.95 MHz 8.5762 (10.82); 8.3193 (0.33); 8.3082 (0.60); 8.2935 (1.16); 8.2792 (0.59); 7.6841 (1.40); 7.6797 (1.55); 7.6650 (1.51); 7.6606 (1.59); 7.4666 (0.78); 7.4621 (0.80); 7.4443 (1.42); 7.4275 (0.93); 7.4229 (0.89); 7.1108 (2.30); 7.0900 (1.99); 7.0196 (1.26); 7.0009 (2.19); 6.9822 (1.07); 3.9043 (3.36); 3.8071 (16.00); 3.7650 (0.45); 3.6117 (0.95); 3.5954 (2.72); 3.5795 (2.84); 3.5634 (1.09); 3.3783 (0.65); 3.3428 (209.28); 3.1923 (1.91); 3.1757 (3.84); 3.1590 (1.71); 2.6758 (0.44); 2.6719 (0.58); 2.6680 (0.46); 2.5421 (0.44); 2.5072 (67.19); 2.5029 (89.05); 2.4986 (69.26); 2.4925 (0.54); 2.3254 (0.41); 1.2732 (0.34); 1.2561 (0.93); 1.2422 (0.54); −0.0002 (1.27)

No. Ic-23, Solvent: <[D$_6$]-DMSO>, Spectrometer: 399.95 MHz 8.6215 (0.80); 8.6070 (1.50); 8.5918 (0.94); 8.5774 (15.20); 7.5947 (2.95); 7.5685 (0.85); 7.5647 (0.81); 7.5589 (1.36); 7.5562 (1.41); 7.5468 (1.18); 7.3479 (0.42); 7.3288 (3.60); 7.3176 (4.45); 7.3152 (4.42); 3.9044 (4.62); 3.5708 (1.04); 3.5542 (3.00); 3.5386 (3.12); 3.5223 (1.20); 3.3939 (0.33); 3.3423 (251.84); 3.1835 (2.25); 3.1742 (1.04); 3.1669 (4.56); 3.1500 (1.97); 2.6767 (0.50); 2.6721 (0.68); 2.6675 (0.50); 2.5424 (0.33); 2.5255 (1.94); 2.5120 (40.67); 2.5076 (82.25); 2.5031 (109.10); 2.4986 (82.16); 2.4942 (42.20); 2.3640 (0.94); 2.3399 (16.00); 2.3254 (1.23); 1.2742 (0.96); 1.2579 (2.11); 1.2431 (1.51); 1.2253 (0.38); −0.0002 (1.21)

No. Ic-24, Solvent: <[D$_6$]-DMSO>, Spectrometer: 399.95 MHz 8.6528 (0.77); 8.6394 (1.34); 8.6248 (1.03); 8.6041 (0.34); 8.5904 (16.00); 8.3191 (0.34); 7.6119 (0.92); 7.6049 (1.38); 7.6011 (1.13); 7.5941 (1.46); 7.5904 (0.93); 7.5833 (2.03); 7.5773 (2.87); 7.5721 (2.39); 7.5623 (2.36); 7.5556 (1.36); 7.3765 (2.27); 7.3523 (2.61); 7.3300 (1.69); 3.9044 (6.00); 3.5711 (1.17); 3.5546 (3.31); 3.5389 (3.49); 3.5227 (1.37); 3.3406 (241.25); 3.1858 (2.45); 3.1693 (4.94); 3.1617 (1.22); 3.1524 (2.08); 2.6766 (0.69); 2.6721 (0.94); 2.6676 (0.71); 2.5253 (3.24); 2.5118 (54.48); 2.5076 (108.08); 2.5030 (142.51); 2.4985 (107.50); 2.4943 (55.39); 2.3343 (0.64); 2.3298 (0.90); 2.3253 (0.65); 1.2554 (0.88); 1.2346 (0.39); 1.2107 (0.78); 1.1944 (0.75); −0.0002 (2.26)

No. Ic-25, Solvent: <[D$_6$]-DMSO>, Spectrometer: 399.95 MHz 8.5812 (16.00); 8.5585 (1.18); 8.5456 (0.64); 7.6127 (1.69); 7.5923 (3.36); 7.5721 (2.12); 7.5546 (2.00); 7.5497 (2.11); 7.5287 (1.97); 7.5238 (2.07); 7.3869 (2.03); 7.3823 (2.04); 7.3660 (1.68); 7.3614 (1.71); 3.9044 (4.83); 3.5738 (1.00); 3.5576 (2.95); 3.5419 (3.11); 3.5258 (1.19); 3.3843 (0.38); 3.3746 (0.80); 3.3416 (244.93); 3.3032 (0.35); 3.1843 (2.27); 3.1678 (4.57); 3.1511 (1.97); 2.6767 (0.57); 2.6722 (0.78); 2.6676 (0.59); 2.5476 (0.43); 2.5254 (2.46); 2.5120 (44.34); 2.5076 (89.18); 2.5031 (117.74); 2.4985 (87.67); 2.4941 (44.10); 2.3345 (0.54); 2.3298 (0.74); 2.3252 (0.57); 1.2730 (0.37); 1.2558 (1.01); 1.2426 (0.62); 1.2106 (0.45); 1.1944 (0.43); −0.0002 (2.22)

No. Ic-26, Solvent: <[D$_6$]-DMSO>, Spectrometer: 399.95 MHz 8.7944 (0.91); 8.7800 (1.77); 8.7656 (0.90); 8.5845 (16.00); 7.8306 (0.97); 7.8256 (1.05); 7.8112 (1.04); 7.8058 (1.19); 7.8019 (1.17); 7.7966 (1.10); 7.7821 (0.96); 7.7770 (1.01); 7.6827 (0.79); 7.6724 (0.86); 7.6657 (1.09); 7.6615 (1.17); 7.6553 (1.09); 7.6509 (1.12); 7.5847 (1.18); 7.5640 (1.73); 7.5587 (1.35); 7.5428 (1.03); 7.5378 (1.74); 7.5168 (0.81); 3.9044 (2.95); 3.5804 (1.24); 3.5640 (3.60); 3.5484 (3.79); 3.5321 (1.46); 3.3395 (193.72); 3.1820 (2.65); 3.1748 (1.08); 3.1655 (5.35); 3.1487 (2.30); 2.6764 (0.54); 2.6721 (0.72); 2.6680 (0.56); 2.5074 (82.52); 2.5031 (108.08); 2.4988 (82.86); 2.3341 (0.51); 2.3296 (0.71); 2.3257 (0.54); 0.0075 (1.01); −0.0002 (28.08); −0.0081 (1.49)

No. Ic-27, Solvent: <[D$_6$]-DMSO>, Spectrometer: 399.95 MHz 8.5935 (14.26); 8.4246 (0.71); 8.4096 (1.38); 8.3949 (0.71); 7.3272 (0.66); 7.3236 (0.78); 7.3107 (0.92); 7.3055 (2.19); 7.2916 (2.45); 7.2871 (2.09); 7.2751 (2.54); 7.2252 (4.55); 7.2069 (3.86); 7.1889 (0.71); 3.9042 (2.75); 3.5685 (1.06); 3.5521 (3.18); 3.5362 (3.35); 3.5200 (1.27); 3.3390 (158.79); 3.3073 (0.37); 3.1764 (2.41); 3.1600 (4.88); 3.1431 (2.00); 2.6758 (0.42); 2.6717 (0.58); 2.6671 (0.43); 2.5246 (2.01); 2.5111 (34.25); 2.5070 (66.90); 2.5025 (87.56); 2.4980 (65.83); 2.4938 (33.96); 2.3338 (0.44); 2.3292 (0.58); 2.3248 (0.43); 2.2733 (16.00); 0.0078 (0.68); −0.0002 (17.89); −0.0082 (0.81)

No. Ic-28, Solvent: <[D$_6$]-DMSO>, Spectrometer: 399.95 MHz 8.6411 (0.86); 8.6262 (1.66); 8.6115 (1.05); 8.5979 (16.00); 7.4913 (1.72); 7.4719 (3.91); 7.4539 (1.30); 7.4428 (2.67); 7.4316 (2.34); 7.4232 (1.45); 7.4119 (1.75); 7.4031 (0.66); 7.3906 (7.16); 7.3811 (4.36); 3.9044 (2.81); 3.5578 (1.24); 3.5409 (3.58); 3.5251 (3.73); 3.5085 (1.49); 3.3388 (157.84); 3.3155 (0.62); 3.1827 (2.73); 3.1740 (1.19); 3.1657 (5.35); 3.1485 (2.27); 2.6763 (0.55); 2.6720 (0.75); 2.6674 (0.58); 2.5249 (2.85); 2.5114 (42.86); 2.5072 (83.76); 2.5028 (109.60); 2.4983 (83.23); 2.3339 (0.51); 2.3295 (0.69); 2.3251 (0.52); 0.0079 (1.26); −0.0002 (33.16); −0.0082 (1.44)

No. Ic-29, Solvent: <[D$_6$]-DMSO>, Spectrometer: 399.95 MHz 8.6662 (0.80); 8.6514 (1.59); 8.6366 (0.82); 8.5960 (16.00); 7.5098 (2.08); 7.5035 (2.18); 7.4872 (2.14); 7.4809 (2.20); 7.4751 (1.93); 7.4595 (1.91); 7.4536 (2.39); 7.4381 (2.21); 7.3122 (1.34); 7.3058 (1.26); 7.2909 (2.35); 7.2845

(2.17); 7.2696 (1.08); 7.2633 (1.00); 3.9043 (4.34); 3.5521 (1.10); 3.5352 (3.17); 3.5194 (3.35); 3.5028 (1.33); 3.3939 (0.33); 3.3426 (250.44); 3.1772 (2.43); 3.1607 (5.37); 3.1433 (2.01); 2.6765 (0.47); 2.6720 (0.66); 2.6674 (0.51); 2.5251 (2.14); 2.5117 (37.29); 2.5074 (75.08); 2.5029 (99.83); 2.4983 (75.63); 2.4940 (39.21); 2.3341 (0.46); 2.3296 (0.63); 2.3252 (0.48); −0.0002 (1.50)

No. Ic-30, Solvent: <[$D_6$]-DMSO>, Spectrometer: 399.95 MHz 8.9154 (0.87); 8.9009 (1.73); 8.8860 (0.85); 8.5823 (16.00); 7.9748 (3.43); 7.9544 (4.87); 7.8592 (5.21); 7.8385 (3.70); 3.9047 (4.08); 3.6134 (1.09); 3.5972 (3.23); 3.5815 (3.40); 3.5656 (1.32); 3.3826 (0.36); 3.3408 (222.36); 3.3049 (0.38); 3.2042 (2.37); 3.1879 (4.70); 3.1714 (2.20); 3.1623 (0.61); 2.6770 (0.48); 2.6725 (0.69); 2.6682 (0.52); 2.5425 (0.39); 2.5257 (2.21); 2.5120 (40.38); 2.5079 (80.10); 2.5034 (105.92); 2.4990 (80.58); 2.3345 (0.51); 2.3302 (0.70); 2.3257 (0.54); −0.0002 (1.87)

No. Ic-31, Solvent: <[$D_6$]-DMSO>, Spectrometer: 399.95 MHz 8.9518 (0.79); 8.9372 (1.56); 8.9223 (0.79); 8.5871 (16.00); 8.1095 (3.03); 8.0899 (1.73); 8.0700 (1.86); 7.9125 (1.48); 7.8931 (1.81); 7.7382 (1.44); 7.7186 (2.43); 7.6992 (1.08); 3.9046 (4.64); 3.6115 (1.07); 3.5950 (3.14); 3.5796 (3.28); 3.5634 (1.25); 3.3413 (256.61); 3.2061 (2.34); 3.1894 (4.74); 3.1726 (2.13); 2.6769 (0.55); 2.6724 (0.73); 2.6678 (0.55); 2.5427 (0.55); 2.5256 (2.30); 2.5120 (42.41); 2.5078 (84.93); 2.5033 (112.19); 2.4988 (84.37); 2.4945 (43.36); 2.3346 (0.53); 2.3300 (0.73); 2.3256 (0.55); −0.0002 (2.12)

No. Ic-32, Solvent: <[$D_6$]-DMSO>, Spectrometer: 399.95 MHz 8.7082 (0.81); 8.6932 (1.63); 8.6787 (0.80); 8.5956 (16.00); 7.6775 (4.12); 7.6726 (4.32); 7.5115 (2.03); 7.5065 (1.89); 7.4909 (3.13); 7.4859 (3.09); 7.4225 (5.09); 7.4019 (3.26); 3.9042 (3.92); 3.5542 (1.08); 3.5374 (3.08); 3.5216 (3.22); 3.5050 (1.28); 3.3401 (184.88); 3.1762 (2.34); 3.1594 (4.63); 3.1422 (1.96); 2.6763 (0.44); 2.6719 (0.62); 2.6673 (0.47); 2.5251 (2.05); 2.5115 (35.63); 2.5073 (70.89); 2.5028 (93.25); 2.4983 (70.15); 2.4941 (36.03); 2.3339 (0.42); 2.3296 (0.58); 2.3251 (0.44); −0.0002 (1.86)

No. Ic-33, Solvent: <[$D_6$]-DMSO>, Spectrometer: 399.95 MHz 8.9156 (0.87); 8.9007 (1.74); 8.8863 (0.88); 8.5925 (16.00); 7.8156 (1.68); 7.8108 (3.93); 7.8063 (3.58); 7.7894 (11.38); 7.7847 (8.20); 3.9044 (3.67); 3.5792 (1.10); 3.5627 (3.25); 3.5471 (3.44); 3.5309 (1.33); 3.3392 (225.17); 3.3129 (0.82); 3.1834 (2.45); 3.1745 (1.50); 3.1669 (4.95); 3.1500 (2.13); 2.6765 (0.57); 2.6723 (0.79); 2.6677 (0.62); 2.5252 (2.49); 2.5076 (90.58); 2.5031 (120.42); 2.4987 (92.44); 2.3344 (0.58); 2.3299 (0.80); 2.3254 (0.60); 0.0079 (1.32); −0.0002 (38.37); −0.0083 (1.95)

No. Ic-34, Solvent: <[$D_6$]-DMSO>, Spectrometer: 399.95 MHz 8.5764 (14.66); 8.5109 (0.79); 8.4964 (1.58); 8.4817 (0.77); 7.3753 (1.96); 7.3710 (2.21); 7.3549 (2.13); 7.3506 (2.47); 7.2957 (4.10); 7.2917 (3.79); 6.9784 (4.09); 6.9581 (3.71); 6.1553 (0.58); 6.0853 (16.00); 3.9045 (4.23); 3.5511 (0.97); 3.5346 (2.85); 3.5191 (2.99); 3.5031 (1.19); 3.3401 (210.82); 3.1739 (0.58); 3.1646 (2.22); 3.1481 (4.33); 3.1314 (1.86); 2.6766 (0.53); 2.6721 (0.73); 2.6677 (0.56); 2.5421 (0.48); 2.5254 (2.33); 2.5118 (42.24); 2.5075 (85.09); 2.5030 (113.06); 2.4985 (86.09); 2.4945 (45.17); 2.3343 (0.53); 2.3298 (0.74); 2.3253 (0.58); 1.2735 (0.81); 1.2564 (1.78); 1.2427 (1.23); 0.0080 (1.00); −0.0002 (31.22); −0.0084 (1.43)

No. Ic-35, Solvent: <[$D_6$]-DMSO>, Spectrometer: 399.95 MHz 8.5860 (1.06); 8.5736 (16.00); 8.5589 (0.92); 7.7037 (4.79); 7.6832 (5.31); 7.2858 (4.84); 7.2653 (4.39); 3.9044 (3.42); 3.5740 (1.05); 3.5575 (2.96); 3.5419 (3.09); 3.5259 (1.20); 3.3402 (209.32); 3.1808 (2.20); 3.1743 (1.02); 3.1642 (4.51); 3.1476 (2.03); 3.1372 (0.46); 2.6766 (0.75); 2.6675 (1.88); 2.6485 (3.90); 2.6295 (4.02); 2.6107 (1.45); 2.5422 (0.47); 2.5253 (2.44); 2.5119 (44.58); 2.5076 (88.21); 2.5030 (115.94); 2.4986 (87.01); 2.4943 (44.94); 2.3343 (0.56); 2.3297 (0.76); 2.3253 (0.57); 1.2760 (1.95); 1.2596 (4.04); 1.2441 (2.72); 1.2275 (0.71); 1.2054 (5.89); 1.1864 (12.34); 1.1674 (5.70); 0.0079 (0.93); −0.0002 (27.20); −0.0083 (1.23)

No. Ic-36, Solvent: <[$D_6$]-DMSO>, Spectrometer: 399.95 MHz 8.6175 (0.33); 8.5816 (16.00); 8.5159 (0.69); 8.5003 (1.37); 8.4885 (0.62); 8.3196 (0.37); 7.6769 (0.89); 7.6601 (1.05); 7.6555 (1.81); 7.6387 (1.80); 7.6344 (1.14); 7.6174 (0.91); 7.3650 (1.00); 7.3589 (1.07); 7.3413 (1.14); 7.3358 (1.44); 7.3318 (1.21); 7.3143 (0.96); 7.3081 (0.98); 7.1903 (0.88); 7.1844 (0.83); 7.1697 (1.56); 7.1638 (1.49); 7.1480 (0.77); 7.1422 (0.72); 3.9045 (5.11); 3.6215 (0.33); 3.6119 (0.36); 3.5726 (1.12); 3.5564 (3.17); 3.5406 (3.33); 3.5246 (1.31); 3.3454 (336.90); 3.1853 (2.36); 3.1687 (5.34); 3.1524 (2.20); 3.1363 (0.41); 3.1257 (0.36); 2.7314 (0.54); 2.6768 (0.60); 2.6722 (0.84); 2.6678 (0.64); 2.5256 (2.58); 2.5120 (47.71); 2.5077 (96.72); 2.5032 (128.99); 2.4987 (97.66); 2.4945 (50.67); 2.3344 (0.59); 2.3299 (0.82); 2.3254 (0.62); 1.2760 (2.48); 1.2596 (5.12); 1.2437 (3.22); 1.2275 (0.74); −0.0002 (1.33)

No. Ic-37, Solvent: <[$D_6$]-DMSO>, Spectrometer: 399.95 MHz 8.6998 (0.77); 8.6852 (1.52); 8.6704 (0.78); 8.5906 (0.51); 8.5784 (16.00); 7.8634 (0.35); 7.8559 (2.76); 7.8505 (1.19); 7.8420 (3.04); 7.8337 (3.27); 7.8253 (1.21); 7.8199 (2.96); 7.8127 (0.36); 7.3159 (0.40); 7.3086 (3.11); 7.3034 (1.08); 7.2914 (1.22); 7.2863 (5.94); 7.2812 (1.27); 7.2692 (0.98); 7.2641 (2.92); 7.2567 (0.38); 3.9045 (4.49); 3.5790 (1.06); 3.5625 (3.13); 3.5469 (3.31); 3.5307 (1.28); 3.3960 (0.35); 3.3431 (259.36); 3.1832 (2.33); 3.1746 (1.15); 3.1667 (4.72); 3.1499 (2.03); 2.6769 (0.48); 2.6723 (0.67); 2.6678 (0.48); 2.5257 (1.86); 2.5122 (37.92); 2.5078 (77.47); 2.5033 (103.55); 2.4987 (78.35); 2.4943 (40.51); 2.3345 (0.51); 2.3301 (0.69); 2.3254 (0.52); 1.2555 (0.83); −0.0002 (1.46)

No. Ic-38, Solvent: <[$D_6$]-DMSO>, Spectrometer: 399.95 MHz 9.0167 (0.81); 9.0022 (1.59); 8.9876 (0.80); 8.5845 (16.00); 8.3374 (2.43); 8.3322 (1.54); 8.3258 (5.86); 8.3207 (2.88); 8.3153 (3.36); 8.3086 (2.36); 8.3036 (6.52); 8.2978 (0.91); 8.1868 (0.49); 8.1813 (3.04); 8.1763 (0.94); 8.1639 (0.82); 8.1591 (2.26); 8.0166 (0.93); 8.0109 (6.25); 8.0060 (2.00); 7.9934 (1.83); 7.9887 (5.44); 7.9829 (0.71); 3.9046 (6.52); 3.6197 (1.07); 3.6037 (3.08); 3.5880 (3.22); 3.5722 (1.27); 3.3421 (162.07); 3.2088 (2.27); 3.1923 (4.46); 3.1756 (2.10); 2.6770 (0.65); 2.6725 (0.89); 2.6681 (0.66); 2.5426 (0.68); 2.5257 (2.90); 2.5122 (51.70); 2.5079 (102.36); 2.5034 (134.23); 2.4989 (100.05); 2.4946 (50.87); 2.3346 (0.63); 2.3301 (0.87); 2.3257 (0.64); 1.2556 (0.81); −0.0002 (2.35)

No. Ic-39, Solvent: <[$D_6$]-DMSO>, Spectrometer: 399.95 MHz 8.7833 (0.74); 8.7687 (1.49); 8.7545 (0.77); 8.5839 (16.00); 8.3207 (0.36); 7.6850 (0.34); 7.6662 (0.39); 7.6373 (1.74); 7.6179 (2.44); 7.5725 (1.09); 7.5663 (1.40); 7.5627 (1.15); 7.5473 (1.35); 7.5404 (2.26); 7.5252 (1.33); 7.5196 (2.00); 7.5050 (1.79); 7.5002 (1.14); 7.4854 (0.98); 7.3950

(0.92); 7.3903 (0.82); 7.3885 (0.84); 7.3743 (1.48); 7.3680 (1.45); 7.3523 (0.84); 7.3480 (0.79); 3.9045 (6.60); 3.5879 (1.11); 3.5715 (3.26); 3.5558 (3.42); 3.5397 (1.34); 3.3424 (105.00); 3.1892 (2.47); 3.1727 (5.10); 3.1559 (2.16); 2.9443 (0.36); 2.6766 (0.61); 2.6722 (0.85); 2.6676 (0.64); 2.5424 (0.72); 2.5255 (2.79); 2.5119 (46.96); 2.5076 (94.04); 2.5031 (124.49); 2.4986 (93.39); 2.4943 (47.55); 2.3343 (0.59); 2.3299 (0.81); 2.3254 (0.60); 1.2554 (0.97); −0.0002 (1.91)

No. Ic-40, Solvent: <[$D_6$]-DMSO>, Spectrometer: 399.95 MHz 8.7615 (0.77); 8.7466 (1.55); 8.7317 (0.78); 8.5909 (0.59); 8.5852 (0.49); 8.5756 (16.00); 8.3197 (0.40); 7.8244 (0.60); 7.8037 (0.76); 7.7265 (2.86); 7.7214 (1.32); 7.7100 (1.86); 7.7047 (8.36); 7.6805 (8.72); 7.6752 (2.07); 7.6639 (1.29); 7.6587 (3.15); 7.6051 (0.33); 3.9045 (5.78); 3.5777 (1.05); 3.5613 (2.97); 3.5457 (3.15); 3.5296 (1.25); 3.3424 (176.27); 3.1811 (2.23); 3.1645 (4.44); 3.1479 (1.91); 2.6766 (0.67); 2.6722 (0.93); 2.6676 (0.70); 2.5425 (0.70); 2.5254 (2.92); 2.5119 (53.03); 2.5076 (106.07); 2.5031 (139.97); 2.4986 (105.34); 2.4942 (53.97); 2.3343 (0.66); 2.3299 (0.91); 2.3253 (0.69); 1.2554 (0.85); 0.0080 (0.68); −0.0002 (20.52); −0.0085 (0.86)

No. Ic-41, Solvent: <[$D_6$]-DMSO>, Spectrometer: 399.95 MHz 8.5903 (0.36); 8.5796 (11.35); 8.5407 (0.62); 8.5263 (1.23); 8.5115 (0.62); 7.4078 (1.21); 7.4028 (1.56); 7.3870 (1.17); 7.3821 (2.11); 7.3730 (3.29); 7.3683 (2.16); 7.0100 (2.66); 6.9892 (2.39); 3.9044 (3.14); 3.7960 (15.86); 3.7783 (16.00); 3.5628 (0.76); 3.5463 (2.08); 3.5308 (2.21); 3.5144 (0.92); 3.3978 (0.33); 3.3429 (198.92); 3.1794 (1.63); 3.1746 (1.46); 3.1620 (3.68); 3.1457 (1.36); 2.6767 (0.47); 2.6723 (0.62); 2.6678 (0.45); 2.5422 (0.50); 2.5253 (2.21); 2.5118 (36.52); 2.5076 (70.76); 2.5031 (91.77); 2.4986 (68.50); 2.4944 (35.01); 2.3344 (0.43); 2.3299 (0.57); 2.3255 (0.41); 1.2554 (0.40); 0.0080 (0.45); −0.0002 (11.83); −0.0084 (0.51)

No. Ic-42, Solvent: <[$D_6$]-DMSO>, Spectrometer: 399.95 MHz 8.9141 (0.81); 8.8991 (1.53); 8.8844 (0.80); 8.6404 (0.35); 8.6201 (0.37); 8.5902 (16.00); 7.5411 (0.53); 7.5245 (1.06); 7.5201 (1.02); 7.5077 (0.76); 7.5034 (2.00); 7.4868 (1.01); 7.4823 (1.17); 7.4658 (0.53); 7.1799 (0.76); 7.1728 (3.51); 7.1530 (4.87); 7.1325 (2.84); 7.1252 (0.57); 3.9043 (3.66); 3.5705 (1.25); 3.5535 (3.33); 3.5372 (3.45); 3.5205 (1.49); 3.3433 (216.18); 3.1660 (2.75); 3.1486 (5.00); 3.1311 (2.25); 2.6766 (0.66); 2.6721 (0.89); 2.6677 (0.68); 2.5253 (2.96); 2.5117 (51.72); 2.5075 (102.01); 2.5030 (134.03); 2.4986 (101.33); 2.3342 (0.60); 2.3298 (0.84); 2.3253 (0.64); 1.2552 (0.92); 0.0079 (0.91); −0.0002 (26.73); −0.0084 (1.26)

No. Ic-43, Solvent: <[$D_6$]-DMSO>, Spectrometer: 399.95 MHz 8.9105 (0.77); 8.8961 (1.48); 8.8818 (0.74); 8.5891 (16.00); 8.3199 (0.34); 8.1822 (2.25); 8.1784 (3.83); 8.1751 (2.49); 8.1012 (1.29); 8.0982 (1.80); 8.0941 (1.29); 8.0814 (1.43); 8.0781 (1.90); 8.0743 (1.40); 8.0176 (1.33); 8.0144 (1.90); 8.0110 (1.27); 7.9983 (1.55); 7.9947 (2.14); 7.9917 (1.37); 7.7140 (1.95); 7.6945 (3.39); 7.6748 (1.58); 3.9045 (5.38); 3.6015 (1.05); 3.5849 (2.99); 3.5693 (3.13); 3.5531 (1.23); 3.3445 (238.06); 3.1971 (2.21); 3.1805 (4.53); 3.1635 (2.03); 2.9446 (1.61); 2.7843 (1.20); 2.6770 (0.57); 2.6726 (0.79); 2.6680 (0.58); 2.5429 (0.69); 2.5258 (2.40); 2.5124 (44.63); 2.5080 (90.29); 2.5034 (119.98); 2.4989 (90.10); 2.4945 (45.78); 2.3348 (0.55); 2.3301 (0.77); 2.3257 (0.57); 1.9581 (1.26); 1.2555 (0.76); −0.0002 (1.11)

No. Ic-44, Solvent: <[$D_6$]-DMSO>, Spectrometer: 399.95 MHz 8.5718 (3.99); 8.4684 (0.51); 8.4544 (0.98); 8.4406 (0.52); 8.4213 (2.59); 8.4090 (2.64); 7.7874 (0.40); 7.7803 (3.50); 7.7753 (1.18); 7.7631 (1.12); 7.7581 (3.76); 7.7510 (0.44); 7.3753 (2.03); 7.3630 (1.99); 6.9976 (0.44); 6.9904 (3.77); 6.9854 (1.22); 6.9731 (1.13); 6.9682 (3.58); 6.9610 (0.43); 3.9045 (2.37); 3.8238 (0.81); 3.7982 (16.00); 3.5660 (0.73); 3.5490 (1.89); 3.5342 (1.91); 3.5173 (0.82); 3.3433 (137.20); 3.0064 (1.47); 2.9893 (2.94); 2.9719 (1.32); 2.6723 (0.39); 2.5255 (1.23); 2.5121 (21.43); 2.5077 (43.36); 2.5032 (57.55); 2.4987 (43.22); 2.4943 (22.12); 2.3298 (0.36); −0.0002 (0.83)

No. Ic-45, Solvent: <[$D_6$]-DMSO>, Spectrometer: 399.95 MHz 8.9584 (1.98); 8.9446 (3.84); 8.9304 (2.03); 8.5796 (15.49); 8.4326 (9.56); 8.4203 (9.94); 8.3307 (1.68); 8.3249 (13.18); 8.3200 (5.35); 8.3075 (4.77); 8.3027 (16.00); 8.2970 (2.52); 8.0294 (2.12); 8.0237 (15.10); 8.0190 (5.42); 8.0062 (4.49); 8.0016 (13.68); 7.9959 (2.12); 7.4043 (8.18); 7.3920 (8.03); 3.9046 (8.63); 3.6230 (2.95); 3.6061 (7.98); 3.5912 (8.11); 3.5746 (3.33); 3.3422 (470.77); 3.0396 (5.97); 3.0226 (12.10); 3.0055 (5.41); 2.6767 (1.07); 2.6723 (1.49); 2.6679 (1.15); 2.5252 (5.40); 2.5076 (169.60); 2.5032 (224.06); 2.4987 (170.80); 2.3344 (1.03); 2.3299 (1.44); 2.3256 (1.09); 1.3377 (0.53); −0.0002 (3.69)

No. Ic-46, Solvent: <[$D_6$]-DMSO>, Spectrometer: 399.95 MHz 8.5714 (6.74); 8.5331 (0.83); 8.5192 (1.57); 8.5055 (0.81); 8.4207 (4.23); 8.4085 (4.36); 7.7022 (5.18); 7.6818 (5.75); 7.3767 (3.47); 7.3644 (3.36); 7.2595 (4.66); 7.2396 (4.26); 3.9045 (3.35); 3.5741 (1.28); 3.5571 (3.31); 3.5422 (3.37); 3.5253 (1.41); 3.3762 (0.32); 3.3409 (155.21); 3.1746 (0.45); 3.1615 (0.46); 3.0112 (2.57); 2.9940 (5.14); 2.9768 (2.28); 2.6765 (0.37); 2.6721 (0.51); 2.6677 (0.39); 2.5253 (1.72); 2.5119 (30.53); 2.5076 (61.15); 2.5030 (80.57); 2.4985 (60.37); 2.4943 (30.91); 2.3397 (16.00); 1.3381 (0.38); −0.0002 (1.45)

No. Ic-47, Solvent: <[$D_6$]-DMSO>, Spectrometer: 399.95 MHz 8.5720 (10.33); 8.5202 (0.57); 8.5058 (1.14); 8.4911 (0.57); 7.7677 (0.43); 7.7604 (3.62); 7.7558 (1.25); 7.7385 (3.88); 7.7313 (0.47); 6.9932 (0.50); 6.9860 (3.94); 6.9639 (3.74); 6.9569 (0.47); 3.9043 (1.78); 3.7980 (16.00); 3.5616 (0.71); 3.5451 (2.05); 3.5297 (2.15); 3.5136 (0.84); 3.3827 (0.35); 3.3423 (160.48); 3.1738 (1.86); 3.1564 (3.09); 3.1398 (1.32); 2.6723 (0.43); 2.5253 (1.56); 2.5075 (51.23); 2.5031 (66.51); 2.4986 (49.88); 2.4946 (25.65); 2.3342 (0.34); 2.3297 (0.46); 2.3255 (0.34); 1.2554 (0.53); 0.0077 (0.68); −0.0002 (18.18); −0.0081 (0.84)

No. Ic-48, Solvent: <[$D_6$]-DMSO>, Spectrometer: 399.95 MHz 8.9372 (0.85); 8.9224 (1.68); 8.9073 (0.84); 8.5817 (16.00); 7.9707 (3.21); 7.9543 (2.21); 7.9494 (8.73); 7.9230 (8.39); 7.9016 (3.13); 3.9047 (2.76); 3.6053 (1.08); 3.5891 (3.17); 3.5734 (3.33); 3.5574 (1.28); 3.3822 (0.37); 3.3414 (193.84); 3.3048 (0.33); 3.1955 (2.33); 3.1791 (4.63); 3.1624 (2.07); 2.6769 (0.49); 2.6723 (0.65); 2.6678 (0.49); 2.5255 (2.31); 2.5120 (39.51); 2.5078 (76.57); 2.5033 (99.56); 2.4989 (74.64); 2.3345 (0.48); 2.3299 (0.64); 2.3255 (0.47); 0.0079 (1.62); −0.0002 (41.86); −0.0084 (1.93)

No. Ic-49, Solvent: <[$D_6$]-DMSO>, Spectrometer: 399.95 MHz 8.8640 (0.84); 8.8494 (1.65); 8.8352 (0.85); 8.5904 (16.00); 7.4969 (0.33); 7.4794 (5.83); 7.4714 (2.25); 7.4606 (5.36); 7.4550 (3.52); 7.4413 (1.16); 7.4360 (0.90); 7.4297 (0.35); 3.9044 (3.18); 3.5865 (1.19); 3.5700 (3.47); 3.5544

(3.64); 3.5383 (1.38); 3.4047 (0.36); 3.3440 (282.22); 3.1865 (2.59); 3.1700 (5.19); 3.1617 (1.58); 3.1533 (2.24); 2.6770 (0.52); 2.6726 (0.68); 2.6682 (0.53); 2.5120 (43.74); 2.5079 (83.27); 2.5034 (107.58); 2.4990 (80.56); 2.4950 (41.51); 2.3346 (0.52); 2.3301 (0.71); 2.3258 (0.52); 0.0078 (1.13); −0.0002 (28.17); −0.0083 (1.33)

No. Ic-50, Solvent: <[D$_6$]-DMSO>, Spectrometer: 399.95 MHz 8.6100 (0.47); 8.5962 (0.95); 8.5826 (0.52); 8.0579 (2.10); 8.0449 (2.21); 7.8862 (1.82); 7.8808 (0.76); 7.8723 (2.02); 7.8640 (2.20); 7.8556 (0.83); 7.8502 (2.04); 7.3126 (2.06); 7.3074 (0.67); 7.2956 (0.75); 7.2903 (4.00); 7.2852 (0.92); 7.2734 (0.71); 7.2681 (2.05); 7.2605 (0.42); 6.8735 (1.40); 6.8703 (1.53); 6.8604 (1.42); 6.8573 (1.52); 6.6792 (2.64); 3.9045 (2.73); 3.8229 (0.44); 3.8106 (16.00); 3.5268 (0.81); 3.5094 (1.88); 3.4949 (1.91); 3.4774 (0.97); 3.3463 (134.26); 2.8406 (1.52); 2.8228 (2.90); 2.8051 (1.39); 2.6770 (0.42); 2.6725 (0.53); 2.6680 (0.40); 2.5258 (1.55); 2.5123 (27.87); 2.5079 (56.12); 2.5034 (74.19); 2.4989 (55.35); 2.4945 (28.09); 2.3345 (0.34); 2.3301 (0.47); 2.3256 (0.35); 1.3496 (0.54); −0.0002 (0.89)

No. Ic-51, Solvent: <[D$_6$]-DMSO>, Spectrometer: 399.95 MHz 8.4293 (0.45); 8.4153 (0.89); 8.4015 (0.44); 8.3195 (11.46); 8.0546 (2.16); 8.0415 (2.22); 7.7995 (0.40); 7.7922 (3.47); 7.7874 (1.21); 7.7750 (1.14); 7.7702 (3.75); 7.7630 (0.46); 6.9995 (0.43); 6.9922 (3.78); 6.9874 (1.28); 6.9749 (1.12); 6.9701 (3.64); 6.9632 (0.45); 6.8674 (1.42); 6.8644 (1.52); 6.8543 (1.42); 6.8513 (1.49); 6.6719 (2.68); 3.9044 (2.55); 3.8097 (15.30); 3.7984 (16.00); 3.7767 (0.75); 3.5076 (0.70); 3.4902 (1.58); 3.4759 (1.71); 3.4586 (0.86); 3.3436 (132.92); 3.3199 (5.62); 2.8316 (1.45); 2.8137 (2.76); 2.7961 (1.34); 2.6766 (0.36); 2.6720 (0.49); 2.6677 (0.38); 2.5421 (0.36); 2.5254 (1.44); 2.5118 (25.75); 2.5075 (51.93); 2.5030 (69.21); 2.4985 (52.63); 2.4944 (27.57); 2.3298 (0.42); 2.3253 (0.33); 1.2888 (0.33); −0.0002 (1.04)

No. Ic-52, Solvent: <[D$_6$]-DMSO>, Spectrometer: 399.95 MHz 8.7704 (0.62); 8.7574 (1.17); 8.7433 (0.62); 8.0608 (2.32); 8.0477 (2.51); 8.0284 (2.75); 8.0245 (2.84); 7.7978 (0.60); 7.7934 (0.49); 7.7769 (2.78); 7.7724 (3.03); 7.7662 (4.48); 7.7453 (0.78); 6.8732 (1.63); 6.8703 (1.64); 6.8602 (1.59); 6.8573 (1.58); 6.6816 (2.99); 3.9049 (3.13); 3.8122 (16.00); 3.5345 (0.86); 3.5173 (2.07); 3.5026 (2.15); 3.4853 (1.05); 3.3427 (165.20); 3.1614 (0.35); 2.8407 (1.62); 2.8231 (3.18); 2.8054 (1.50); 2.6768 (0.51); 2.6727 (0.69); 2.6681 (0.51); 2.5427 (0.46); 2.5079 (70.21); 2.5035 (90.46); 2.4990 (68.19); 2.3345 (0.43); 2.3303 (0.56); 2.3257 (0.44); −0.0002 (1.39)

No. Ic-53, Solvent: <[D$_6$]-DMSO>, Spectrometer: 399.95 MHz 8.4040 (0.71); 8.0695 (2.09); 8.0564 (2.14); 7.5573 (0.56); 7.5529 (0.74); 7.5388 (1.39); 7.5343 (1.75); 7.5254 (0.58); 7.5200 (1.33); 7.5156 (1.34); 7.5062 (0.79); 7.4997 (0.83); 7.4948 (0.44); 7.4861 (0.51); 7.4816 (0.38); 7.2937 (1.03); 7.2796 (1.20); 7.2772 (1.45); 7.2728 (1.10); 7.2691 (1.20); 7.2663 (1.18); 7.2608 (2.05); 7.2588 (1.72); 7.2480 (0.84); 7.2458 (0.90); 7.2422 (1.06); 6.8920 (1.47); 6.8889 (1.53); 6.8790 (1.44); 6.8758 (1.47); 6.6965 (2.64); 3.9044 (3.59); 3.8373 (0.67); 3.8208 (16.00); 3.8135 (1.18); 3.7876 (0.66); 3.5236 (0.82); 3.5062 (2.02); 3.4914 (2.04); 3.4741 (0.93); 3.3407 (146.64); 2.8301 (1.58); 2.8126 (3.08); 2.7951 (1.43); 2.6765 (0.46); 2.6719 (0.60); 2.6673 (0.48); 2.5420 (0.44); 2.5252 (1.83); 2.5117 (32.20); 2.5074 (64.11); 2.5028 (84.34); 2.4983 (63.12); 2.4940 (32.21); 2.3340 (0.40); 2.3296 (0.52); 2.3250 (0.40); 1.3499 (0.53); 0.0079 (0.45); −0.0002 (14.48); −0.0084 (0.62)

No. Ic-54, Solvent: <[D$_6$]-DMSO>, Spectrometer: 399.95 MHz 8.4814 (0.39); 8.0562 (0.74); 8.0432 (0.77); 7.7405 (1.13); 7.7193 (1.35); 7.4710 (1.35); 7.4498 (1.17); 6.8704 (0.50); 6.8676 (0.53); 6.8573 (0.50); 6.8545 (0.51); 6.6764 (0.95); 3.9043 (0.83); 3.8100 (5.01); 3.5050 (0.64); 3.4903 (0.65); 3.3421 (40.75); 2.8373 (0.50); 2.8197 (0.97); 2.8020 (0.46); 2.5251 (0.60); 2.5116 (10.71); 2.5074 (21.15); 2.5030 (27.87); 2.4985 (21.12); 1.2888 (16.00); −0.0002 (7.71); −0.0083 (0.38)

No. Ic-55, Solvent: <[D$_6$]-DMSO>, Spectrometer: 399.95 MHz 8.5199 (0.60); 8.0631 (1.12); 8.0500 (1.19); 6.9490 (2.89); 6.9433 (3.11); 6.8720 (0.79); 6.8691 (0.84); 6.8588 (0.82); 6.8560 (0.86); 6.6777 (1.50); 6.6354 (0.79); 6.6297 (1.47); 6.6241 (0.84); 3.9044 (1.30); 3.8119 (8.03); 3.7849 (0.47); 3.7704 (16.00); 3.7128 (0.61); 3.5084 (0.41); 3.4913 (0.99); 3.4764 (0.97); 3.4592 (0.46); 3.3475 (129.12); 2.8340 (0.78); 2.8163 (1.51); 2.7986 (0.73); 2.5078 (34.02); 2.5033 (44.27); 2.4989 (33.69); −0.0002 (2.70)

No. Ic-56, Solvent: <[D$_6$]-DMSO>, Spectrometer: 399.95 MHz 8.8483 (0.53); 8.8345 (1.09); 8.8209 (0.60); 8.1263 (2.14); 8.1155 (1.47); 8.0950 (1.40); 8.0634 (2.29); 8.0504 (2.42); 7.9135 (1.06); 7.8940 (1.30); 7.7395 (1.01); 7.7200 (1.72); 7.7005 (0.80); 6.8858 (1.51); 6.8829 (1.64); 6.8727 (1.53); 6.8699 (1.64); 6.6913 (2.93); 3.9046 (1.88); 3.8109 (16.00); 3.5633 (0.84); 3.5460 (2.03); 3.5313 (2.04); 3.5140 (0.98); 3.4003 (0.36); 3.3930 (0.53); 3.3504 (295.05); 2.8621 (1.63); 2.8445 (3.16); 2.8268 (1.52); 2.6776 (0.45); 2.6731 (0.59); 2.6689 (0.45); 2.5262 (1.80); 2.5125 (32.43); 2.5084 (63.76); 2.5040 (83.74); 2.4995 (63.47); 2.3352 (0.39); 2.3307 (0.53); 2.3263 (0.41); 1.3501 (0.45); −0.0002 (4.25)

No. Ic-57, Solvent: <[D$_6$]-DMSO>, Spectrometer: 399.95 MHz 8.4129 (0.53); 8.3992 (1.05); 8.3850 (0.54); 8.0559 (2.15); 8.0428 (2.22); 7.4053 (1.36); 7.4010 (1.54); 7.3850 (1.48); 7.3807 (1.75); 7.3610 (0.41); 7.3569 (0.40); 7.3338 (2.94); 7.3297 (2.65); 7.0144 (0.38); 6.9939 (0.42); 6.9845 (2.86); 6.9641 (2.64); 6.8628 (1.46); 6.8598 (1.53); 6.8498 (1.42); 6.8467 (1.49); 6.6686 (2.66); 6.1228 (1.67); 6.0848 (11.21); 6.0501 (0.40); 3.9041 (3.15); 3.8111 (16.00); 3.4967 (0.82); 3.4794 (1.82); 3.4648 (1.86); 3.4473 (0.93); 3.3431 (197.53); 2.8225 (1.46); 2.8048 (2.80); 2.7872 (1.34); 2.6767 (0.40); 2.6721 (0.52); 2.6677 (0.40); 2.5424 (0.45); 2.5254 (1.69); 2.5120 (28.33); 2.5076 (56.46); 2.5031 (74.69); 2.4986 (56.17); 2.4942 (28.71); 2.3344 (0.34); 2.3298 (0.47); 2.3254 (0.34); 1.3497 (0.54); −0.0002 (0.93)

No. Ic-58, Solvent: <[D$_6$]-DMSO>, Spectrometer: 399.95 MHz 8.4947 (0.57); 8.4808 (1.11); 8.4670 (0.57); 8.0559 (2.32); 8.0430 (2.36); 7.8403 (0.32); 7.8204 (0.35); 7.7333 (3.53); 7.7128 (3.90); 7.2924 (3.60); 7.2719 (3.29); 6.8704 (1.59); 6.8675 (1.66); 6.8574 (1.55); 6.8544 (1.58); 6.6759 (2.93); 3.9044 (3.18); 3.8097 (16.00); 3.5195 (0.86); 3.5021 (2.01); 3.4873 (2.05); 3.4701 (0.97); 3.3443 (128.72); 2.8377 (1.62); 2.8200 (3.06); 2.8022 (1.46); 2.6766 (0.57); 2.6683 (1.35); 2.6623 (0.65); 2.6496 (2.91); 2.6306 (3.04); 2.6119 (1.18); 2.5423 (0.37); 2.5254 (1.75); 2.5120 (31.12); 2.5078 (61.17); 2.5033 (79.91); 2.4988 (59.97); 2.3345 (0.38); 2.3300 (0.52); 2.3257 (0.38); 1.3501 (0.53); 1.2029 (4.21); 1.1839 (8.82); 1.1650 (4.04); −0.0002 (1.18)

No. Ic-59, Solvent: <[D$_6$]-DMSO>, Spectrometer: 399.95 MHz 8.2052 (0.45); 8.1914 (0.85); 8.1784 (0.48); 8.0867 (2.15); 8.0736 (2.14); 7.7105 (1.28); 7.7060 (1.40); 7.6914 (1.39); 7.6868 (1.43); 7.4735 (0.70); 7.4689 (0.72); 7.4551 (0.93);

7.4525 (1.11); 7.4508 (1.10); 7.4482 (0.97); 7.4344 (0.90); 7.4297 (0.87); 7.1179 (1.82); 7.0972 (1.59); 7.0336 (0.96); 7.0314 (1.00); 7.0146 (1.70); 7.0129 (1.73); 6.9962 (0.88); 6.9940 (0.90); 6.9085 (1.46); 6.9053 (1.52); 6.8955 (1.42); 6.8922 (1.49); 6.7149 (2.58); 3.9043 (3.43); 3.8391 (0.74); 3.8278 (16.00); 3.8117 (15.88); 3.7778 (0.65); 3.7546 (0.57); 3.5541 (0.82); 3.5368 (2.09); 3.5221 (2.11); 3.5050 (0.93); 3.3417 (161.70); 2.8361 (1.53); 2.8187 (3.07); 2.8013 (1.42); 2.6764 (0.36); 2.6719 (0.48); 2.6675 (0.36); 2.5253 (1.34); 2.5118 (26.55); 2.5074 (53.59); 2.5028 (71.13); 2.4983 (53.53); 2.4939 (27.37); 2.3340 (0.34); 2.3296 (0.47); 2.3250 (0.36); 1.3496 (0.35); −0.0002 (1.21)

No. Ic-60, Solvent: <[D$_6$]-DMSO>, Spectrometer: 399.95 MHz 8.8187 (0.60); 8.8052 (1.15); 7.7918 (0.59); 8.0620 (2.39); 8.0489 (2.48); 7.9999 (2.45); 7.9794 (3.28); 7.8601 (3.51); 7.8393 (2.58); 6.8820 (1.62); 6.8791 (1.69); 6.8689 (1.57); 6.8660 (1.62); 6.6903 (3.01); 3.9046 (2.28); 3.8428 (0.35); 3.8117 (16.00); 3.7893 (0.35); 3.5608 (0.86); 3.5435 (2.09); 3.5288 (2.10); 3.5115 (0.97); 3.3912 (0.44); 3.3839 (0.42); 3.3440 (219.39); 3.3080 (0.41); 2.8596 (1.62); 2.8420 (3.18); 2.8243 (1.47); 2.6772 (0.45); 2.6726 (0.59); 2.6682 (0.45); 2.5257 (2.01); 2.5079 (63.83); 2.5035 (83.81); 2.4991 (63.48); 2.3347 (0.39); 2.3303 (0.53); 2.3261 (0.40); 1.3501 (0.40); 0.0079 (0.66); −0.0002 (19.35); −0.0079 (0.91)

No. Ic-61, Solvent: <[D$_6$]-DMSO>, Spectrometer: 399.95 MHz 8.5199 (0.56); 8.5064 (1.03); 8.4930 (0.55); 8.0590 (2.22); 8.0459 (2.28); 7.6127 (2.21); 7.5922 (0.68); 7.5831 (0.99); 7.5805 (1.03); 7.5708 (0.85); 7.3339 (2.51); 7.3224 (3.30); 7.3202 (3.23); 6.8742 (1.55); 6.8712 (1.61); 6.8612 (1.51); 6.8582 (1.54); 6.6787 (2.80); 3.9044 (2.08); 3.8117 (16.00); 3.5215 (0.84); 3.5041 (1.99); 3.4893 (2.01); 3.4719 (0.97); 3.3444 (181.26); 2.8397 (1.60); 2.8219 (3.04); 2.8043 (1.45); 2.6765 (0.38); 2.6722 (0.50); 2.6678 (0.37); 2.5253 (1.37); 2.5117 (26.70); 2.5076 (52.59); 2.5031 (69.14); 2.4987 (52.20); 2.3639 (0.47); 2.3442 (11.80); 2.3302 (0.68); 2.3252 (0.53); 2.2700 (0.41); 1.3499 (0.54); 0.0080 (0.33); −0.0002 (10.74); −0.0083 (0.51)

No. Ic-62, Solvent: <[D$_6$]-DMSO>, Spectrometer: 399.95 MHz 8.4149 (0.79); 8.0665 (2.12); 8.0534 (2.21); 7.6462 (0.60); 7.6294 (0.71); 7.6250 (1.24); 7.6082 (1.24); 7.6039 (0.84); 7.5870 (0.67); 7.3704 (0.64); 7.3643 (0.67); 7.3466 (0.78); 7.3410 (0.93); 7.3375 (0.83); 7.3199 (0.67); 7.3137 (0.68); 7.1851 (0.58); 7.1804 (0.54); 7.1643 (1.04); 7.1586 (1.03); 7.1426 (0.53); 7.1381 (0.50); 6.8864 (1.51); 6.8833 (1.60); 6.8734 (1.49); 6.8702 (1.58); 6.6907 (2.73); 3.9044 (2.12); 3.8346 (0.59); 3.8195 (16.00); 3.7976 (0.61); 3.5183 (0.84); 3.5011 (2.06); 3.4862 (2.09); 3.4691 (0.96); 3.4066 (0.33); 3.3481 (199.38); 2.8243 (1.56); 2.8068 (3.09); 2.7893 (1.44); 2.6771 (0.41); 2.6726 (0.53); 2.6682 (0.41); 2.5257 (1.56); 2.5122 (27.46); 2.5079 (54.84); 2.5034 (72.29); 2.4989 (54.54); 2.4946 (28.23); 2.3302 (0.46); 2.3257 (0.34); 1.3497 (0.36); 0.0080 (0.36); −0.0002 (10.34); −0.0085 (0.43)

No. Ic-63, Solvent: <[D$_6$]-DMSO>, Spectrometer: 399.95 MHz 8.7609 (0.52); 8.7474 (0.98); 8.7339 (0.52); 8.3192 (0.57); 8.0641 (2.17); 8.0511 (2.23); 7.5134 (1.26); 7.5078 (2.14); 7.4920 (1.96); 7.4870 (2.03); 7.4762 (0.58); 7.4653 (0.99); 7.4595 (1.21); 7.4537 (0.51); 7.4426 (0.47); 7.4369 (0.61); 6.8765 (1.51); 6.8734 (1.56); 6.8634 (1.50); 6.8603 (1.51); 6.6857 (2.80); 3.9045 (1.70); 3.8134 (16.00); 3.5391 (0.86); 3.5217 (1.98); 3.5072 (2.00); 3.4897 (0.94); 3.4083 (0.35); 3.3518 (240.84); 2.8422 (1.55); 2.8245 (3.04); 2.8069 (1.43); 2.6774 (0.35); 2.6730 (0.45); 2.6685 (0.35); 2.5262 (1.49); 2.5127 (25.93); 2.5085 (51.13); 2.5040 (67.14); 2.4995 (50.48); 2.4954 (26.01); 2.3308 (0.43); −0.0002 (7.53); −0.0085 (0.34)

No. Ic-64, Solvent: <[D$_6$]-DMSO>, Spectrometer: 399.95 MHz 8.5421 (0.90); 8.0708 (2.18); 8.0577 (2.23); 7.6013 (0.65); 7.5942 (0.87); 7.5905 (0.78); 7.5834 (0.87); 7.5791 (0.82); 7.5722 (1.00); 7.5685 (0.86); 7.5614 (0.91); 7.5284 (1.41); 7.5215 (1.22); 7.5134 (1.47); 7.5065 (1.17); 7.3752 (1.48); 7.3513 (1.91); 7.3287 (1.25); 6.8907 (1.54); 6.8877 (1.63); 6.8777 (1.50); 6.8746 (1.57); 6.6922 (2.80); 3.9042 (3.05); 3.8382 (0.70); 3.8233 (16.00); 3.8137 (1.17); 3.8066 (0.82); 3.5172 (0.87); 3.4999 (2.19); 3.4850 (2.22); 3.4679 (1.06); 3.3436 (177.03); 3.1615 (0.32); 2.8239 (1.61); 2.8065 (3.18); 2.7890 (1.49); 2.6766 (0.41); 2.6722 (0.55); 2.6678 (0.44); 2.5428 (0.40); 2.5253 (1.87); 2.5118 (30.85); 2.5076 (61.13); 2.5031 (81.16); 2.4986 (63.04); 2.4945 (34.46); 2.3344 (0.37); 2.3298 (0.51); 2.3254 (0.39); 1.3497 (0.50); −0.0002 (1.05)

No. Ic-65, Solvent: <[D$_6$]-DMSO>, Spectrometer: 399.95 MHz 8.7007 (0.55); 8.6869 (1.06); 8.6735 (0.55); 8.0613 (2.18); 8.0482 (2.24); 7.9694 (1.51); 7.9650 (2.64); 7.9607 (1.65); 7.8089 (1.30); 7.8055 (1.04); 7.7887 (1.44); 7.7403 (0.93); 7.7380 (1.10); 7.7355 (1.05); 7.7332 (0.93); 7.7203 (1.13); 7.7181 (1.22); 7.7155 (1.27); 7.4532 (1.59); 7.4335 (2.71); 7.4138 (1.27); 6.8746 (1.53); 6.8716 (1.57); 6.8616 (1.49); 6.8585 (1.53); 6.6803 (2.78); 3.9044 (3.06); 3.8133 (16.00); 3.5315 (0.85); 3.5141 (1.99); 3.4994 (2.02); 3.4821 (0.99); 3.3922 (0.33); 3.3432 (187.48); 3.1746 (0.70); 3.1615 (0.69); 2.8420 (1.57); 2.8244 (3.05); 2.8068 (1.45); 2.6765 (0.41); 2.6722 (0.56); 2.6676 (0.42); 2.5255 (1.69); 2.5118 (30.33); 2.5076 (59.87); 2.5031 (78.61); 2.4986 (58.80); 2.4943 (29.92); 2.3344 (0.36); 2.3299 (0.50); 2.3255 (0.36); −0.0002 (1.18)

No. Ic-66, Solvent: <[D$_6$]-DMSO>, Spectrometer: 399.95 MHz 8.6640 (0.58); 8.6504 (1.12); 8.6366 (0.57); 8.0562 (2.22); 8.0432 (2.26); 7.7550 (2.87); 7.7503 (1.14); 7.7384 (1.46); 7.7335 (5.45); 7.7282 (0.99); 7.6899 (0.90); 7.6847 (5.59); 7.6798 (1.48); 7.6678 (1.10); 7.6631 (2.95); 6.8692 (1.57); 6.8661 (1.63); 6.8560 (1.54); 6.8529 (1.58); 6.6762 (2.89); 3.9044 (3.03); 3.8097 (16.00); 3.5257 (0.82); 3.5082 (2.01); 3.4935 (2.01); 3.4763 (0.94); 3.3421 (156.50); 2.8386 (1.58); 2.8208 (3.05); 2.8032 (1.44); 2.6767 (0.38); 2.6724 (0.53); 2.6679 (0.41); 2.5254 (1.57); 2.5118 (29.40); 2.5077 (57.51); 2.5032 (75.00); 2.4987 (55.92); 2.3343 (0.34); 2.3299 (0.47); 2.3256 (0.35); −0.0002 (1.31)

No. Ic-67, Solvent: <[D$_6$]-DMSO>, Spectrometer: 399.95 MHz 8.8224 (0.51); 8.8092 (0.94); 8.7961 (0.50); 8.0666 (2.17); 8.0535 (2.23); 7.5317 (0.33); 7.5150 (0.66); 7.5106 (0.64); 7.4982 (0.47); 7.4939 (1.28); 7.4772 (0.63); 7.4728 (0.78); 7.4562 (0.34); 7.1768 (0.41); 7.1690 (2.14); 7.1492 (2.84); 7.1291 (1.82); 7.1214 (0.33); 6.8948 (1.49); 6.8917 (1.60); 6.8817 (1.45); 6.8786 (1.55); 6.6950 (2.77); 3.9041 (1.84); 3.8335 (0.51); 3.8221 (16.00); 3.7863 (0.34); 3.5232 (0.86); 3.5061 (2.24); 3.4914 (2.25); 3.4745 (0.95); 3.3425 (158.00); 2.8094 (1.57); 2.7923 (3.23); 2.7751 (1.46); 2.6762 (0.32); 2.6719 (0.41); 2.5250 (1.21); 2.5116 (22.29); 2.5073 (44.89); 2.5028 (59.74); 2.4983 (45.58); 2.4941 (23.93); 2.3296 (0.39); 0.0079 (0.39); −0.0002 (11.84); −0.0083 (0.55)

No. Ic-68, Solvent: <[D$_6$]-DMSO>, Spectrometer: 399.95 MHz 8.7951 (0.52); 8.7816 (1.01); 8.7676 (0.53); 8.3195 (10.72); 8.2053 (2.61); 8.2022 (1.71); 8.1175 (1.32); 8.1137 (0.96); 8.1006 (1.06); 8.0975 (1.44); 8.0940 (1.07); 8.0640

(2.21); 8.0509 (2.28); 8.0180 (0.93); 8.0149 (1.36); 8.0116 (0.93); 7.9986 (1.08); 7.9953 (1.57); 7.7128 (1.36); 7.6933 (2.43); 7.6736 (1.11); 6.8844 (1.53); 6.8813 (1.63); 6.8713 (1.53); 6.8682 (1.57); 6.6913 (2.88); 3.9046 (1.79); 3.8135 (16.00); 3.5560 (0.78); 3.5386 (1.91); 3.5241 (1.99); 3.5068 (0.93); 3.3451 (148.24); 3.3215 (6.78); 2.8519 (1.59); 2.8343 (3.13); 2.8167 (1.47); 2.6725 (0.45); 2.6683 (0.34); 2.5257 (1.36); 2.5080 (47.49); 2.5035 (62.58); 2.4990 (47.30); 2.3303 (0.40); −0.0002 (8.66); −0.0083 (0.39)

No. Ic-69, Solvent: <[D$_6$]-DMSO>, Spectrometer: 399.95 MHz 8.5530 (0.56); 8.5395 (1.12); 8.5255 (0.61); 8.0707 (2.26); 8.0577 (2.35); 7.5022 (1.48); 7.4959 (1.50); 7.4796 (1.51); 7.4733 (1.50); 7.4125 (1.17); 7.3970 (1.26); 7.3912 (1.70); 7.3756 (1.60); 7.2918 (0.99); 7.2855 (0.94); 7.2706 (1.68); 7.2643 (1.58); 7.2493 (0.76); 7.2430 (0.69); 6.9024 (1.57); 6.8994 (1.65); 6.8893 (1.59); 6.8863 (1.64); 6.7046 (2.96); 3.9042 (2.13); 3.8345 (0.61); 3.8218 (16.00); 3.8012 (0.53); 3.5082 (0.94); 3.4910 (2.29); 3.4762 (2.37); 3.4593 (1.09); 3.3488 (256.64); 2.8220 (1.67); 2.8047 (3.33); 2.7875 (1.52); 2.6765 (0.41); 2.6723 (0.53); 2.6678 (0.42); 2.5077 (58.84); 2.5032 (76.72); 2.4988 (57.84); 2.3343 (0.35); 2.3301 (0.48); 2.3254 (0.35); 0.0079 (0.53); −0.0002 (13.34); −0.0083 (0.56)

No. Ic-70, Solvent: <[D$_6$]-DMSO>, Spectrometer: 399.95 MHz 8.8383 (0.57); 8.8248 (1.09); 8.8110 (0.57); 8.0593 (2.23); 8.0463 (2.29); 7.9751 (1.08); 7.9731 (0.86); 7.9693 (0.60); 7.9533 (8.15); 7.9461 (7.98); 7.9301 (0.56); 7.9242 (1.06); 6.8768 (1.57); 6.8737 (1.63); 6.8637 (1.54); 6.8606 (1.57); 6.6856 (2.85); 3.9044 (1.60); 3.8104 (16.00); 3.5534 (0.84); 3.5360 (2.02); 3.5215 (2.06); 3.5041 (0.95); 3.4024 (0.48); 3.3533 (219.71); 3.3176 (0.54); 3.1621 (0.32); 2.8510 (1.56); 2.8334 (3.04); 2.8158 (1.42); 2.6731 (0.39); 2.5261 (1.37); 2.5128 (22.31); 2.5085 (43.72); 2.5040 (57.22); 2.4995 (42.92); 2.4953 (22.03); 2.3308 (0.36); 0.0079 (0.33); −0.0002 (9.55); −0.0084 (0.43)

No. Ic-71, Solvent: <[D$_6$]-DMSO>, Spectrometer: 399.95 MHz 8.9204 (0.59); 8.9065 (1.15); 8.8930 (0.60); 8.3327 (0.49); 8.3267 (3.96); 8.3220 (1.38); 8.3094 (1.40); 8.3046 (4.64); 8.2991 (0.67); 8.0635 (2.37); 8.0505 (2.48); 8.0404 (0.69); 8.0346 (4.55); 8.0298 (1.52); 8.0172 (1.30); 8.0124 (3.90); 8.0067 (0.58); 6.8847 (1.59); 6.8817 (1.66); 6.8716 (1.56); 6.8687 (1.64); 6.6936 (2.98); 3.9046 (2.68); 3.8122 (16.00); 3.5692 (0.85); 3.5519 (2.08); 3.5372 (2.11); 3.5201 (0.96); 3.3890 (0.51); 3.3489 (227.87); 2.8640 (1.61); 2.8465 (3.20); 2.8289 (1.51); 2.6729 (0.43); 2.6685 (0.33); 2.5260 (1.37); 2.5125 (25.35); 2.5083 (50.35); 2.5038 (66.56); 2.4993 (50.41); 2.4953 (26.44); 2.3305 (0.43); 2.3259 (0.32); −0.0002 (0.58)

No. Ic-72, Solvent: <[D$_6$]-DMSO>, Spectrometer: 399.95 MHz 8.6756 (0.52); 8.6620 (1.00); 8.6481 (0.53); 8.0617 (2.21); 8.0487 (2.28); 7.6627 (1.25); 7.6433 (1.64); 7.6022 (0.77); 7.5960 (0.96); 7.5923 (0.76); 7.5771 (0.77); 7.5709 (0.94); 7.5670 (0.76); 7.5437 (0.67); 7.5291 (0.73); 7.5235 (1.21); 7.5089 (1.21); 7.5040 (0.77); 7.4892 (0.67); 7.4008 (0.54); 7.3988 (0.60); 7.3941 (0.54); 7.3923 (0.54); 7.3784 (0.95); 7.3720 (0.89); 7.3582 (0.44); 7.3562 (0.46); 7.3517 (0.41); 6.8770 (1.52); 6.8740 (1.61); 6.8640 (1.49); 6.8609 (1.57); 6.6839 (2.82); 3.9045 (2.04); 3.8121 (16.00); 3.5370 (0.85); 3.5196 (2.01); 3.5050 (2.03); 3.4876 (0.97); 3.3438 (157.75); 2.8454 (1.62); 2.8276 (3.12); 2.8100 (1.47); 2.6723 (0.37); 2.5255 (1.17); 2.5119 (21.60); 2.5077 (43.33); 2.5032 (57.34); 2.4987 (43.26); 2.4944 (22.30); 2.3300 (0.37); −0.0002 (0.87)

No. Ic-73, Solvent: <[D$_6$]-DMSO>, Spectrometer: 399.95 MHz 8.6887 (0.58); 8.6753 (1.06); 8.6613 (0.56); 8.0603 (2.24); 8.0472 (2.30); 7.8645 (0.62); 7.8593 (0.66); 7.8448 (0.67); 7.8395 (0.77); 7.8356 (0.75); 7.8302 (0.70); 7.8158 (0.62); 7.8107 (0.64); 7.7128 (0.58); 7.7052 (0.56); 7.7015 (0.59); 7.6945 (0.76); 7.6912 (0.75); 7.6859 (0.68); 7.6836 (0.69); 7.6798 (0.68); 7.5863 (0.71); 7.5655 (1.09); 7.5601 (0.80); 7.5444 (0.67); 7.5393 (1.06); 7.5182 (0.50); 6.8728 (1.56); 6.8699 (1.66); 6.8597 (1.53); 6.8568 (1.59); 6.6812 (2.90); 3.9046 (2.00); 3.8118 (16.00); 3.5318 (0.86); 3.5145 (2.07); 3.4998 (2.12); 3.4824 (0.98); 3.3430 (136.84); 2.8381 (1.67); 2.8205 (3.21); 2.8028 (1.52); 2.6724 (0.39); 2.5077 (47.30); 2.5033 (61.16); 2.4988 (46.03); 2.3399 (0.36); 2.3346 (0.33); 2.3301 (0.41); −0.0002 (0.99)

No. Ic-74, Solvent: <[D$_6$]-DMSO>, Spectrometer: 399.95 MHz 8.5336 (0.52); 8.5203 (0.98); 8.5059 (0.51); 8.0725 (2.20); 8.0594 (2.25); 7.4855 (0.86); 7.4824 (1.07); 7.4656 (1.94); 7.4626 (2.10); 7.4436 (0.87); 7.4391 (0.97); 7.4259 (1.41); 7.4212 (1.50); 7.4063 (0.80); 7.4014 (0.88); 7.3891 (0.88); 7.3854 (0.83); 7.3704 (1.63); 7.3671 (1.64); 7.3525 (0.94); 7.3491 (0.87); 7.3277 (1.85); 7.3234 (1.76); 7.3092 (1.05); 7.3046 (0.86); 6.9066 (1.53); 6.9035 (1.60); 6.8935 (1.50); 6.8905 (1.55); 6.7088 (2.79); 4.1169 (0.75); 4.1038 (0.77); 3.9040 (1.87); 3.8235 (16.00); 3.5112 (0.88); 3.4940 (2.24); 3.4793 (2.28); 3.4622 (0.98); 3.3434 (173.90); 3.1744 (2.73); 3.1613 (2.68); 2.8267 (1.62); 2.8094 (3.26); 2.7920 (1.47); 2.6719 (0.38); 2.5249 (1.31); 2.5114 (22.31); 2.5072 (44.38); 2.5027 (58.72); 2.4982 (44.67); 2.4940 (23.31); 2.3294 (0.38); −0.0002 (8.93); −0.0084 (0.42)

No. Ic-75, Solvent: <[D$_6$]-DMSO>, Spectrometer: 399.95 MHz 8.7040 (0.55); 8.6901 (1.02); 8.6766 (0.54); 8.0623 (2.21); 8.0493 (2.27); 7.8332 (1.44); 7.8287 (2.55); 7.8243 (1.75); 7.7701 (1.37); 7.7507 (1.55); 7.6108 (0.73); 7.6084 (0.88); 7.6057 (0.81); 7.6032 (0.78); 7.5908 (1.17); 7.5883 (1.26); 7.5857 (1.32); 7.5833 (1.10); 7.5192 (1.76); 7.4996 (2.53); 7.4799 (1.05); 6.8761 (1.53); 6.8731 (1.60); 6.8630 (1.50); 6.8600 (1.56); 6.6830 (2.83); 3.9048 (1.61); 3.8129 (16.00); 3.5349 (0.85); 3.5174 (2.04); 3.5029 (2.05); 3.4855 (0.95); 3.3389 (69.67); 2.8441 (1.61); 2.8264 (3.15); 2.8088 (1.48); 2.6722 (0.39); 2.5254 (1.26); 2.5118 (21.91); 2.5076 (43.44); 2.5031 (57.19); 2.4987 (43.40); 2.3300 (0.36); 0.0079 (0.90); −0.0002 (26.05); −0.0083 (1.26)

No. Ic-76, Solvent: <[D$_6$]-DMSO>, Spectrometer: 399.95 MHz 8.6151 (0.54); 8.6012 (1.02); 8.5879 (0.54); 8.0787 (2.24); 8.0656 (2.29); 7.7739 (1.28); 7.7546 (1.68); 7.7230 (0.56); 7.7049 (1.42); 7.6867 (1.03); 7.6489 (1.01); 7.6298 (1.27); 7.6112 (0.47); 7.4185 (1.49); 7.3999 (1.31); 6.8989 (1.54); 6.8959 (1.63); 6.8858 (1.51); 6.8828 (1.58); 6.6969 (2.86); 3.9041 (1.78); 3.8255 (16.00); 3.5078 (0.88); 3.4904 (2.17); 3.4757 (2.22); 3.4586 (1.04); 3.3489 (220.78); 2.8102 (1.59); 2.7927 (3.19); 2.7752 (1.47); 2.6722 (0.42); 2.5254 (1.45); 2.5118 (24.92); 2.5077 (49.52); 2.5032 (65.46); 2.4987 (49.73); 2.4946 (26.04); 2.3301 (0.43); −0.0002 (8.30); −0.0083 (0.40)

No. Ic-77, Solvent: <[D$_6$]-DMSO>, Spectrometer: 399.95 MHz 8.4468 (0.44); 8.4334 (0.92); 8.4193 (0.49); 8.3180 (0.39); 8.0609 (2.02); 8.0478 (2.18); 7.4383 (1.03); 7.4333 (1.27); 7.4175 (0.97); 7.4124 (1.46); 7.3931 (2.38); 7.3882 (1.93); 7.0143 (2.24); 6.9933 (1.97); 6.8734 (1.31); 6.8702 (1.43); 6.8602 (1.36); 6.8571 (1.50); 6.6768 (2.41); 3.9043 (2.36); 3.8798 (0.33); 3.8197 (1.76); 3.8114 (16.00); 3.7960 (13.14); 3.7864 (13.44); 3.7675 (0.70); 3.7606 (0.67); 3.7051 (0.37);

3.5104 (0.70); 3.4930 (1.58); 3.4780 (1.60); 3.4608 (0.85); 3.3557 (234.82); 3.3019 (0.57); 2.8359 (1.27); 2.8182 (2.37); 2.8004 (1.20); 2.6773 (0.47); 2.6729 (0.59); 2.6685 (0.45); 2.5429 (0.43); 2.5262 (1.79); 2.5127 (29.03); 2.5084 (57.83); 2.5038 (75.93); 2.4993 (56.68); 2.4949 (28.72); 2.3350 (0.34); 2.3306 (0.47); 2.3260 (0.34); 1.3498 (0.77); 1.2736 (0.39); 0.0080 (0.33); −0.0002 (8.43)

No. Ic-79, Solvent: <[$D_6$]-DMSO>, Spectrometer: 399.95 MHz 8.6622 (0.81); 8.6496 (1.56); 8.6365 (0.89); 8.5187 (0.45); 8.3246 (2.56); 8.3120 (2.69); 7.8975 (2.26); 7.8824 (2.81); 7.8761 (3.31); 7.8620 (2.70); 7.3133 (2.29); 7.2915 (4.52); 7.2694 (2.33); 7.1270 (3.80); 7.0582 (2.23); 7.0454 (2.13); 3.5230 (1.11); 3.5052 (2.74); 3.4893 (2.83); 3.4729 (1.35); 3.3482 (367.89); 2.8365 (2.27); 2.8185 (4.15); 2.8007 (2.12); 2.6726 (1.17); 2.5036 (171.29); 2.4159 (16.00); 2.3302 (1.17); −0.0002 (6.39)

No. Ic-80, Solvent: <[$D_6$]-DMSO>, Spectrometer: 399.95 MHz 8.5395 (0.64); 8.5257 (1.25); 8.5127 (0.74); 8.3400 (2.43); 8.3274 (2.58); 7.4886 (1.07); 7.4854 (1.34); 7.4688 (2.39); 7.4656 (2.71); 7.4457 (0.99); 7.4412 (1.18); 7.4279 (1.70); 7.4233 (1.94); 7.4083 (1.01); 7.4035 (1.15); 7.3926 (1.08); 7.3889 (1.16); 7.3739 (2.00); 7.3706 (2.22); 7.3559 (1.15); 7.3526 (1.20); 7.3282 (2.26); 7.3237 (2.31); 7.3099 (1.37); 7.3052 (1.25); 7.1533 (3.25); 7.0909 (1.73); 7.0793 (1.75); 3.5118 (1.09); 3.4945 (2.81); 3.4797 (2.77); 3.4626 (1.27); 3.3436 (188.70); 2.8899 (0.64); 2.8272 (2.08); 2.8097 (4.09); 2.7922 (1.95); 2.7299 (0.56); 2.6713 (0.47); 2.6669 (0.39); 2.5067 (51.98); 2.5024 (69.63); 2.4980 (55.75); 2.4310 (16.00); 2.3292 (0.47); 2.3246 (0.38); −0.0002 (3.20)

No. Ic-81, Solvent: <[$D_6$]-DMSO>, Spectrometer: 399.95 MHz 8.5983 (0.83); 8.5849 (1.56); 8.5713 (0.86); 8.3392 (2.59); 8.3266 (2.72); 8.3201 (1.07); 7.6746 (3.08); 7.6699 (3.22); 7.4945 (1.65); 7.4912 (1.45); 7.4896 (1.54); 7.4739 (2.21); 7.4706 (1.98); 7.4690 (2.11); 7.3635 (3.52); 7.3429 (2.61); 7.1483 (3.62); 7.0874 (1.94); 7.0750 (1.94); 3.5119 (1.10); 3.4949 (2.91); 3.4796 (3.01); 3.4632 (1.29); 3.4019 (0.45); 3.3481 (233.56); 2.8912 (0.36); 2.8219 (2.13); 2.8044 (4.21); 2.7871 (1.98); 2.7317 (0.35); 2.6720 (0.53); 2.5031 (79.16); 2.4295 (16.00); 2.3297 (0.53); 0.0016 (0.91); −0.0002 (1.08)

No. Ic-82, Solvent: <[$D_6$]-DMSO>, Spectrometer: 399.95 MHz 8.6880 (0.80); 8.6748 (1.53); 8.6610 (0.84); 8.3221 (3.59); 8.3118 (2.74); 7.8301 (4.31); 7.8089 (5.46); 7.7841 (0.50); 7.5485 (5.17); 7.5271 (4.74); 7.2589 (0.46); 7.2377 (0.46); 7.1241 (3.59); 7.0550 (1.91); 7.0427 (1.92); 3.5254 (1.12); 3.5081 (2.66); 3.4921 (2.71); 3.4757 (1.38); 3.3501 (198.24); 2.8905 (0.35); 2.8345 (2.16); 2.8164 (3.94); 2.7987 (2.02); 2.6724 (0.59); 2.5074 (62.66); 2.5033 (85.22); 2.4992 (72.28); 2.4393 (0.35); 2.4158 (16.00); 2.3303 (0.57); −0.0002 (3.14)

No. Ic-83, Solvent: <[$D_6$]-DMSO>, Spectrometer: 399.95 MHz 8.5086 (0.79); 8.4953 (1.51); 8.4816 (0.83); 8.3231 (2.50); 8.3105 (2.63); 7.8376 (1.74); 7.8176 (1.89); 7.7151 (4.16); 7.6949 (4.61); 7.2999 (1.59); 7.2800 (1.55); 7.2650 (4.12); 7.2452 (3.83); 7.1232 (3.52); 7.0535 (1.89); 7.0417 (1.91); 3.5135 (1.25); 3.4962 (2.76); 3.4808 (2.83); 3.4635 (1.59); 3.3555 (130.60); 2.8909 (0.97); 2.8308 (2.17); 2.8127 (3.86); 2.7949 (1.98); 2.7315 (0.84); 2.6725 (0.55); 2.5037 (77.91); 2.4159 (16.00); 2.3663 (5.84); 2.3418 (13.45); −0.0002 (0.34)

No. Ic-84, Solvent: <[$D_6$]-DMSO>, Spectrometer: 399.95 MHz 8.4163 (1.14); 8.3370 (2.55); 8.3244 (2.67); 7.5528 (0.92); 7.5348 (2.19); 7.5280 (0.98); 7.5163 (1.87); 7.5079 (1.25); 7.5023 (1.17); 7.4878 (0.68); 7.2965 (1.33); 7.2813 (1.76); 7.2758 (1.62); 7.2633 (2.87); 7.2465 (1.63); 7.1412 (3.53); 7.0772 (1.98); 7.0650 (1.99); 3.5225 (1.22); 3.5053 (2.92); 3.4897 (2.93); 3.4726 (1.44); 3.3577 (249.10); 2.8910 (0.56); 2.8281 (2.28); 2.8104 (4.26); 2.7927 (2.09); 2.7313 (0.48); 2.6729 (0.48); 2.5039 (65.74); 2.4287 (16.00); 2.3302 (0.43); −0.0002 (0.47)

No. Ic-85, Solvent: <[$D_6$]-DMSO>, Spectrometer: 399.95 MHz 8.4929 (0.51); 8.3250 (0.82); 8.3125 (0.84); 7.7408 (1.34); 7.7199 (1.55); 7.4735 (1.58); 7.4526 (1.35); 7.1284 (1.09); 7.0534 (0.58); 7.0414 (0.57); 3.5205 (0.33); 3.5031 (0.78); 3.4880 (0.78); 3.4704 (0.37); 3.3411 (33.71); 2.8908 (0.40); 2.8314 (0.64); 2.8133 (1.18); 2.7956 (0.60); 2.7315 (0.36); 2.5071 (17.42); 2.5029 (22.34); 2.4996 (17.79); 2.4194 (5.09); 1.2892 (16.00); −0.0002 (1.16)

No. Ic-86, Solvent: <[$D_6$]-DMSO>, Spectrometer: 399.95 MHz 20.0038 (1.14); 8.6741 (1.13); 8.6148 (0.77); 8.3299 (2.01); 8.3171 (2.16); 7.6618 (1.42); 7.6433 (1.99); 7.5956 (1.16); 7.5722 (1.17); 7.5262 (1.23); 7.5115 (1.30); 7.3799 (1.18); 7.1312 (2.85); 7.0600 (1.47); 7.0492 (1.61); 3.5170 (2.29); 3.5022 (2.39); 3.4834 (1.55); 3.3415 (5739.85); 2.8398 (2.22); 2.8213 (3.69); 2.8028 (2.20); 2.6716 (16.00); 2.5068 (1843.93); 2.5025 (2321.81); 2.4983 (1770.85); 2.4183 (14.24); 2.3293 (15.15); 1.2356 (0.75); −0.0002 (113.32)

No. Ic-87, Solvent: <[$D_6$]-DMSO>, Spectrometer: 399.95 MHz 8.8632 (0.81); 8.8503 (1.51); 8.8362 (0.84); 8.3314 (2.60); 8.3188 (2.69); 8.1272 (3.12); 8.0969 (1.94); 7.9162 (1.49); 7.8968 (1.81); 7.7413 (1.31); 7.7219 (2.21); 7.7028 (1.00); 7.1368 (3.61); 7.0705 (1.94); 7.0582 (1.91); 3.5597 (1.07); 3.5421 (2.65); 3.5264 (2.67); 3.5098 (1.27); 3.3826 (0.69); 3.3460 (245.64); 2.8559 (2.15); 2.8378 (4.01); 2.8201 (2.02); 2.6728 (0.55); 2.5034 (78.20); 2.4995 (67.27); 2.4397 (0.34); 2.4158 (16.00); 2.3304 (0.52); −0.0002 (3.03); −0.0019 (2.43)

No. Ic-88, Solvent: <[$D_6$]-DMSO>, Spectrometer: 399.95 MHz 8.5058 (0.77); 8.4922 (1.53); 8.4789 (0.86); 8.3237 (2.48); 8.3112 (2.61); 7.7335 (4.14); 7.7130 (4.77); 7.2947 (4.24); 7.2742 (4.05); 7.1251 (3.49); 7.0533 (1.85); 7.0414 (1.89); 3.5167 (1.10); 3.4995 (2.50); 3.4839 (2.51); 3.4669 (1.26); 3.3976 (0.36); 3.3472 (205.91); 2.8313 (2.13); 2.8132 (3.81); 2.7954 (1.97); 2.6696 (1.56); 2.6504 (3.55); 2.6315 (3.65); 2.6128 (1.40); 2.5072 (52.43); 2.5031 (67.83); 2.4990 (54.27); 2.4172 (16.00); 2.3299 (0.45); 1.2027 (4.65); 1.1940 (1.19); 1.1838 (9.58); 1.1647 (4.46); −0.0002 (2.84)

No. Ic-89, Solvent: <[$D_6$]-DMSO>, Spectrometer: 399.95 MHz 8.3541 (1.81); 8.3415 (1.85); 8.2141 (0.43); 8.2012 (0.78); 8.1883 (0.45); 7.7123 (1.31); 7.7078 (1.41); 7.6931 (1.41); 7.6886 (1.45); 7.4744 (0.81); 7.4698 (0.81); 7.4559 (0.93); 7.4533 (1.11); 7.4518 (1.07); 7.4491 (0.93); 7.4352 (0.87); 7.4306 (0.82); 7.1547 (2.25); 7.1204 (1.96); 7.0995 (1.87); 7.0941 (1.37); 7.0804 (1.19); 7.0351 (0.98); 7.0330 (0.96); 7.0163 (1.69); 7.0145 (1.67); 6.9978 (0.90); 6.9956 (0.85); 6.9855 (0.33); 3.9050 (1.10); 3.8086 (16.00); 3.5580 (0.85); 3.5405 (1.99); 3.5258 (2.02); 3.5082 (1.00); 3.3358 (55.29); 2.8326 (1.54); 2.8149 (2.97); 2.7972 (1.41); 2.6759 (0.34); 2.6714 (0.47); 2.6669 (0.35); 2.5247 (1.50); 2.5112 (26.66); 2.5068 (52.90); 2.5023 (70.07); 2.4978 (52.92); 2.4935 (27.14); 2.4349 (12.42); 2.3335 (0.33); 2.3291 (0.45); 2.3246 (0.34); 0.0081 (0.89); −0.0002 (26.75); −0.0084 (1.07)

No. Ic-90, Solvent: <[D$_6$]-DMSO>, Spectrometer: 399.95 MHz 8.8319 (0.80); 8.8189 (1.51); 8.8052 (0.80); 8.3304 (2.54); 8.3177 (2.61); 7.9994 (3.15); 7.9791 (4.19); 7.8628 (4.34); 7.8422 (3.27); 7.1366 (3.46); 7.0662 (1.84); 7.0541 (1.80); 3.5577 (1.09); 3.5403 (2.56); 3.5248 (2.57); 3.5079 (1.25); 3.4042 (0.33); 3.3461 (260.63); 3.2945 (0.38); 2.8540 (2.06); 2.8360 (3.84); 2.8183 (1.94); 2.6725 (0.60); 2.5075 (65.69); 2.5034 (87.06); 2.4998 (71.81); 2.4432 (0.37); 2.4199 (16.00); 2.3303 (0.58); −0.0002 (3.62)

No. Ic-91, Solvent: <[D$_6$]-DMSO>, Spectrometer: 399.95 MHz 8.7185 (0.75); 8.7051 (1.41); 8.6916 (0.79); 8.3298 (2.54); 8.3172 (2.64); 7.8747 (0.76); 7.8575 (0.34); 7.8268 (3.15); 7.7697 (1.76); 7.7504 (2.06); 7.6108 (1.22); 7.6086 (1.21); 7.5909 (1.71); 7.5885 (1.82); 7.5212 (2.10); 7.5015 (3.07); 7.4820 (1.31); 7.1288 (3.46); 7.0611 (1.83); 7.0487 (1.83); 3.5314 (1.16); 3.5139 (2.89); 3.4984 (2.70); 3.4815 (1.40); 3.4586 (0.33); 3.3504 (98.15); 2.8381 (2.15); 2.8200 (3.95); 2.8022 (2.00); 2.6720 (0.47); 2.5033 (66.97); 2.4993 (54.96); 2.4193 (16.00); 2.3299 (0.44); −0.0002 (2.34)

No. Ic-92, Solvent: <[D$_6$]-DMSO>, Spectrometer: 399.95 MHz 8.8157 (0.80); 8.8026 (1.51); 8.7896 (0.82); 8.3338 (2.56); 8.3212 (2.65); 7.9535 (0.45); 7.9147 (0.80); 7.8631 (2.02); 7.8597 (1.73); 7.8101 (12.00); 7.1312 (3.53); 7.0643 (1.89); 7.0522 (1.89); 3.5328 (1.44); 3.5156 (3.04); 3.5004 (3.17); 3.4833 (1.88); 3.3601 (116.66); 2.8919 (2.65); 2.8353 (2.17); 2.8175 (3.99); 2.7998 (2.00); 2.7322 (2.41); 2.6734 (0.57); 2.5046 (84.12); 2.4561 (0.39); 2.4223 (16.00); 2.3311 (0.55)

No. Ic-93, Solvent: <[D$_6$]-DMSO>, Spectrometer: 399.95 MHz 8.5340 (0.77); 8.5204 (1.44); 8.5066 (0.81); 8.3271 (2.49); 8.3145 (2.62); 7.6126 (3.04); 7.5928 (0.92); 7.5900 (0.92); 7.5818 (1.46); 7.5718 (1.28); 7.3555 (0.41); 7.3360 (3.07); 7.3244 (4.20); 7.3224 (4.79); 7.1266 (3.48); 7.0573 (1.86); 7.0449 (1.85); 3.5184 (1.09); 3.5009 (2.54); 3.4842 (2.54); 3.4682 (1.28); 3.3425 (95.37); 2.8329 (2.14); 2.8147 (3.86); 2.7969 (1.99); 2.6719 (0.41); 2.5072 (43.88); 2.5029 (60.03); 2.4988 (50.28); 2.4188 (16.00); 2.3458 (15.04); −0.0002 (2.97)

No. Ic-94, Solvent: <[D$_6$]-DMSO>, Spectrometer: 399.95 MHz 8.4242 (1.09); 8.3348 (2.47); 8.3222 (2.59); 7.6466 (0.69); 7.6254 (1.53); 7.6085 (1.49); 7.6045 (1.13); 7.5873 (0.79); 7.3734 (0.80); 7.3672 (0.87); 7.3494 (1.01); 7.3440 (1.27); 7.3406 (1.13); 7.3228 (0.83); 7.3167 (0.88); 7.1881 (0.74); 7.1832 (0.76); 7.1674 (1.39); 7.1620 (1.41); 7.1456 (0.84); 7.1346 (3.49); 7.0699 (1.79); 7.0576 (1.79); 3.5164 (1.09); 3.4991 (2.65); 3.4839 (2.67); 3.4666 (1.26); 3.3447 (88.40); 2.8216 (2.11); 2.8037 (4.01); 2.7861 (1.96); 2.6723 (0.45); 2.5075 (48.38); 2.5031 (63.37); 2.4989 (49.92); 2.4266 (16.00); 2.3297 (0.40); −0.0002 (3.09)

No. Ic-95, Solvent: <[D$_6$]-DMSO>, Spectrometer: 399.95 MHz 8.7667 (0.77); 8.7540 (1.39); 8.7402 (0.77); 8.3334 (2.53); 8.3208 (2.60); 7.5247 (0.50); 7.5081 (2.95); 7.4926 (3.31); 7.4878 (2.88); 7.4763 (0.76); 7.4704 (1.52); 7.4647 (1.54); 7.4478 (0.63); 7.4421 (0.78); 7.1315 (3.41); 7.0625 (1.83); 7.0498 (1.82); 3.5364 (1.12); 3.5192 (2.57); 3.5041 (2.58); 3.4865 (1.26); 3.3429 (73.33); 2.8913 (1.02); 2.8372 (2.21); 2.8192 (3.90); 2.8013 (1.99); 2.7319 (0.90); 2.6726 (0.41); 2.5075 (49.94); 2.5034 (62.04); 2.4199 (16.00); 2.3299 (0.43); −0.0002 (2.53)

No. Ic-96, Solvent: <[D$_6$]-DMSO>, Spectrometer: 399.95 MHz 8.5914 (0.73); 8.5779 (1.31); 8.5640 (0.70); 8.0711 (2.43); 8.0581 (2.47); 7.6725 (2.76); 7.6677 (2.79); 7.4911 (1.49); 7.4861 (1.41); 7.4706 (2.02); 7.4656 (1.92); 7.3630 (3.36); 7.3425 (2.47); 6.8990 (1.84); 6.8882 (1.78); 6.7046 (3.36); 3.8214 (16.00); 3.8043 (0.67); 3.5108 (0.99); 3.4938 (2.53); 3.4788 (2.60); 3.4620 (1.11); 3.3374 (72.52); 2.8904 (0.64); 2.8203 (1.83); 2.8030 (3.63); 2.7858 (1.70); 2.7309 (0.57); 2.6713 (0.48); 2.6672 (0.37); 2.5066 (54.26); 2.5024 (68.54); 2.4982 (52.98); 2.3293 (0.44); −0.0002 (3.72)

No. Ic-97, Solvent: <[D$_6$]-DMSO>, Spectrometer: 399.95 MHz 8.4928 (0.68); 8.4790 (1.26); 8.4650 (0.66); 8.0547 (2.32); 8.0417 (2.37); 7.8287 (0.55); 7.8084 (0.60); 7.7140 (3.60); 7.6936 (3.99); 7.2820 (0.49); 7.2622 (3.73); 7.2424 (3.12); 6.8661 (1.82); 6.8559 (1.63); 6.8530 (1.76); 6.6735 (3.14); 3.8088 (16.00); 3.5153 (0.94); 3.4980 (2.21); 3.4830 (2.21); 3.4660 (1.06); 3.3412 (65.07); 2.8903 (0.86); 2.8359 (1.73); 2.8182 (3.30); 2.8007 (1.62); 2.7304 (0.73); 2.6717 (0.44); 2.5072 (48.56); 2.5028 (65.10); 2.4984 (52.31); 2.3597 (1.91); 2.3399 (11.16); −0.0002 (3.49)

No. Ic-98, Solvent: <[D$_6$]-DMSO>, Spectrometer: 399.95 MHz 8.3146 (0.87); 8.3016 (1.57); 8.2890 (0.97); 8.0709 (2.51); 8.0580 (2.68); 7.3169 (0.54); 7.3104 (0.65); 7.2968 (1.43); 7.2926 (1.42); 7.2814 (1.22); 7.2765 (1.46); 7.2098 (6.28); 7.1952 (3.68); 7.1731 (0.78); 7.1493 (0.51); 6.8951 (2.25); 6.8823 (2.31); 6.6939 (3.94); 3.8208 (16.00); 3.7826 (0.57); 3.5152 (1.37); 3.4985 (3.32); 3.4834 (3.45); 3.4670 (1.72); 3.3489 (100.35); 2.8905 (0.37); 2.8266 (2.26); 2.8096 (4.30); 2.7926 (2.13); 2.7302 (0.35); 2.6720 (0.64); 2.5028 (80.08); 2.4451 (2.27); 2.3297 (0.58); 2.2229 (14.11); −0.0002 (2.35)

No. Ic-99, Solvent: <[D$_6$]-DMSO>, Spectrometer: 399.95 MHz 8.8037 (0.70); 8.7905 (1.37); 8.7770 (0.76); 8.3192 (1.36); 8.0637 (2.43); 8.0507 (2.54); 7.8097 (16.00); 6.8733 (2.03); 6.8602 (2.02); 6.6830 (3.53); 3.8145 (15.95); 3.5350 (0.95); 3.5177 (2.39); 3.5028 (2.39); 3.4860 (1.13); 3.3531 (239.97); 2.8910 (1.09); 2.8387 (1.84); 2.8212 (3.59); 2.8036 (1.73); 2.7309 (0.97); 2.6727 (0.45); 2.5082 (47.10); 2.5039 (64.66); 2.4998 (54.89); 2.3307 (0.44); −0.0002 (2.24)

No. Ic-100, Solvent: <[D$_6$]-DMSO>, Spectrometer: 399.95 MHz 8.4744 (1.04); 8.3207 (0.97); 8.0676 (2.40); 8.0546 (2.46); 7.5804 (1.22); 7.5606 (3.76); 7.5398 (1.75); 7.5354 (1.71); 7.5306 (1.60); 7.3819 (1.62); 7.3770 (1.54); 7.3611 (1.32); 7.3561 (1.27); 6.8858 (1.84); 6.8832 (1.72); 6.8727 (1.80); 6.6916 (3.31); 3.8343 (0.59); 3.8193 (16.00); 3.8007 (0.51); 3.5197 (0.91); 3.5027 (2.30); 3.4876 (2.38); 3.4706 (1.00); 3.3421 (101.47); 2.8233 (1.78); 2.8058 (3.49); 2.7883 (1.62); 2.6722 (0.41); 2.5073 (48.31); 2.5029 (60.55); 2.4985 (45.52); 2.3299 (0.40); −0.0002 (3.29)

No. Ic-101, Solvent: <[D$_6$]-DMSO>, Spectrometer: 399.95 MHz 8.4281 (0.84); 8.4145 (1.59); 8.4011 (0.86); 8.3247 (2.54); 8.3121 (2.65); 7.4062 (1.77); 7.4021 (1.87); 7.3859 (1.92); 7.3818 (2.07); 7.3350 (3.82); 7.3315 (3.38); 7.1181 (3.52); 7.0473 (1.87); 7.0354 (1.90); 6.9882 (3.34); 6.9679 (3.05); 6.0865 (12.92); 3.4944 (1.09); 3.4772 (2.51); 3.4618 (2.59); 3.4444 (1.23); 3.3441 (173.45); 2.8909 (0.42); 2.8169 (2.11); 2.7988 (3.80); 2.7810 (1.95); 2.7315 (0.40); 2.6722 (0.45); 2.5071 (54.72); 2.5030 (68.01); 2.4175 (16.00); 2.3299 (0.45); −0.0002 (2.87)

No. Ic-102, Solvent: <[D$_6$]-DMSO>, Spectrometer: 399.95 MHz 8.4417 (0.74); 8.4281 (1.39); 8.4146 (0.77); 8.3236 (2.21); 8.3110 (2.28); 7.7936 (3.85); 7.7715 (4.09); 7.1218 (3.12); 7.0521 (1.69); 7.0394 (1.69); 6.9950 (4.13); 6.9730 (3.91); 3.7993 (16.00); 3.5054 (0.98); 3.4883 (2.22); 3.4726 (2.33); 3.4554 (1.13); 3.3474 (151.20); 2.8909 (0.47); 2.8256 (1.87); 2.8076 (3.34); 2.7897 (1.74); 2.7317 (0.42); 2.6722 (0.38); 2.5032 (56.46); 2.4169 (13.85); 2.3300 (0.39); −0.0002 (2.09)

No. Ic-103, Solvent: <[D$_6$]-DMSO>, Spectrometer: 399.95 MHz 8.9318 (0.76); 8.9185 (1.45); 8.9045 (0.81); 8.3296 (5.90); 8.3197 (3.14); 8.3072 (5.51); 8.0339 (5.14); 8.0116 (4.58); 7.1396 (3.35); 7.0694 (1.77); 7.0573 (1.79); 3.5661 (1.05);

3.5487 (2.50); 3.5334 (2.52); 3.5163 (1.21); 3.4048 (0.32); 3.3886 (0.54); 3.3490 (217.85); 2.8911 (1.77); 2.8588 (2.06); 2.8409 (3.83); 2.8231 (1.95); 2.7314 (1.50); 2.6769 (0.35); 2.6725 (0.44); 2.6689 (0.35); 2.5079 (49.33); 2.5036 (64.55); 2.4994 (51.21); 2.4439 (0.32); 2.4214 (16.00); 2.3303 (0.43); 2.3262 (0.35); −0.0002 (2.64)

No. Ic-104, Solvent: <[D$_6$]-DMSO>, Spectrometer: 399.95 MHz 8.3376 (2.60); 8.3249 (3.14); 8.3072 (1.47); 8.2934 (0.79); 7.3181 (0.53); 7.3101 (0.56); 7.3043 (0.77); 7.2976 (1.24); 7.2917 (1.10); 7.2834 (1.06); 7.2773 (1.31); 7.2111 (6.16); 7.2037 (3.09); 7.1965 (3.63); 7.1761 (0.38); 7.1414 (3.47); 7.0813 (1.82); 7.0690 (1.85); 3.5166 (1.16); 3.4994 (2.98); 3.4844 (2.95); 3.4675 (1.31); 3.3801 (0.72); 3.3474 (193.07); 3.3030 (0.43); 2.8900 (0.41); 2.8259 (2.19); 2.8085 (4.25); 2.7910 (2.01); 2.7300 (0.37); 2.6715 (0.37); 2.5068 (42.64); 2.5025 (56.75); 2.4983 (45.92); 2.4279 (16.00); 2.3293 (0.38); 2.2251 (14.99); −0.0002 (2.33)

No. Ic-105, Solvent: <[D$_6$]-DMSO>, Spectrometer: 399.95 MHz 8.6632 (0.68); 8.6497 (1.26); 8.6360 (0.67); 8.0582 (2.41); 8.0452 (2.48); 7.8270 (4.04); 7.8055 (4.54); 7.5480 (4.73); 7.5266 (3.89); 6.8721 (1.79); 6.8591 (1.77); 6.6792 (3.28); 3.8100 (16.00); 3.5295 (0.96); 3.5123 (2.33); 3.4974 (2.42); 3.4801 (1.17); 3.3522 (227.85); 2.8913 (1.92); 2.8409 (1.77); 2.8232 (3.43); 2.8055 (1.66); 2.7319 (1.69); 2.6771 (0.33); 2.6730 (0.40); 2.5081 (48.56); 2.5038 (61.15); 2.4995 (46.32); 2.3307 (0.40); −0.0002 (2.38)

No. Ic-106, Solvent: <[D$_6$]-DMSO>, Spectrometer: 399.95 MHz 8.5791 (0.72); 8.5659 (1.32); 8.5528 (0.76); 8.3184 (0.59); 8.0607 (2.43); 8.0478 (2.54); 7.8032 (3.34); 7.7855 (3.67); 7.5355 (0.54); 7.5175 (1.75); 7.4994 (1.62); 7.4704 (2.82); 7.4516 (3.71); 7.4339 (1.43); 6.8779 (1.95); 6.8655 (1.95); 6.6850 (3.56); 3.8109 (16.00); 3.5344 (1.09); 3.5172 (2.58); 3.5021 (2.65); 3.4851 (1.30); 3.3569 (313.73); 3.2775 (0.40); 2.8482 (2.00); 2.8305 (3.80); 2.8129 (1.89); 2.6728 (0.48); 2.5038 (70.94); 2.3308 (0.47); −0.0002 (0.70)

No. Ic-107, Solvent: <[D$_6$]-DMSO>, Spectrometer: 399.95 MHz 8.5856 (16.00); 8.5665 (4.63); 8.5527 (2.59); 8.4591 (9.13); 8.4469 (9.47); 7.4846 (4.04); 7.4651 (8.76); 7.4433 (12.12); 7.4309 (13.60); 7.4115 (3.07); 7.4063 (3.50); 7.3964 (3.10); 7.3929 (3.00); 7.3776 (6.56); 7.3747 (6.63); 7.3602 (4.71); 7.3566 (5.58); 7.3527 (8.73); 7.3480 (8.20); 7.3340 (3.36); 7.3292 (2.77); 3.8097 (0.58); 3.7980 (0.93); 3.5808 (3.54); 3.5641 (9.69); 3.5489 (10.06); 3.5324 (4.29); 3.3477 (627.52); 3.2563 (0.39); 3.0062 (7.11); 2.9892 (14.00); 2.9722 (6.60); 2.8908 (1.37); 2.7312 (1.20); 2.6722 (1.25); 2.5070 (145.79); 2.5031 (185.98); 2.4992 (150.12); 2.3297 (1.25); −0.0002 (7.24)

No. Ic-108, Solvent: <[D$_6$]-DMSO>, Spectrometer: 601.6 MHz 8.5872 (2.38); 8.5781 (4.34); 8.5691 (2.34); 8.3223 (11.25); 8.3139 (11.44); 7.7653 (6.55); 7.7523 (7.93); 7.7173 (3.00); 7.7050 (7.13); 7.6925 (4.51); 7.6426 (4.39); 7.6298 (6.46); 7.6172 (2.60); 7.4273 (13.17); 7.4265 (13.22); 7.4059 (7.12); 7.3934 (6.53); 7.3285 (7.38); 7.3264 (7.05); 7.3201 (7.23); 7.3180 (6.78); 3.9026 (8.22); 3.5487 (4.53); 3.5376 (11.20); 3.5278 (11.37); 3.5168 (4.82); 3.3172 (360.46); 3.1722 (0.99); 3.1635 (0.97); 2.8807 (8.05); 2.8694 (16.00); 2.8582 (7.52); 2.6185 (1.53); 2.6156 (3.11); 2.6125 (4.28); 2.6095 (3.11); 2.6066 (1.49); 2.5401 (1.17); 2.5218 (9.07); 2.5188 (11.15); 2.5156 (11.72); 2.5068 (234.71); 2.5038 (493.13); 2.5008 (673.77); 2.4978 (492.69); 2.4948 (230.18); 2.3910 (1.30); 2.3880 (2.87); 2.3850 (3.98); 2.3820 (2.80); 2.3791 (1.23); 1.2362 (0.46); 0.0965 (1.98); 0.0200 (0.36); 0.0052 (16.40); −0.0002 (483.17); −0.0057 (15.23); −0.1000 (1.97)

No. Ic-109, Solvent: <[D$_6$]-DMSO>, Spectrometer: 399.95 MHz 8.8744 (2.27); 8.8502 (2.40); 8.3175 (1.28); 7.7482 (3.28); 7.7335 (4.35); 7.7285 (5.09); 7.7165 (2.82); 7.6489 (2.42); 7.6294 (3.15); 7.6108 (1.34); 7.3008 (3.72); 7.2810 (3.02); 4.5767 (1.53); 4.5535 (1.51); 3.9039 (16.00); 3.5063 (1.08); 3.4624 (2.31); 3.4544 (1.70); 3.4285 (2.77); 3.3493 (2090.58); 3.1742 (0.87); 3.1611 (0.76); 2.8910 (0.38); 2.7110 (1.42); 2.6766 (2.85); 2.6721 (3.86); 2.6677 (2.94); 2.5075 (445.81); 2.5031 (581.82); 2.4986 (439.71); 2.4247 (0.83); 2.3918 (1.17); 2.3627 (1.15); 2.3342 (3.09); 2.3298 (4.07); 2.3254 (3.14); 1.8532 (1.48); 1.8353 (2.10); 1.8106 (4.24); 1.7791 (3.94); 1.7357 (1.65); 1.7103 (1.49); 1.5723 (0.32); 1.5286 (1.74); 1.5047 (1.15); 1.4051 (1.11); 1.3762 (1.02); 1.2976 (0.40); 1.2580 (0.66); 1.2349 (1.39); 0.8401 (2.15); 0.8349 (2.19); 0.8268 (0.98); 0.0079 (1.57); −0.0002 (38.93); −0.0084 (1.55)

The following tables D to F illustrate in a non limiting manner intermediates of formula (II) which can be used for the preparation of compounds of formula (I).

TABLE D

Compounds of formula (IIa)

(IIa)

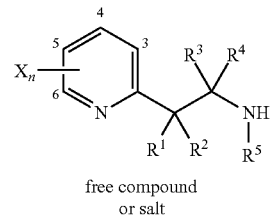

free compound
or salt

| No. | X$_n$ | R$^1$ | R$^2$ | R$^3$ | R$^4$ | R$^5$ | salt | Reference or phys. chem. data |
|---|---|---|---|---|---|---|---|---|
| IIa-1 | 3-Cl 5-CF$_3$ | C$_2$H$_5$ | H | H | H | H | HCl-salt | P2 P10 |
| IIa-2 | 3-Cl 5-CF$_3$ | CH$_3$ | H | H | H | H | | according to P2, not isolated |
| IIa-3 | 5-CF$_3$ | CH$_3$ | H | H | H | H | HCl-salt | NMR |
| IIa-4 | 5-CF$_3$ 6-Cl | CH$_3$ | H | H | H | H | | according to P2, not isolated |
| IIa-5 | 5-Cl | CH$_3$ | H | H | H | H | | P11 |

TABLE D-continued

Compounds of formula (IIa)

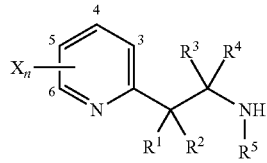

(IIa)

free compound
or salt

| No. | $X_n$ | $R^1$ | $R^2$ | $R^3$ | $R^4$ | $R^5$ | salt | Reference or phys. chem. data |
|---|---|---|---|---|---|---|---|---|
| IIa-6 | 3-Cl<br>5-Cl | $CH_3$ | H | H | H | H | | NMR |
| IIa-7 | 3-Cl<br>5-$CF_3$ | n-Pr | H | H | H | H | | according to P10, not isolated |
| IIa-8 | 5-Cl | $C_6H_5$ | H | H | H | H | | |
| IIa-9 | 3-Cl<br>5-$CF_3$ | NHC(O)—$CH_3$ | H | H | H | H | | P2<br>P10 |
| IIa-10 | 3-Cl<br>5-$CF_3$ | NHC(O)—2-$C_6H_4Cl$ | H | H | H | H | | according to P2, P10 |
| IIa-11 | 3-Cl<br>5-$CF_3$ | NHC(O)—2,6-$C_6H_3Cl_2$ | H | H | H | H | | according to P2, P10 |
| IIa-12 | 3-Cl<br>5-$CF_3$ | OH | H | $COOC_2H_5$ | H | H | | |
| IIa-13 | 3-Cl<br>5-$CF_3$ | OH | H | H | H | H | | P2<br>P10 |
| IIa-14 | 3-Cl<br>5-$CF_3$ | F | F | H | H | H | | NMR<br>see Examples |
| IIa-15 | 3-Cl<br>5-Cl | F | F | H | H | H | | NMR<br>see Examples |
| IIa-16 | 3-Cl<br>5-$CF_3$ | $CH_3$ | H | $CH_3$ | H | H | | NMR<br>see Examples |
| IIa-17 | 3-Cl<br>5-$CF_3$ | $CH_2$-cyclo-Pr | H | $CH_3$ | H | H | | NMR |
| IIa-18 | 3-Cl<br>5-$CF_3$ | $CH_2$—CH=$CH_2$ | H | $CH_3$ | H | H | | NMR |
| IIa-19 | 3-Cl<br>5-$CF_3$ | $CH_2$—C≡CH | H | $CH_3$ | H | H | | NMR |
| IIa-20 | 3-Cl<br>5-$CF_3$ | H | H | $C_2H_5$ | H | H | | P2<br>P10 |
| IIa-21 | 3-Cl<br>5-$CF_3$ | H | H | $CH_3$ | H | H | | according to P2, P10 |
| IIa-22 | 3-Cl<br>5-Cl | H | H | $CH_3$ | H | H | | [M + 1] = 205 |
| IIa-23 | 6-Cl<br>5-$CF_3$ | H | H | $CH_3$ | H | H | | [M + 1] = 239 |
| IIa-24 | 3-Cl<br>5-$CF_3$ | H | H | $CH_3$ | H | cyclo-Pr | HCl salt | P2<br>P10<br>NMR |
| IIa-25 | 3-Cl<br>5-$CF_3$ | H | H | $C_6H_5$ | H | H | | P2<br>P10 |
| IIa-26 | 3-Cl<br>5-$CF_3$ | H | H | COOH | H | H | | comm av.<br>CAS-No. 317377-64-3<br>NMR |
| IIa-27 | 3-Cl<br>5-$CF_3$ | H | H | COOMe | H | H | | P1<br>comm av.<br>CAS-No. 1008232-30-1 |
| IIa-28 | 3-Cl<br>5-$CF_3$ | H | H | COOEt | H | H | | according to P1 |
| IIa-29 | 3-Cl<br>5-$CF_3$ | H | H | CONHMe | H | H | | according to P1 |
| IIa-30 | 3-Cl<br>5-$CF_3$ | H | H | CONHEt | H | H | | according to P1<br>NMR |
| IIa-31 | 5-$CF_3$ | $CH_2$—$CH_2$ | | H | H | H | | |
| IIa-32 | 3-Cl<br>5-Cl | $CH_2$—$CH_2$ | | H | H | H | — | |
| IIa-33 | 5-Cl | $CH_2$—$CH_2$ | | H | H | H | — | |
| IIa-34 | 5-Cl | $(CH_2)_4$ | | H | H | H | — | |
| IIa-35 | 3-Cl<br>5-Cl | H | | $CH_2$<br>H | H | COO—$C_4H_9$-t | — | P5 |
| IIa-36 | 3-Cl<br>5-Cl | H | | $(CH_2)_4$ | H | H | — | P5 |

TABLE D-continued

Compounds of formula (IIa)

(IIa)

free compound or salt

| No. | $X_n$ | $R^1$ | $R^2$ | $R^3$ | $R^4$ | $R^5$ | salt | Reference or phys. chem. data |
|---|---|---|---|---|---|---|---|---|
| IIa-37 | 3-Cl 5-CF$_3$ | H | (CH$_2$)$_4$ | | H | H | — | P4 |
| IIa-38 | 3-Cl 5-CF$_3$ | H | (CH$_2$)$_5$ | | H | H | — | P4 |
| IIa-39 | 3-Cl 5-CF$_3$ | H | H | H | H | cyclo-Pr | — | P9 |
| IIa-40 | 3-Cl 5-CF$_3$ | N(CH$_3$)$_2$ | H | H | H | H | 2 HCl | According to J. Amer. Chem. Soc. 72, 2804-6 (1950); WO 1984/03278 WO 2008/06479 THL 45, 7407-08 (2004) NMR |
| IIa-41 | 3-Cl 5-CF$_3$ | morpholino (N-CH$_2$CH$_2$-O-CH$_2$CH$_2$) | | H | H | H | 2 HCl | According to J. Amer. Chem. Soc. 72, 2804-6 (1950); WO 1984/03278 WO 2008/06479 THL 45, 7407-08 (2004) NMR |

$^1$H-NMR Data

No. IIa-3, Solvent: <[D$_6$]-DMSO>, Spectrometer: 399.95 MHz 8.9425 (4.53); 8.5297 (0.55); 8.3132 (0.37); 8.3081 (0.36); 8.2919 (0.35); 8.2871 (0.34); 8.2274 (2.43); 8.2220 (2.47); 8.2066 (2.63); 8.2014 (2.57); 7.9233 (3.03); 7.9035 (1.80); 7.8274 (0.51); 7.6396 (4.25); 7.6190 (3.98); 7.3355 (0.94); 7.2080 (1.11); 7.0806 (0.95); 3.9056 (6.21); 3.5088 (0.47); 3.3780 (460.23); 3.3398 (2.99); 3.3213 (1.08); 3.3038 (0.56); 3.2802 (0.50); 3.2660 (0.94); 3.2515 (1.14); 3.2344 (1.49); 3.2202 (1.32); 3.2154 (1.20); 3.2005 (0.91); 3.1668 (2.48); 3.1300 (0.34); 3.1160 (1.18); 3.1012 (1.89); 3.0859 (1.76); 3.0701 (1.36); 3.0550 (0.71); 2.6777 (1.01); 2.6732 (1.39); 2.6687 (1.05); 2.6173 (0.39); 2.5383 (15.01); 2.5244 (34.14); 2.5127 (88.01); 2.5087 (171.64); 2.5041 (220.28); 2.4996 (165.79); 2.4953 (85.87); 2.3354 (1.00); 2.3308 (1.41); 2.3264 (1.01); 2.0215 (0.61); 1.4956 (2.91); 1.2936 (16.00); 1.2762 (15.82); −0.0002 (1.03)

No. IIa-6, Solvent: <[D$_6$]-DMSO>, Spectrometer: 250 MHz 8.5963 (8.43); 8.2402 (10.03); 8.1164 (7.73); 5.3630 (6.41); 3.6596 (3.33); 3.4600 (0.33); 3.2465 (2.97); 3.0224 (2.94); 2.4999 (4.52); 1.1822 (16.00); 0.9220 (0.39)

No. IIa-17, Solvent: <CDCl$_3$>, Spectrometer: 250 MHz 8.9941 (2.31); 8.9630 (0.34); 8.1671 (3.06); 8.1606 (2.59); 7.5175 (16.00); 5.5564 (0.32); 3.9536 (0.69); 3.7988 (0.70); 3.7839 (0.96); 3.7718 (0.94); 3.7565 (1.47); 3.7409 (0.76); 3.7291 (0.99); 3.7140 (0.88); 3.7011 (0.63); 3.6746 (0.72); 3.6478 (0.48); 3.5960 (0.37); 3.5702 (1.39); 3.5440 (1.89); 3.5178 (1.27); 2.2067 (0.53); 2.1840 (0.70); 2.1558 (1.59); 2.1299 (2.84); 2.1145 (3.46); 2.0400 (0.86); 2.0115 (0.72); 1.9919 (0.95); 1.9754 (1.13); 1.9497 (0.99); 1.9382 (1.01); 1.9106 (0.97); 1.8963 (0.69); 1.8588 (0.34); 1.5092 (1.77); 1.4234 (3.14); 1.3975 (3.07); 1.2784 (8.41); 1.2526 (8.28); 1.2064 (0.53); 1.1338 (0.43); 1.1081 (0.40); 1.0670 (0.55); 1.0434 (0.55); 0.9228 (0.36); 0.7034 (0.40); 0.6727 (0.65); 0.6423 (0.86); 0.6352 (0.88); 0.6164 (1.21); 0.5976 (1.53); 0.5835 (1.25); 0.5621 (1.09); 0.5265 (0.65); 0.5116 (0.84); 0.4908 (1.06); 0.4746 (1.28); 0.4604 (1.03); 0.4450 (0.92); 0.4378 (0.80); 0.4077 (0.47); 0.3041 (0.41); 0.2821 (0.68); 0.2671 (1.08); 0.2469 (1.08); 0.2339 (0.94); 0.0354 (0.52); 0.0164 (1.14); 0.0006 (1.38); 0.0203 (1.36); 0.0372 (0.95); 0.0580 (0.55)

No. IIa-18, Solvent: <CDCl$_3$>, Spectrometer: 250 MHz 8.9427 (3.26); 8.0878 (4.75); 7.4633 (16.00); 5.8995 (0.57); 5.8721 (1.11); 5.8589 (0.73); 5.8440 (0.67); 5.8314 (1.96); 5.8036 (2.06); 5.7908 (0.90); 5.7757 (0.84); 5.7635 (1.57); 5.7353 (0.80); 5.1250 (2.37); 5.1181 (2.31); 5.0738 (1.08); 5.0563 (3.92); 5.0193 (2.01); 3.7000 (1.05); 3.6740 (1.88); 3.6485 (1.68); 3.6408 (1.67); 3.6150 (1.40); 3.5866 (0.93); 3.5604 (1.19); 3.5494 (0.72); 3.5338 (0.83); 3.5235 (2.12); 3.4975 (2.89); 3.4713 (1.78); 3.4452 (0.46); 2.8940 (1.26); 2.8800 (1.38); 2.8592 (3.43); 2.8305 (2.50); 2.7877 (1.03); 2.7576 (1.18); 2.7350 (0.58); 1.6222 (4.44); 1.4911 (0.38); 1.4546 (0.73); 1.3640 (5.48); 1.3382 (5.36); 1.2214 (13.13); 1.1957 (13.11); 1.0405 (0.42); 1.0155 (0.41)

No. IIa-19, Solvent: <CDCl$_3$>, Spectrometer: 250 MHz 8.7504 (1.99); 8.6893 (4.95); 8.6001 (0.38); 7.8894 (1.68); 7.8607 (5.20); 7.2799 (0.39); 7.1935 (23.30); 7.1061 (0.38); 5.2314 (0.41); 4.6008 (0.71); 4.5754 (0.71); 4.5664 (0.95); 4.5408 (0.72); 3.7272 (0.50); 3.6408 (12.39); 3.6111 (1.01); 3.5983 (0.95); 3.5841 (1.01); 3.5704 (2.26); 3.5550 (0.83);

3.5429 (2.36); 3.5146 (1.18); 3.4216 (0.80); 3.3972 (1.87); 3.3691 (0.78); 3.3295 (2.53); 3.3188 (3.16); 3.2921 (1.80); 3.2660 (2.53); 3.2400 (1.75); 3.2143 (0.44); 3.1658 (2.39); 3.1554 (2.78); 3.0945 (1.45); 3.0843 (1.58); 2.9965 (0.81); 2.9859 (0.92); 2.9709 (0.85); 2.9622 (1.30); 2.9534 (1.01); 2.9284 (0.79); 2.9180 (0.85); 2.8956 (0.32); 2.7528 (3.63); 2.7425 (4.09); 2.7241 (3.84); 2.7136 (4.02); 2.6655 (1.86); 2.6549 (2.06); 2.6365 (1.78); 2.6261 (1.83); 2.0260 (16.00); 1.9003 (2.38); 1.8896 (5.18); 1.8789 (2.85); 1.8466 (1.03); 1.8358 (2.11); 1.8255 (1.13); 1.8040 (0.97); 1.7937 (2.02); 1.7835 (1.09); 1.7571 (2.12); 1.7466 (4.21); 1.7360 (2.41); 1.5540 (11.55); 1.4134 (0.99); 1.3886 (0.90); 1.3419 (0.75); 1.3156 (0.74); 1.2598 (0.50); 1.2366 (0.57); 1.1844 (1.92); 1.0994 (0.52); 1.0785 (5.55); 1.0523 (5.50); 0.9865 (11.03); 0.9607 (10.95); 0.9008 (0.59); 0.8333 (0.50); 0.8112 (0.59); 0.7824 (0.57); 0.7502 (0.55); 0.7245 (0.46); 0.6433 (0.34); 0.6177 (0.34)

No. IIa-24, Solvent: <[D$_6$]-DMSO>, Spectrometer: 399.95 MHz 9.1652 (0.94); 9.0728 (1.01); 8.9503 (6.07); 8.9477 (5.98); 8.5288 (6.13); 8.5250 (6.03); 3.9453 (1.35); 3.9054 (5.68); 3.5449 (1.73); 3.5325 (1.70); 3.5062 (2.40); 3.4935 (2.26); 3.3867 (0.60); 3.3436 (264.78); 3.3065 (3.05); 3.2849 (2.60); 3.2674 (2.09); 3.2459 (1.91); 3.1667 (0.97); 2.8120 (1.66); 2.6810 (0.39); 2.6769 (0.81); 2.6723 (1.13); 2.6678 (0.85); 2.5426 (0.72); 2.5257 (3.49); 2.5121 (66.26); 2.5078 (134.10); 2.5032 (177.17); 2.4987 (132.59); 2.4943 (67.64); 2.3390 (0.41); 2.3344 (0.84); 2.3300 (1.15); 2.3255 (0.86); 1.3351 (0.36); 1.3158 (15.96); 1.2994 (16.00); 1.2490 (0.33); 1.2342 (0.32); 0.9477 (0.49); 0.9389 (0.89); 0.9174 (6.40); 0.9081 (5.02); 0.8945 (1.34); 0.8853 (0.82); 0.8753 (0.70); 0.8534 (0.52); 0.8376 (0.78); 0.8323 (0.56); 0.8224 (1.44); 0.8071 (4.83); 0.7889 (4.82); 0.7662 (0.83); 0.7508 (0.37); 0.0080 (0.39); −0.0002 (12.25); −0.0085 (0.53)

No. IIa-26, Solvent: <[D$_6$]-DMSO>, Spectrometer: 399.95 MHz 8.8717 (15.40); 8.8694 (15.54); 8.4864 (15.85); 8.4825 (15.76); 8.3229 (0.39); 8.2695 (0.42); 8.0777 (0.43); 7.7065 (0.38); 4.1514 (4.63); 4.1387 (3.79); 3.9052 (16.00); 3.6150 (5.91); 3.6033 (6.10); 3.5730 (8.21); 3.5613 (8.15); 3.3562 (72.65); 3.1669 (6.89); 2.6767 (3.03); 2.6721 (4.09); 2.6677 (3.09); 2.5254 (12.41); 2.5119 (232.26); 2.5076 (463.05); 2.5031 (607.50); 2.4986 (454.95); 2.4944 (234.67); 2.3343 (2.90); 2.3298 (3.98); 2.3253 (2.98); 1.2582 (0.35); 1.2486 (0.52); 1.2353 (0.57); 0.8750 (0.45); 0.0079 (0.73); −0.0002 (20.80); −0.0083 (0.88)

No. IIa-30, Solvent: <[D$_6$]-DMSO>, Spectrometer: 399.95 MHz 8.8681 (3.65); 8.8491 (0.41); 8.6288 (0.37); 8.4069 (3.72); 8.4024 (3.41); 8.1943 (0.35); 8.1890 (0.35); 7.9500 (0.92); 7.9366 (1.46); 7.9233 (0.80); 5.5399 (0.79); 3.9050 (5.32); 3.7490 (1.58); 3.7358 (1.88); 3.7276 (1.96); 3.7144 (1.76); 3.4459 (0.40); 3.3410 (284.43); 3.2952 (1.33); 3.2820 (1.17); 3.2585 (1.65); 3.2454 (1.60); 3.1740 (1.00); 3.1609 (0.95); 3.1525 (0.32); 3.1282 (0.50); 3.1135 (1.08); 3.1028 (2.50); 3.0955 (2.31); 3.0819 (4.30); 3.0652 (3.50); 3.0508 (2.32); 3.0456 (2.22); 3.0329 (0.97); 3.0182 (0.41); 2.6765 (0.85); 2.6719 (1.15); 2.6673 (0.85); 2.5252 (4.14); 2.5118 (68.50); 2.5074 (134.85); 2.5029 (175.39); 2.4983 (128.97); 2.4939 (64.49); 2.3341 (1.17); 2.3296 (1.48); 2.3251 (1.19); 1.2350 (0.41); 1.0955 (0.63); 1.0853 (0.53); 1.0773 (1.24); 1.0591 (0.66); 1.0381 (0.44); 1.0300 (0.52); 1.0205 (0.63); 1.0059 (7.75); 0.9879 (16.00); 0.9699 (7.79); 0.9536 (1.46); 0.9356 (0.72); 0.9119 (0.48); 0.8940 (0.60); 0.8761 (0.33); −0.0002 (9.34); −0.0084 (0.44)

TABLE E

Compounds of formula (IIb)

(IIb)

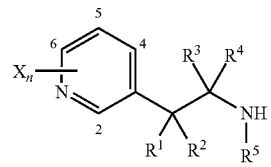

| No. | X$_n$ | R$^1$ | R$^2$ | R$^3$ | R$^4$ | R$^5$ | optical information | Reference of synthesis procedure or phys. chem. data |
|---|---|---|---|---|---|---|---|---|
| IIb-1 | 6-Cl | H | H | COOH | H | H | | comm av. CAS-No. 188916-07-6 |
| IIb-2 | 5-Cl 6-OMe | H | H | COOH | H | H | | comm av. CAS-No. 1270318-19-8 |
| IIb-3 | 5-Cl 6-OMe | H | H | COOMe | H | H | — | according to P1 |
| IIb-4 | 5-Cl 6-OMe | H | H | COOMe | H | H | R-enantiomer | comm av. CAS-No. 1212838-31-7 |
| IIb-5 | 5-Cl 6-OMe | H | H | COOMe | H | H | S-enantiomer | comm av. CAS-No. 1213663-26-3 |
| IIb-6 | 5-Cl 6-OMe | H | H | COOEt | H | H | — | according to P1 |
| IIb-7 | 5-Cl 6-OMe | H | H | CONHMe | H | H | — | according to P1 |
| IIb-8 | 5-Cl 6-OMe | H | H | CONHEt | H | H | — | according to P1 |
| IIb-9 | 6-Cl | H | H | H | H | H | — | P4 |
| IIb-10 | 6-CF$_3$ | H | H | H | H | H | — | according to P4 comm av. CAS-No. 765287-34-1 |
| IIb-11 | 2-Cl 4-Cl | H | H | H | H | H | — | according to P4 |

TABLE E-continued

Compounds of formula (IIb)

(IIb)

| No. | $X_n$ | $R^1$ | $R^2$ | $R^3$ | $R^4$ | $R^5$ | optical information | Reference of synthesis procedure or phys. chem. data |
|---|---|---|---|---|---|---|---|---|
| IIb-12 | 6-Cl | $CH_3$ | H | H | H | H | | |
| IIb-13 | 6-Cl | $CH_3$ | $CH_3$ | H | H | H | — | comm av. CAS-No. 1060812-06-7 |
| IIb-14 | 6-$CH_3$ | $CH_3$ | $CH_3$ | H | H | H | — | comm av. CAS-No. 1060806-41-8 |
| IIb-15 | 6-OMe | $CH_3$ | $CH_3$ | H | H | H | — | comm av. CAS-No. 1060807-33-1 |
| IIb-16 | 6-Cl | F | F | H | H | H | — | comm av. CAS-No. 1204235-05-1 |
| IIb-17 | 6-$CF_3$ | H | H | $CH_3$ | H | H | — | comm av. CAS-No. 910414-32-3 |
| IIb-18 | 2-Cl | H | H | $CH_3$ | H | H | — | comm av. CAS-No. 910413-05-7 |
| IIb-19 | 6-Cl | H | H | $CH_3$ | H | H | | comm av. CAS-No. 910398-62-8 |
| IIb-20 | 2-OMe 5-Br | H | H | $C_2H_5$ | H | H | — | comm av. CAS-No. 910407-42-0 |
| IIb-21 | 6-$CF_3$ | H | H | $C_2H_5$ | H | H | — | comm av. CAS-No. 910386-05-9 |
| IIb-22 | 6-Cl | H | H | $C_2H_5$ | H | H | — | comm av. CAS-No. 910387-17-6 |
| IIb-23 | 5-$CF_3$ | $CH_2$—$CH_2$ | | H | H | H | — | comm av. CAS-No. 1245915-95-0 |
| IIb-24 | 6-Cl | $CH_2$—$CH_2$ | | H | H | H | — | comm av. CAS-No. 1060811-84-8 |
| IIb-25 | 2-Br | $CH_2$—$CH_2$ | | H | H | H | — | comm av. CAS-No. 1060811-52-0 |
| IIb-26 | 4-F | $CH_2$—$CH_2$ | | H | H | H | — | comm av. CAS-No. 1060809-53-1 |
| IIb-27 | 6-$CF_3$ | $CH_2$—$CH_2$ | | H | H | H | — | comm av. CAS-No. 1060811-04-2 |
| IIb-28 | 6-Br | $CH_2$—$CH_2$ | | H | H | H | — | comm av. CAS-No. 1060811-50-8 |
| IIb-29 | 2-OMe | $CH_2$—$CH_2$ | | H | H | H | — | comm av. CAS-No. 1060807-12-6 |
| IIb-30 | 4-$CH_3$ | $CH_2$—$CH_2$ | | H | H | H | — | comm av. CAS-No. 1060804-94-5 |
| IIb-31 | 5-F | H | | $(CH_2)_3$ | H | H | | comm av. CAS-No. 1247729-51-6 |
| IIb-32 | 5-F | H | | $(CH_2)_4$ | H | H | | comm av. CAS-No. 1249152-50-8 |
| IIb-33 | 5-F | H | | $(CH_2)_5$ | H | H | | comm av. CAS-No. 1247860-65-6 |
| IIb-34 | 4-Cl 6-$CF_3$ | H | H | H | H | H | | CAS-No. 1393584-52-5 Synthesis c.f. experimental part |
| IIb-35 | 2-Cl 6-$CF_3$ | H | H | H | H | H | | Synthesis c.f. experimental part |
| IIb-36 | 2-Cl 6-$CF_3$ | H | H | $CH_3$ | H | H | | CAS-No. 1337694-11-7 |

TABLE F

Compounds of formula (IIc)

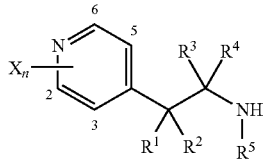

(IIc)

| No. | $X_n$ | $R^1$ | $R^2$ | $R^3$ | $R^4$ | $R^5$ | Reference of synthesis procedure or phys. chem. data |
|---|---|---|---|---|---|---|---|
| IIc-1 | 2-F 3-F 5-F 6-F | H | H | H | H | H | P8 |
| IIc-2 | 2-Me 5-Cl | H | H | H | H | H | according to P8 |
| IIc-3 | 2-F 5-F | H | H | H | H | H | according to P8 |
| IIc-4 | 2-F 3-F 5-F 6-F | H | H | COOH | H | H | comm. av. CAS-No. 1270314-19-6 |
| IIc-5 | 2-F 3-F 5-F 6-F | H | (CH$_2$)$_4$ | | H | H | according to P5 |
| IIc-6 | 3-F 5-F | H | H | H | H | H | comm av. CAS-No. 1314907-15-7 |
| IIc-7 | 2-CF$_3$ 3-OMe | H | H | H | H | H | comm av. CAS-No. 1211539-23-9 |
| IIc-8 | 2-CF$_3$ | H | H | H | H | H | comm. av. CAS-No. 1060811-11-1 |
| IIc-9 | 3-Cl 5-Cl | H | H | H | H | H | comm. av. CAS-No. 910391-44-5 |
| IIc-10 | 3-Cl | H | H | H | H | H | comm. av. CAS-No. 910410-77-4 |
| IIc-11 | 2-OMe | H | H | H | H | H | comm. av. CAS-No. 764708-27-2 |
| IIc-12 | 2-Me | H | H | H | H | H | comm. av. CAS-No. 625438-03-1 |
| IIc-13 | 2-Cl | H | H | H | H | H | comm. av. CAS-No. 910388-12-4 |
| IIc-14 | 3-Cl 5-Cl | H | H | CH$_3$ | H | H | comm. av. CAS-No. 910389-65-0 |
| IIc-15 | 3-F 5-Fl | H | H | CH$_3$ | H | H | comm. av. CAS-No. 910402-24-3 |
| IIc-16 | 3-Cl 6-Cl | H | H | CH$_3$ | H | H | comm. av. CAS-No. 910407-17-9 |
| IIc-17 | 3-F | H | H | CH$_3$ | H | H | comm. av. CAS-No. 910389-92-3 |
| IIc-18 | 3-Cl | H | H | CH$_3$ | H | H | comm. av. CAS-No. 910389-80-9 |
| IIc-19 | 2-OMe | CH$_3$ | CH$_3$ | H | H | H | comm. av. CAS-No. 1060807-35-3 |
| IIc-20 | 2-OMe | CH$_2$—CH$_2$ | | H | H | H | comm. av. CAS-No. 1060807-10-4 |
| IIc-21 | 2-Me | CH$_2$—CH$_2$ | | H | H | H | comm. av. CAS-No. 1060806-23-6 |
| IIc-22 | 2-CF$_3$ | CH$_2$—CH$_2$ | | H | H | H | comm. av. CAS-No. 1060811-06-4 |
| IIc-23 | 2-Cl | CH$_2$—CH$_2$ | | H | H | H | comm. av. CAS-No. 1060811-85-9 |
| IIc-24 | 3-Cl 5-Cl | H | H | COOH | H | H | comm. av. CAS-No. 1270326-34-5 |
| IIc-25 | 2-Me | CH$_3$ | CH$_3$ | H | H | H | comm. av. CAS-No. 1060806-42-9 |
| IIc-26 | 2-Cl | CH$_3$ | CH$_3$ | H | H | H | comm. av. CAS-No. 1060812-07-8 |

EXAMPLES

Abbreviations which are used in the text and in the formulae:

Int=Intermediate

Synthesis of N-{2-[3-chloro-5-(trifluoromethyl)pyridin-2-yl]-2-methylpropyl}-2-(trifluoromethyl)benzamide (Ia-93)

Step 1: Synthesis of 2-[3-chloro-5-(trifluoromethyl)pyridin-2-yl]-2-methylpropanenitrile (Int-2)

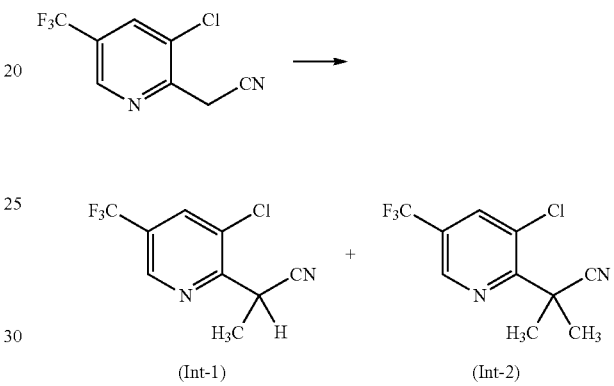

Under Argon, 20.2 g (0.091 mol) of 3-chloro-5-(trifluoromethyl)pyridin-2-ylacetonitrile (P10, prep. example 7, page 59) were dissolved in 0.1 L of tetrahydrofuran (THF) at 5° C. 350 mL of a 1N solution of potassium 2-methylpropan-2-olate (0.35 mol) in tetrahydrofuran were slowly added to the reaction medium. After 2 h, 42.1 g (0.297 mol) of methyl iodide were added dropwise to the reaction mixture, which was stirred for three days at room temperature. 500 mL of water were added to the reaction mixture. After separation, the aqueous phase was extracted twice with 300 mL of diethyl ether. The organic phase was washed with 300 mL of water, dried over magnesium sulfate, filtered and concentrated in vacuo to yield 20 g of crude product which was chromatographed over silica gel to yield 6.10 g (32%) of 2-[3-chloro-5-(trifluoromethyl)pyridin-2-yl]propanenitrile (Int-1) and 5.12 g (22%) of 2-[3-chloro-5-(trifluoromethyl)pyridin-2-yl]-2-methylpropanenitrile (Int-2).

(Int-1), Solvent: <CDCl$_3$>, Spectrometer: 250 MHz 8.8851 (2.85); 8.8810 (2.90); 8.0597 (3.16); 8.0531 (3.03); 7.3468 (0.43); 4.6887 (0.86); 4.6601 (2.73); 4.6314 (2.77); 4.6028 (0.92); 1.9535 (0.37); 1.8201 (16.00); 1.7915 (15.84); 1.6816 (1.04); 1.3985 (0.39); 1.3699 (0.41); 1.3263 (2.32); 0.9654 (0.63); 0.9398 (2.11); 0.9121 (0.74)

(Int-2), Solvent: <CDCl$_3$>, Spectrometer: 250 MHz 8.8501 (0.70); 8.8470 (0.81); 8.8429 (0.82); 8.8399 (0.72); 8.0975 (0.87); 8.0908 (0.87); 2.7950 (0.75); 1.9777 (16.00); 1.3467 (1.18); 0.9585 (1.01); 0.9309 (0.35)

Step 2: Synthesis of tert-butyl 2-[3-chloro-5-(trifluoromethyl)pyridin-2-yl]-2-methylpropyl carbamate (Int-3)

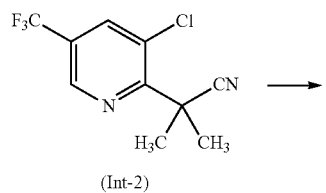

(Int-2)

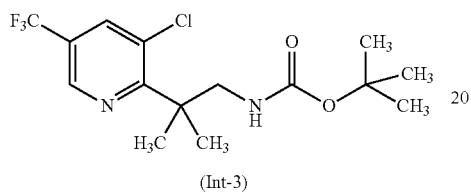

(Int-3)

270 mg of 2-[3-chloro-5-(trifluoromethyl)pyridin-2-yl]-2-methylpropanenitrile (Int-2) (1.08 mMol), 470 mg (2.16 mMol) of di-tert-butyl carbonate, 256 mg (1.08 mMol) of nickel-(II)-chloride-hexahydrate were stirred in 7 mL of methanol at room temperature. 284 mg (7.6 mMol) of sodium borohydride were added portionwise. After 2 hours of stirring, 20 mL of ethyl acetate were added to the reaction mixture, followed by 5 mL of an aqueous solution of sodium bicarbonate. After separation, the organic phase was washed with 5 mL of an aqueous solution of sodium bicarbonate, dried over magnesium sulfate, filtered and concentrated to yield 283 mg (48%) of crude material, which was purified over silica gel to produce 185 mg of desired product tert-butyl {2-[3-chloro-5-(trifluoromethyl)pyridin-2-yl]-2-methylpropyl}carbamate (Int-3).

(Int-3), Solvent: <CDCl$_3$>, Spectrometer: 250 MHz 8.6142 (1.38); 7.8087 (1.59); 7.1968 (0.42); 5.3003 (0.41); 3.5212 (2.11); 3.4946 (2.03); 1.6795 (0.65); 1.4510 (3.37); 1.4297 (18.21); 1.3873 (1.28); 1.3387 (16.00); 1.2821 (0.82); 1.1813 (0.64); 1.0122 (0.48)

Step 3: Synthesis of 2-[3-chloro-5-(trifluoromethyl)pyridin-2-yl]-2-methylpropan-1-amine hydrochloride (Int-4) (not isolated)

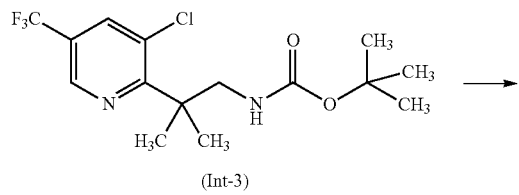

(Int-3)

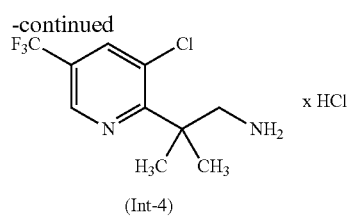

(Int-4)

according to P10, prep. example 7, page 60 and

Step 4: Synthesis of N-{2-[3-chloro-5-(trifluoromethyl)pyridin-2-yl]-2-methylpropyl}-2-(trifluoromethyl)benzamide (Ia-93)

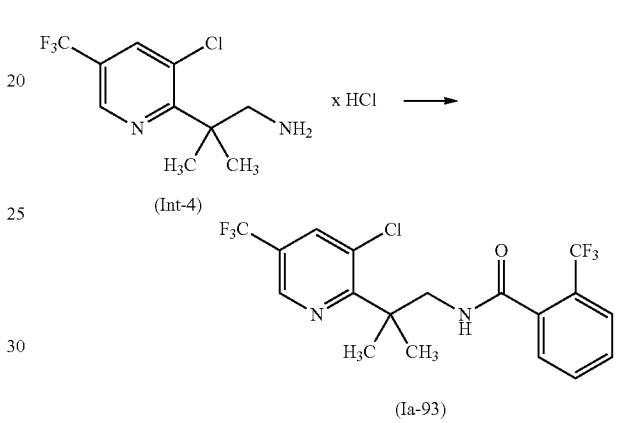

(Ia-93)

according to P10, e.g. prep. example 2, page 56, in a one-pot reaction

In a similar manner the final products (Ia-94), (Ia-95), (Ia-96), (Ia-97) and (Ia-106) can be prepared.

Synthesis of N-{2-[3-chloro-5-(trifluoromethyl)pyridin-2-yl]-1-methoxyethyl}-2-(trifluoromethyl)benzamide (Ia-111)

Step 1: Synthesis of N-{2-[3-chloro-5-(trifluoromethyl)pyridin-2-yl]ethylidene}-2-(trifluoromethyl)benzamide (Int-6)

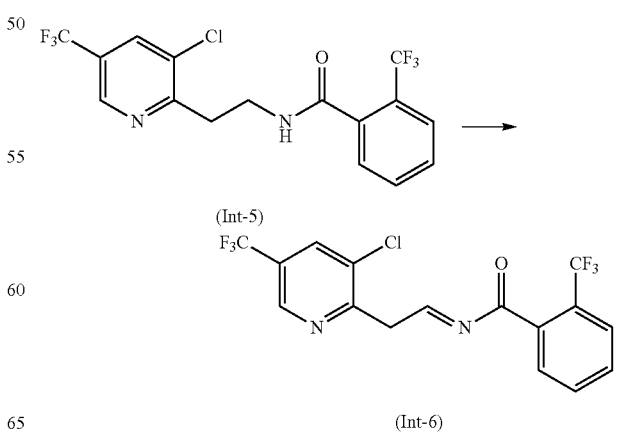

(Int-6)

2.00 g of N-{2-[3-chloro-5-(trifluoromethyl)pyridin-2-yl]ethyl}-2-(trifluoromethyl)benzamide (Int-5), (known from WO 2004/016088), were dissolved in 20 mL of methanol. 1 mL of concentrated bleach was added to the reaction mixture at room temperature. The reaction mixture was stirred for 24 hours at room temperature. 20 mL of a 1N aqueous solution of sodium hydroxide were added to the reaction mixture which was then extracted twice with diethyl ether. The combined organic phases were dried over magnesium sulphate, concentrated in vacuo to yield 1.41 g of crude product which was purified by chromatography on silica gel with ethyl acetate/heptane (3/7 v/v) as eluting phase. 340 mg (17%) of desired N-{2-[3-chloro-5-(trifluoromethyl)pyridin-2-yl]ethylidene}-2-(trifluoromethyl)benzamide (Int-6) were obtained, [M+1]=395.

(Int-6), Solvent: <CDCl$_3$>, Spectrometer: 250 MHz 8.9332 (9.79); 8.9300 (10.02); 8.1058 (10.17); 8.0994 (10.79); 8.0590 (0.59); 8.0405 (4.14); 8.0293 (4.93); 8.0053 (5.61); 7.8799 (4.19); 7.8553 (5.39); 7.8433 (6.53); 7.8254 (1.03); 7.8135 (0.43); 7.7616 (1.08); 7.7531 (2.30); 7.7313 (7.59); 7.7224 (10.49); 7.7082 (16.00); 7.6941 (8.42); 7.6624 (1.16); 7.3731 (2.26); 6.3219 (5.33); 6.2909 (6.05); 6.2819 (6.18); 6.2509 (5.77); 4.6899 (3.46); 4.6499 (3.13); 4.6312 (10.24); 4.5911 (10.09); 4.5750 (10.55); 4.5440 (10.16); 4.5161 (3.62); 4.4853 (3.08); 4.2001 (0.84); 4.1747 (0.34); 3.9138 (2.48); 3.7663 (0.44); 3.5945 (1.93); 3.5203 (0.71); 2.1563 (1.20); 1.7637 (14.75); 1.3752 (2.57); 1.0440 (0.56); 1.0153 (0.88); 0.9906 (2.20); 0.9629 (0.84)

Step 2: Synthesis of N-{2-[3-chloro-5-(trifluoromethyl)pyridin-2-yl]-1-methoxyethyl}-2-(trifluoromethyl)benzamide (Ia-111)

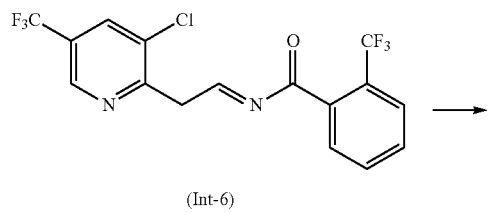

(Int-6)

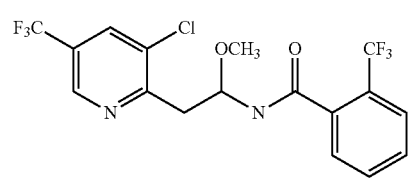

(Ia-111)

0.16 g of N-{2-[3-chloro-5-(trifluoromethyl)pyridin-2-yl]ethylidene}-2-(trifluoromethyl)benzamide (Int-6) were diluted in 2 mL of methanol. 50 μL of sulfuric acid 99% were added. The reaction mixture was stirred at room temperature for 48 hours. A mixture of dichloromethane (10 mL) and water (5 mL) was added. After separation, the aqueous phase was extracted twice with dichloromethane. The combined organic phases were washed with 5 mL of water, dried over magnesium sulfate, filtered, concentrated to yield to 0.150 g of crude material, which was purified by chromatography on silica gel to yield 0.107 g (63%) of desired product N-{2-[3-chloro-5-(trifluoromethyl)pyridin-2-yl]-1-methoxyethyl}-2-(trifluoromethyl)benzamide (Ia-111), [M+1]=427.

(Ia-111), Solvent: <CDCl$_3$>, Spectrometer: 250 MHz 12.1063 (0.36); 12.0712 (1.19); 12.0521 (0.95); 12.0171 (0.38); 11.9822 (0.38); 8.8855 (0.60); 8.1085 (16.00); 7.8954 (0.37); 7.7656 (0.49); 7.2610 (0.36); 6.0372 (0.33); 5.6296 (0.39)

Synthesis of 2-[3-chloro-5-(trifluoromethyl)pyridin-2-yl]-1-{[2-(trifluoromethyl)benzoyl]amino}ethyl acetate (Ia-112)

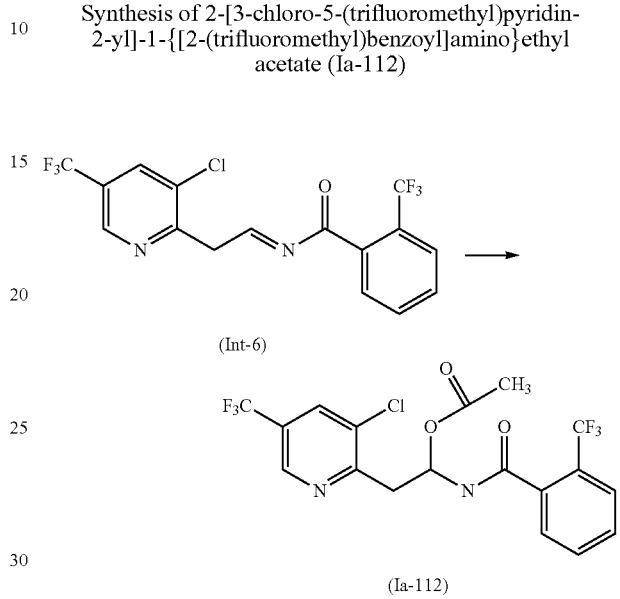

0.16 g of N-{2-[3-chloro-5-(trifluoromethyl)pyridin-2-yl]ethylidene}-2-(trifluoromethyl)benzamide (Int-6) were diluted in 2 mL of acetic acid. The reaction mixture was stirred for two days at room temperature and then heated to 90° C. for one day and left at room temperature for four days. After concentration in vacuo, the crude product was purified by chromatography on silica gel to yield 0.045 g (24%) of desired product 2-[3-chloro-5-(trifluoromethyl)pyridin-2-yl]-1-{[2-(trifluoromethyl)benzoyl]amino}ethyl acetate (Ia-112), [M+1]=455.

(Ia-112), Solvent: <CDCl$_3$>, Spectrometer: 250 MHz 8.7470 (0.39); 8.6387 (1.99); 7.9142 (2.37); 7.9078 (2.10); 7.6281 (0.97); 7.6011 (1.38); 7.5952 (1.39); 7.5508 (0.70); 7.5391 (0.62); 7.5255 (1.49); 7.5013 (2.27); 7.4927 (2.11); 7.4625 (1.11); 7.4431 (1.65); 7.4120 (0.74); 7.1939 (0.35); 6.4536 (0.68); 6.2788 (0.95); 6.2616 (1.19); 6.2555 (1.23); 6.2384 (0.96); 4.1809 (0.48); 4.1640 (0.52); 4.1544 (0.51); 4.1375 (0.51); 4.1235 (0.73); 4.1067 (0.74); 4.0970 (0.74); 4.0802 (0.66); 3.8884 (0.67); 3.8658 (1.13); 3.8431 (0.71); 3.8313 (0.54); 3.8084 (0.79); 3.7859 (0.47); 3.4015 (0.59); 2.0705 (16.00); 1.9568 (0.34); 1.1896 (0.99); 0.8053 (0.74); 0.7776 (0.33)

Synthesis of intermediates (IIa-15) and (IIa-14)

Step 1: Preparation of ethyl (3,5-dichloropyridin-2-yl)(difluoro)acetate (Int-7)

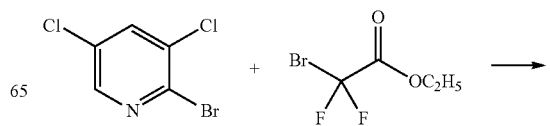

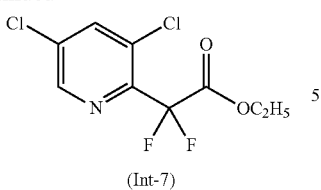

(Int-7)

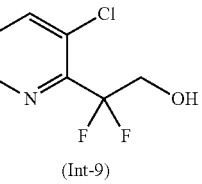

(Int-9)

To a solution of 56 g (0.246 mol) of 2-bromo-3,5-dichloropyridine in 500 mL of dry dimethylsulfoxide, were added 53 g (0.261 mol) of ethyl bromodifluoroacetate followed by 94 g (0.518 mol) of copper bronze (200 mesh). The beige suspension was heated at 50° C. for 5 hours. After cooling of the reaction mixture, a solution of 44 g (0.328 mol) of potassium monophosphate in 280 mL of water was added and stirred for 1 hour. The black mixture was then filtered over a cake of Supercel™, and the cake was washed three times by 200 mL of ethyl acetate. The organic phases were collected, washed with brine and dried over magnesium sulfate. Evaporation of the solvent under vacuum gave 57.6 g of brown oil. After purification by column chromatography on silica gel (heptane/ethyl acetate 9/1) 40 g (57%) of ethyl (3,5-dichloropyridin-2-yl)(difluoro)acetate (Int-7) were obtained as a yellow oil, (M+1)=270, $^{19}$F-NMR (235 MHz, CDCl$_3$) δ (ppm): −104.21 (CF$_2$).

Preparation of ethyl[3-chloro-5-(trifluoromethyl)pyridin-2-yl](difluoro)acetate (Int-8)

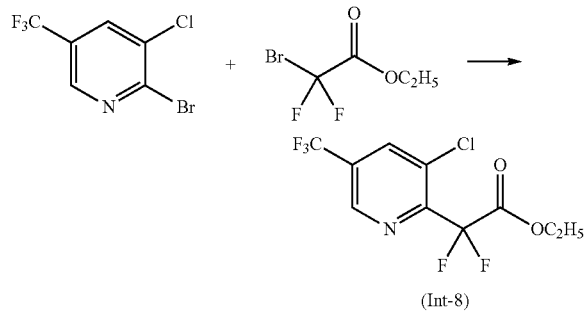

(Int-8)

Under the same conditions, 47 g of 2-bromo-3-chloro-5-(trifluoromethyl)pyridine, yields 46.7 g (46%) of ethyl[3-chloro-5-(trifluoromethyl)pyridin-2-yl](difluoro)acetate (Int-8) as a yellow oil.

Step 2: Preparation of 2-(3,5-dichloropyridin-2-yl)-2,2-difluoroethanol (Int-9)

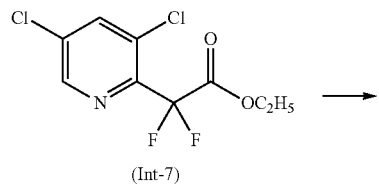

(Int-7)

To a solution of 10 g (37 mmol) of ethyl (3,5-dichloropyridin-2-yl)(difluoro)acetate (Int-7) in 60 mL of ethanol, were added portionwise at 0° C., 1.05 g (27.7 mmol) of sodium borohydride. The reaction mixture was stirred below 10° C. for 2 hours. 30 mL of 1 N HCl were then slowly added followed by 500 mL of water. The aequeous phase was extracted three times by 300 mL of ethyl acetate and the organic phase was successively washed with brine, water and dried over magnesium sulfate. After evaporation of the solvent under vacuum 8.5 g of yellow oil were obtained. After trituration in diisopropyl ether and filtration 6.8 g (80%) of 2-(3,5-dichloropyridin-2-yl)-2,2-difluoroethanol (Int-9) were obtained as a white solid. Mp (melting point)=56° C. (M+1)=228. $^{19}$F-NMR (235 MHz, CDCl$_3$) δ (ppm): −105.85 (CF$_2$).

Preparation of 2-[3-chloro-5-(trifluoromethyl)pyridin-2-yl]-2,2-difluoroethanol (Int-10)

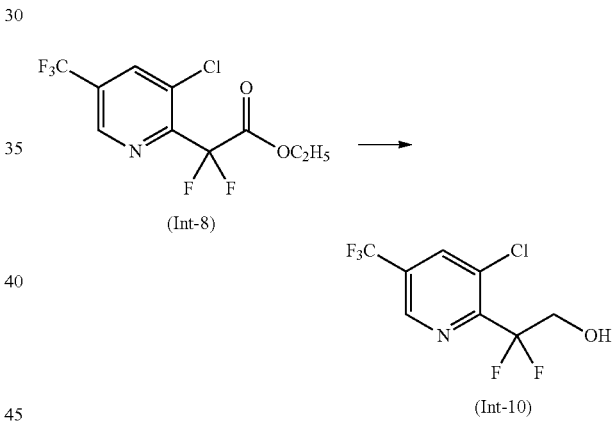

(Int-8)

(Int-10)

Under the same conditions, reduction of 12 g of ethyl[3-chloro-5-(trifluoromethyl)pyridin-2-yl](difluoro)acetate (Int-8), resulted in 6.8 g (65%) of 2-[3-chloro-5-(trifluoromethyl)pyridin-2-yl]-2,2-difluoroethanol (Int-10) as a yellow oil, (M+1)=262, $^{19}$F-NMR (235 MHz, CDCl$_3$) δ (ppm): −106.74 (CF$_2$); −63.18 (CF$_3$).

Step 3: Preparation of 2-(3,5-dichloropyridin-2-yl)-2,2-difluoroethanamine (IIa-15)

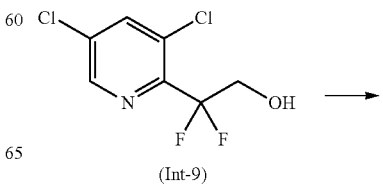

(Int-9)

-continued

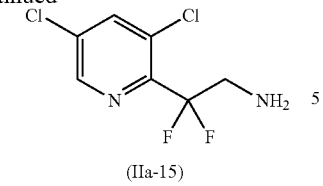

(IIa-15)

To a solution of 1.3 g (5.7 mmol) of 2-(3,5-dichloropyridin-2-yl)-2,2-difluoroethanol (Int-9) in dry acetonitrile under argon, were added 0.744 mL (9.12 mmol) of dry pyridine. The reaction mixture was cooled to 0° C. and 1.06 mL (6.27 mmol) of triflic anhydride were added dropwise in 15 min while maintaining the temperature below 8° C. The reaction mixture was stirred at 0° C. for additional 30 min 9.9 mL of a 28% w/w aqueous solution of ammonia (144 mmol) were added and the reaction mixture was stirred at room temperature for 2 days. The reaction mixture was diluted with 50 mL of brine and the product extracted three times with 25 mL of ethyl acetate. The organic phases were collected, washed three times with 40 mL of brine and dried over magnesium sulfate. Afater evaporation of the solvent under vacuum 1.09 g of brown oil were obtained. After purification by column chromatography on silica gel (heptane/ethyl acetate gradient) 0.65 g (50%) of 2-(3,5-dichloropyridin-2-yl)-2,2-difluoroethanamine (IIa-15) were obtained as a yellow oil, (M+1)=227, $^{19}$F-NMR (235 MHz, CDCl$_3$) δ (ppm): −104.80 (CF$_2$).

Preparation of 2-[3-chloro-5-(trifluoromethyl)pyridin-2-yl]-2,2-difluoroethanamine (IIa-14)

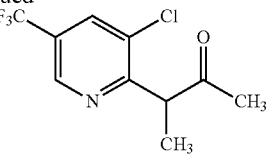

(Int-10)

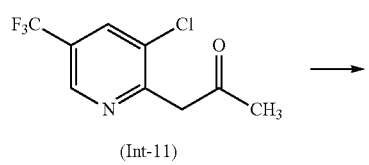

(IIa-14)

Under the same conditions, amination of 1.5 g of 2-[3-chloro-5-(trifluoromethyl)pyridin-2-yl]-2,2-difluoroethanol (Int-10), produced 0.4 g (27%) of 2-[3-chloro-5-(trifluoromethyl)pyridin-2-yl]-2,2-difluoroethanamine (IIa-14) as a yellow oil, (M+1)=261, $^{19}$F-NMR (235 MHz, CDCl$_3$) δ (ppm): −105.48 (CF$_2$); −62.97 (CF$_3$).

Synthesis of intermediate (IIa-16)

Step 1: Preparation of 3-[3-chloro-5-(trifluoromethyl)pyridin-2-yl]butan-2-one (Int-12)

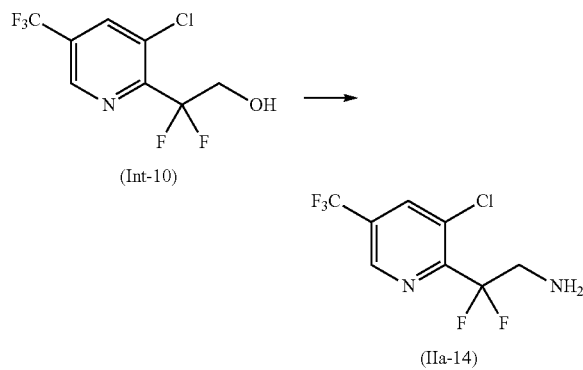

(Int-11)

-continued (Int-12)

6.00 g of 1-[3-chloro-5-(trifluoromethyl)pyridin-2-yl]acetone (Int-11) (27 mMol) (synthesis according to P10 and comm av.) and 5.75 g of methyl iodide (40.5 mMol) were diluted in 120 mL of dimethoxyethane. 3.03 g of potassium hydroxide were added portionwise at room temperature. After cooling, 100 mL of water were added to the reaction mixture which was extracted twice with 150 mL of ethyl acetate. The organic phase was washed twice with 100 mL of water, dried over magnesium sulfate and concentrated. After purification on silica, 0.67 g (39%) of desired product 3-[3-chloro-5-(trifluoromethyl)pyridin-2-yl]butan-2-one (Int-12) were obtained, [M+1]=252.

Step 2: Preparation of 3-[3-chloro-5-(trifluoromethyl)pyridin-2-yl]butan-2-amine (IIa-16)

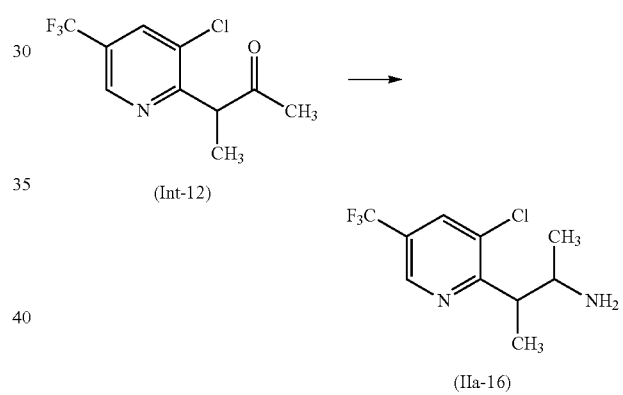

(Int-12)

(IIa-16)

0.64 g of 1-[3-chloro-5-(trifluoromethyl)pyridin-2-yl]butan-2-one (Int-12) (0.0025 mol) were diluted in 5 mL of methanol. 7.0 g of molecular sieves 3 Å, 1.90 g (0.025 mol) of ammonium acetate and 0.39 g (0.0052 mol) of sodium cyanoborohydride were added. The reaction medium was stirred overnight at room temperature. After filtration, the pH was adjusted to 9 with an aqueous solution of 1 N sodium hydroxide. The reaction mixture was concentrated to dryness and 30 mL of ethyl acetate were added. The organic phase was washed with an aqueous solution of 1 N sodium hydroxide, brine and water; dried over magnesium sulfate, filtered and concentrated to dryness. The crude material was dissolved in 15 mL of 1 N hydrochloric acid and extracted with 15 mL of ethyl acetate. An aqueous solution of 1 N sodium hydroxide was added to the aqueous phase, which was subsequently extracted twice with 15 mL of ethyl acetate. The organic phase was dried over magnesium sulfate, filtered and concentrated to dryness. 0.21 g (32%) of desired product 1-[3-chloro-5-(trifluoromethyl)pyridin-2-yl]butan-2-amine (IIa-16) were obtained, [M+1]=253.

(IIa-16), Solvent: <CDCl$_3$>, Spectrometer: 250 MHz 8.8007 (1.26); 8.7474 (4.38); 8.7114 (0.96); 8.6750 (0.36); 7.9494 (0.94); 7.9165 (5.80); 7.8572 (0.64); 7.2852 (4.01);

4.4592 (0.43); 4.4301 (0.35); 3.7320 (3.86); 3.5142 (0.35); 3.4764 (0.56); 3.4505 (1.77); 3.4238 (3.16); 3.3975 (3.05); 3.3807 (1.53); 3.3561 (2.58); 3.3312 (3.03); 3.3063 (1.80); 3.2810 (0.52); 3.0742 (0.39); 3.0493 (0.38); 2.1316 (7.72); 1.6759 (0.81); 1.6137 (16.00); 1.5889 (2.25); 1.5492 (0.55); 1.5133 (1.30); 1.4535 (4.53); 1.3733 (1.83); 1.3369 (13.49); 1.3099 (13.31); 1.2792 (4.17); 1.2534 (4.91); 1.2219 (4.68); 1.1978 (3.94); 1.1754 (0.82); 1.0772 (12.77); 1.0519 (12.76); 0.9908 (1.18); 0.9655 (1.06); 0.9102 (0.50); 0.8863 (0.66); 0.8671 (0.49); 0.7657 (0.94); 0.7408 (0.83)

In a similar manner compound (IIa-24) can be prepared by reacting 1-[3-chloro-5-(trifluoromethyl)pyridin-2-yl]acetone (Int-11) and cyclopropylamine.

Synthesis of intermediate (IIa-40)

Preparation according to known methods (cf. J. Amer. Chem. Soc. 72, 2804-6 (1950); WO 1984/03278; WO 2008/06479; THL 45, 7407-08 (2004))

Figure 17:
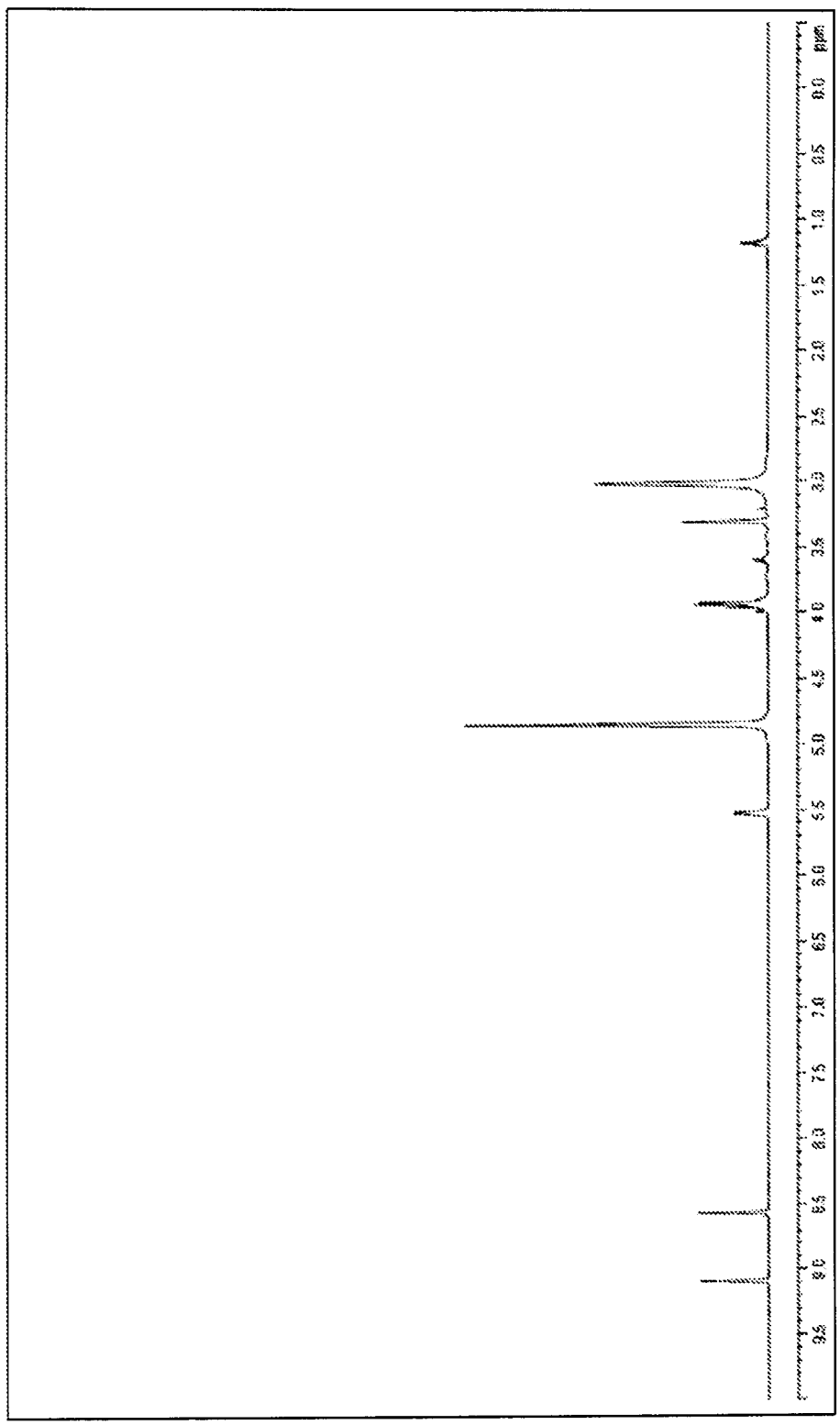
FIGS. 17 and 18 show chemical structures and mass spectrometry graphs for Compound Nos. IIa40 and IIa41, respectively, as further described herein.

(IIa40), Solvent: <CDCl$_3$>, Spectrometer: 400 MHz
See FIG. 17

Synthesis of Intermediate (IIa-41)

Preparation according to known methods (cf. J. Amer. Chem. Soc. 72, 2804-6 (1950); WO 1984/03278; WO 2008/06479; THL 45, 7407-08 (2004))

Figure 18:
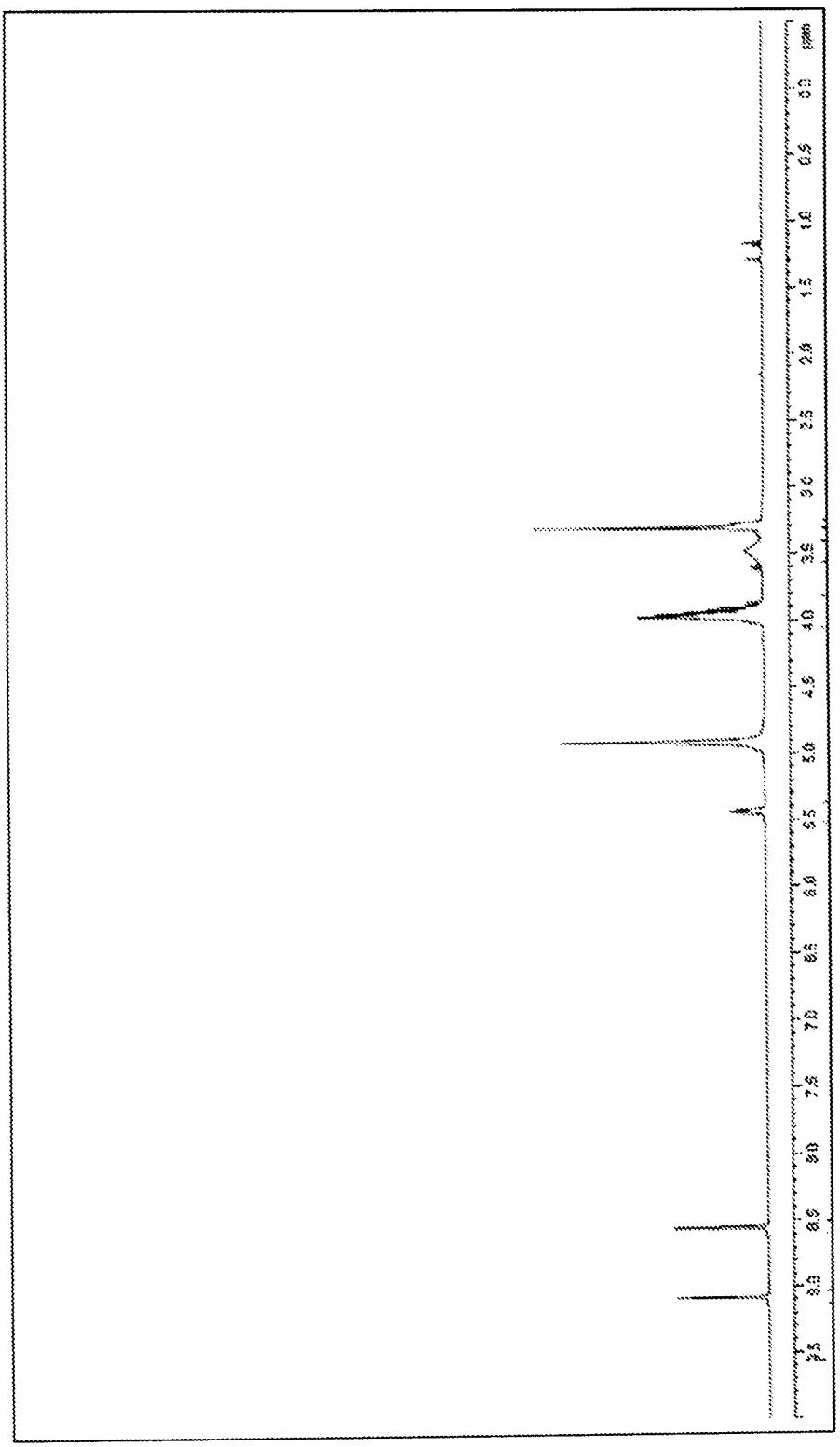

(IIa41), Solvent: <CDCl$_3$>, Spectrometer: 400 MHz
See FIG. 18

Synthesis of Intermediate (IIb-34)

Step 1: Preparation of 4-chloro-6-(trifluoromethyl)nicotinic acid (Int-11)

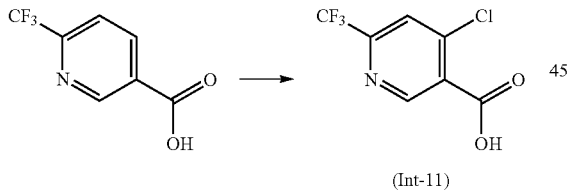

(Int-11)

A solution of 2,2,6,6-tetramethylpiperidin (198.8 g, 1.41 mol) in tetrahydrofuran (1.5 L) was added n-butyl-lithium (564 mL, 1.41 mol) dropwise at −78° C. Then the mixture was stirred from −78° C.~−30° C. for 30 minutes. Then the mixture was cooled to −78° C. and a solution of 6-(trifluoromethyl)nicotinic acid (90 g, 1.47 mol) in tetrahydrofuran (2.5 L) added dropwise at −78° C., then the mixture was stirred from −78° C.--40° C. for 1 hour. The mixture was cooled to −78° C. and a solution of hexachloroethane (222.5 g, 0.94 mol) was added to the reaction mixture dropwise. The mixture was stirred at −78° C. for 3 hours. Aqueous ammoniumchloride (1500 mL) was added to the mixture slowly at −78° C. and the mixture was stirred at room temperature for 20 minutes. The mixture was extracted with ethyl acetate (1 L*3). The combined organic layer was concentrated and the residue was purified by silica gel chromatography eluted with dichloromethane: methanol=20:1 to yield 4-chloro-6-(trifluoromethyl)nicotinic acid (Int-11) (85 g, 80%) as a brown solid.

Figure 19:
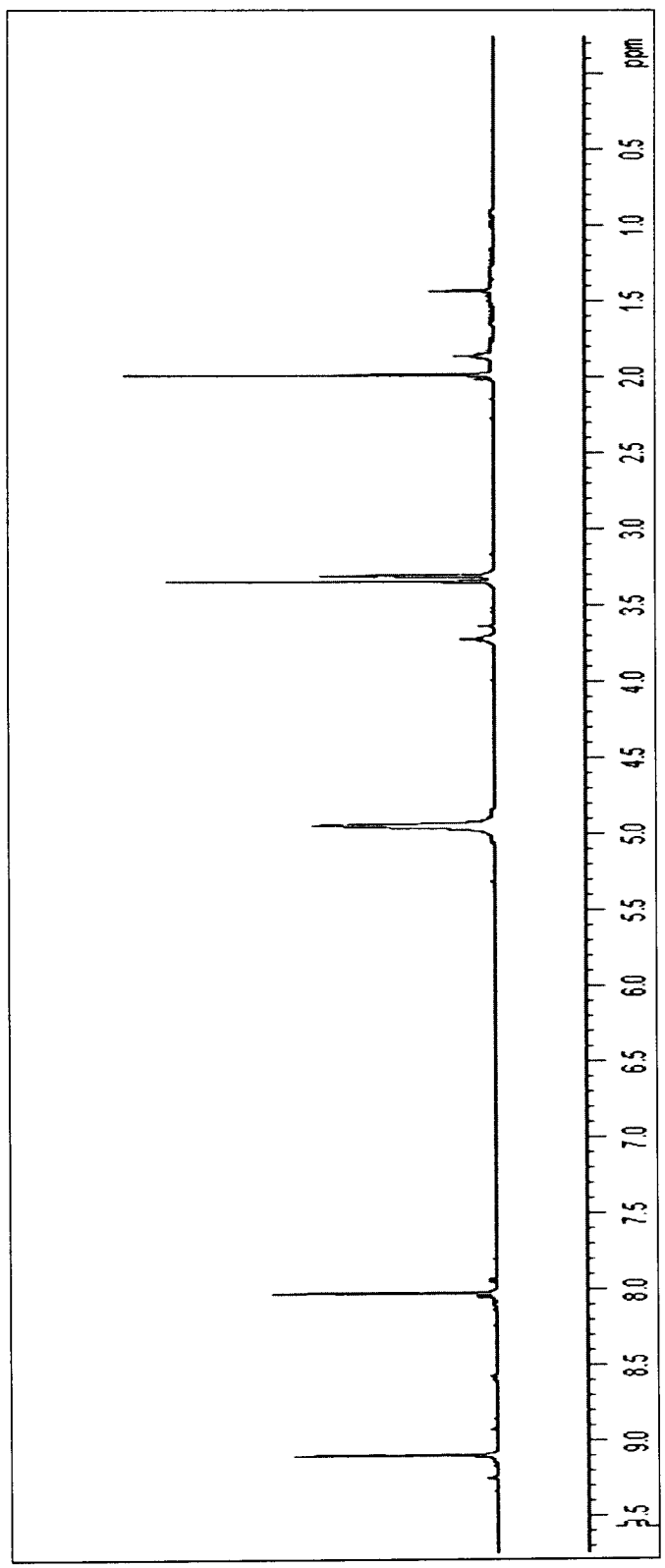
FIG. 19 shows mass spectrometry graph for Compound No. Int-11, as further described herein.

(Int-11), Solvent: <CD$_3$OD>, Spectrometer: 400 MHz
See FIG. 19

Step 2: Preparation of [4-chloro-6-(trifluoromethyl)pyridin-3-yl]methanol (Int-12)

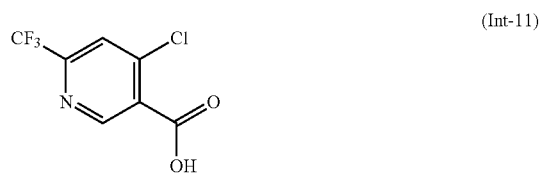

(Int-11)

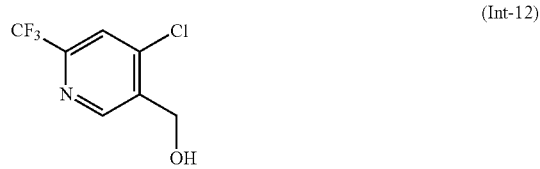

(Int-12)

To a mixture of 4-chloro-6-(trifluoromethyl)nicotinic acid (Int-11) (85 g, 0.377 mol) in tetrahydrofuran (1.5 L) was added BH$_3$-THF (755 mL, 0.755 mol, 1M in THF) slowly with ice bath. The mixture was stirred at room temperature overnight. Aqueous NH$_4$Cl (500 mL) was added to the mixture slowly with ice bath and the mixture was poured into water (1 L). The mixture was extracted with Ethyl acetate (1L*3). The combined organic layer was washed with brine, dried over Na$_2$SO$_4$ and concentrated to give crude[4-chloro-6-(trifluoromethyl)pyridin-3-yl]methanol (Int-12) (90 g, 100%) as brown syrup, which was used for the next step without further purification.

Figure 20:
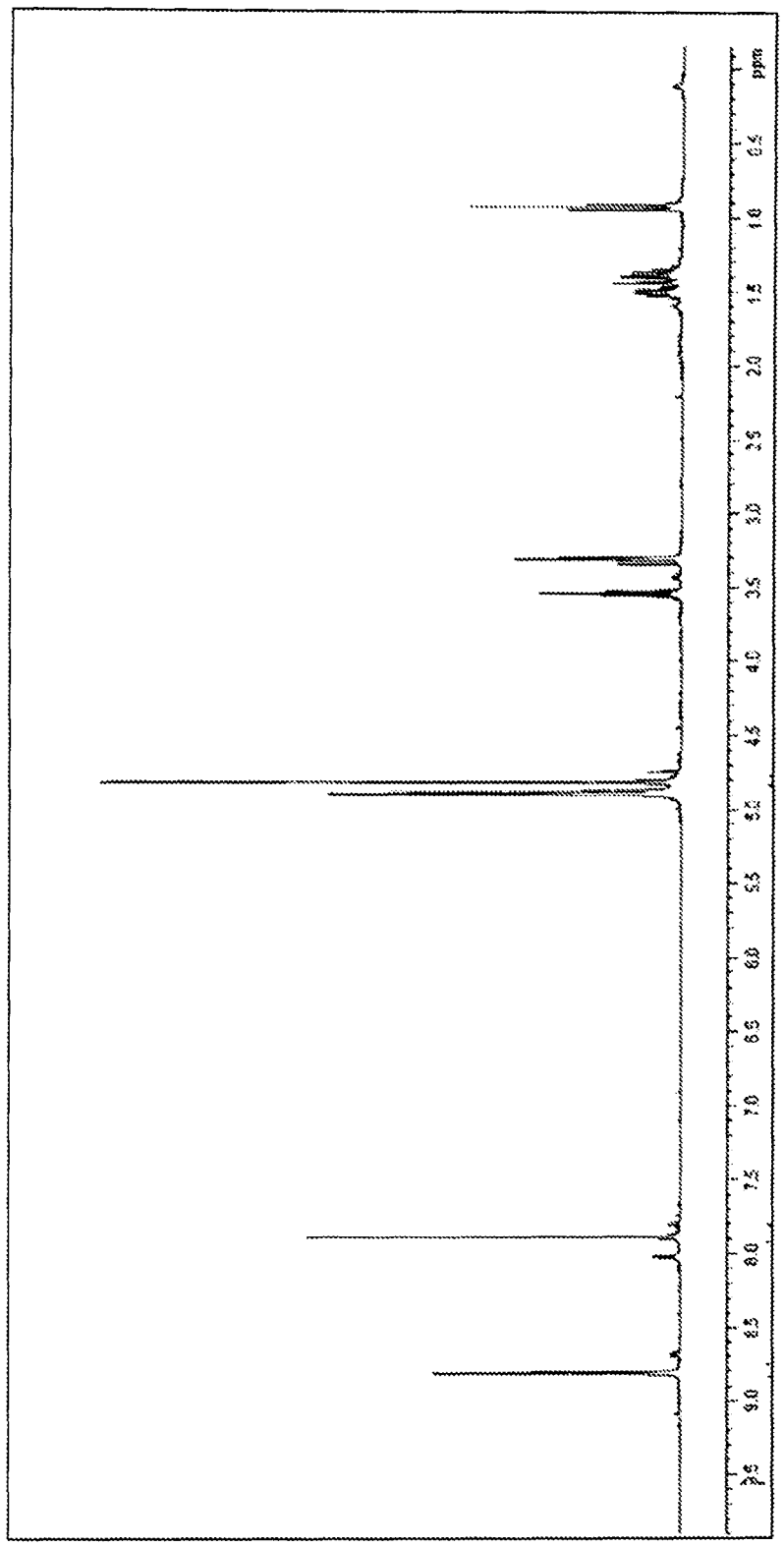
FIGS. 20-22 show chemical structures and mass spectrometry graphs for Compound Nos. Int-12 through Int-14, respectively, as further described herein.

(Int-12), Solvent: <CD$_3$OD>, Spectrometer: 400 MHz
See FIG. 20

Step 3: Preparation of 4-chloro-5-(chloromethyl)-2-(trifluoromethyl)pyridine (Int-13)

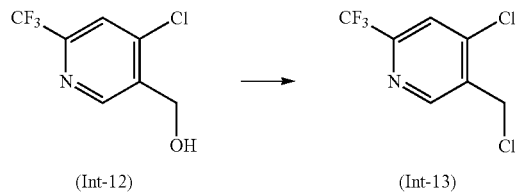 [SMILES: OCc1cnc(C(F)(F)F)cc1Cl ; FC(F)(F)c1cc(Cl)c(CCl)cn1]

(Int-12)     (Int-13)

[4-Chloro-6-(trifluoromethyl)pyridin-3-yl]methanol (Int-12) (90 g, 0.426 mol) was added to SOCl$_2$ (700 mL) slowly with ice bath, the mixture was refluxed for 1 hour. The mixture was concentrated and the residue was poured into water (1 L). The mixture was adjusted to pH=7-8 with solid NaHCO$_3$. The mixture was extracted with ethyl acetate (500 mL*3). The combined organic layer was concentrated to yield 4-chloro-5-(chloromethyl)-2-(trifluoromethyl)pyridine (Int-13) (80 g, 87%) as brown syrup which was used for the next step without further purification.

Figure 21:
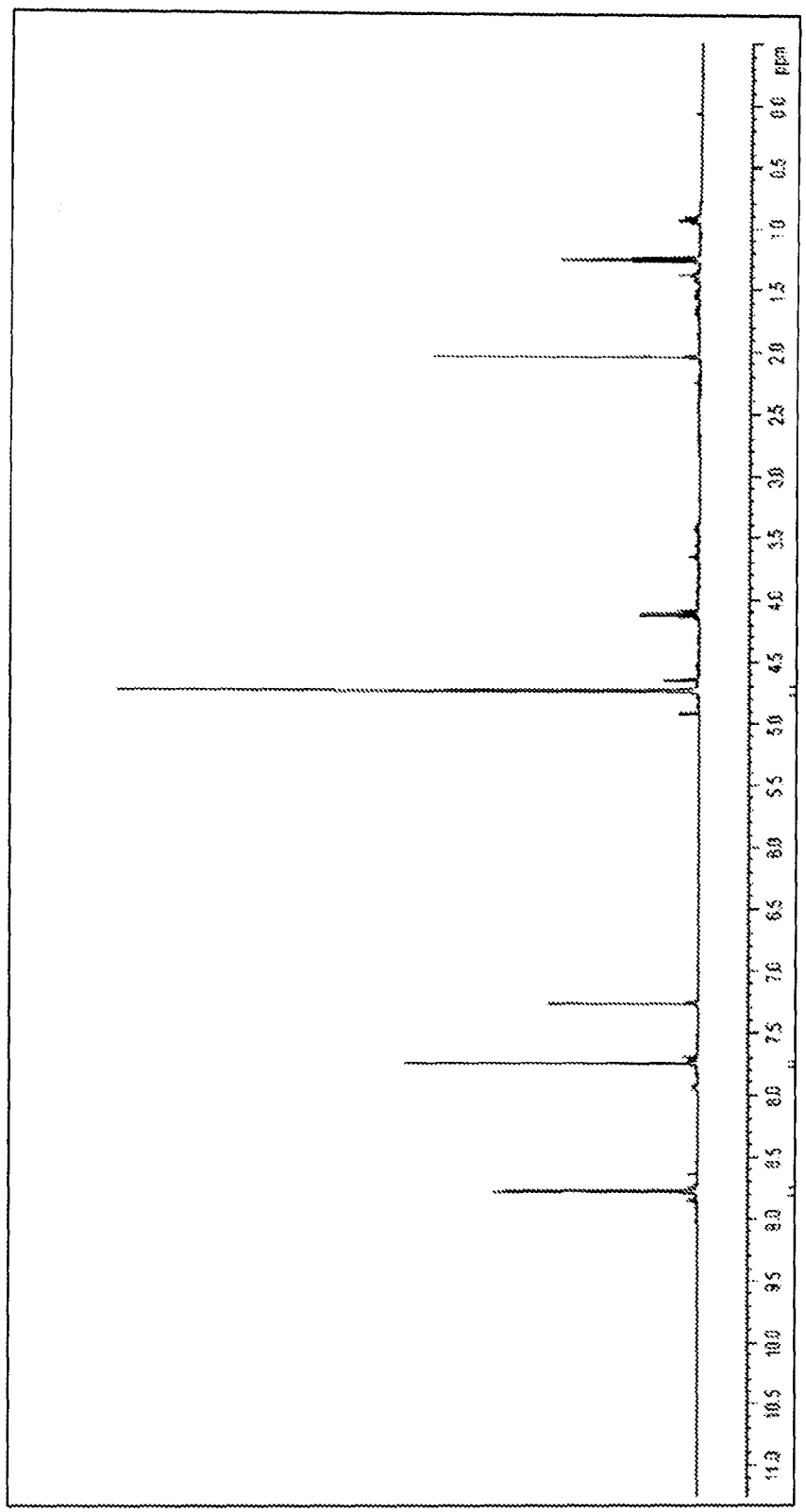

(Int-13), Solvent: <CDCl$_3$>, Spectrometer: 400 MHz
See FIG. 21

Step 4: Preparation of [4-chloro-6-(trifluoromethyl)pyridin-3-yl]acetonitrile (Int-14)

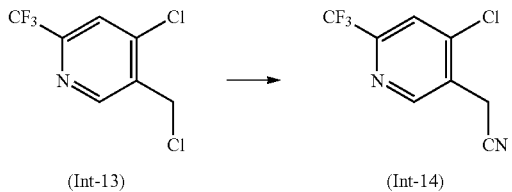 [SMILES: FC(F)(F)c1cc(Cl)c(CCl)cn1 ; N#CCc1cnc(C(F)(F)F)cc1Cl]

Trimethylsilylcyanid (TMSCN) (69.3 g, 0.7 mol) was added to a solution of 4-chloro-5-(chloromethyl)-2-(trifluoromethyl)pyridine (Int-13) (80 g, 0.348 mol) and Tetra-n-butylammoniumfluoride (129.5 g, 0.7 mol) in acetonitrile (1.5 L) slowly. Then the mixture was stirred at 20-30° C. for 2 hours. Thin layer chromatography (petroleum ether: EtOAc=3:1) showed all of starting material was consumed. The mixture was concentrated and the residue was purified by silica gel chromatography eluted with petroleum ether: EtOAc=20:1~3:1 to yield [4-chloro-6-(trifluoromethyl)pyridin-3-yl]acetonitrile (Int-14) (50 g, 60% from NMR, 39% of yield) as yellow syrup.

Figure 22:
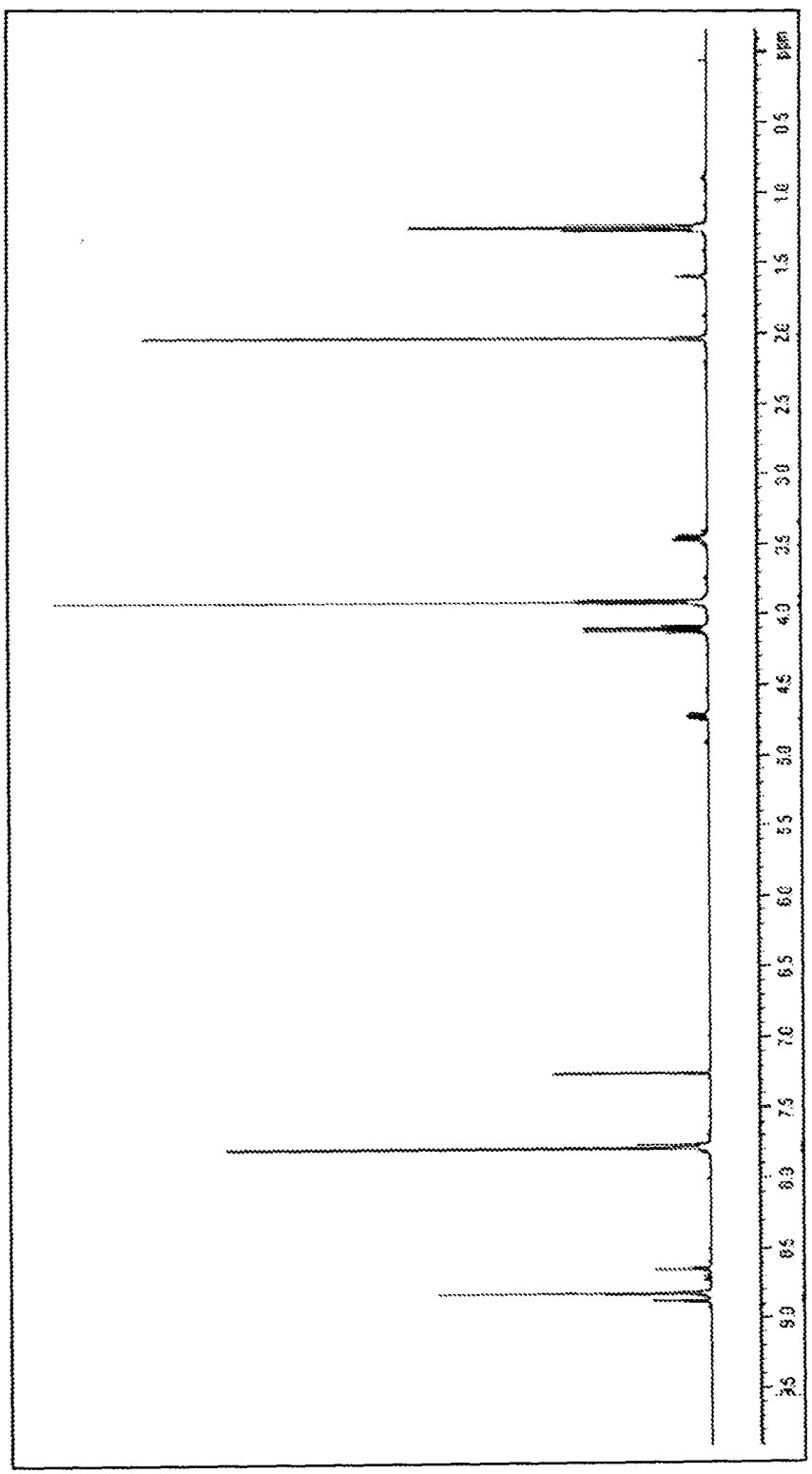

(Int-14), Solvent: <CDCl$_3$>, Spectrometer: 400 MHz
See FIG. 22

Step 5: Preparation of 2-[4-chloro-6-(trifluoromethyl)pyridin-3-yl]ethanamine (IIb-34) hydrochloride

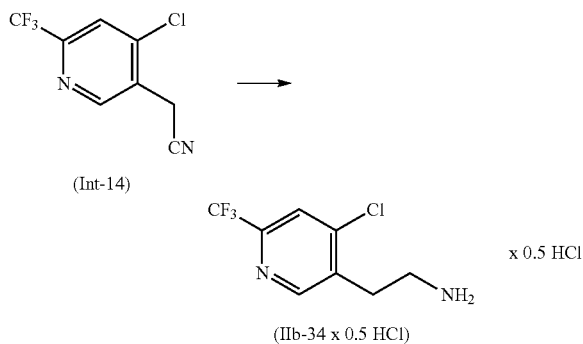

To a mixture of [4-chloro-6-(trifluoromethyl)pyridin-3-yl]acetonitrile (Int-14) (50 g, 0.227 mol) in THF (1.5 L) was added BH$_3$-THF (908 mL, 0.908 mol, 1N in THF) slowly with ice bath. Then the mixture was stirred at room temperature for 3 hours. Methanol (500 mL) was added to the mixture slowly with ice bath. The mixture was concentrated and the residue was purified by silica gel chromatography eluted with dichloromethane: methanol=20:1~10:1 to give crude 2-[4-chloro-6-(trifluoromethyl)pyridin-3-yl]ethanamine (IIb-34× HCl) (20 g), which was poured into HCl-ethyl acetate (300 mL) and stirred at room temperature for 1 hour. The mixture was filtered and the filter cake was washed with methyl-t-butylether (20 mL*3) and dried to yield 2-[4-chloro-6-(trifluoromethyl)pyridin-3-yl]ethanamine (IIb-34×HCl) (14 g, 46%, hydrochloride salt) as off-white solid.

Figure 23:
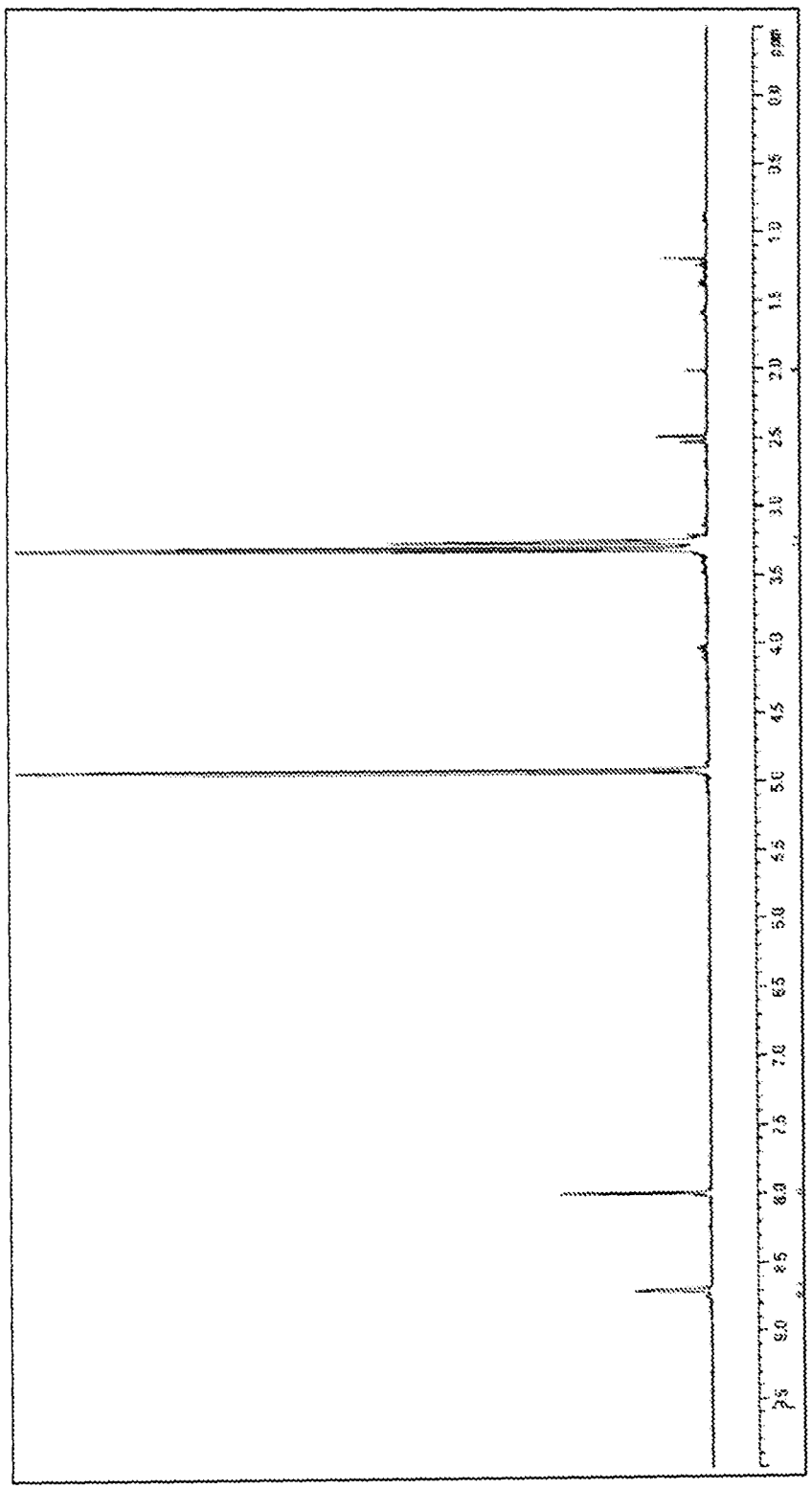
FIG. 23 shows chemical structure and mass spectrometry graph for Compound No. IIb-34×HCl, as further described herein.

(IIb-34×HCl), Solvent: <CD$_3$OD>, Spectrometer: 400 MHz
See FIG. 23

Synthesis of Intermediate (IIb-35)

Step 1: Preparation of 2-chloro-6-(trifluoromethyl)nicotinic acid (Int-15)

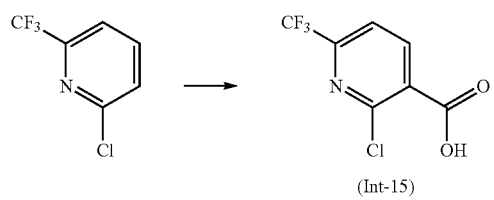 [SMILES: FC(F)(F)c1cccc(Cl)n1 ; O=C(O)c1ccc(C(F)(F)F)nc1Cl]

To a stirred solution of 2-chloro-6-(trifluoromethyl)pyridine (50.0 g, 1.0 eq.) in tetrahydrofuran (1.01) was added drop wise lithium diisopropylamide (LDA) (44.2 g, 1.5 eq.) at −78° C. After 2 h dry carbondioxide (500 g) was added at −78° C. The resulting reaction mixture was allowed to room temperature and stirred for 10 min. The reaction progress was monitored by TLC. After completion of reaction, the reaction mixture was acidified with 1 N HCl up to pH 2 and extracted with ethyl acetate (2×500 mL). The combined organic layer was washed with water (500 mL), brine (500 mL), dried over anhydrous sodium sulfate and concentrated under reduced pressure to get crude product which was triturated with pet ether to get pure 2-chloro-6-(trifluoromethyl)nicotinic acid (Int-15) (40.0 g, 64.6%).

Figure 24:
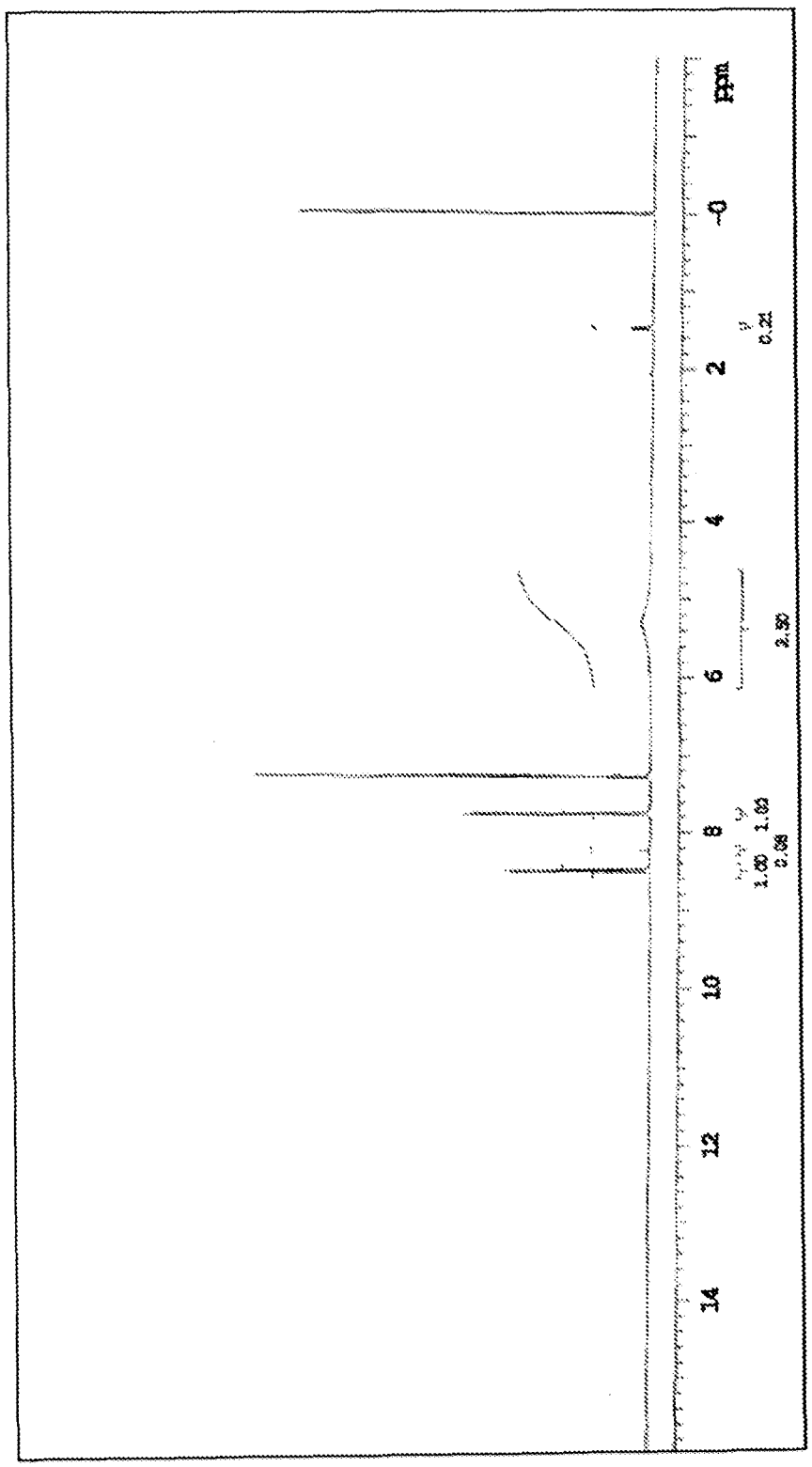
FIGS. 24-27 show chemical structures and mass spectrometry graphs for Compound No. Int-15, Int-16, Int-18, and Int-19, respectively, as further described herein.

(Int-15), Solvent: <CDCl$_3$>, Spectrometer: 400 MHz
See FIG. 24

Step 2: Preparation of [2-chloro-6-(trifluoromethyl)pyridin-3-yl]methanol (Int-16)

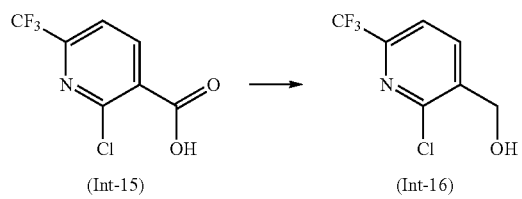 [SMILES: O=C(O)c1ccc(C(F)(F)F)nc1Cl ; OCc1ccc(C(F)(F)F)nc1Cl]

To a stirred solution of e 2-chloro-6-(trifluoromethyl)nicotinic acid (Int-15) (40 g, 1.0 eq.) in THF (400 mL) was added BH$_3$-THF (266.6 mL, 1.5 eq) at room temperature. The progress of the reaction was monitored by TLC. After 16 h the reaction mixture was concentrated under reduced pressure to remove THF. The resulting reaction mixture was diluted with 10% NaHCO$_3$ (500 mL) and extracted with ethyl acetate (2×500 mL). The combined organic layers were washed with water (500 mL), brine (500 mL), dried over anhydrous sodium sulfate and the solvent was removed under reduced pressure to get crude [2-chloro-6-(trifluoromethyl)pyridin-3-yl]methanol (Int-16) as light yellow liquid, 32 g (85.5%).

Figure 25:
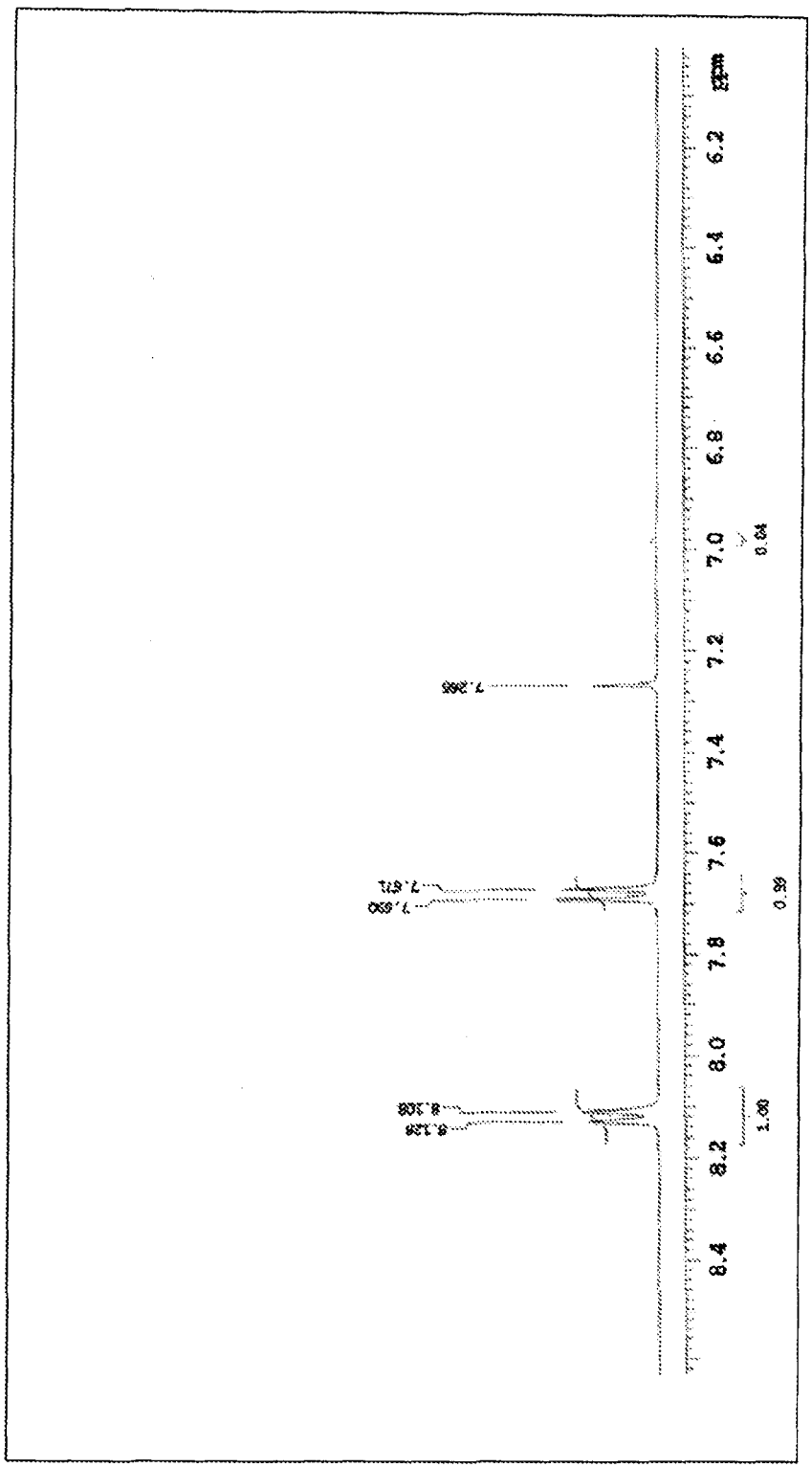

(Int-16), Solvent: <CDCl$_3$>, Spectrometer: 400 MHz
See FIG. 25

Step 3: Preparation of 2-chloro-6-(trifluoromethyl)nicotinaldehyde (Int-17)

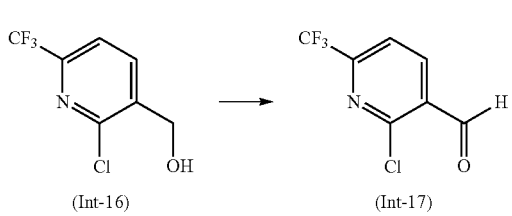 [SMILES: OCc1ccc(C(F)(F)F)nc1Cl ; O=Cc1ccc(C(F)(F)F)nc1Cl]

To a stirred solution of [2-chloro-6-(trifluoromethyl)pyridin-3-yl]methanol (Int-16) (80.0 g, 1.0 eq.) in dichloromethane (700 ml) was added pyridinium chlorochromate (160.0 g, 2.0 eq), silicium dioxide (240 g) at room temperature and stirred for 4 h. The progress of the reaction was monitored by TLC. After completion of reaction, reaction mixture was filtered through silica gel bed and washed the bed with excess 90% ethyl acetate in pet ether and filtrate was concentrated under reduced pressure to get crude 2-chloro-6-(trifluoromethyl)nicotinaldehyde (Int-17) as yellow liquid (70.0 g, 88.3%). GC-MS: m/z 209 ([M]).

Step 4: Preparation of 1-[2-chloro-6-(trifluoromethyl)pyridin-3-yl]-2-nitroethanol (Int-18)

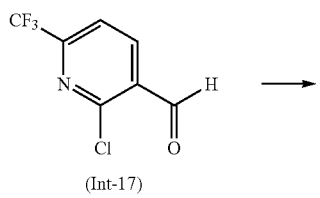

To a stirred solution of 2-chloro-6-(trifluoromethyl)nicotinaldehyde (Int-17) (70 g, 1.0 eq.) in nitro methane (700 mL) was added sodium hydroxide (6.7 g, 0.5 eq.) at room temperature. The resulting reaction mixture was heated to 100° C. and stirred for 2 h. The progress of the reaction was monitored by TLC. After completion of reaction, the reaction mixture was concentrated under reduced pressure to remove nitro methane quenched with ice water (500 mL) and extracted with ethyl acetate (2×1.0 L). The combined organic layer was washed with water (500 mL), brine (500 mL), dried over anhydrous sodium sulfate and concentrated under reduced pressure to get pure 1-[2-chloro-6-(trifluoromethyl)pyridin-3-yl]-2-nitroethanol (Int-18) (65.0 g, 72.0%).

Figure 26:
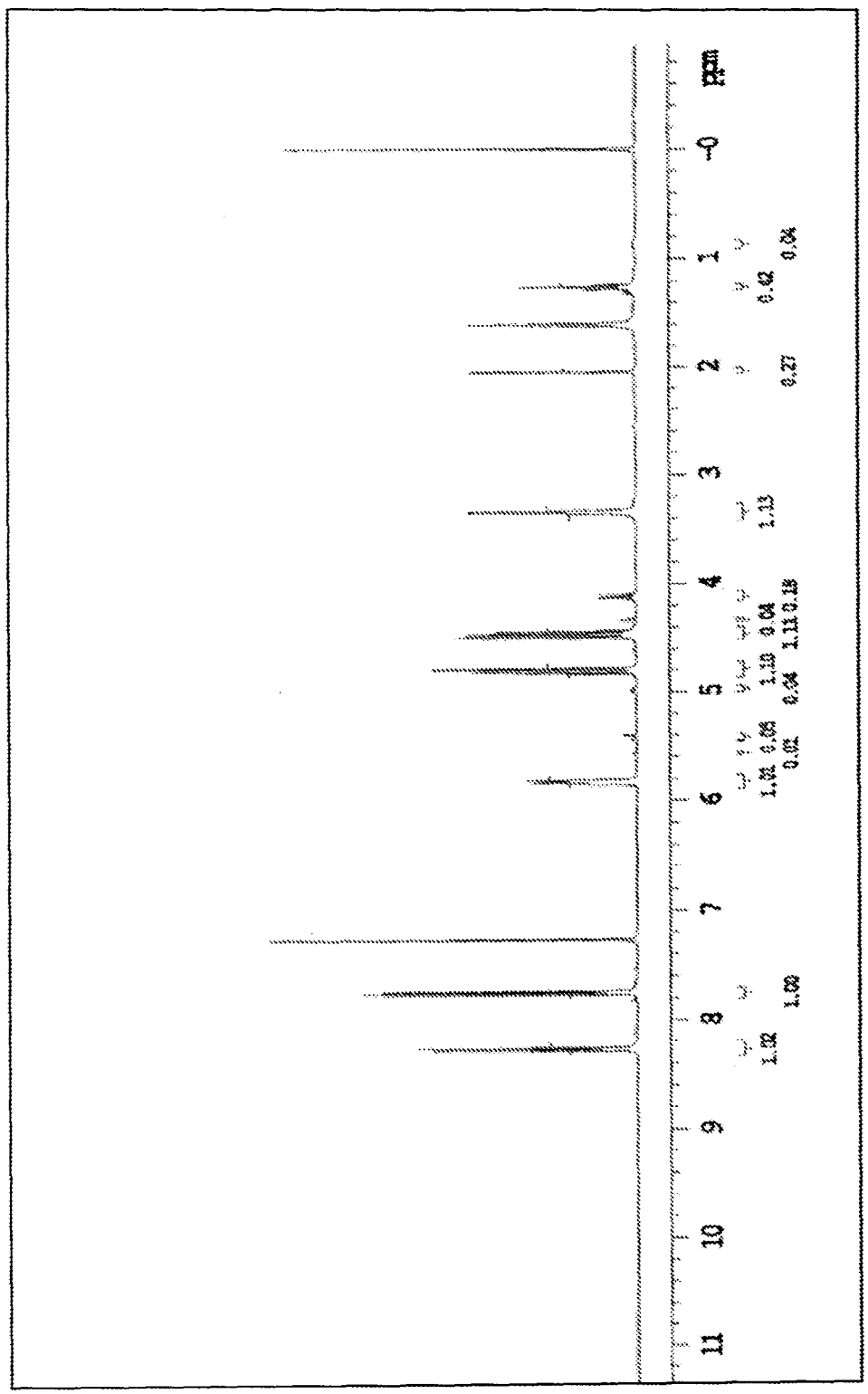

(Int-18), Solvent: <CDCl$_3$>, Spectrometer: 400 MHz
See FIG. 26

Step 5: Preparation of 2-chloro-3-[(E)-2-nitrovinyl]-6-(trifluoromethyl)pyridine (Int-19)

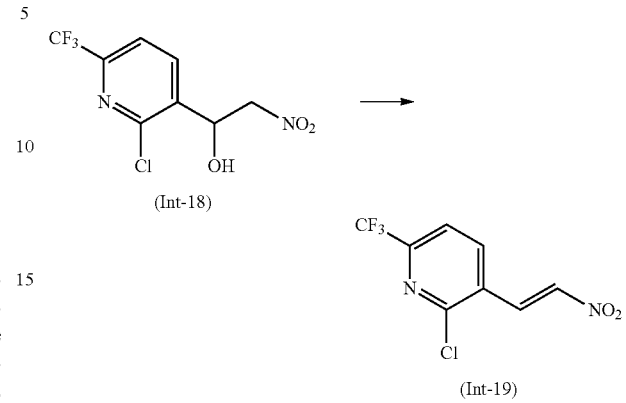

To a stirred solution of 1-[2-chloro-6-(trifluoromethyl)pyridin-3-yl]-2-nitroethanol (Int-18) (27 g, 1.0 eq.) in dichloromethane (270 mL) was added 4-dimethylamino pyridine (13.5 g, 1.1 eq.) followed by drop wise addition of acetic anhydride (13.5 g, 1.3 eq) at 0° C. and stirred for 15 min. The progress of the reaction was monitored by TLC. After completion of reaction, the reaction mixture was quenched with ice water and extracted with dichloromethane (2×200 mL). The combined organic layer was washed with water (200 mL), brine (200 mL), dried over anhydrous sodium sulfate and the solvent was removed under reduced pressure to get crude 2-chloro-3-[(E)-2-nitrovinyl]-6-(trifluoromethyl)pyridine (Int-19) (22.0 g, 87.6%).

Figure 27:
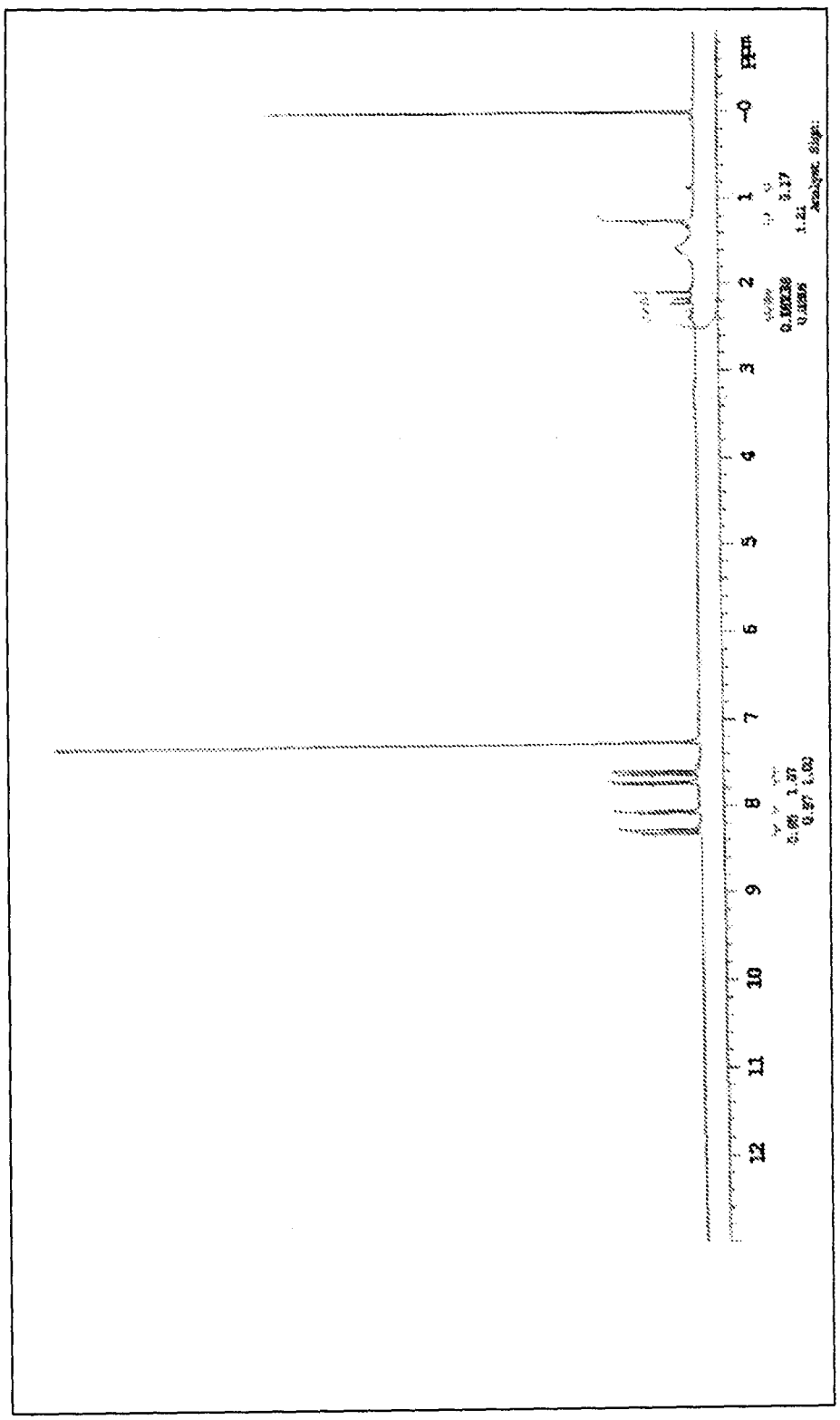

(Int-19), Solvent: <CDCl$_3$>, Spectrometer: 400 MHz
See FIG. 27

Step 5: Preparation of 2-[2-chloro-6-(trifluoromethyl)pyridin-3-yl]ethanamine (IIb-35) hydrochloride

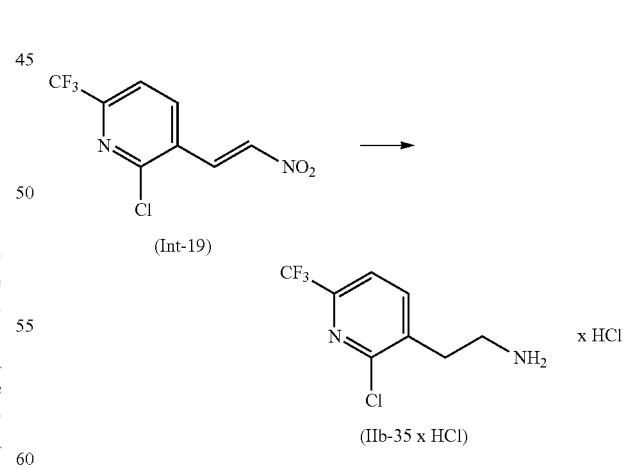

To a stirred solution of NaBH$_4$ (16.0 g, 4.2 eq.) in tetrahydrofuran (125 mL) was added BF$_3$ etherate (125 mL) at 0° C. The resulting reaction mixture was allowed to room temperature and stirred for 15 min 2-Chloro-3-[(E)-2-nitrovinyl]-6-(trifluoromethyl)pyridine (Int-19) (25.0 g, 1.0 eq) in tetrahydrofuran (125 mL) was added to above reaction mixture at room temperature. The reaction mixture was heated to 70° C. and stirred for 2 h. The resulting reaction mixture was allowed to room temperature and stirred for 16 h. The progress of the reaction was monitored by TLC. After completion of reaction, the reaction mixture was quenched in ice water (200 mL) and extracted with ethyl acetate (3×200 mL). The combined organic layers were washed with water (1×100 mL), brine (1×100 mL), dried over anhydrous sodium sulfate and the solvent was removed under reduced pressure to get crude amine. The amine compound was dissolved in ethanolic HCl (50 mL) and stirred at room temperature for 2.0 h. The reaction mixture was concentrated under reduced pressure to get crude 2-[2-chloro-6-(trifluoromethyl)pyridin-3-yl]ethanamine (IIb-35) hydrochloride (15.0 g, 58.3%).

(IIIb-35×HCl), Solvent: <[$D_6$]-DMSO>, Spectrometer: 400 MHz

Figure 28:
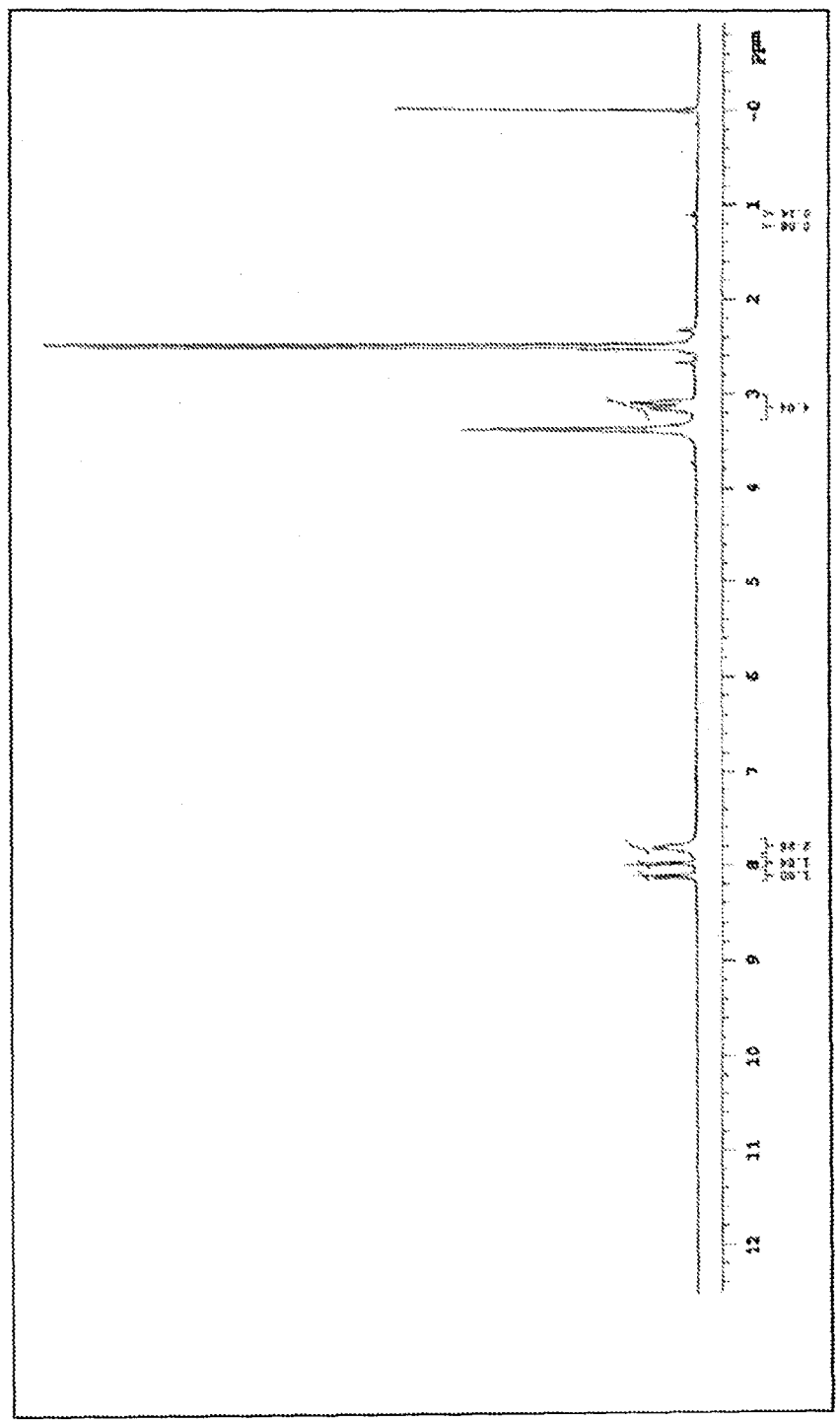
FIG. 28 shows chemical structure and mass spectrometry graph for Compound No. IIb-35×HCl, as further described herein.

See FIG. 28

BIOLOGICAL EXAMPLES

*Meloidogyne Incognita*—Test

Solvent: 125.0 parts by weight of acetone

To produce a suitable preparation of active compound, 1 part by weight of active compound is mixed with the stated amount of solvent, and the concentrate is diluted with water to the desired concentration. Vessels are filled with sand, a solution of the active ingredient, a suspension containing eggs and larvae of *Meloidogyne incognita* and salad seeds. The salad seeds germinate and the seedlings grow. Galls develop in the roots.

After 14 days the nematicidal activity is determined on the basis of the percentage of gall formation. 100% means that no galls were found; 0% means that the number of galls found on the roots of the treated plants was equal to that in untreated control plants.

In this test, for example, the following compounds from the preparation examples showed an activity of 100% at an application rate of 20 ppm: Ia-3, Ia-43, Ia-46, Ia-47, Ia-50, Ia-70, Ia-92, Ia-93, Ia-110, Ia-113, Ia-114, Ia-122, Ia-126, Ia-127, Ia-131, Ia-137, Ia-140, Ia-141, Ia-142, Ia-143, Ia-147, Ia-148, Ia-153, Ia-154, Ia-177, Ic-1, Ic-2, Ic-7.

In this test, for example, the following compounds from the preparation examples showed an activity of 90% at an application rate of 20 ppm: Ia-170, Ia-172, Ia-174, Ia-196, Ia-211, Ia-212, Ib-47, Ib-58, Ic-5.

In this test, for example, the following compounds from the preparation examples showed good activity of 70% at an application rate of 20 ppm: Ib-50, Ib-51.

In this test, for example, the following compounds from the preparation examples showed an activity of 100% at an application rate of 4 ppm: Ic-8.

*Cooperia Curticei*-Test (COOPCU)
Solvent: dimethyl sulfoxide

To produce a suitable preparation of active compound, 10 mg of active compound are dissolved in 0.5 ml solvent, and the concentrate is diluted with "Ringer's solution" to the desired concentration.

Approximately 40 *Cooperia curticei* larvae are transferred into a test tube containing compound solution. After 5 days percentage of larval mortality are recorded. 100% efficacy means all larvae are killed; 0% efficacy means no larvae are killed.

In this test for example, the following compounds from the preparation examples showed good activity of 100% at an application rate of 100 ppm: Ia-1, Ia-4, Ia-5, Ia-6, Ia-48, Ib-47, Ib-49, Ib-50, Ib-51, Ib-52, Ic-1, Ic-7.

In this test for example, the following compounds from the preparation examples showed good activity of 90% at an application rate of 100 ppm: Ib-48, Ic-59, Ic-60, Ic-75.

In this test for example, the following compounds from the preparation examples showed good activity of 80% at an application rate of 100 ppm: Ic-26, Ic-58.

*Haemonchus contortus*—Test (HAEMCO)
Solvent: dimethyl sulfoxide

To produce a suitable preparation of active compound, 10 mg of active compound are dissolved in 0.5 ml solvent, and the concentrate is diluted with "Ringer's solution" to the desired concentration.

Approximately 40 *Haemonchus contortus* larvae are transferred into a test tube containing compound solution. After 5 days percentage of larval mortality are recorded. 100% efficacy means all larvae are killed, 0% efficacy means no larvae are killed.

In this test for example, the following compounds from the preparation examples showed good activity of 100% at an application rate of 100 ppm: Ib-47, Ib-49, Ib-50, Ic-1, Ic-7.

In this test for example, the following compounds from the preparation examples showed good activity of 90% at an application rate of 100 ppm: Ia-1, Ib-48, Ib-51.

In this test for example, the following compounds from the preparation examples showed good activity of 80% at an application rate of 100 ppm: Ia-5, Ia-6, Ia-48.

In this test for example, the following compounds from the preparation examples showed good activity of 80% at an application rate of 20 ppm: Ib-52.

The invention claimed is:
1. A compound of formula

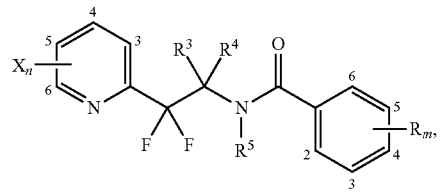

wherein
X is selected from the group consisting of halogen, nitro, cyano, hydroxy, amino, —SH, —SF$_5$, —CHO, —OCHO, —NHCHO, —COOH, —CONH$_2$, —CONH (OH), —OCONH$_2$, (hydroxyimino)-C$_1$-C$_6$-alkyl, C$_1$-C$_8$-alkyl, C$_1$-C$_8$-halogenoalkyl having 1 to 5 halogen atoms, C$_2$-C$_8$-alkenyl, C$_2$-C$_8$-alkynyl, C$_1$-C$_8$-alkylamino, di-(C$_1$-C$_8$)-alkylamino, C$_1$-C$_8$-alkoxy, C$_1$-C$_8$-halogenoalkoxy having 1 to 5 halogen atoms, C$_2$-C$_8$-alkenyloxy, C$_2$-C$_8$-halogenoalkenyloxy having 1 to 5 halogen atoms, C$_8$-C$_8$-alkynyloxy, C$_3$-C$_8$-halogenoalkynyloxy having 1 to 5 halogen atoms, C$_3$-C$_8$-cycloalkyl, C$_3$-C$_8$-halogenocycloalkyl having 1 to 5 halogen atoms, C$_1$-C$_8$-alkylcarbonyl, C$_1$-C$_8$-halogenoalkylcarbonyl having 1 to 5 halogen atoms, —CONH(C$_1$-C$_8$-alkyl), —CON(C$_1$-C$_8$-alkyl)$_2$, —CONH(OC$_1$-C$_8$-alkyl), —CON(OC$_1$-C$_8$-alkyl)(C$_1$-C$_8$-alkyl), C$_1$-C$_8$-alkoxycarbonyl, C$_1$-C$_8$-halogenoalkoxycarbonyl having 1 to 5 halogen atoms, C$_1$-C$_8$-alkylcarbonyloxy, C$_1$-C$_8$-halogenoalkylcarbonyloxy having 1 to 5 halogen atoms, C$_1$-C$_8$-alkylcarbonylamino, C$_1$-C$_8$-halogenoalkylcarbonylamino having 1 to 5 halogen atoms, —OCONH(C$_1$-C$_8$-alkyl), —OCON(C$_1$-C$_8$-alkyl)$_2$, —OCONH(OC$_1$-C$_8$-alkyl), —OCO(OC$_1$-C$_8$-alkyl), —S—C$_1$-C$_8$-alkyl, —S—C$_1$-C$_8$-halogenoalkyl having 1 to 5 halogen atoms, —S(O)—C$_1$-C$_8$-alkyl, —S(O)—C$_1$-C$_8$-halogenoalkyl having 1 to 5 halogen atoms, —S(O)$_2$—C$_1$-C$_8$-alkyl, —S(O)$_2$—C$_1$-C$_8$-halogenoalkyl having 1 to 5 halogen atoms, (C$_1$-C$_6$-alkoxyimino)-C$_1$-C$_6$-alkyl, (C$_2$-C$_6$-alkenyloxyimino)-C$_1$-C$_6$-alkyl, (C$_3$-C$_6$-alkynyloxyimino)-C$_1$-C$_6$-alkyl, (benzyloxyimino)-C$_1$-C$_6$-alkyl, benzyloxy, —S-benzyl, benzylamino, phenoxy, —S-phenyl and phenylamino, n is 1, 2, 3 or 4 and if n is 2, 3, or 4 then the substituents X may be the same or different, R$^3$ and R$^4$ are the same or different and are selected from the group consisting of hydrogen, halogen, cyano, hydroxy, amino, —SH, —CHO, —COOH, —CONH$_2$, —CONH(OH), —OCONH$_2$, (hydroxyimino)-C$_1$-C$_6$-alkyl, C$_1$-C$_6$-alkyl, C$_2$-C$_6$-alkenyl, C$_2$-C$_6$-alkynyl, C$_1$-C$_6$-alkylamino, di-(C$_1$-C$_6$-alkyl)amino, C$_1$-C$_6$-alkoxy, hydroxy-C$_1$-C$_6$-alkyl, C$_1$-C$_6$-alkoxy-C$_1$-C$_6$-alkyl, C$_1$-C$_6$-halogenoalkyl having 1 to 5 halogen atoms, C$_1$-C$_6$-halogenoalkoxy having 1 to 5 halogen atoms, C$_2$-C$_6$-alkenyloxy, C$_2$-C$_6$-halogenoalkenyloxy having 1 to 5 halogen atoms, C$_3$-C$_6$-alkynyloxy, C$_3$-C$_6$-halogenoalkynyloxy having 1 to 5 halogen atoms, C$_3$-C$_6$-cycloalkyl, C$_3$-C$_6$-halogenocycloalkyl having 1 to 5 halogen atoms, C$_1$-C$_6$-alkylcarbonyl, C$_1$-C$_6$-halogenoalkylcarbonyl having 1 to 5 halogen atoms, —CONH(C$_1$-C$_6$-alkyl), —CON(C$_1$-C$_6$-alkyl)$_2$, —CONH(OC$_1$-C$_6$-alkyl), —CON(OC$_1$-C$_6$-alkyl)(C$_1$-C$_6$-alkyl), C$_1$-C$_6$-alkoxycarbonyl, C$_1$-C$_6$-halogenoalkoxycarbonyl having 1 to 5 halogen atoms, —OC(O)—C$_1$-C$_6$-alkyl, —OC(O)—C$_1$-C$_6$-halogenoalkyl having 1 to 5 halogen atoms, —NHC(O)—C$_1$-C$_6$-alkyl, —NHC(O)—C$_1$-C$_6$-halogenoalkyl having 1 to 5 halogen atoms, —OCONH(C$_1$-C$_6$-alkyl), —OCON(C$_1$-C$_6$-alkyl)$_2$, —OCONH(OC$_1$-C$_6$-alkyl), OCO(OC$_1$-C$_6$-alkyl), —S—C$_1$-C$_6$-alkyl, —S—C$_1$-C$_6$-halogenoalkyl having 1 to 5 halogen atoms, —S(O)—C$_1$-C$_6$-alkyl, —S(O)—C$_1$-C$_6$-halogenoalkyl having 1 to 5 halogen atoms, —S(O)$_2$—C$_1$-C$_6$-alkyl, —S(O)$_2$—C$_1$-C$_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2-chlorophenyl-carbonylamino, 2,6-dichlorophenyl-carbonylamino and phenyl;

R$^5$ is selected from the group consisting of hydrogen, cyano, —CHO, —OH, C$_1$-C$_6$-alkyl, C$_1$-C$_6$-halogenoalkyl having 1 to 5 halogen atoms, C$_1$-C$_6$-alkoxy, C$_1$-C$_6$-halogenoalkoxy having 1 to 5 halogen atoms, C$_3$-C$_7$-cycloalkyl, C$_3$-C$_7$-halogenocycloalkyl having 1 to 5 halogen atoms, C$_2$-C$_6$-alkenyl, C$_2$-C$_6$-alkynyl, C$_1$-C$_6$-alkoxy-C$_1$-C$_6$-alkyl, C$_3$-C$_7$-cycloalkyl-C$_1$-C$_6$-alkyl, cyano-C$_1$-C$_6$-alkyl, amino-C$_1$-C$_6$-alkyl, C$_1$-C$_6$-alkylamino-C$_1$-C$_6$-alkyl, di-C$_1$-C$_6$-alkylamino-C$_1$-C$_6$-alkyl, C$_1$-C$_6$-alkylcarbonyl, C$_1$-C$_6$-halogenoalkylcarbonyl having 1 to 5 halogen atoms, C$_1$-C$_6$-alkoxycarbonyl, benzyloxycarbonyl, C$_1$-C$_6$-alkoxy-C$_1$-C$_6$-alkylcarbonyl, —S(O)$_2$—C$_1$-C$_6$-alkyl, and —S(O)$_2$—C$_1$-C$_6$-halogenoalkyl having 1 to 5 halogen atoms;

R is selected from the group consisting of halogen, nitro, —OH, NH$_2$, SH, SF$_8$, CHO, OCHO, NHCHO, COOH, cyano, C$_1$-C$_8$-alkyl, C$_1$-C$_8$-halogenoalkyl having 1 to 5 halogen atoms, C$_2$-C$_8$-alkenyl, C$_2$-C$_8$-alkynyl, C$_3$-C$_6$-cycloalkyl, —S—C$_1$-C$_8$-alkyl, —S—C$_1$-C$_8$-halogenoalkyl having 1 to 5 halogen atoms, C$_1$-C$_8$-alkoxy, C$_1$-C$_8$-halogenoalkoxy having 1 to 5 halogen atoms, C$_1$-C$_8$-alkoxy-C$_2$-C$_8$-alkenyl, C$_1$-C$_8$-alkoxycarbonyl, C$_1$-C$_8$-halogenoalkoxycarbonyl having 1 to 5 halogen atoms, C$_1$-C$_8$-alkylcarbonyloxy, C$_1$-C$_8$-halogenoalkylcarbonyloxy having 1 to 5 halogen atoms, —S(O)—C$_1$-C$_8$-alkyl, —S(O)—C$_1$-C$_8$-halogenoalkyl having 1 to 5 halogen atoms, —S(O)$_2$—C$_1$-C$_8$-alkyl, —S(O)$_2$—C$_1$-C$_8$-halogenoalkyl having 1 to 5 halogen atoms, C$_1$-C$_8$-alkylsulfonamide, —NH(C$_1$-C$_8$-alkyl), N(C$_1$-C$_8$-alkyl)$_2$, phenyl (optionally substituted by C$_1$-C$_6$-alkoxy) and phenoxy, or two R bonded to adjacent carbon atoms together represent —O(CH$_2$)$_p$O—, wherein p represents 1 or 2, m is 0, 1, 2, 3, 4 or 5 and if m is 2, 3, 4, or 5 then the substituents R may be the same or different.

2. A compound according to claim 1, in which R$^3$, R$^4$, R$^5$ represent hydrogen, n represents 2 and X represent 3-Cl and 5-CF$_3$.

3. A compound according to claim 1, in which R$^3$, R$^4$, R$^5$ represent hydrogen, n represents 2 and X represent 3-Cl and 5-Cl.

4. A method of controlling nematodes comprising applying to a plant, surroundings of a plant, habitat of a plant, or storage space of a plant a compound according to claim 1.

5. A method of controlling nematodes comprising applying to a plant, surroundings of a plant, habitat of a plant, or storage space of a plant a compound according to claim 2.

6. A method of controlling nematodes comprising applying to a plant, surroundings of a plant, habitat of a plant, or storage space of a plant a compound according to claim 3.

7. A compound according to claim 1, wherein the compound is an anthelmintic.

8. A method of controlling human or animal parasitic worm comprising administering a compound according to claim 1 to a human or animal.

9. A compound according to claim 2, wherein the compound is an anthelmintic.

10. A method of controlling human or animal parasitic worm comprising administering a compound according to claim 2 to a human or animal.

11. A compound according to claim 3, wherein the compound is an anthelmintic.

12. A method of controlling human or animal parasitic worm comprising administering a compound according to claim 3 to a human or animal.

* * * * *